US009222086B2

(12) United States Patent
Judge et al.

(10) Patent No.: US 9,222,086 B2
(45) Date of Patent: Dec. 29, 2015

(54) COMPOSITIONS AND METHODS FOR SILENCING GENES EXPRESSED IN CANCER

(75) Inventors: Adam Judge, Vancouver (CA); Yun-Han Lee, Rockville, MD (US); Ian MacLachlan, Mission (CA); Snorri S. Thorgeirsson, Bethesda, MD (US)

(73) Assignees: PROTIVA BIOTHERAPEUTICS, INC., Burnaby, BC (CA); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 236 days.

(21) Appl. No.: 13/497,789

(22) PCT Filed: Sep. 23, 2010

(86) PCT No.: PCT/US2010/050077
§ 371 (c)(1),
(2), (4) Date: Nov. 9, 2012

(87) PCT Pub. No.: WO2011/038160
PCT Pub. Date: Mar. 31, 2011

(65) Prior Publication Data
US 2013/0065939 A1 Mar. 14, 2013

Related U.S. Application Data

(60) Provisional application No. 61/245,143, filed on Sep. 23, 2009, provisional application No. 61/377,439, filed on Aug. 26, 2010.

(51) Int. Cl.
A61K 31/70 (2006.01)
C07H 21/02 (2006.01)
C07H 21/04 (2006.01)
C12N 15/113 (2010.01)
C12Q 1/68 (2006.01)
A61K 31/713 (2006.01)
A61K 31/7105 (2006.01)

(52) U.S. Cl.
CPC .......... *C12N 15/113* (2013.01); *C12N 15/1137* (2013.01); *A61K 31/713* (2013.01); *A61K 31/7105* (2013.01); *C12N 2310/14* (2013.01); *C12N 2310/344* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| 2004/0259247 A1* | 12/2004 | Tuschl et al. ................. 435/375 |
| 2005/0255487 A1* | 11/2005 | Khvorova et al. ................ 435/6 |
| 2007/0249819 A1* | 10/2007 | Khvorova et al. ........... 536/24.1 |
| 2011/0071208 A1* | 3/2011 | MacLachlan et al. ...... 514/44 A |

FOREIGN PATENT DOCUMENTS

| WO | 2005/031002 A2 | 4/2005 |
| WO | 2006/043938 A1 | 4/2006 |
| WO | 2006/108584 A2 | 10/2006 |
| WO | 2007/012191 A1 | 2/2007 |
| WO | 2007/051303 A1 | 5/2007 |
| WO | 2009/129319 A2 | 10/2009 |

OTHER PUBLICATIONS

Iorns et al., "Integrated Functional, Gene Expression and Genomic Analysis for the Identification of Cancer Targets," PLOS One, Apr. 2009, vol. 4(4), pp. 1-11.
Judge et al., "Confirming the RNAi-mediated mechanism of action of siRNA-based cancer therapeutics in mice," Journal of Clinical Investigation, Mar. 2009, vol. 119(3), pp. 661-673.
Judge et al., "Design of Noninflammatory Synthetic siRNA Mediating Potent Gene Silencing in Vivo," Molecular Therapy, Mar. 2006, vol. 13(3), pp. 494-505.
Lee et al., "Definition of Ubiquitination Modulator COP1 as a Novel Therapeutic Target in Human Hepatocellular Carcinoma," Cancer Research, Nov. 2010, vol. 70(21), pp. 8264-8269.
Yi et al., "COP1-from plant photomorphogenesis to mammalian tumorigenesis," Trends in Cell Biology, Nov. 2005, vol. 15(11), pp. 618-625.

* cited by examiner

*Primary Examiner* — Sean McGarry
(74) *Attorney, Agent, or Firm* — Kilpatrick Townsend & Stockton LLP

(57) ABSTRACT

The present invention provides therapeutic nucleic acids such as interfering RNA (e.g., siRNA) that target the expression of genes associated with tumorigenesis and/or cell transformation, lipid particles (e.g., nucleic acid-lipid particles) comprising one or more (e.g., a cocktail) of the therapeutic nucleic acids, methods of making the lipid particles, and methods of delivering and/or administering the lipid particles, e.g., for the treatment of a cell proliferative disorder such as cancer.

8 Claims, 70 Drawing Sheets

*Light Microscopy (96 h)*
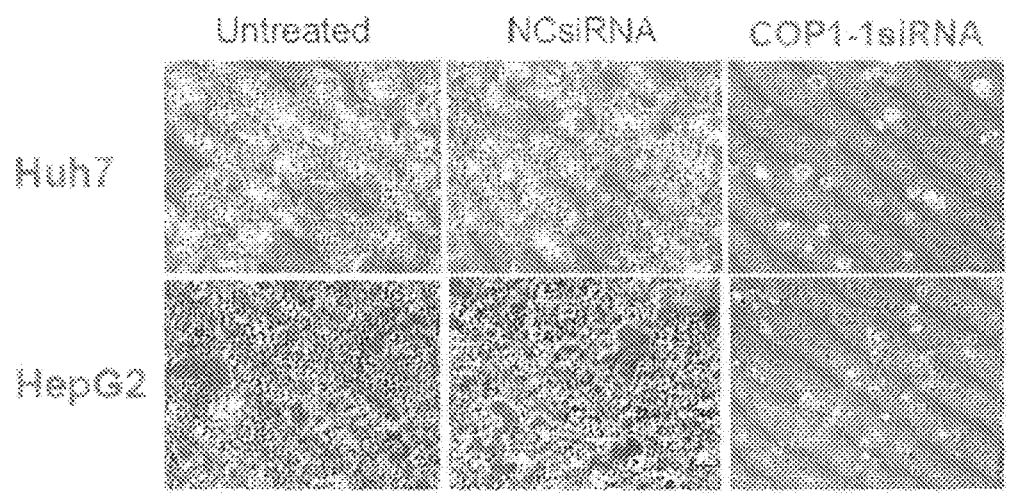
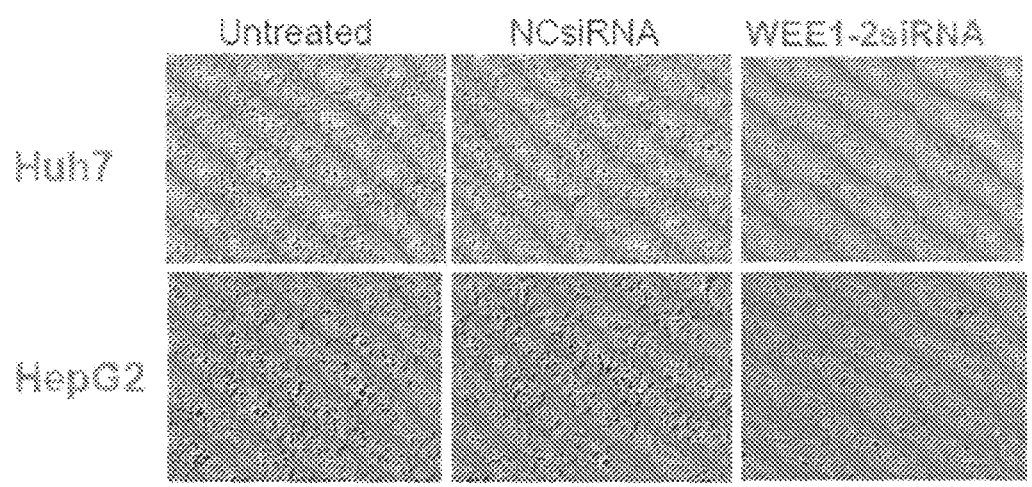
*X100 magnification*
*FIG. 3*

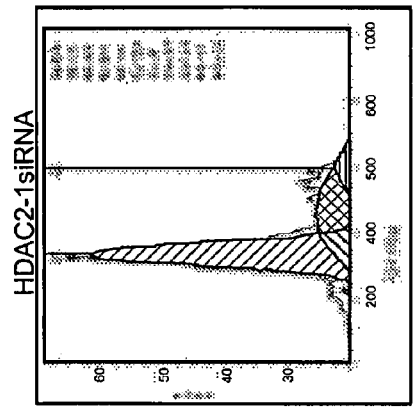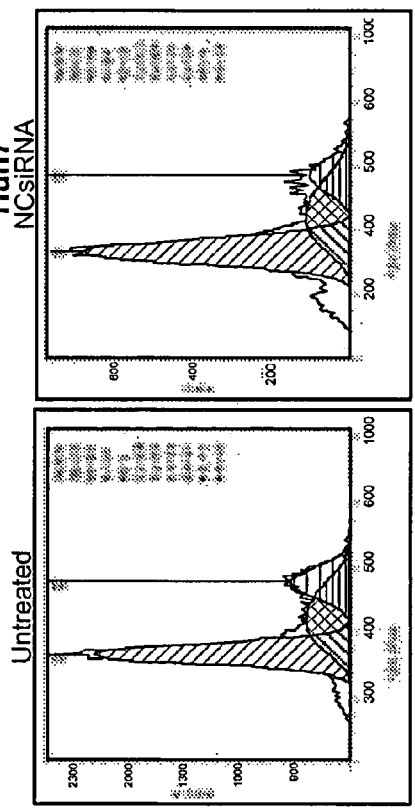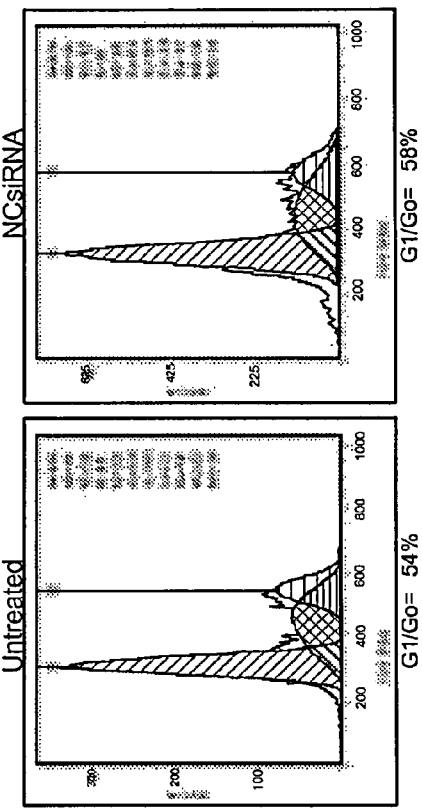
FIG. 18

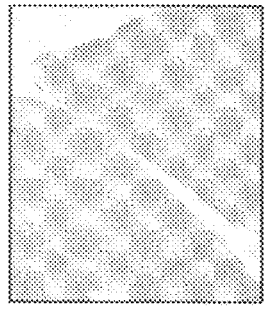
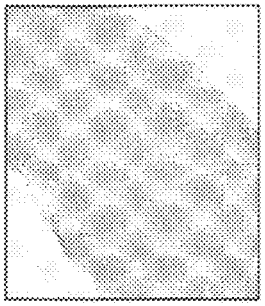
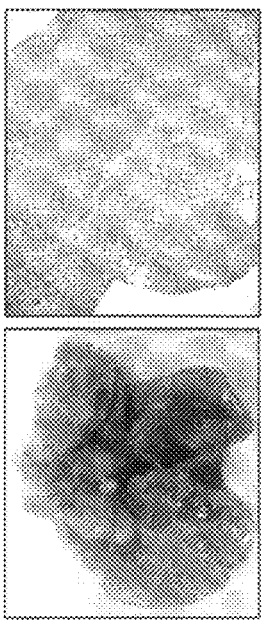
FIG. 26

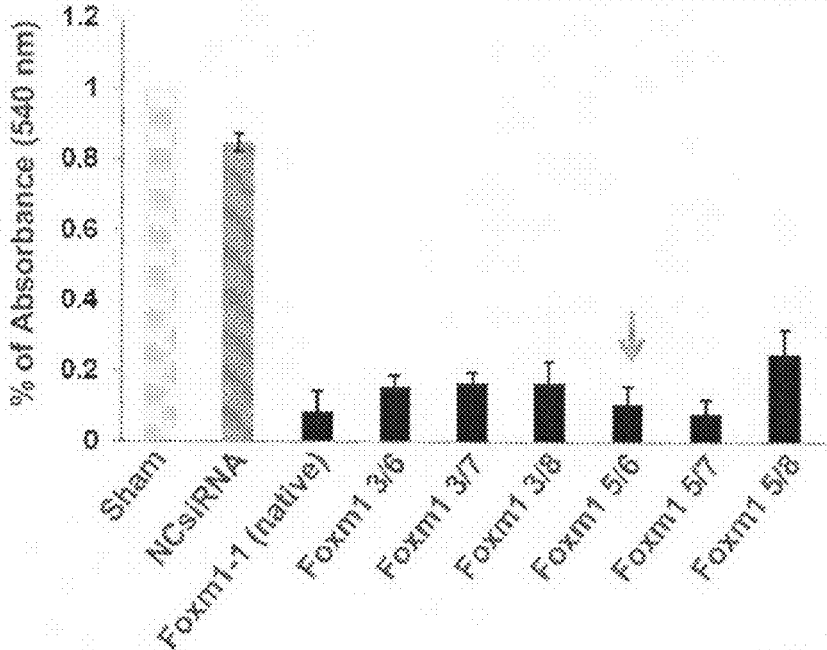
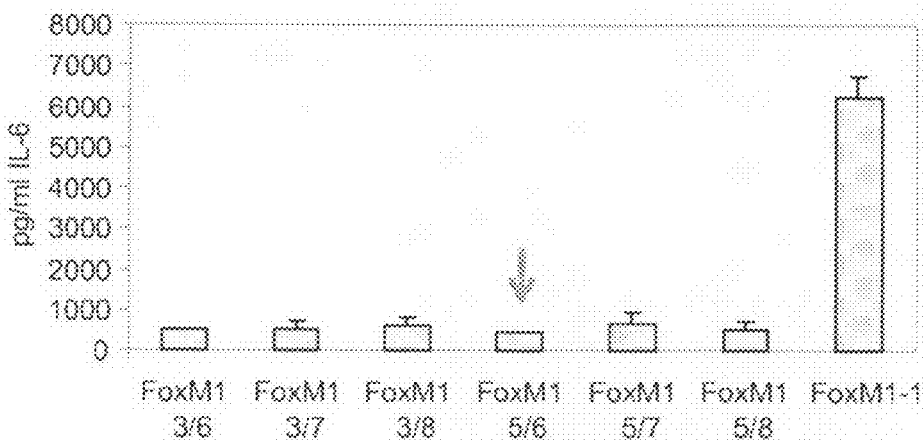
FIG. 32

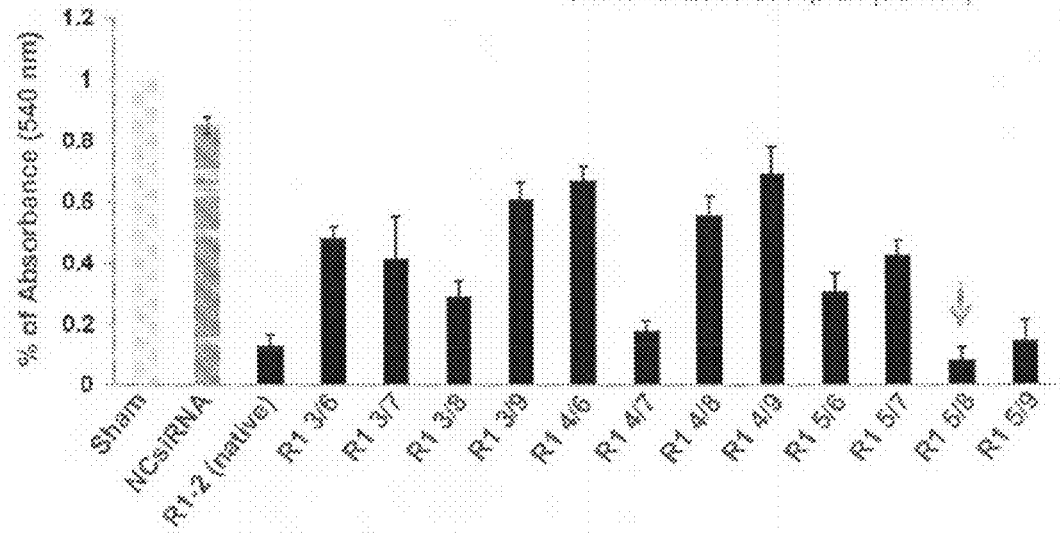
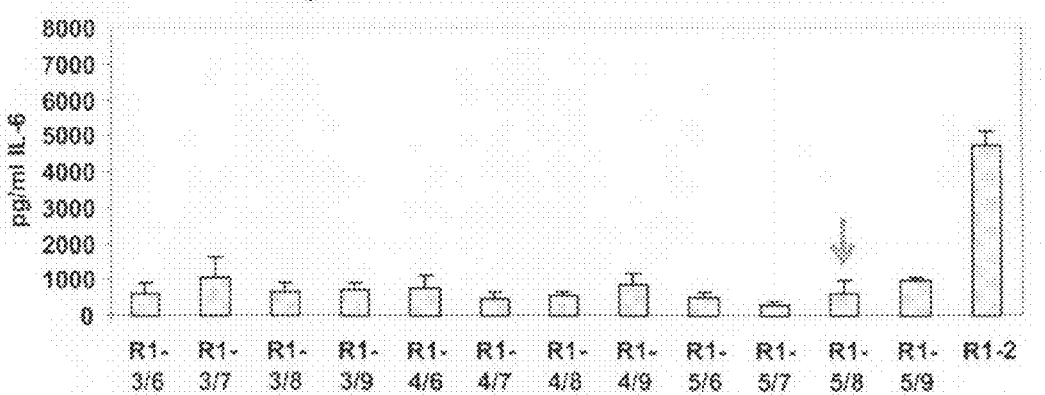
FIG. 33

| Gene symbol | GenBank Accession | Gene Description | Average log ratio* | P value |
|---|---|---|---|---|
| *Upregulated* | | | | |
| Apoptosis (GOID GO:0006915) *P*-value 0.0002 | | | | |
| PAK2 | NM_002577 | p21 (CDKN1A)-activated kinase 2 | 0.619229 | 0.0014 |
| HSPA1B | NM_005345 | heat shock 70kDa protein 1B | 0.855933 | 0 |
| BAG3 | NM_004281 | BCL2-associated athanogene 3 | 0.739676 | 0 |
| GAS1 | AL158149 | growth arrest-specific 1 | 1.05045 | 0.0031 |
| JAG2 | NM_145159 | jagged 2 | 0.650559 | 0 |
| PHLDA1 | NM_007350 | pleckstrin homology-like domain, family A, member 1 | 0.595623 | 0.0109 |
| DIDO1 | NM_080797 | death inducer-obliterator 1 | 0.695141 | 0.0009 |
| CEBPG | NM_001806 | CCAAT/enhancer binding protein (C/EBP), gamma | 0.635062 | 0.0003 |
| PPP2CB | NM_004156 | protein phosphatase 2, catalytic subunit, beta isoform | 1.397829 | 0.0072 |
| HSPE1 | NG_008914 | heat shock 10kDa protein 1 (chaperonin 10) | 0.614883 | 0.0438 |
| PMAIP1 | NM_021127 | phorbol-12-myristate-13-acetate-induced protein 1 | 0.644866 | 0.0188 |
| PCSK9 | NG_009061 | proprotein convertase subtilisin/kexin type 9 | 0.695368 | 0.0052 |
| RNF130 | NM_018434 | ring finger protein 130 | 0.621086 | 0.0159 |
| CROP | NM_006107 | cisplatin resistance-associated overexpressed protein | 0.998734 | 0.0069 |
| Intracellular signaling cascade (GOID GO:0007242) *P*-value 0.00012 | | | | |
| DUSP1 | NM_004417 | dual specificity phosphatase 1 | 0.92518 | 0.0067 |
| DUSP8 | NM_004420 | dual specificity phosphatase 8 | 0.619338 | 0.0345 |
| LATS2 | NM_014572 | LATS, large tumor suppressor, homolog 2 (Drosophila) | 0.623350 | 0 |
| RAD1 | NR_026591 | RAD1 homolog (S. pombe) | 0.622815 | 0.0105 |
| RHOB | NM_004040 | ras homolog gene family, member B | 0.990665 | 0.0004 |
| NLK | NM_016231 | nemo-like kinase | 0.713408 | 0.0458 |
| *Downregulated* | | | | |
| Inflammatory response (GOID GO:0006954) *P*-value 0.00034 | | | | |
| FGG | NM_000509 | fibrinogen gamma chain, transcript variant gamma-A | -1.046564 | 0.0382 |
| CCL5 | NM_002985 | chemokine (C-C motif) ligand 5 | -1.637715 | 0.0148 |
| CXCR4 | NM_003467 | chemokine (C-X-C motif) receptor 4 | -0.842814 | 0.0048 |
| SERPINA3 | NM_001085 | serpin peptidase inhibitor, clade A, member 3 | -2.202251 | 0.0082 |
| NUPR1 | NM_012385 | nuclear protein 1 | -0.777396 | 0.0129 |
| ANXA2 | NM_004039 | annexin A2 | -0.622098 | 0 |
| Response to stress (GOID GO:0006950) *P*-value 0.00021 | | | | |
| PCNA | NM_182649 | proliferating cell nuclear antigen | -0.660795 | 0.0186 |
| CLDN3 | NM_001306 | claudin 3 | -1.095438 | 0.0037 |
| Antigen processing and presentation of exogenous peptide antigen (GOID GO:0002478) *P*-value 0.00143 | | | | |
| IFI30 | NM_006332 | interferon, gamma-inducible protein 30 | -0.638862 | 0.0057 |
| CTSE | NM_148964 | cathepsin E | -0.92357 | 0.0483 |

*Shown here are the means of the intensity log ratios of 6 separate experiments by comparing SNALP-COP1 4/7 vs. SNALP-βgal478 treated tumors.

*FIG. 47*

| Network ID | Score* | # of focus genes | Genes in network and their top functions |
|---|---|---|---|
| 1 | 53 | 32 | ↑ADNP, ↓ALOX5AP, ↓APH1B, ↓APOBEC3B, ↑BTG3, ↑CEBPD, ↑CEBPG, ↑CENPJ, ↑COL7A1, ↓CSF1R, ↑CTSZ (includes EG:1522), ↓DAZAP1, ↑DMBT1, ↓DUSP10, Fcer1, ↓IFI6, ↓ITPR2, ↑JAG2, ↓LAMA3, ↓LAMC2, ↑MAFF, ↓MEOX1, ↓NFAT5, ↓NFS1, ↓OASL, peptidase, ↓PI3, ↑PLAA, ↓PSENEN, ↓RARRES2, Secretase gamma, ↓TNF, ↑UBQLN2, ↑WNT10B, ↓WWOX |
| | | | Connective tissue development and function, lipid metabolism, dermatological diseases and conditions |
| 2 | 43 | 28 | ↑ACSL4, ↓ACTA2, ↑ADARB1, Alpha actin, ↓ANXA2, ↑BAG3, Bcl9-Cbp/p300-Ctnnb1-Lef/Tcf, ↑CLIP1, Cofilin, ↑CYFIP2 (includes EG:26999), ↓ETV3, F Actin, ↑G3BP1, ↑GAA, ↑GAS1, ↓HERC5, ↑HSPA1B, ↑HSPH1, Ige, ↑MYC, ↑PERP, ↑PHLDA1, ↑RCC1 (includes EG:1104), ↑RPL14, ↓RPL34, ↓SCPEP1, ↑SRM, ↓STMN1, Tni, ↓TNNC1, ↓TNNT2, ↓TPM1, Tropomyosin, ↑TUBA4A, ↑VARS |
| | | | Skeletal and muscular system development and function, tissue morphology, cardiovascular system development and function |
| 3 | 38 | 27 | Akt, ↓C4BPB, ↑CAST, ↓CDC25C, ↑CDKN1C, ↑CHMP4C, ↓CSF2RA (includes EG:1438), ↓CSTF1, ↓CTDP1, Cyclin A, Cyclin B, Cyclin D, Cyclin E, ↑DDX11, E2f, E3 RING, ↑EP400, ↑GPBP1, ↑INPP5E, ↑LATS2, ↓MDM2, ↓NUPR1, ↓PCNA, ↑PRKDC, ↑PROS1, ↓PRRG2, Rb, ↑SLBP, ↓TBC1D19, ↓TJP2, ↑UNG, ↑USP8, ↑USP6NL, ↓XIAP, ↑YAP1 |
| | | | DNA replication, recombination, and repair, cell cycle, respiratory system development and function |
| 4 | 36 | 25 | ↓AIF1, ↑AMH, ↑BHLHB2, ↓BTG2, ↓CCL5, ↑CNN2, ERK, GC-GCR dimer, ↑HSPE1, I kappa b kinase, ↑IL11, ↑IL27RA, JAK, ↑KITLG (includes EG:4254), ↑KLF5, ↑LIFR, ↓LIMS1, ↓LOX, ↓MPL, NfkB-RelA, ↑NPTX1, ↑PLXNA1, ↓PTPRR, ↑RPS6KA3 (includes EG:6197), Rsk, SAA@, ↑SEMA3F, STAT, STAT5a/b, ↑TAF1C, Tgf beta, ↑TGFA, ↓TNFRSF14, ↑TSC22D3, ↓UGCGL1 |
| | | | Cellular growth and proliferation, cancer, embryonic development |
| 5 | 36 | 25 | Calcineurin protein(s), ↓CFB, ↑CHP, ↑EXOSC10, ↓FGG, ↑GNA13, ↓HAX1, IFN Beta, IL12, Interferon alpha, IRAK, ↑IRAK1, IRF, ↓ISG20, ↓ITCH, ↓LTB, ↓MX1, NFkB, ↑PMAIP1, ↓RARRES3, Ras homolog, ↓RBCK1, ↑RHOB, ↑RNF19B, Rock, ↓SERPINA5, ↓SGK3, ↑STK40, ↑TACSTD1, ↑TICAM1, ↓TNFRSF25, ↑TOLLIP, ↑UBAP2L, ↑XRN2 |
| | | | RNA damage and repair, antigen presentation, antimicrobial response |

*The score is a numerical value used to rank networks according to how relevant they are to the genes in input dataset (540 genes). The score takes into account the number of genes in network and the size of the network to approximate how relevant this network is to input gene list. Up- and downregulated genes in each network are indicated in red and green arrow, respectively.

FIG. 48

| Canonical Pathways | P-value | Gene Symbol | Entrez Gene Name | Log Ratio* |
|---|---|---|---|---|
| p53 Signaling | 0.00646 | BCL2 | B-cell CLL/lymphoma 2 | -0.743 |
| | | MDM2 | Mdm2 p53 binding protein homolog (mouse) | -0.72 |
| | | PCNA | proliferating cell nuclear antigen | -0.661 |
| | | PERP | PERP, TP53 apoptosis effector | 0.919 |
| | | PIK3C3 | phosphoinositide-3-kinase, class 3 | 0.591 |
| | | PMAIP1 | phorbol-12-myristate-13-acetate-induced protein 1 | 0.645 |
| | | PRKDC | protein kinase, DNA-activated, catalytic polypeptide | 1.051 |
| | | SERPINB5 | serpin peptidase inhibitor, clade B (ovalbumin), member 5 | -0.693 |
| Wnt/β-catenin Signaling | 0.00275 | AXIN1 | axin 1 | 0.668 |
| | | CDH3 | cadherin 3, type 1, P-cadherin (placental) | -0.816 |
| | | FZD4 | frizzled homolog 4 (Drosophila) | 1.333 |
| | | GJA1 | gap junction protein, alpha 1, 43kDa | 0.6 |
| | | MDM2 | Mdm2 p53 binding protein homolog (mouse) | -0.72 |
| | | MMP7 | matrix metallopeptidase 7 (matrilysin, uterine) | -1.177 |
| | | MYC | v-myc myelocytomatosis viral oncogene homolog (avian) | 0.722 |
| | | NLK | nemo-like kinase | 0.713 |
| | | PPP2CB | protein phosphatase 2, catalytic subunit, beta isoform | 1.398 |
| | | PPP2R2B | protein phosphatase 2, regulatory subunit B, beta isoform | -0.694 |
| | | SOX9 | SRY (sex determining region Y)-box 9 | -0.811 |
| | | WNT10B | wingless-type MMTV integration site family, member 10B | 0.882 |
| Death Receptor Signaling | 0.0398 | BCL2 | B-cell CLL/lymphoma 2 | -0.743 |
| | | IKBKE | inhibitor of kappa light polypeptide gene enhancer in B-cells, kinase epsilon | -0.819 |
| | | TNF | tumor necrosis factor (TNF superfamily, member 2) | -0.639 |
| | | TNFRSF25 | tumor necrosis factor receptor superfamily, member 25 | -1.08 |
| | | XIAP | X-linked inhibitor of apoptosis | -0.695 |

*Shown here are the means of the intensity log ratios of 6 separate experiments by comparing SNALP-COP1 4/7 vs. SNALP-βgal478 treated tumors.

*FIG. 49*

| Serial No. | Target gene (Locus ID) | Size (base) | Sequence |
|---|---|---|---|
| COP1-1 | COP1 (64326) | 21<br>21 | S; 5'-GGACACCGUAAAGCAGUCUtt-3'<br>AS; 5'-AGACUGCUUUACGGUGUCCtt-3 |
| COP1-2 | COP1 (64326) | 21<br>21 | S; 5'-GGAAUGCUUGUCCAAGUUtt-3'<br>AS; 5'-AAACUUGGACAAGCAUUCCtg-3' |
| COP1-3 | COP1 (64326) | 21<br>21 | S; 5'-GCAACGACUUCGUAUGCCtt-3'<br>AS; 5'-GGGCAUACGAAGUCGUUGCtt-3' |
| CSN5-1 | CSN5 (10987) | 21<br>21 | S; 5'-CCAUUACUUUAAGUACUGCtt-3'<br>AS; 5'-GCAGUACUUUAAGUAAUGGtg-3' |
| CSN5-2 | CSN5 (10987) | 21<br>21 | S; 5'-GGAUCACCAUUACUUUAAGtt-3'<br>AS; 5'-CUUAAAGUAAUGGUGAUCCtt-3' |
| CSN5-3 | CSN5 (10987) | 21<br>21 | S; 5'-CCGAAAUCAGAAGACAAAtt-3'<br>AS; 5'-UUUGUCUUCUGAUUUCGGtc-3' |
| βgal478 | None | 21<br>21 | S; 5'-mGAAGmGCCAGACmGCmGAAUUAdTdT-3'<br>AS; 5'-UAAUmUCGCGmUCUGGCCmUUCdTdT-3' |
| COP1 4/7 | COP1 (64326) | 21 | S; 5'-GmGACACCmGUAAAmGCAmGUCUdTdT-3'<br>AS; 5'-AGACUGCmUUUACGGmUGmUCCdTdT-3' |
| CSN5 3/8 | CSN5 (10987) | 21<br>21 | S; 5'-GGAmUCACCAUmUACmUUmUAAGUU-3'<br>AS; 5'-CUUAAAmGUAAUGmGUmGAUCCUU-3' |

Abbreviation: *S*, sense; *AS*, antisense; *mU*, 2'O-methyl uridine; *mG*, 2'O-methyl guanosine; and *dT*, dexoy-thymidine.

*FIG. 51*

| Serial No. | Target gene (Locus ID) | Size (base) | Sequence |
|---|---|---|---|
| COP1-1 | COP1 (64326) | 21<br>21 | S: 5'-GGACACCGUAAAGCAGUCUtt-3'<br>AS: 5'-AGACUGCUUUACGGUGUCCtt-3 |
| COP1-2 | COP1 (64326) | 21<br>21 | S: 5'-GGAAUGCUUGUCCAAGUUUtt-3'<br>AS: 5'-AAACUUGGACAAGCAUUCCtg-3' |
| COP1-3 | COP1 (64326) | 21<br>21 | S: 5'-GCAACGACUUCGUAUGCCCtt-3'<br>AS: 5'-GGGCAUACGAAGUCGUUGCtt-3' |
| βgal478 | None | 21<br>21 | S: 5'-mGAAGmGCCAGACmGCmGAAUUAdTdT-3'<br>AS: 5'-UAAUmUCGCGmUCUGGCCmUUCdTdT-3' |
| COP1 4/7 | COP1 (64326) | 21<br>21 | S: 5'-GmGACACCmGUAAAmGCAmGUCUdTdT-3'<br>AS: 5'-AGACUGCmUUUACGGmUGmUCCdTdT-3' |

Abbreviation : S, sense; AS, antisense; mU, 2'O-methyl uridine; mG, 2'O-methyl guanosine; and dT, deoxy-thymidine.

FIG. 52

| Gene Symbol | Gene Description (*Homo Sapiens*) | Huh7 | | HepG2 | |
|---|---|---|---|---|---|
| | | Fold Changes (Log2) | *p*-value | Fold Changes (Log2) | *p*-value |
| AARS | alanyl-tRNA synthetase | -1.061 | 0.0000 | -1.024 | 0.0000 |
| ABL1 | c-abl oncogene 1 | -1.006 | 0.0000 | -1.307 | 0.0004 |
| ALDH18A1 | aldehyde dehydrogenase 18 family, member A1 | -1.526 | 0.0007 | -1.268 | 0.0006 |
| ARIH2 | ariadne homolog 2 (Drosophila) | -1.112 | 0.0000 | -1.064 | 0.0018 |
| B4GALT5 | UDP-Gal:betaGlcNAc beta 1,4- galactosyltransferase, polypeptide 5 | -1.115 | 0.0086 | -1.214 | 0.0014 |
| BOLA3 | bolA homolog 3 (E. coli) | -1.991 | 0.0092 | -1.746 | 0.0000 |
| C11orf48 | chromosome 11 open reading frame 48 | -3.487 | 0.0032 | -2.268 | 0.0034 |
| C17orf58 | chromosome 17 open reading frame 58 | -1.207 | 0.0000 | -1.515 | 0.0002 |
| C1orf225 | chromosome 1 open reading frame 225 | -2.184 | 0.0000 | -1.173 | 0.0000 |
| C6orf106 | chromosome 6 open reading frame 106 | -1.423 | 0.0078 | -1.287 | 0.0000 |
| CANX | calnexin | -3.083 | 0.0000 | -3.516 | 0.0006 |
| CCNI | cyclin I | -1.819 | 0.0000 | -1.688 | 0.0000 |
| CETN2 | centrin, EF-hand protein, 2 | -1.160 | 0.0006 | -1.173 | 0.0000 |
| COMMD1 | copper metabolism (Murr1) domain containing 1 | -2.195 | 0.0028 | -1.315 | 0.0000 |
| COQ9 | coenzyme Q9 homolog (S. cerevisiae) | -2.017 | 0.0000 | -1.490 | 0.0004 |
| COX7A2 | cytochrome c oxidase subunit VIIa polypeptide 2 (liver) | -2.826 | 0.0000 | -2.216 | 0.0016 |
| CPD | carboxypeptidase D | -1.321 | 0.0050 | -1.602 | 0.0012 |
| CTDSPL | CTD (carboxy-terminal domain, RNA polymerase II, polypeptide A) small phosphatase-like | -2.911 | 0.0000 | -1.088 | 0.0004 |
| CTRC | chymotrypsin C (caldecrin) | -1.373 | 0.0010 | 1.286 | 0.0037 |
| EPB41L4B | erythrocyte membrane protein band 4.1 like 4B | -2.199 | 0.0000 | -1.091 | 0.0000 |
| ETV4 | ets variant 4 | -3.142 | 0.0000 | -1.127 | 0.0000 |
| FADD | Fas (TNFRSF6)-associated via death domain | -1.684 | 0.0061 | -1.836 | 0.0016 |
| FAM168B | family with sequence similarity 168, member B | -1.118 | 0.0000 | -1.086 | 0.0000 |
| FBXW4 | F-box and WD repeat domain containing 4 | -1.030 | 0.0035 | -1.085 | 0.0000 |
| FHL2 | four and a half LIM domains 2 | 1.138 | 0.0000 | 1.036 | 0.0004 |
| FLJ45032 | similar to F40B5.2b | 1.151 | 0.0038 | 1.662 | 0.0000 |
| FOXJ3 | forkhead box J3 | -1.335 | 0.0000 | -1.707 | 0.0002 |
| FOXO3 | forkhead box O3 | -1.372 | 0.0082 | -1.109 | 0.0048 |
| FZD9 | frizzled homolog 9 (Drosophila) | -3.333 | 0.0000 | -1.455 | 0.0002 |
| GLIPR1 | GLI pathogenesis-related 1 | 3.002 | 0.0003 | 1.860 | 0.0006 |
| GLUD1 | glutamate dehydrogenase 1 | -1.500 | 0.0097 | -1.716 | 0.0037 |
| GPER | G protein-coupled estrogen receptor 1 | -1.830 | 0.0018 | -0.953 | 0.0002 |
| HIST1H2AC | histone cluster 1, H2ac | 1.366 | 0.0089 | 1.192 | 0.0000 |
| IDH1 | isocitrate dehydrogenase 1 (NADP+), soluble | -1.017 | 0.0080 | -1.515 | 0.0000 |
| KIAA0152 | KIAA0152 | -1.782 | 0.0000 | -1.378 | 0.0000 |
| LEPROT | leptin receptor overlapping transcript | -1.980 | 0.0014 | -1.820 | 0.0000 |
| LETM1 | leucine zipper-EF-hand containing transmembrane protein 1 | -1.720 | 0.0003 | -1.942 | 0.0000 |
| MORC2 | MORC family CW-type zinc finger 2 | -1.156 | 0.0090 | -1.324 | 0.0000 |
| MRPL18 | mitochondrial ribosomal protein L18 | -2.199 | 0.0049 | -2.069 | 0.0000 |
| NEDD8 | neural precursor cell expressed, developmentally down-regulated 8 | -1.146 | 0.0062 | -1.108 | 0.0000 |
| NETO2 | neuropilin (NRP) and tolloid (TLL)-like 2 | -1.392 | 0.0025 | -3.022 | 0.0006 |
| NFIX | nuclear factor I/X (CCAAT-binding transcription factor) | -2.388 | 0.0000 | -1.425 | 0.0000 |
| NHP2L1 | NHP2 non-histone chromosome protein 2-like 1 (S. cerevisiae) | -1.480 | 0.0000 | -1.129 | 0.0000 |
| NQO1 | NAD(P)H dehydrogenase, quinone 1 | -2.418 | 0.0000 | -2.131 | 0.0000 |
| NUDT2 | nudix (nucleoside diphosphate linked moiety X)-type motif 2 | -1.640 | 0.0000 | -1.186 | 0.0000 |

*FIG. 56*

| | | | | | |
|---|---|---|---|---|---|
| PFDN1 | prefoldin subunit 1 | -1.399 | 0.0075 | -1.912 | 0.0000 |
| PLD1 | phospholipase D1, phosphatidylcholine-specific | -1.536 | 0.0047 | -1.265 | 0.0002 |
| PLEKHB2 | pleckstrin homology domain containing, family B (evectins) member 2 | 1.278 | 0.0066 | 1.044 | 0.0000 |
| POLR2C | polymerase (RNA) II (DNA directed) polypeptide C, 33kDa | -1.091 | 0.0000 | -1.612 | 0.0029 |
| RCC2 | regulator of chromosome condensation 2 | -1.419 | 0.0019 | -2.127 | 0.0000 |
| RFWD2 | ring finger and WD repeat domain 2 | -2.695 | 0.0000 | -2.034 | 0.0000 |
| RPAIN | RPA interacting protein | -1.602 | 0.0015 | -1.116 | 0.0006 |
| RPUSD3 | RNA pseudouridylate synthase domain containing 3 | -1.501 | 0.0025 | -1.192 | 0.0002 |
| SCMH1 | sex comb on midleg homolog 1 (Drosophila) | -1.029 | 0.0068 | -1.061 | 0.0018 |
| SDC1 | syndecan 1 | -2.113 | 0.0000 | -1.255 | 0.0004 |
| SDC4 | syndecan 4 | 1.189 | 0.0059 | 1.044 | 0.0000 |
| SLC31A2 | solute carrier family 31 (copper transporters), member 2 | 1.794 | 0.0000 | 1.047 | 0.0006 |
| SOCS2 | suppressor of cytokine signaling 2 | 2.182 | 0.0008 | 1.195 | 0.0000 |
| SPOCK2 | sparc/osteonectin, cwcv and kazal-like domains proteoglycan (testican) 2 | -2.230 | 0.0000 | -2.314 | 0.0002 |
| ST6GALNAC6 | ST6 (alpha-N-acetyl-neuraminyl-2,3-beta-galactosyl-1,3)-N-acetylgalactosaminide alpha-2,6-sialyltransferase 6 | -1.538 | 0.0036 | -1.190 | 0.0000 |
| SURF4 | surfeit 4 | -1.886 | 0.0000 | -1.914 | 0.0000 |
| TALDO1 | transaldolase 1 | -1.491 | 0.0023 | -1.642 | 0.0018 |
| TAP1 | transporter 1, ATP-binding cassette, sub-family B (MDR/TAP) | 2.000 | 0.0000 | 1.054 | 0.0000 |
| TFPI | tissue factor pathway inhibitor | -1.280 | 0.0085 | -1.798 | 0.0018 |
| THAP11 | THAP domain containing 11 | -1.442 | 0.0000 | -1.541 | 0.0000 |
| TIMM23 | translocase of inner mitochondrial membrane 23 homolog (yeast) | -1.399 | 0.0072 | -1.639 | 0.0008 |
| TIMP2 | TIMP metallopeptidase inhibitor 2 | 1.103 | 0.0004 | 1.107 | 0.0000 |
| TMCO3 | transmembrane and coiled-coil domains 3 | -1.705 | 0.0000 | -1.240 | 0.0040 |
| TNFRSF21 | tumor necrosis factor receptor superfamily, member 21 | -1.276 | 0.0000 | -1.871 | 0.0000 |
| TRIM35 | tripartite motif-containing 35 | 1.074 | 0.0028 | 1.117 | 0.0000 |
| TUFT1 | tuftelin 1 | 1.868 | 0.0000 | 1.004 | 0.0000 |
| UBE2G2 | ubiquitin-conjugating enzyme E2G 2 (UBC7 homolog, yeast) | -1.727 | 0.0020 | -2.013 | 0.0012 |
| UBE2Q1 | ubiquitin-conjugating enzyme E2Q (putative) 1 | -1.702 | 0.0000 | -1.897 | 0.0000 |
| UBE2Z | ubiquitin-conjugating enzyme E2Z | -1.468 | 0.0032 | -1.279 | 0.0008 |
| UBFD1 | ubiquitin family domain containing 1 | -1.449 | 0.0021 | -1.081 | 0.0004 |
| UBIAD1 | UbiA prenyltransferase domain containing 1 | -2.501 | 0.0002 | -1.617 | 0.0000 |
| ZHX3 | zinc fingers and homeoboxes 3 | -1.383 | 0.0000 | -1.072 | 0.0012 |
| ZNF358 | zinc finger protein 358 | -2.328 | 0.0019 | -1.140 | 0.0018 |

*FIG. 56 (cont)*

| Network ID | Score* | # of focus genes | Genes in network and their top functions |
|---|---|---|---|
| 1 | 38 | 18 | ↓ABL1, Actin, ↓CANX, CARD8, CASP8AP2, Caspase, Ck2, Collagen type I, ↓COMMD1 (includes EG:150684), DCT, ↓EPB41L4B, ERK, ERK1/2, ↓FADD, ↑FHL2, ↓FOXO3, ↓GPER, H2-LD, MIR1, ↓NETO2, NFkB (complex), ↓NQO1, PDGF BB, peptide-Tap1-Tap2, ↓PFDN1, Pkc(s), ↓PLD1, ↑PLEKHB2, ↓SDC1, ↑SDC4, ↑TAP1, ↓TFPI, ↑TIMP2, TNFRSF23, WASF3 |
| | | | Gene Expression, Cellular Compromise, Post-Translational Modification |
| 2 | 30 | 15 | ↓AARS, beta-estradiol, BRF2, ↓C11ORF48, CBR3, CCNG2, ↓CETN2, ↓COX7A2, CP110, CRADD, EMG1, ↓FOXJ3, GNS, HNF4A, KRT5, LCN2, ↓LEPROT, ↓LETM1, MAPK7, MBD4, MED23, ↓MRPL18, MUC4, NRF1, ↓NUDT2, ↓RPAIN, SGK1, ↓SPOCK2, SSR1, ↓SURF4, TARS, ↓TIMM23, TRAIP, ↑TUFT1, ↓UBIAD1 |
| | | | Gene Expression, Cancer, Cardiovascular Disease |
| 3 | 29 | 15 | AChR, ↓ALDH18A1, ↓ARIH2, ATXN1, CARD17, CBR3, CCNG2, ↓CCNI, CDKN2A, ↓CPD, ↑GLIPR1, ↓GLUD1, hydrogen peroxide, IFNG, IL2, ↓MORC2, MSR1, ↓NHP2L1, RAD17, ↓RFWD2 (includes EG:64326), ↓SCMH1, SERP1, SIPA1, SLC1A6, ↑SOCS2, ↓ST6GALNAC6, STUB1, ↑TAP1, TGFB1, TP53, TYRP1, ↓UBE2Q1, YY1AP1, ZHX2, ↓ZHX3 |
| | | | Cellular Development, Cellular Growth and Proliferation, Connective Tissue Development and Function |
| 4 | 19 | 11 | APP, CD82, CUL1, Cytochrome c oxidase, E2F1, FAF1, FBXO4, ↓FBXW4, HARS, ↑HIST1H2AC, ↓IDH1, KCNH2, MIR214 (includes EG:406996), ↓MLEC, MVP, NAE1, NAIP, ↓NEDD8, NR3C1, ↓POLR2C, RBX1 (includes EG:9978), ↓RCC2, RDBP, RNA polymerase II, SENP8, ↓TALDO1, TCEB1, TCEB2, ↓TMCO3, TNF, ↓TNFRSF21, UBC, ↓UBFD1, UCHL1, VHL |
| | | | Post-Translational Modification, Cell Cycle, Drug Metabolism |
| 5 | 19 | 11 | B4GALT1, ↓B4GALT5, BACE1, BCAP31, CASP3, COX2, ↓CTDSPL, CTNNB1, ↓CTRC, DNAJB1, DVL1, ENPEP, ↓ETV4, F9, ↓FAM168B, Frizzled, ↓FZD9, Galactosyltransferase beta 1.4, GTF2IRD1, HTT, JUP, KRT5, ↓NFIX, Nuclear factor 1, peptidase, PRSS3 (includes EG:5646), RAPSN, RB1, SMAD3, ↓THAP11, TRIM27, ↑TRIM35, ↓UBE2G2, ↓UBE2Z, WNT7A |
| | | | Cell Morphology, Nervous System Development and Function, Carbohydrate Metabolism |

*The score is a numerical value used to rank networks according to how relevant they are to the genes in the input dataset (78 genes). The score takes into account the number of genes in network and the size of the network to approximate how relevant this network is to input gene list. Up- and downregulated genes are indicated.

FIG. 58

COMPOSITIONS AND METHODS FOR SILENCING GENES EXPRESSED IN CANCER

CROSS-REFERENCES TO RELATED APPLICATIONS

The present application claims priority to U.S. Provisional Application No. 61/245,143, filed Sep. 23, 2009, and U.S. Provisional Application No. 61/377,439, filed Aug. 26, 2010, the disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

The Sequence Listing written in file -95-2.TXT, created on Jul. 6, 2012, 90,112 bytes, machine format IBM-PC, MS-Windows operating system, is hereby incorporated by reference in its entirety for all purposes.

This invention was created, in part, in the performance of a Collaboration Agreement with the National Cancer Institute, National Institutes of Health, an agency of the United States Government. The Government of the United States has certain rights in this invention.

BACKGROUND OF THE INVENTION

Cell proliferation and programmed cell death play important roles in the growth and development of an organism. In proliferative diseases such as cancer, the processes of cell proliferation and/or programmed cell death are often perturbed. For example, a cancer cell may have unregulated cell division through either the overexpression of a positive regulator of the cell cycle or the loss of a negative regulator of the cell cycle, perhaps by mutation. Alternatively, a cancer cell may have lost the ability to undergo programmed cell death through the overexpression of a negative regulator of apoptosis. Therefore, there is a need to develop new therapeutic agents that will restore the processes of checkpoint control and programmed cell death to cancerous cells.

RNA interference (RNAi) is an evolutionarily conserved process in which recognition of double-stranded RNA (dsRNA) ultimately leads to posttranscriptional suppression of gene expression. In particular, RNAi induces specific degradation of mRNA through complementary base pairing between the dsRNA and the target mRNA. In several model systems, this natural response has been developed into a powerful tool for the investigation of gene function (see, e.g., Elbashir et al., *Genes Dev.*, 15:188-200 (2001); Hammond et al., *Nat. Rev. Genet.*, 2:110-119 (2001)).

RNAi is generally mediated by short dsRNAs such as small interfering RNA (siRNA) duplexes of 21-23 nucleotides in length or by longer Dicer-substrate dsRNAs of 25-30 nucleotides in length. Unlike siRNAs, Dicer-substrate dsRNAs are cleaved by Dicer endonuclease, a member of the RNase III family, to produce smaller functional 21-mer siRNA duplexes. The 21-mer siRNA (whether synthesized or processed by Dicer) recruits the RNA-induced silencing complex (RISC) and enables effective gene silencing via sequence-specific cleavage of the target sequence.

Although the precise mechanism is still unclear, RNAi provides a powerful approach to downregulate or silence the transcription and translation of a gene of interest. In particular, for the treatment of neoplastic disorders such as cancer, RNAi may be used to modulate (e.g., reduce) the expression of certain genes, e.g., an anti-apoptotic molecule, a growth factor, a growth factor receptor, a mitotic spindle protein, a cell cycle protein, an angiogenic factor, an oncogene, an intracellular signal transducer, a molecular chaperone, and combinations thereof.

However, a safe and effective nucleic acid delivery system is required for RNAi to be therapeutically useful. Viral vectors are relatively efficient gene delivery systems, but suffer from a variety of limitations, such as the potential for reversion to the wild-type as well as immune response concerns. Furthermore, viral systems are rapidly cleared from the circulation, limiting transfection to "first-pass" organs such as the lungs, liver, and spleen. In addition, these systems induce immune responses that compromise delivery with subsequent injections. As a result, nonviral gene delivery systems are receiving increasing attention (Worgall et al., *Human Gene Therapy*, 8:37 (1997); Peeters et al., *Human Gene Therapy*, 7:1693 (1996); Yei et al., *Gene Therapy*, 1:192 (1994); Hope et al., *Molecular Membrane Biology*, 15:1 (1998)).

Complexes of nucleic acid and cationic liposomes (i.e., lipoplexes) are a commonly employed nonviral gene delivery vehicle. For instance, lipoplexes made of an amphipathic compound, a neutral lipid, and a detergent for transfecting insect cells are disclosed in U.S. Pat. No. 6,458,382. Lipoplexes are also disclosed in U.S. Patent Publication No. 20030073640. However, lipoplexes are large, poorly defined systems that are not suited for systemic applications and can elicit considerable toxic side-effects (Harrison et al., *Biotechniques*, 19:816 (1995); Li et al., *The Gene*, 4:891 (1997); Tam et al, *Gene Ther.*, 7:1867 (2000)). As large, positively charged aggregates, lipoplexes are rapidly cleared when administered in vivo, with highest expression levels observed in first-pass organs, particularly the lungs (Huang et al., *Nature Biotechnology*, 15:620 (1997); Templeton et al., *Nature Biotechnology*, 15:647 (1997); Hofland et al., *Pharmaceutical Research*, 14:742 (1997)).

Other liposomal delivery systems include, for example, the use of reverse micelles, anionic liposomes, and polymer liposomes. Reverse micelles are disclosed in U.S. Pat. No. 6,429,200. Anionic liposomes are disclosed in U.S. Patent Publication No. 20030026831. Polymer liposomes that incorporate dextrin or glycerol-phosphocholine polymers are disclosed in U.S. Patent Publication Nos. 20020081736 and 20030082103, respectively. However, such liposomal delivery systems are unsuitable for delivering nucleic acids such as interfering RNA to tumors because they are not of the desired size (i.e., less than about 150 nm diameter), are not preferentially delivered to tumor sites, and do not remain intact in the circulation for an extended period of time in order to achieve delivery to tumor sites. Rather, effective intracellular delivery of nucleic acids such as interfering RNA to tumors requires a highly stable, serum-resistant nucleic acid-containing particle that preferentially targets tumors such as solid tumors and does not interact with cells and other components of the vascular compartment.

Thus, there remains a strong need in the art for novel compositions and methods for preferentially introducing nucleic acids such as interfering RNA into tumor cells. In addition, there is a need in the art for methods of downregulating the expression of genes associated with tumorigenesis or cell transformation to treat or prevent cancer. The present invention addresses these and other needs.

BRIEF SUMMARY OF THE INVENTION

The present invention provides compositions comprising therapeutic nucleic acids (e.g., interfering RNA such as siRNA) that target the expression of genes associated with tumorigenesis or cell transformation (e.g., genes expressed in a cell proliferative disorder such as cancer), lipid particles comprising one or more (e.g., a cocktail) of the therapeutic nucleic acids, methods of making the lipid particles, and methods of delivering and/or administering the lipid particles (e.g., for the treatment of a cell proliferative disorder such as cancer).

More particularly, the present invention provides compositions comprising unmodified and chemically modified interfering RNA (e.g., siRNA) molecules which silence the expression of at least 1, 2, 3, 4, 5, 6, 7, or all 8 of the following genes: COP1, WEE1, HDAC2, RBX1, CDK4, CSN5, FOXM1, and R1 (RAM2). The present invention also provides serum-stable nucleic acid-lipid particles (e.g., SNALP) and formulations thereof comprising one or more (e.g., a cocktail) of the interfering RNA (e.g., siRNA) described herein, a cationic lipid, and a non-cationic lipid, which can further comprise a conjugated lipid that inhibits aggregation of particles. Methods of silencing COP1, WEE1, HDAC2, RBX1, CDK4, CSN5, FOXM1, and/or R1 (RAM2) gene expression by administering the interfering RNA (e.g., siRNA) described herein to a mammalian subject are also provided.

In one aspect, the present invention provides interfering RNA (e.g., siRNA) that target COP1, WEE1, HDAC2, RBX1, CDK4, CSN5, FOXM1, and/or R1 (RAM2) gene expression. In certain embodiments, the present invention provides compositions comprising a combination (e.g., a cocktail) of siRNAs that target multiple genes (e.g., at least 2, 3, 4, 5, 6, 7, or 8 different genes) expressed in cancer. The interfering RNA (e.g., siRNA) molecules of the invention are capable of inhibiting the proliferation of cancer cells and/or inducing cancer cell apoptosis in vitro or in vivo.

In some embodiments, the interfering RNA comprises at least one or a cocktail (e.g., at least 2, 3, 4, 5, 6, 7, 8, 9, 10, or more) of unmodified and/or modified siRNAs that silence one or multiple (e.g., at least 2, 3, 4, 5, 6, 7, 8, 9, 10, or more) genes expressed in cancer. In some instances, a cocktail of siRNA molecules may comprise sequences which target the same gene. In other instances, a cocktail of siRNA molecules may comprise sequences which target different genes. In further instances, the cocktail of siRNA molecules may comprise sequences which target genes associated with different strains, subtypes, or stages of cancer. In certain instances, one or more (e.g., at least 2, 3, 4, 5, 6, 7, 8, 9, 10, or more) modified siRNA sequences that silence cancer gene expression are present in a cocktail with one or more (e.g., at least 2, 3, 4, 5, 6, 7, 8, 9, 10, or more) unmodified siRNA sequences that silence cancer gene expression.

Each of the interfering RNA (e.g., siRNA) sequences present in the compositions of the present invention may independently comprise at least 1, 2, 3, 4, 5, 6, 7, 8, 9, 10, or more modified nucleotides such as 2'OMe nucleotides, e.g., in the sense and/or antisense strand of the double-stranded region. Preferably, uridine and/or guanosine nucleotides are modified with 2'OMe nucleotides. In particular embodiments, each of the interfering RNA (e.g., siRNA) sequences present in the compositions of the invention comprises at least one 2'OMe-uridine nucleotide and at least one 2'OMe-guanosine nucleotide in the sense and/or antisense strands.

In some embodiments, each of the interfering RNA (e.g., siRNA) sequences present in the compositions of the invention may independently comprise a 3' overhang of at least 1, 2, 3, or 4 nucleotides in one or both strands of the interfering RNA or may comprise at least one blunt end. In certain instances, the 3' overhangs in one or both strands of the interfering RNA each independently comprise at least 1, 2, 3, or 4 of any combination of modified and unmodified deoxythymidine (dT) nucleotides, at least 1, 2, 3, or 4 of any combination of modified (e.g., 2'OMe) and unmodified uridine (U) ribonucleotides, or at least 1, 2, 3, or 4 of any combination of modified (e.g., 2'OMe) and unmodified ribonucleotides having complementarity to the target sequence (3' overhang in the antisense strand) or the complementary strand thereof (3' overhang in the sense strand).

In further embodiments, the present invention provides a composition comprising at least one or a cocktail (e.g., at least 2, 3, 4, 5, 6, 7, 8, 9, 10, or more) of the unmodified and/or modified interfering RNA (e.g., siRNA) sequences set forth in Tables 1-30 herein and/or in FIGS. 42-47 from U.S. Provisional Application No. 61/377,439, which figures are herein incorporated by reference in their entirety for all purposes. In particular embodiments, the present invention provides a composition comprising at least one or a cocktail of the interfering RNA (e.g., siRNA) sequences set forth in Tables 1-10. In certain embodiments, at least 1, 2, 3, 4, 5, 6, 7, 8, 9, 10, or more (e.g., all) of these interfering RNAs (e.g., siRNAs) are chemically modified (e.g., 2'OMe-modified). As a non-limiting example, the compositions of the present invention may comprise one or a cocktail (e.g., at least 2, 3, 4, 5, 6, 7, 8, 9, 10, or more) of the 2'OMe-modified interfering RNA (e.g., siRNA) sequences set forth in Tables 13, 14, 16, 18, 20, 22, 24, 26, 28, and 30.

In particularly preferred embodiments, the compositions of the present invention comprise at least 1, 2, 3, 4, 5, 6, 7, or all 8 of the following siRNAs: (1) COP1-1 siRNA, COP1-1181 siRNA, or a 2'OMe-modified variant thereof such as COP1-4/7 siRNA; (2) WEE1-2 siRNA, WEE1-3058 siRNA, or a 2'OMe-modified variant thereof such as WEE1-5/6 siRNA or WEE1-3058-1/5 siRNA; (3) HDAC2-1 siRNA or a 2'OMe-modified variant thereof such as HDAC2-3/7 siRNA; (4) RBX1-2 siRNA or a 2'OMe-modified variant thereof such as RBX1-3/6 siRNA; (5) CDK4-1 siRNA or a 2'OMe-modified variant thereof such as CDK4-3/7 siRNA; (6) CSN5-2 siRNA or a 2'OMe-modified variant thereof such as CSN5-3/8 siRNA; (7) FOXM1-1 siRNA or a 2'OMe-modified variant thereof such as FOXM1-5/6 siRNA; and (8) R1-2 siRNA or a 2'OMe-modified variant thereof such as R1-5/8 siRNA.

The present invention also provides a pharmaceutical composition comprising one or a cocktail of the interfering RNA (e.g., siRNA) described herein and a pharmaceutically acceptable carrier.

In another aspect, the present invention provides a nucleic acid-lipid particle (e.g., SNALP) that targets the expression of one or more (e.g., at least 1, 2, 3, 4, 5, 6, 7, or 8) of the following genes: COP1, WEE1, HDAC2, RBX1, CDK4, CSN5, FOXM1, and R1 (RAM2). The nucleic acid-lipid particle (e.g., SNALP) typically comprises one or more (a cocktail) of the unmodified and/or modified interfering RNA (e.g., siRNA) sequences described herein, a cationic lipid, and a non-cationic lipid. In certain embodiments, the nucleic acid-lipid particle (e.g., SNALP) further comprises a conjugated lipid that inhibits aggregation of particles. In particular embodiments, the nucleic acid-lipid particle (e.g., SNALP) comprises 1, 2, 3, 4, 5, 6, 7, 8, or more of the unmodified and/or modified interfering RNA (e.g., siRNA) molecules described herein, a cationic lipid, a non-cationic lipid, and a conjugated lipid that inhibits aggregation of particles, wherein the interfering RNA (e.g., siRNA) molecules silence the expression of 1, 2, 3, 4, 5, 6, 7, or all 8 of the following genes: COP1, WEE1, HDAC2, RBX1, CDK4, CSN5, FOXM1, and R1 (RAM2).

In some embodiments, the nucleic acid-lipid particle (e.g., SNALP) comprises at least 1, 2, 3, 4, 5, 6, 7, 8, 9, 10, or more of the unmodified and/or modified interfering RNA (e.g., siRNA) sequences set forth in Tables 1-30 herein and/or in FIGS. 42-47 from U.S. Provisional Application No. 61/377, 439. In certain preferred embodiments, the nucleic acid-lipid particle comprises one or a cocktail (e.g., at least 2, 3, 4, 5, 6, 7, 8, 9, 10, or more) of the 2'OMe-modified interfering RNA (e.g., siRNA) sequences set forth in Tables 13, 14, 16, 18, 20, 22, 24, 26, 28, and 30.

In other embodiments, the interfering RNAs (e.g., siRNAs) are fully encapsulated in the nucleic acid-lipid particle (e.g., SNALP). With respect to formulations comprising an interfering RNA cocktail, the different types of interfering RNAs may be co-encapsulated in the same nucleic acid-lipid particle, or each type of interfering RNA species present in the cocktail may be encapsulated in its own nucleic acid-lipid particle. The interfering RNA cocktail may be formulated in the nucleic acid-lipid particles using a mixture of individual interfering RNAs at identical, similar, or different concentrations. In particular embodiments, a cocktail of two or three interfering RNAs may be formulated as a 1:1 mixture or as a 1:1:1 mixture of each interfering RNA species, respectively.

The present invention also provides pharmaceutical compositions comprising a nucleic acid-lipid particle and a pharmaceutically acceptable carrier.

The nucleic acid-lipid particles of the invention (e.g., SNALP) are useful for the therapeutic delivery of interfering RNA (e.g., siRNA) molecules that silence the expression of one or more genes expressed in cancer (e.g., COP1, WEE1, HDAC2, RBX1, CDK4, CSN5, FOXM1, and/or R1). In some embodiments, a cocktail of the interfering RNA (e.g., siRNA) described herein is formulated into the same or different nucleic acid-lipid particles, and the particles are administered to a mammal (e.g., a rodent such as a mouse or a primate such as a human, chimpanzee, or monkey) requiring such treatment. In certain instances, a therapeutically effective amount of the nucleic acid-lipid particles can be administered to the mammal, e.g., for treating a cell proliferative disorder such as cancer. The nucleic acid-lipid particles of the invention are particularly useful for targeting cancer cells such as cells of a solid tumor, and also find utility in targeting non-tumor cells that produce one or more angiogenic and/or growth factors associated with cell proliferation, tumorigenesis, or cell transformation. Administration of the nucleic acid-lipid particle formulation can be by any route known in the art, such as, e.g., oral, intranasal, intravenous, intraperitoneal, intramuscular, intra-articular, intralesional, intratracheal, subcutaneous, or intradermal.

Other objects, features, and advantages of the present invention will be apparent to one of skill in the art from the following detailed description and figures.

BRIEF DESCRIPTION OF THE DRAWINGS

FIG. 3 illustrates that COP1 or WEE1 gene silencing decreased HCC cell survival as detected by light microscopy. The effect of COP1-1 or WEE1-2 siRNA on morphological changes was observed in Huh7 or HepG2 cells treated with 15 nM of the siRNA for 4 days (100× magnification).

Figure 10:
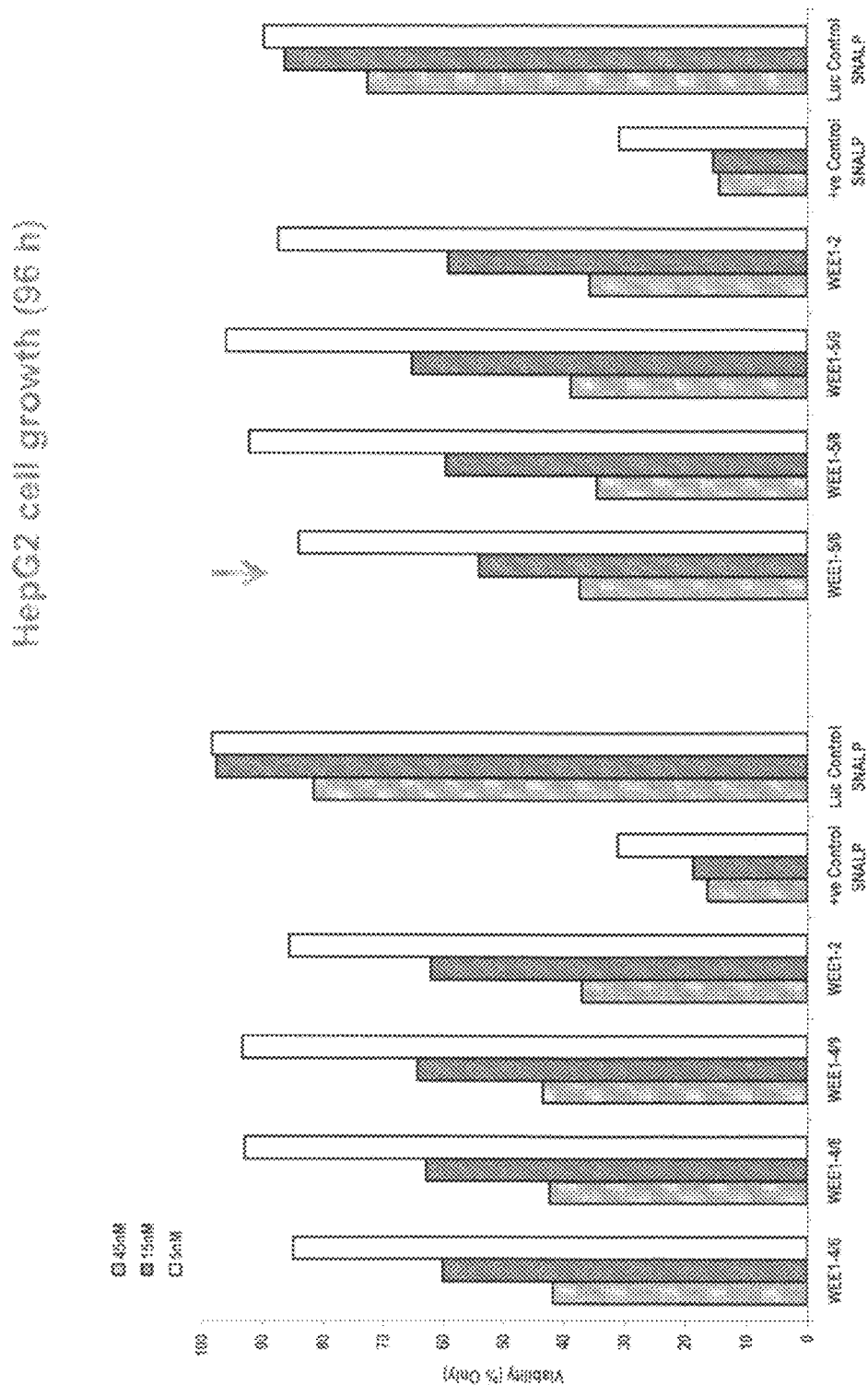

FIG. 10 illustrates the inhibition of HepG2 cell growth after transfection with 5, 15, or 45 nM of SNALP-formulated modified WEE1-2 siRNA. The cells were examined 4 days after the treatment. SNALP containing Luciferase (Luc) siRNA was used as a negative control.

Figure 11:
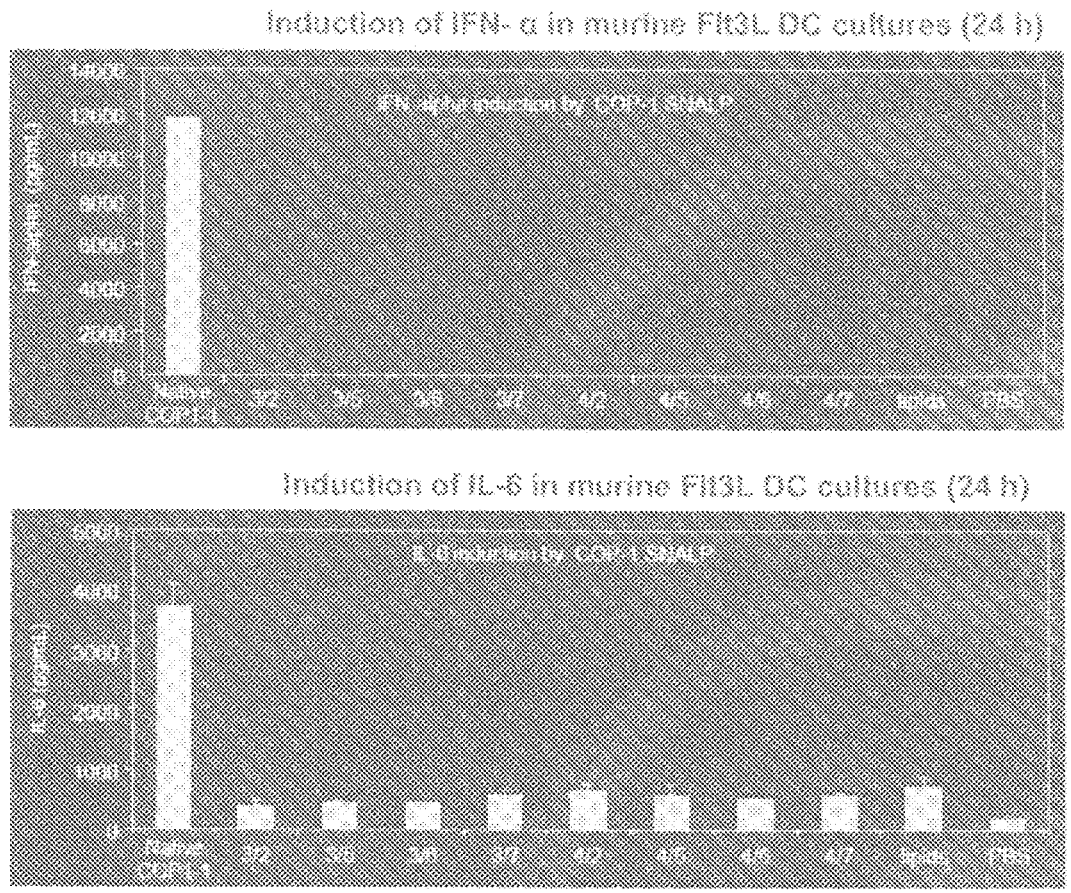

FIG. 11 illustrates that chemically modified COP1-1 siRNA induced a minimal cytokine response in vitro. This figure shows the quantification of IFN-α and IL-6 levels after i.v. administration of SNALP-encapsulated unmodified or modified COP1-1 siRNA into mice. After 24 h of siRNA treatment, culture supernatants of Flt3L-derived dendricytes isolated from mouse bone marrow were assayed for IFN-α or IL-6 by an ELISA method. Each value is the mean±s.d. of triplicate experiments.

Figure 12:
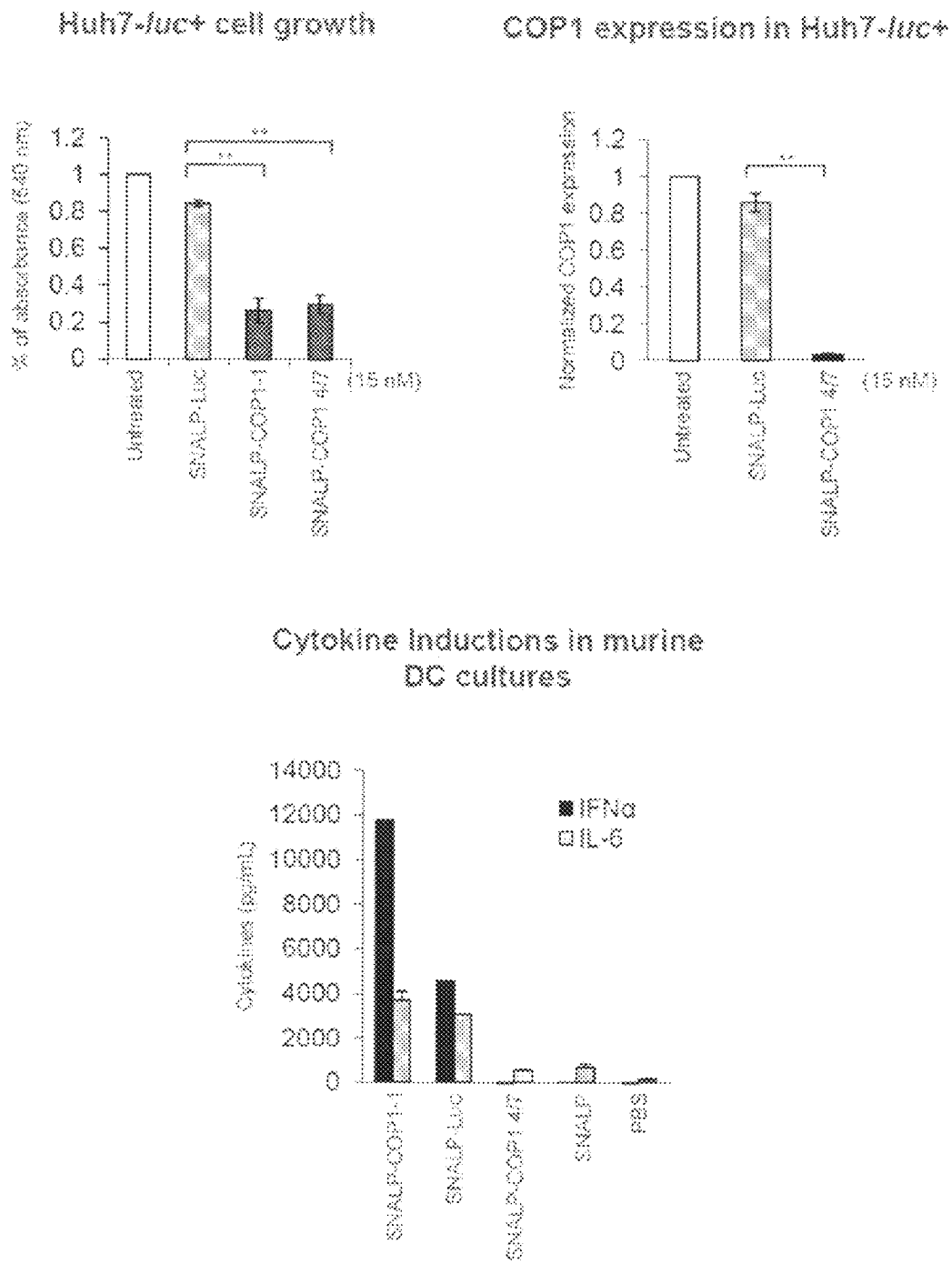

FIG. 12 illustrates that the COP1-4/7 siRNA was selected for in vivo studies in the HCC mouse model because it was comparable in potency to the unmodified COP1-1 siRNA at inhibiting Huh7-luc$^+$ cell growth and at reducing COP1 gene expression, but it induced a minimal cytokine response in murine Flt3L DC cultures.

Figure 13:
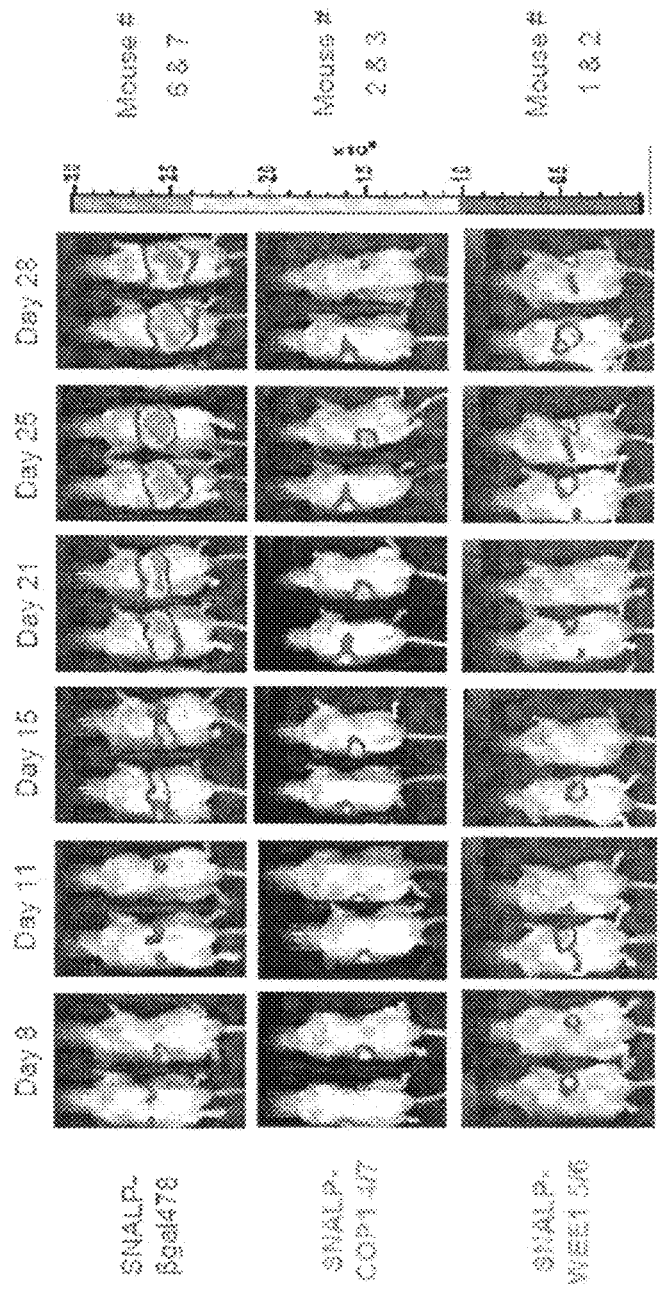
Figure 13:
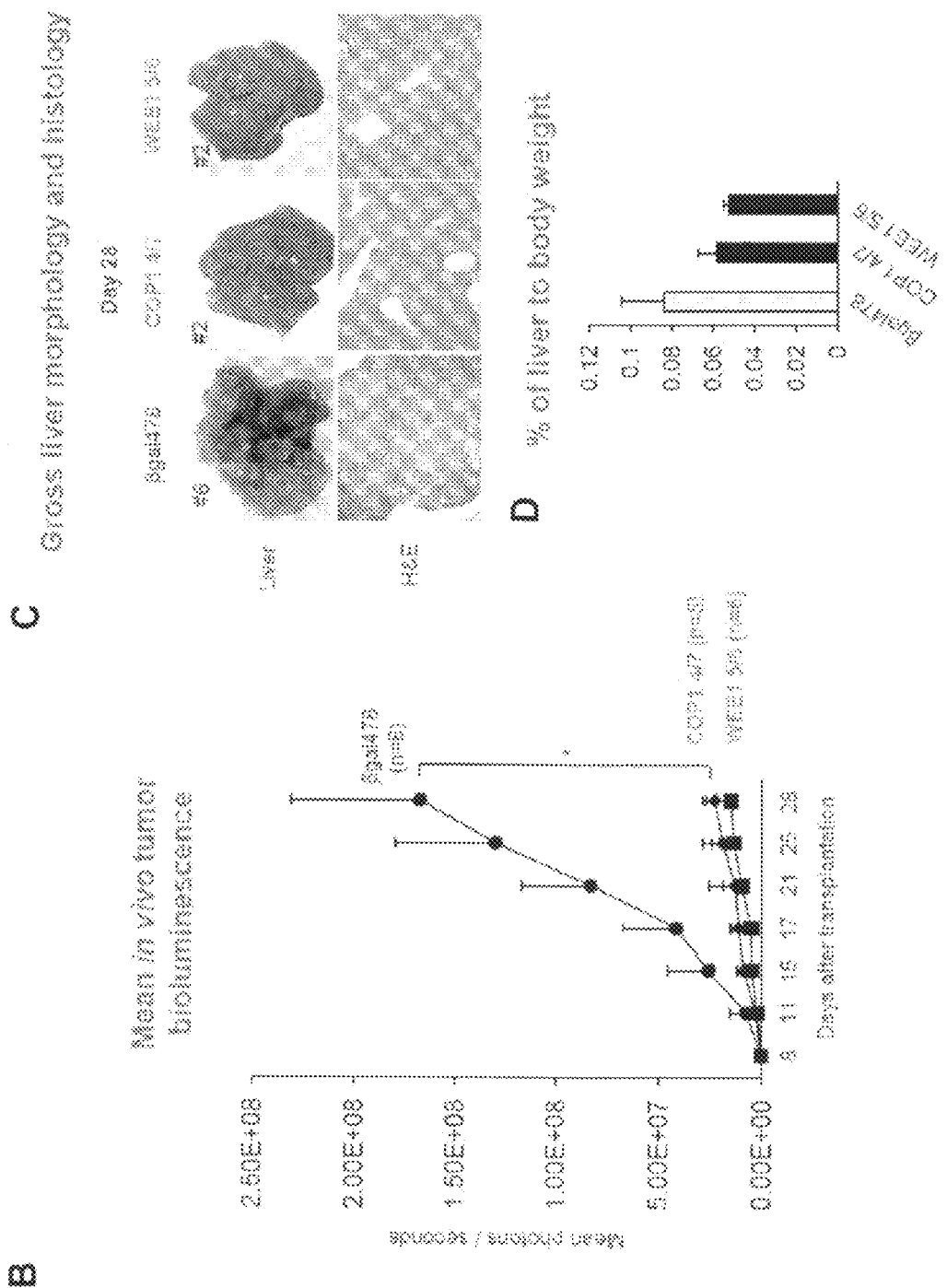

FIG. 13 illustrates that treatment with SNALP containing COP1-4/7 or WEE1-5/6 siRNA effectively suppressed neoplastic growth in a mouse model of metastatic human liver cancer. (A) In vivo monitoring of tumor growth by BLI during and after treatments. Images of two representative mice from each treatment group are shown. On days 8, 11, 14, and 18 after transplantation, SNALP-formulated βgal478, COP1-4/7, or WEE1-5/6 siRNA was injected into the tail vein at a dosage of 2 mg/kg. Images were set at the same pseudocolor scale to show relative bioluminescent changes over time. (B) Measurement of mean in vivo tumor bioluminescence. Bioluminescent signals emitted from the liver tumors of Huh7-luc$^+$ cells were quantified in photons/second at each imaging time point, and mean tumor bioluminescence±s.d. was graphed over time for the mice treated with SNALP-formulated βgal478, COP1-4/7, or WEE1-5/6 siRNA. (C) This panel shows examples of the gross liver morphology and histological analysis of excised livers on day 28 after administration of SNALP-formulated βgal478, COP1-4/7, or WEE1-5/6 siRNA. (D) This panel shows that liver to body weight ratios were lower in SNALP-formulated COP1-4/7 or WEE1-5/6 siRNA-treated versus control mice. Each bar represents the mean ratio of liver:body weight±s.d. from each treatment group.

Figure 14:
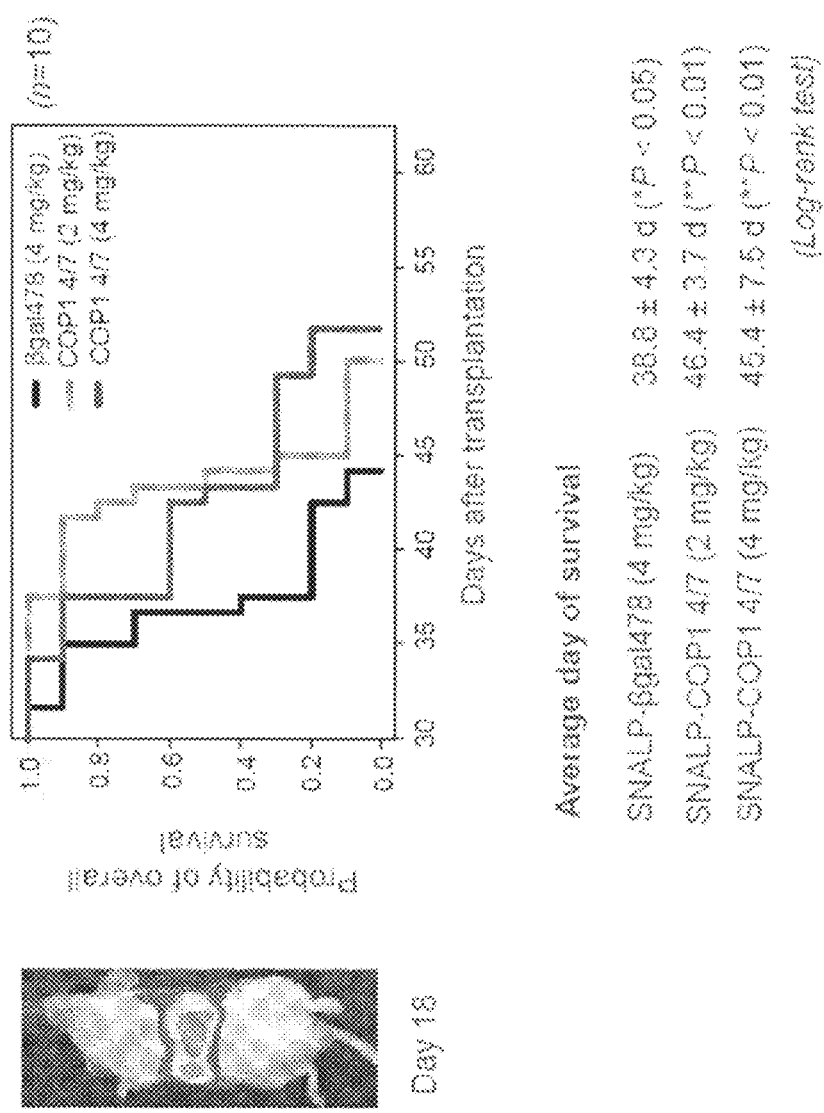

FIG. 14 illustrates the effect of SNALP-formulated COP1-4/7 siRNA treatment on the relative survival of mice bearing Huh7-luc$^+$ orthotopic xenografts. SNALP containing COP1-4/7 siRNA or β-gal siRNA were systemically delivered to the liver through a tail vein injection three times (days 18, 21, and 24) at a dosage of 2 or 4 mg/kg.

Figure 15:
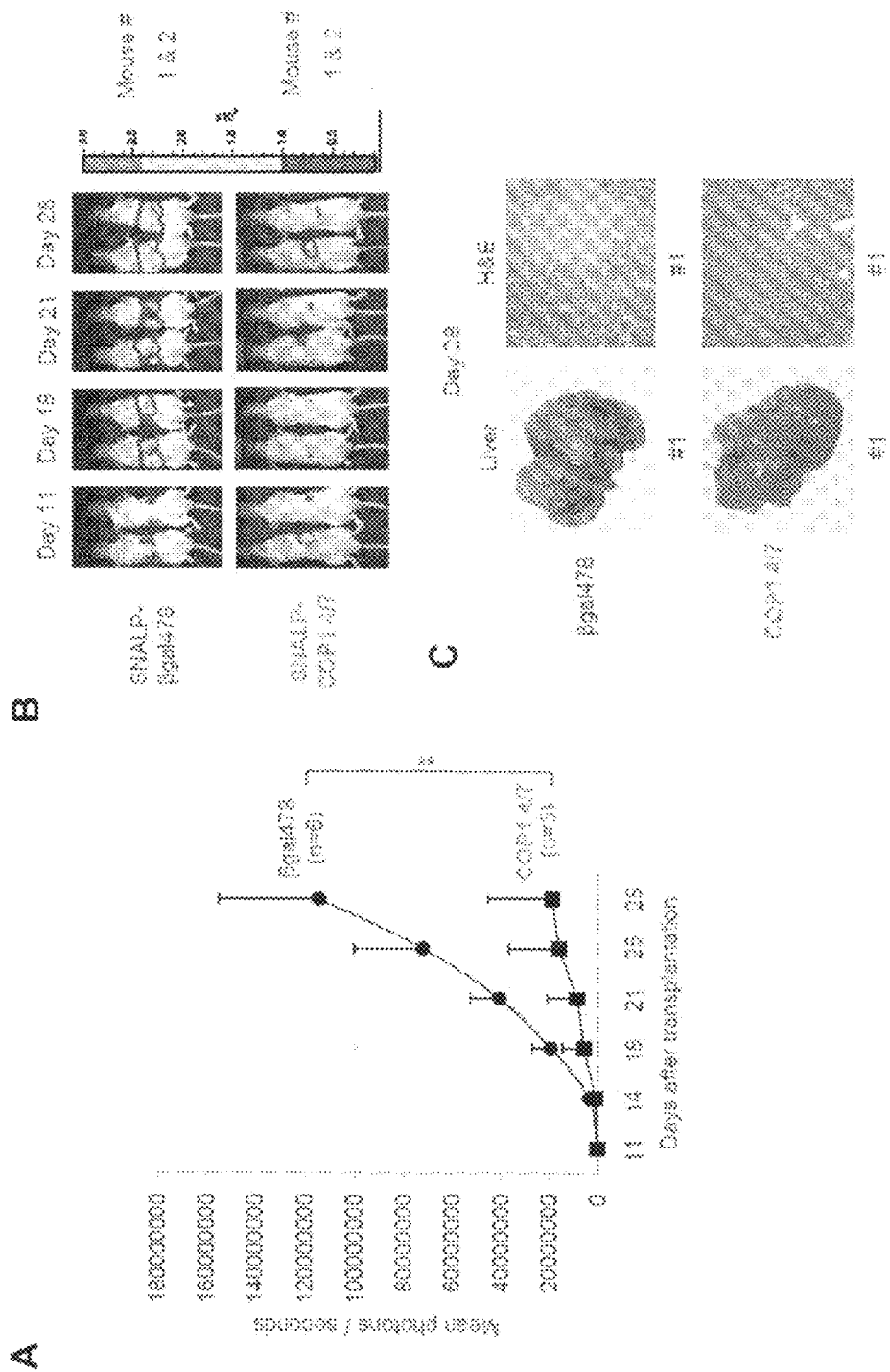

FIG. 15 illustrates the systemic inhibition of HepG2-luc$^+$ orthotopic liver tumors with COP1-4/7 siRNA. Eleven days after transplantation of HepG2-luc$^+$ cells, SNALP containing COP1-4/7 siRNA were systemically delivered to the liver through a tail vein injection four times (days 11, 14, 17, and 21) at a dosage of 2 mg/kg. Tumor relapses were monitored by BLI up to 28 days after cell transplantation. (A) Measurement of mean in vivo tumor bioluminescence. Bioluminescent signals emitted from the liver tumors of HepG2-luc$^+$ cells were quantified in photons/second at each imaging time point, and mean tumor bioluminescence±s.d. was graphed over time for the mice treated with SNALP-formulated βgal478 or COP1-4/7 siRNA. (B) In vivo monitoring of tumor growth by BLI during and after treatments. Images of two representative mice from each treatment group are shown. (C) This panel shows examples of the gross liver morphology and histological analysis of excised livers on day 28 after administration of SNALP-formulated βgal478 or COP1-4/7 siRNA.

Figure 16:
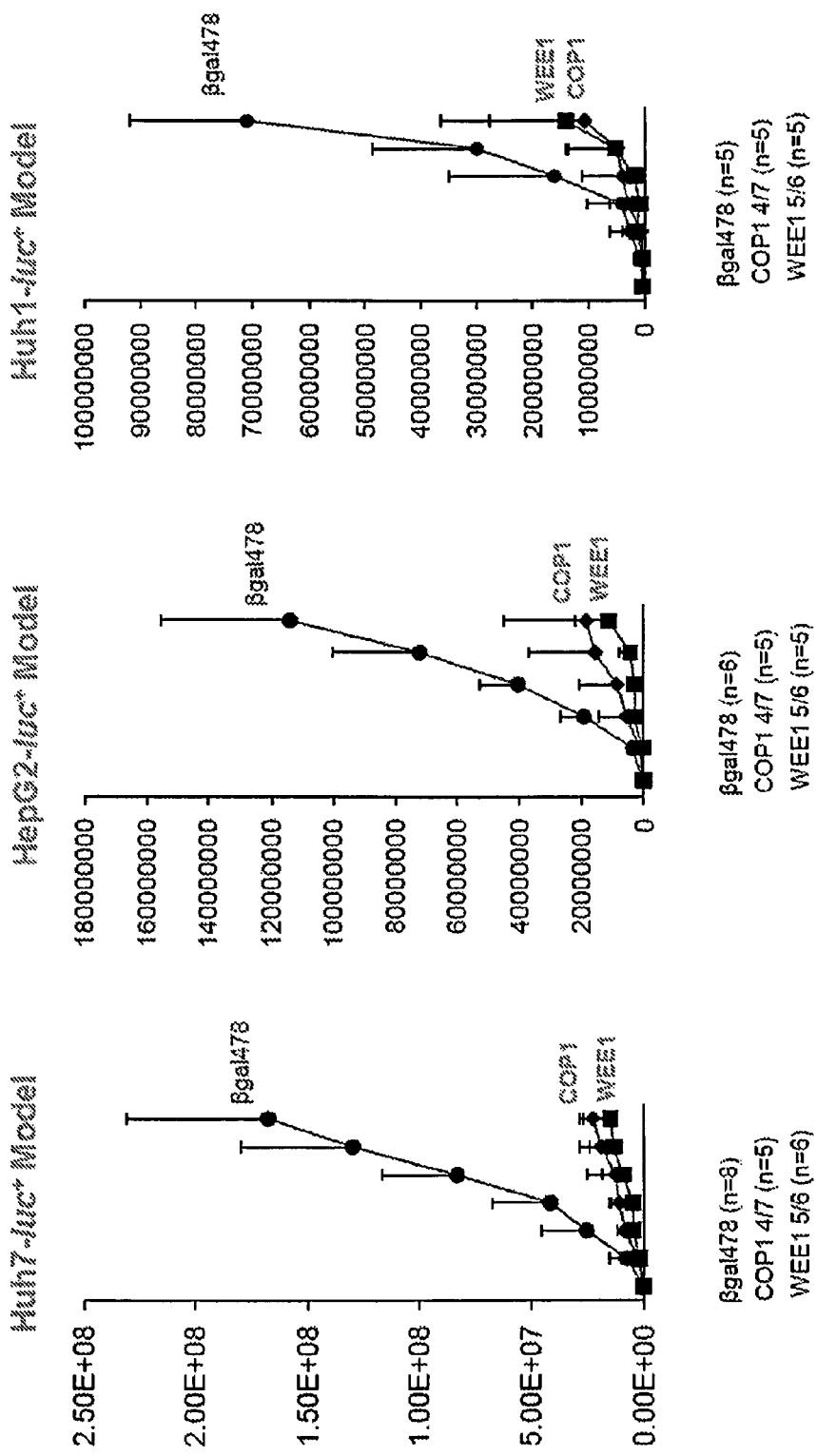

FIG. 16 illustrates the inhibition of liver tumor growth in a variety of different mouse models upon systemic delivery of either SNALP-formulated COP1-4/7 or WEE1-5/6 siRNA.

Figure 17:
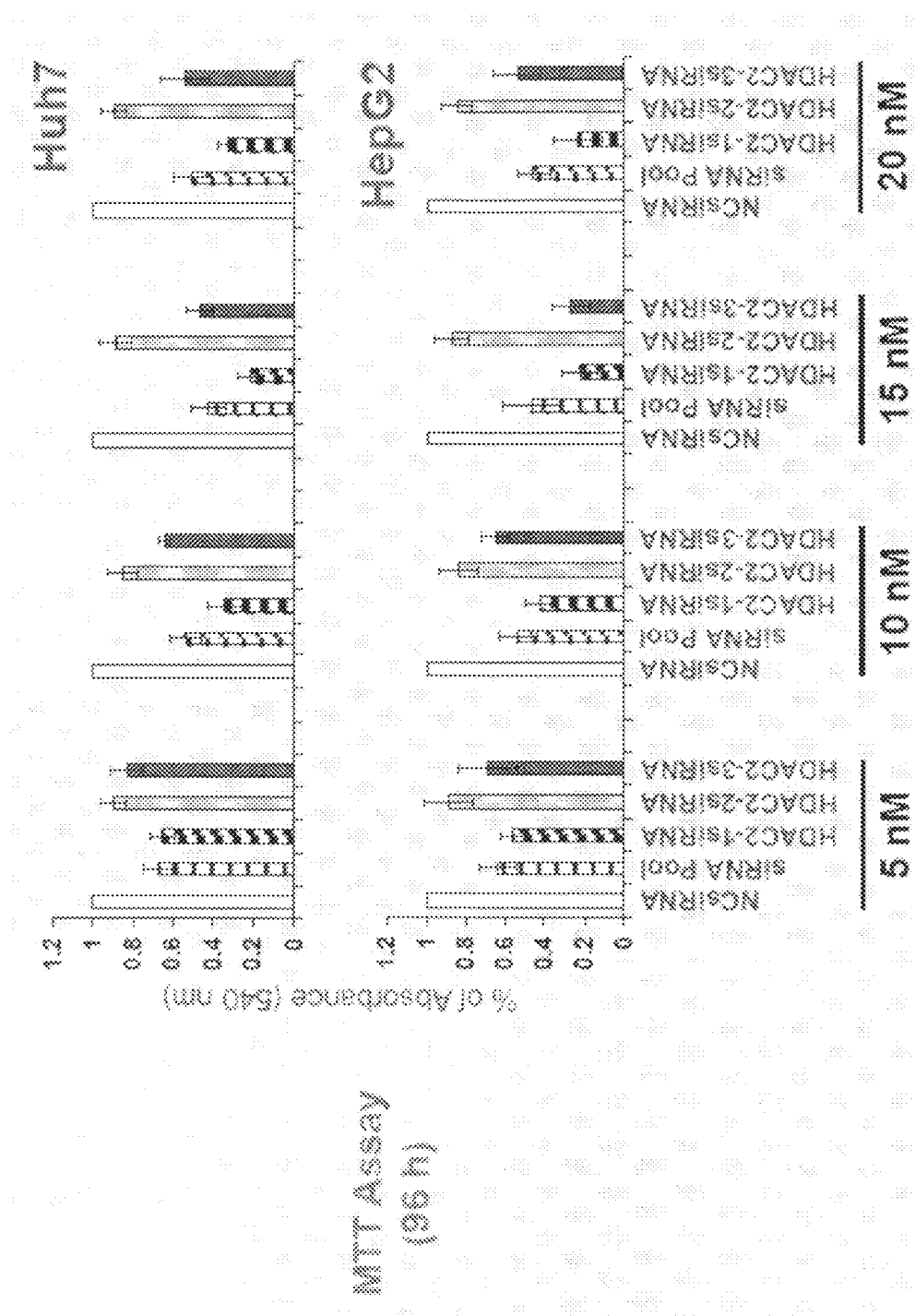

FIG. 17 illustrates that HDAC2 gene silencing decreased HCC cell survival in a cell viability assay. Growth inhibition of Huh7 or HepG2 cells after transfection with 5, 10, 15, or 20 nM of three HDAC2-specific siRNA was examined by an MTT assay 4 days after treatment. Cells that were treated with a pool of HDAC2 siRNA or NCsiRNA were assayed simultaneously. Results are presented as mean percentage of absorbance at 540 nm±s.d.

FIG. 18 illustrates that HDAC2 gene silencing is associated with cell cycle arrest in the G1 phase. The effect of HDAC2-1 siRNA on cell cycle progression of HCC cells was determined by cell cycle analysis after transfection of Huh7 or HepG2 cells with 15 nM of HDAC2-1 siRNA for 48 hours. The analysis was performed on an equal number of cells ($10^4$ events) by flow cytometry after staining of DNA with propium iodide. The cells that were untreated or treated with NCsiRNA were assayed simultaneously.

Figure 19:
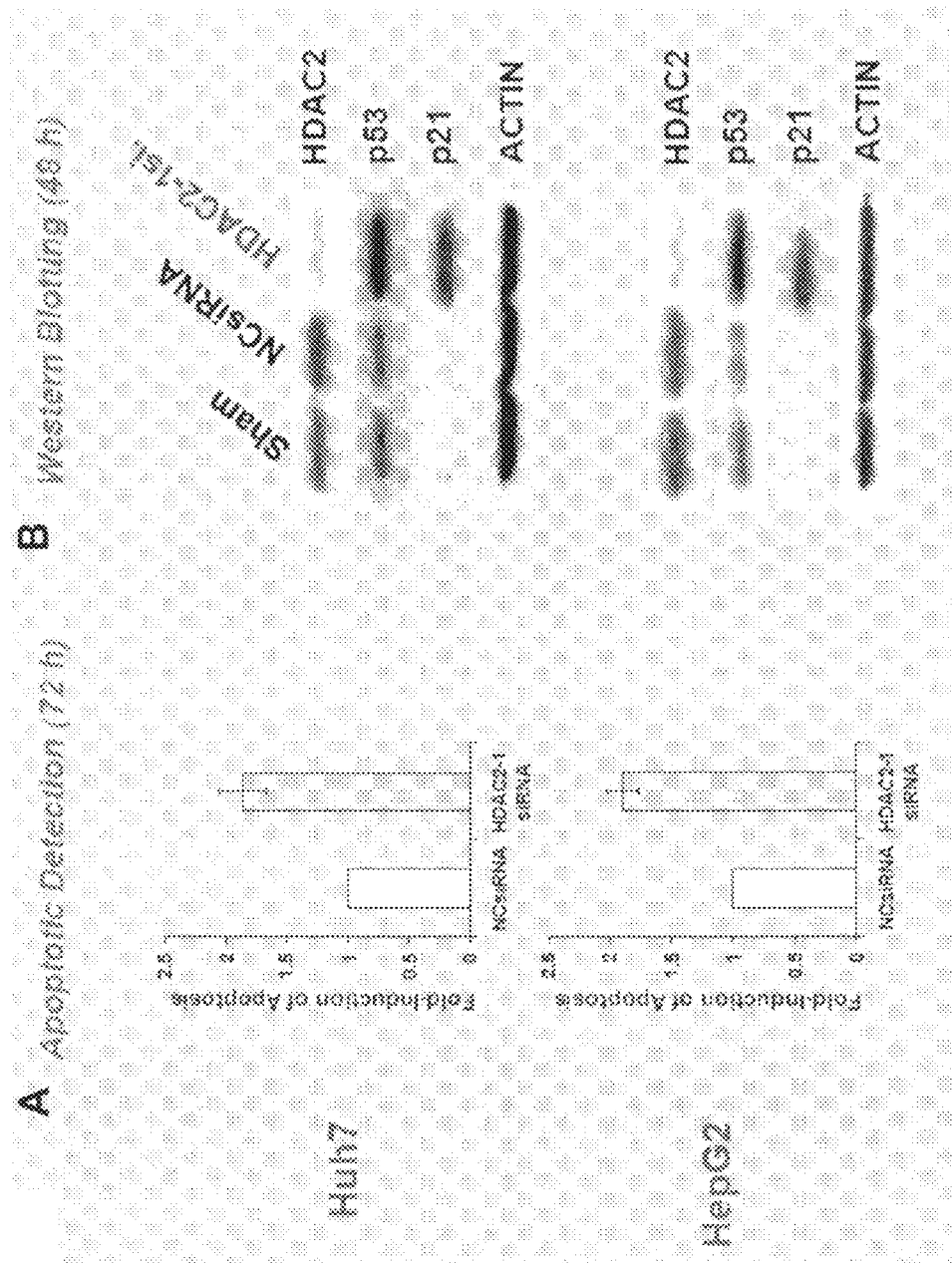

FIG. 19 illustrates that HDAC2 gene silencing increased apoptosis by restoring p53 and p21 levels. (A) Detection of apoptotic progression in Huh7 or HepG2 cells 3 d after transfection with 15 nM of HDAC2-1 siRNA. The cells that were treated with NCsiRNA were assayed simultaneously. Results are shown as the mean fold-induction of apoptosis±s.d. of three independent experiments. (B) Western blot analysis of HDAC2, p53, and p21 protein expression in Huh7 or HepG2 cells that were untreated (Sham) or treated with 15 nM of NCsiRNA or HDAC2-1 siRNA for 48 h.

Figure 20:
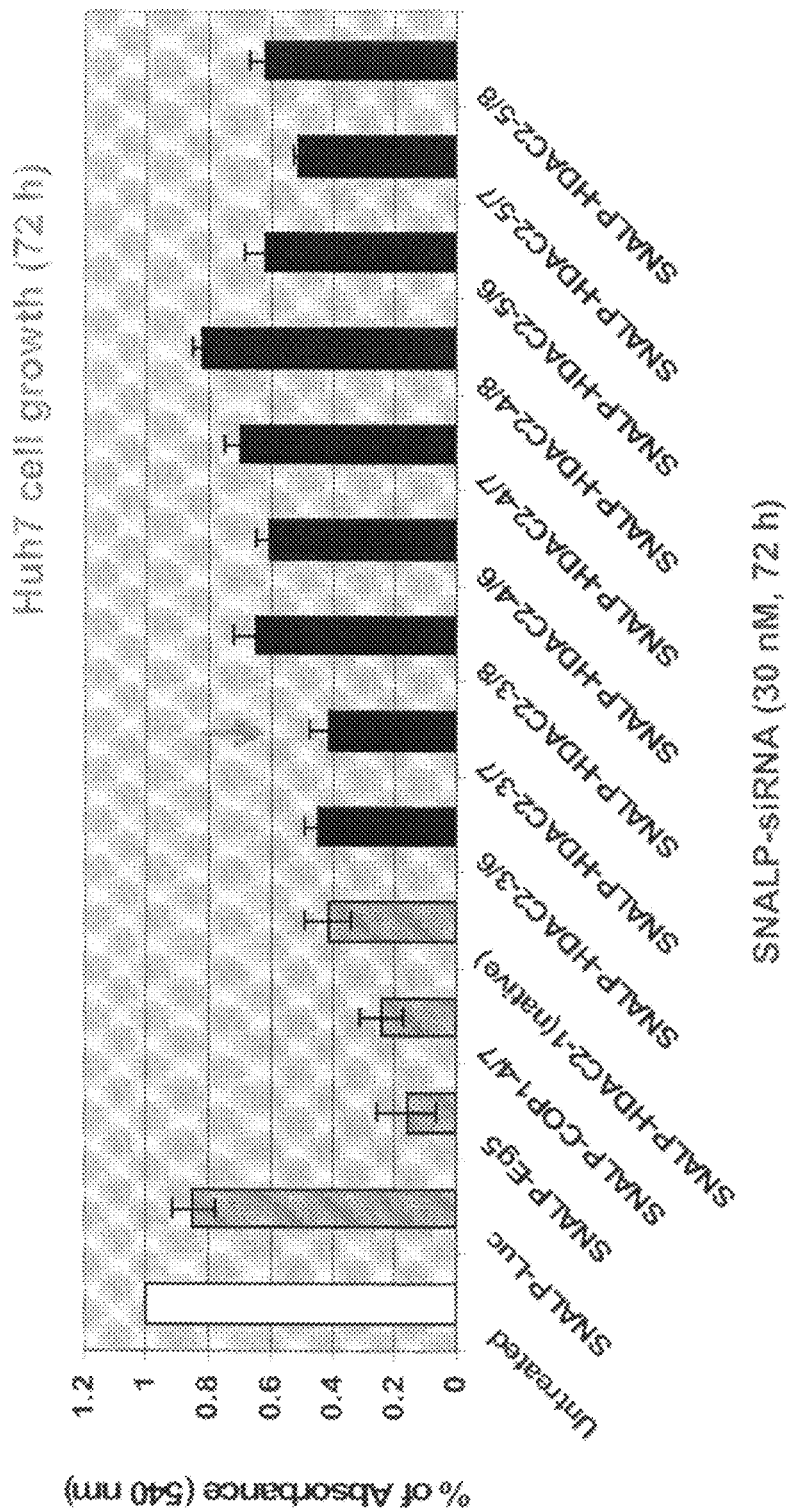

FIG. 20 illustrates the inhibition of Huh7-luc$^+$ cell growth after transfection with 30 nM of SNALP-formulated unmodified or modified HDAC2-1 siRNA. The cells were examined by an MTT assay 3 days after the treatment. SNALP containing Luciferase (Luc) siRNA was used as a negative control, and SNALP containing Eg5 siRNA was used as a positive control. Results are shown as the mean percentage of absorbance at 540 nm±s.d.

Figure 21:
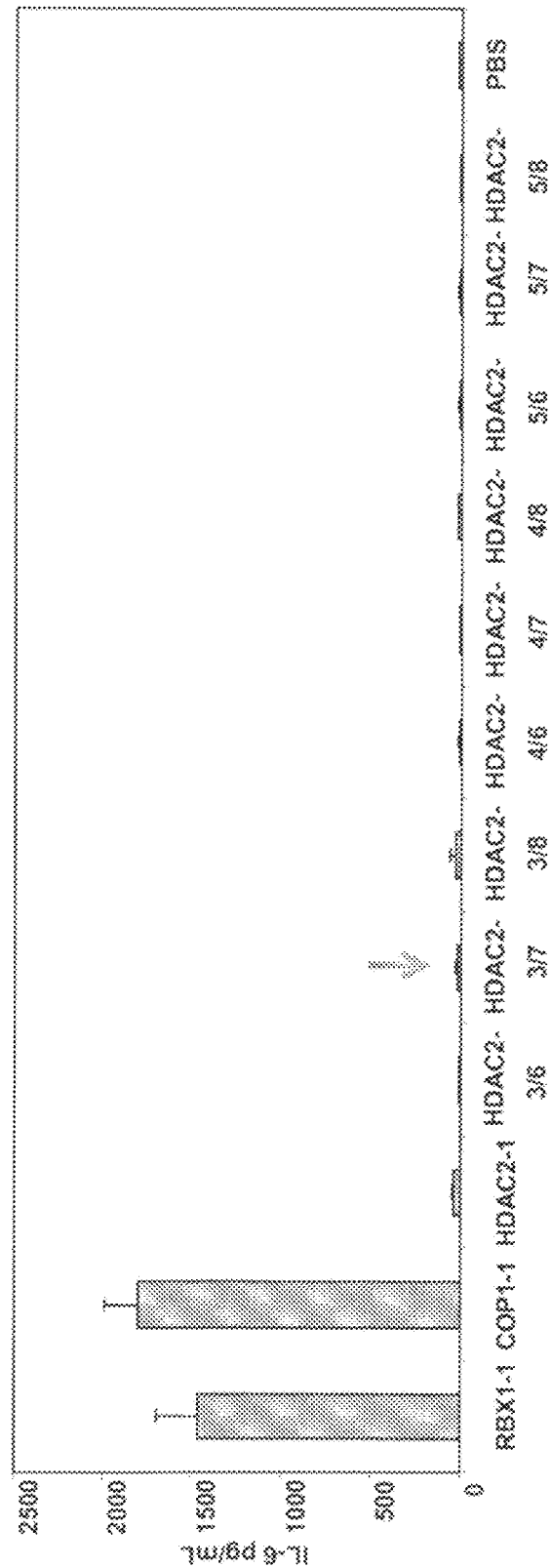

FIG. 21 illustrates that chemically modified HDAC2-1 siRNA induced a minimal cytokine response in vitro. This figure shows the quantification of IL-6 levels after i.v. administration of SNALP-encapsulated unmodified or modified HDAC2-1 siRNA into mice. After 24 h of siRNA treatment, culture supernatants of Flt3L-derived dendricytes isolated from mouse bone marrow were assayed for IL-6 by an ELISA method. Each value is the mean±s.d. of triplicate experiments.

Figure 22:
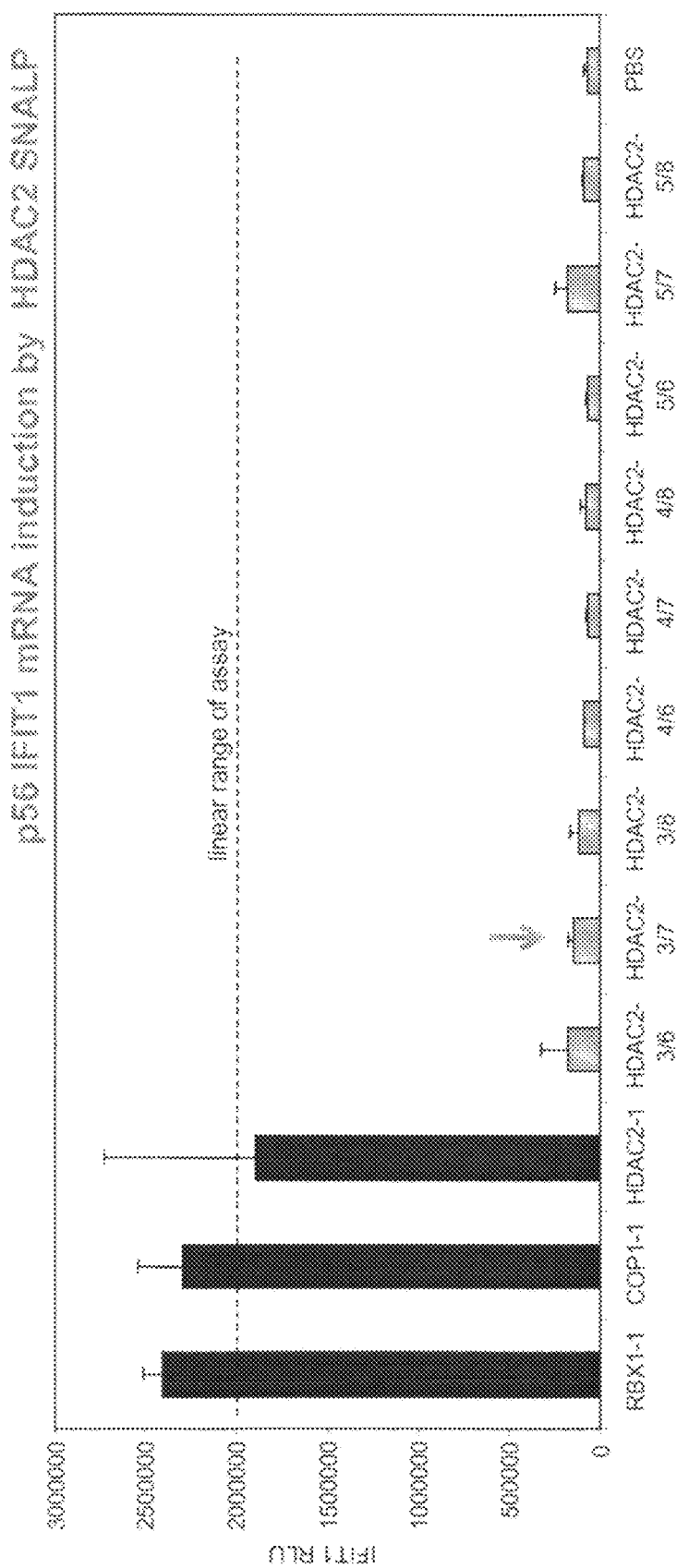

FIG. 22 illustrates that SNALP containing unmodified HDAC2-1 siRNA induced high levels of p56 IFIT1 mRNA in murine Flt3L DC cultures, but 2'OMe-modified variants of HDAC2-1 did not significantly elevate p56 IFIT1 mRNA levels.

Figure 23:
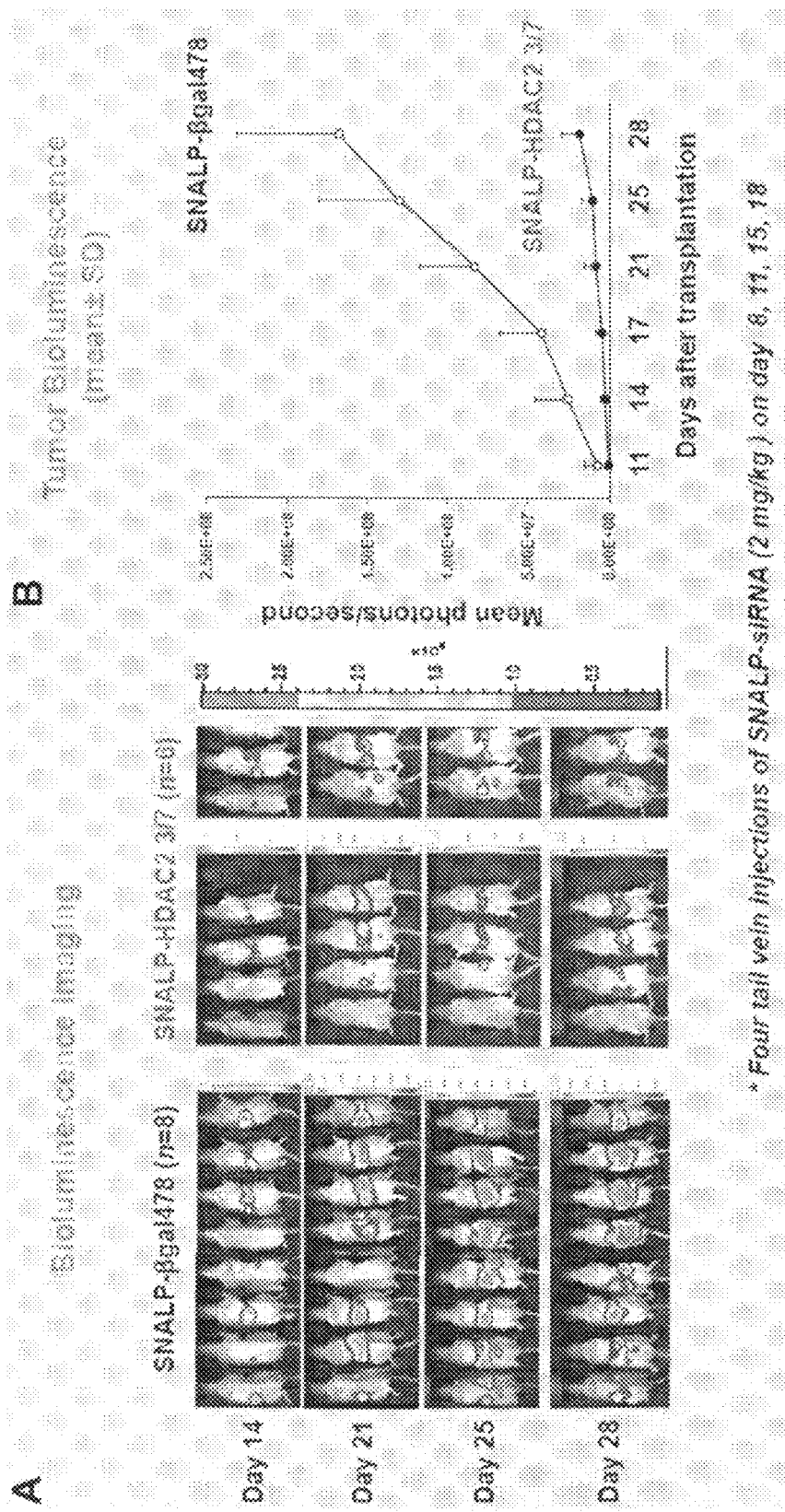
Figure 23:
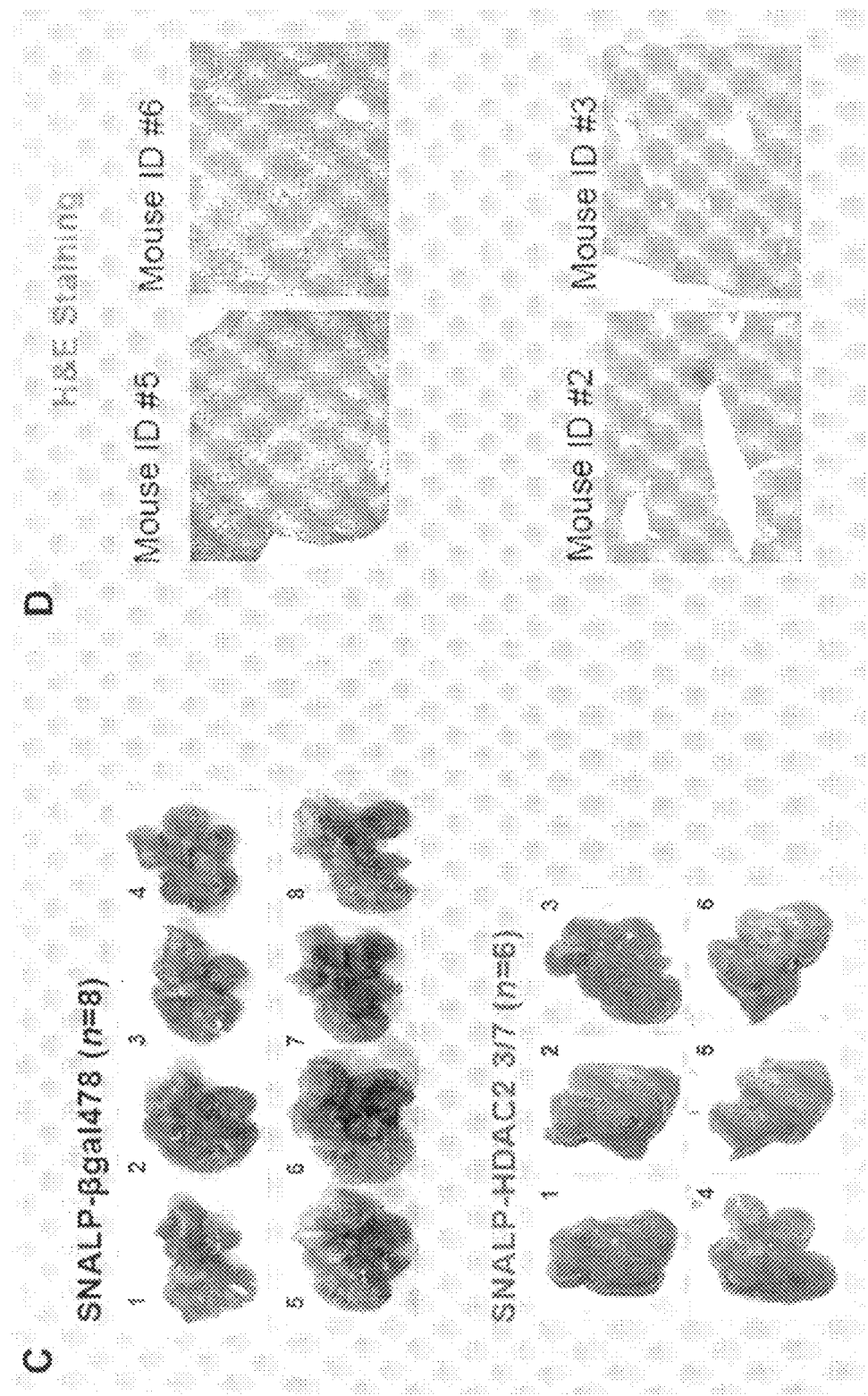

FIG. 23 illustrates that treatment with SNALP containing HDAC2-3/7 siRNA effectively suppressed neoplastic growth in a mouse model of metastatic human liver cancer. (A) In vivo monitoring of tumor growth by BLI during and after treatments. On days 8, 11, 15, and 18 after transplantation, SNALP-formulated βgal478 or HDAC2-3/7 siRNA was injected into the tail vein at a dosage of 2 mg/kg. Images were set at the same pseudocolor scale to show relative bioluminescent changes over time. (B) Measurement of mean in vivo tumor bioluminescence. Bioluminescent signals emitted from the liver tumors of Huh7-luc$^+$ cells were quantified in photons/second at each imaging time point, and mean tumor bioluminescence±s.d. was graphed over time for the mice treated with SNALP-formulated βgal478 or HDAC2-3/7 siRNA. (C) This panel shows the gross liver morphology of excised livers on day 28 after administration of SNALP-formulated βgal478 or HDAC2-3/7 siRNA. (D) This panel shows examples of the histological analysis of excised livers on day 28 after administration of SNALP-formulated βgal478 or HDAC2-3/7 siRNA. Livers from all mice tested were sectioned and stained with H&E to observe the status of tumor growth within tissues.

Figure 24:
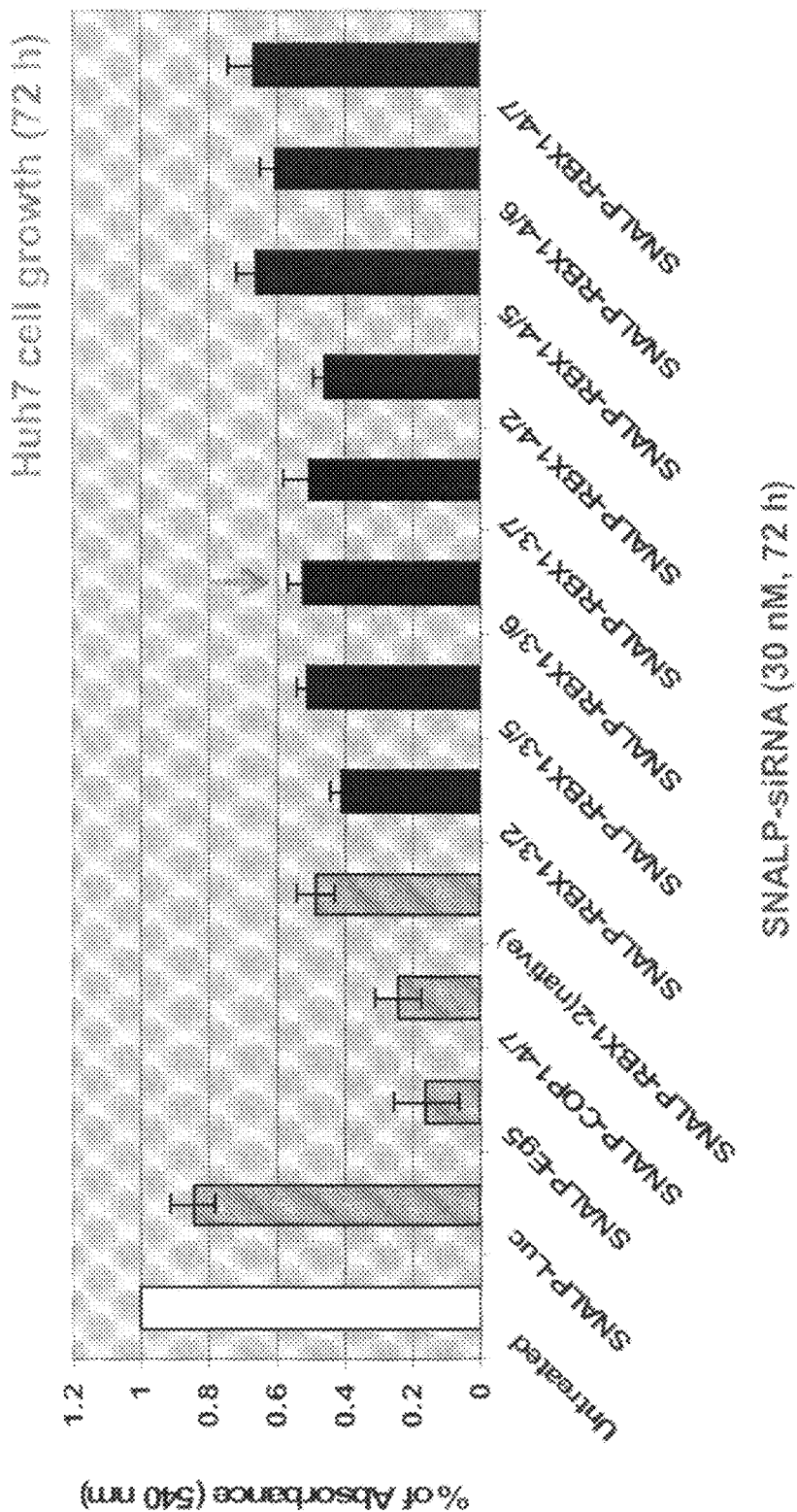

FIG. 24 illustrates the inhibition of Huh7-luc$^+$ cell growth after transfection with 30 nM of SNALP-formulated unmodified or modified RBX1-2 siRNA. The cells were examined by an MTT assay 3 days after the treatment. SNALP containing Luciferase (Luc) siRNA was used as a negative control, and SNALP containing Eg5 siRNA was used as a positive control. Results are shown as the mean percentage of absorbance at 540 nm±s.d.

Figure 25:
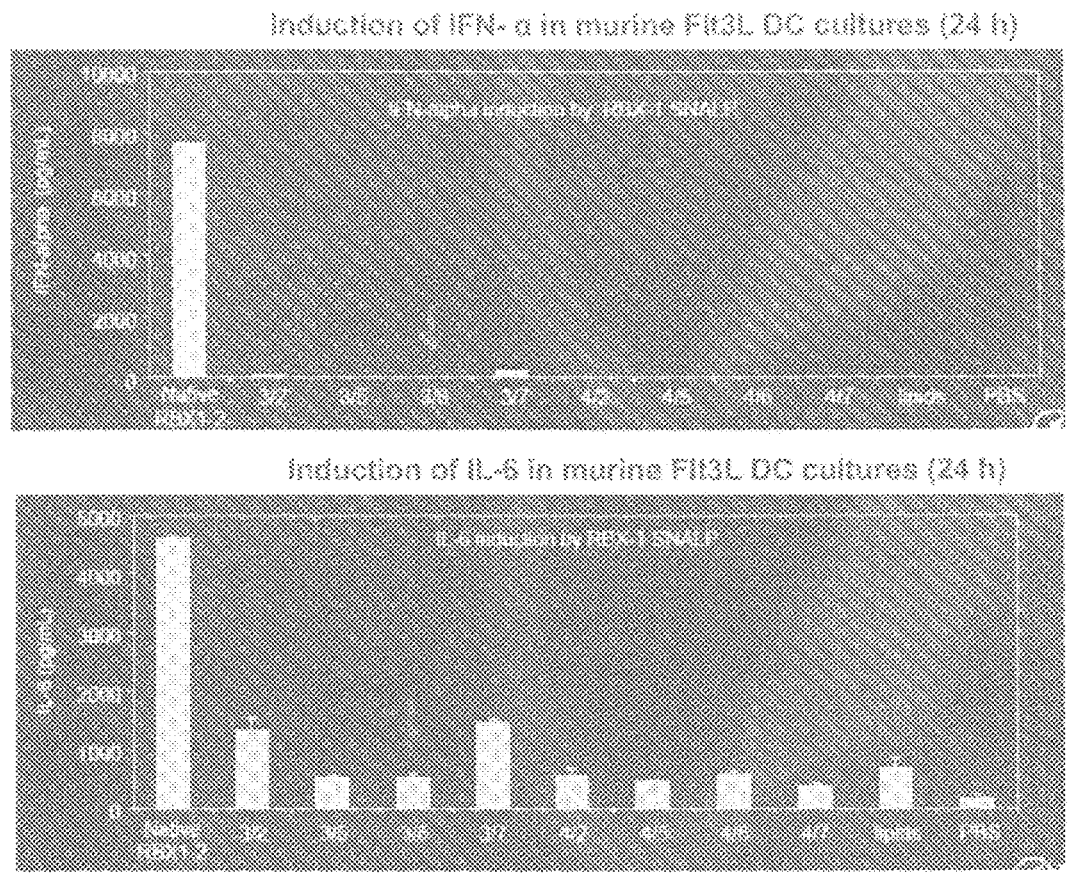

FIG. 25 illustrates that chemically modified RBX1-2 siRNA induced a minimal cytokine response in vitro. This figure shows the quantification of IFN-α and IL-6 levels after i.v. administration of SNALP-encapsulated unmodified or modified RBX1-2 siRNA into mice. After 24 h of siRNA treatment, culture supernatants of Flt3L-derived dendricytes isolated from mouse bone marrow were assayed for IFN-α or IL-6 by an ELISA method. Each value is the mean±s.d. of triplicate experiments.

Figure 26:
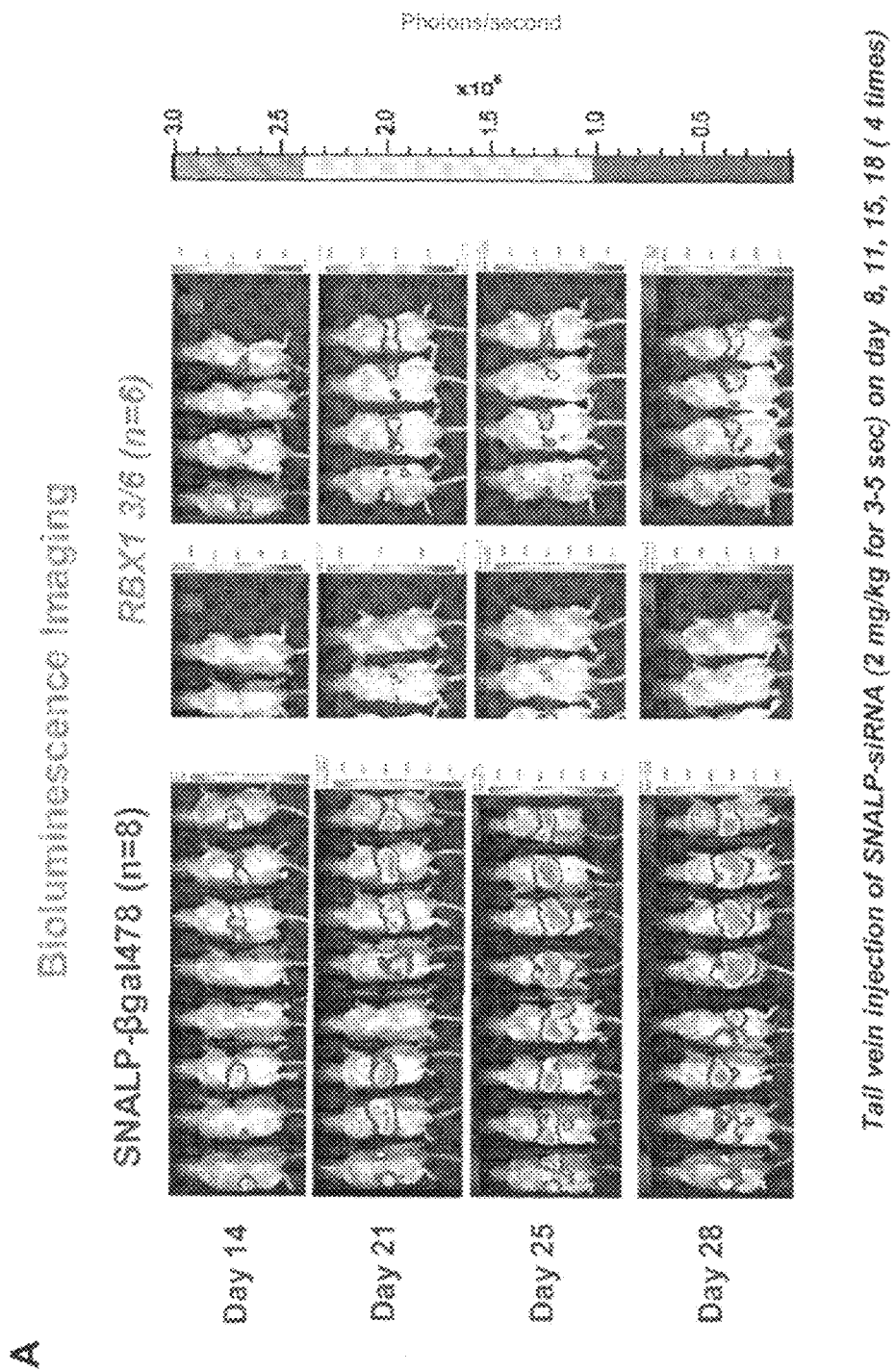
Figure 26:
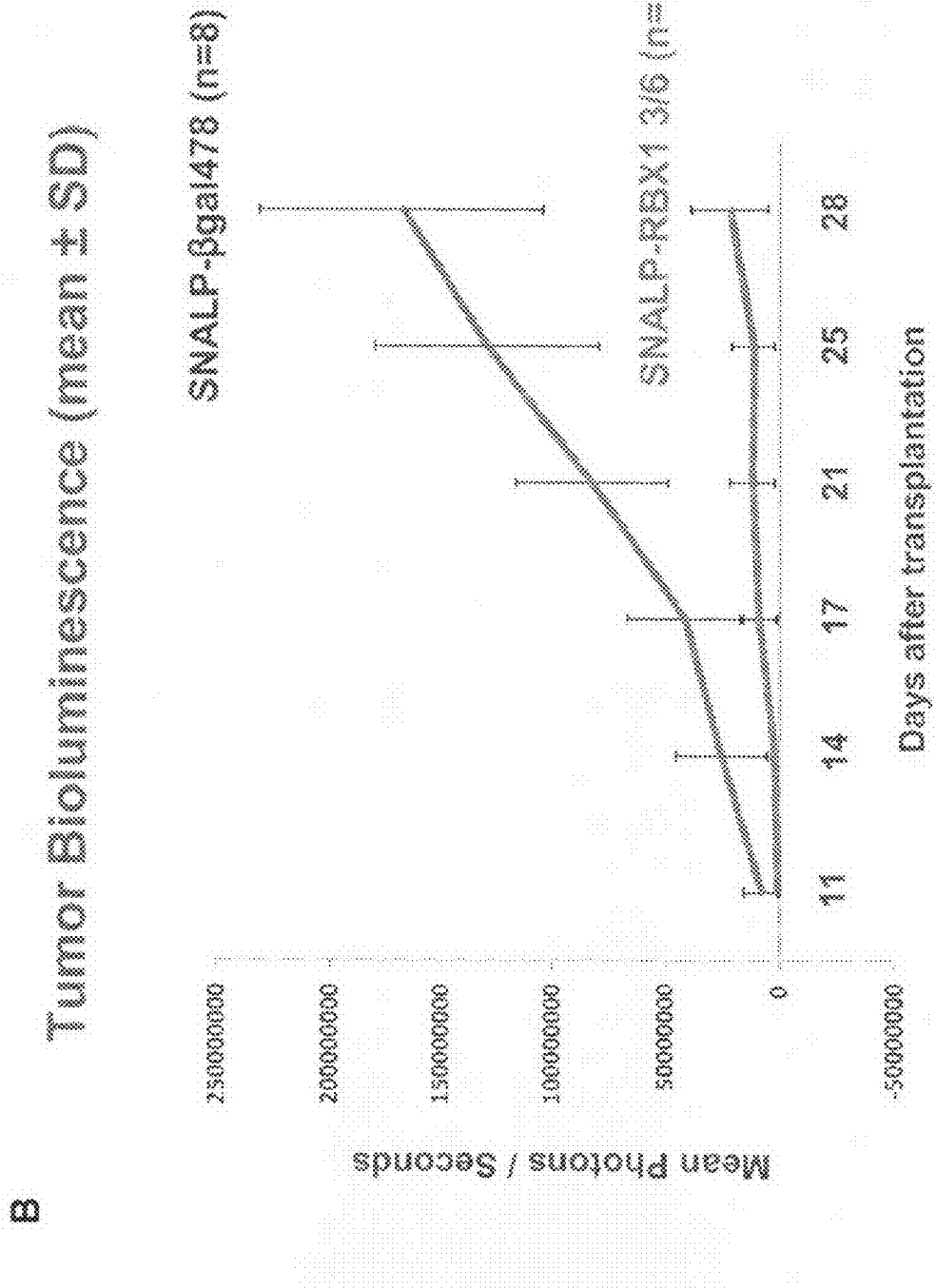

FIG. 26 illustrates that treatment with SNALP containing RBX1-3/6 siRNA effectively suppressed neoplastic growth in a mouse model of metastatic human liver cancer. (A) In vivo monitoring of tumor growth by BLI during and after treatments. On days 8, 11, 15, and 18 after transplantation, SNALP-formulated βgal478 or RBX1-3/6 siRNA was injected into the tail vein at a dosage of 2 mg/kg. Images were set at the same pseudocolor scale to show relative bioluminescent changes over time. (B) Measurement of mean in vivo tumor bioluminescence. Bioluminescent signals emitted from the liver tumors of Huh7-luc$^+$ cells were quantified in photons/second at each imaging time point, and mean tumor bioluminescence±s.d. was graphed over time for the mice treated with SNALP-formulated βgal478 or RBX1-3/6 siRNA. (C) This panel shows examples of the gross liver morphology and histological analysis of excised livers on day 28 after administration of SNALP-formulated βgal478 or RBX1-3/6 siRNA.

Figure 27:
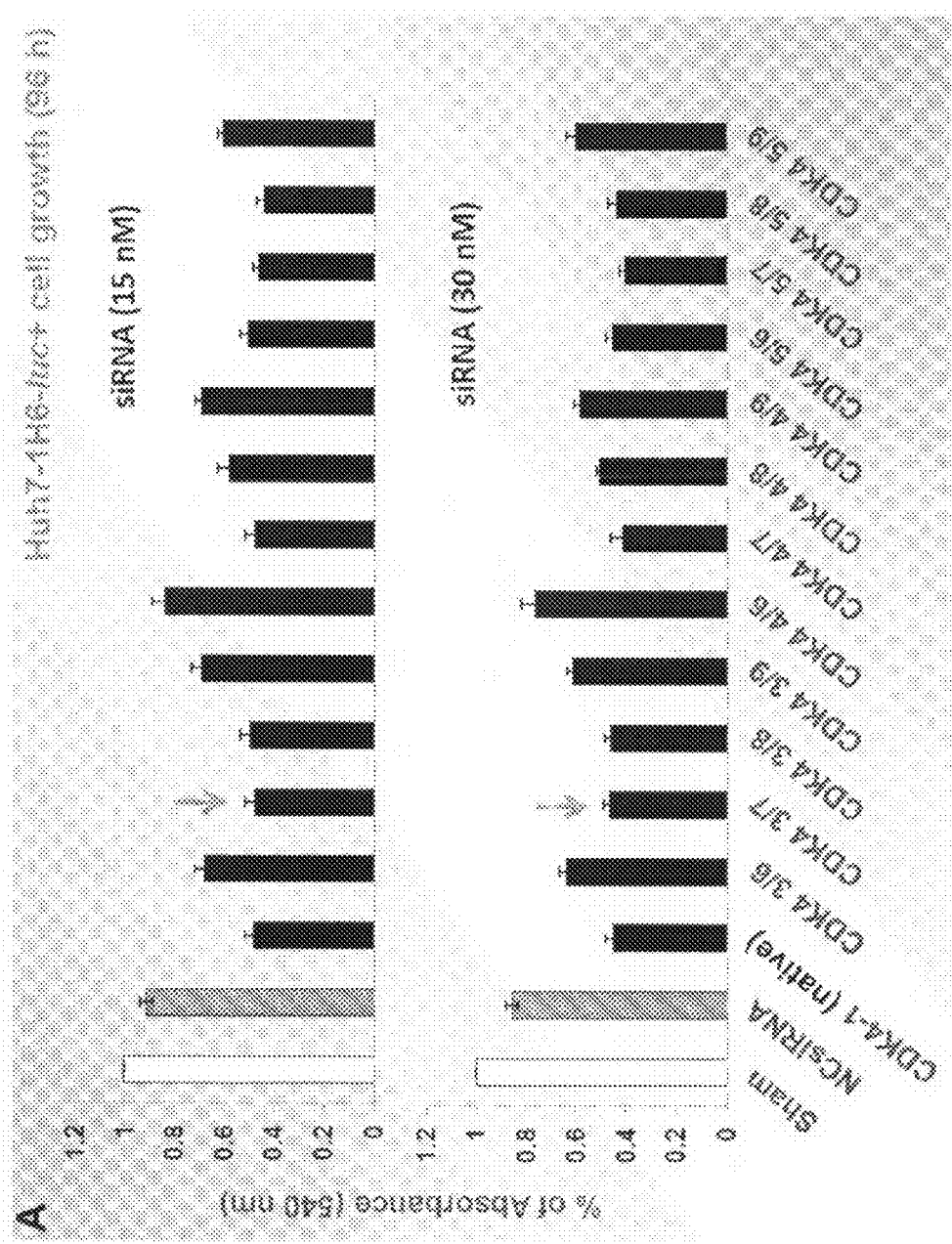
Figure 27:
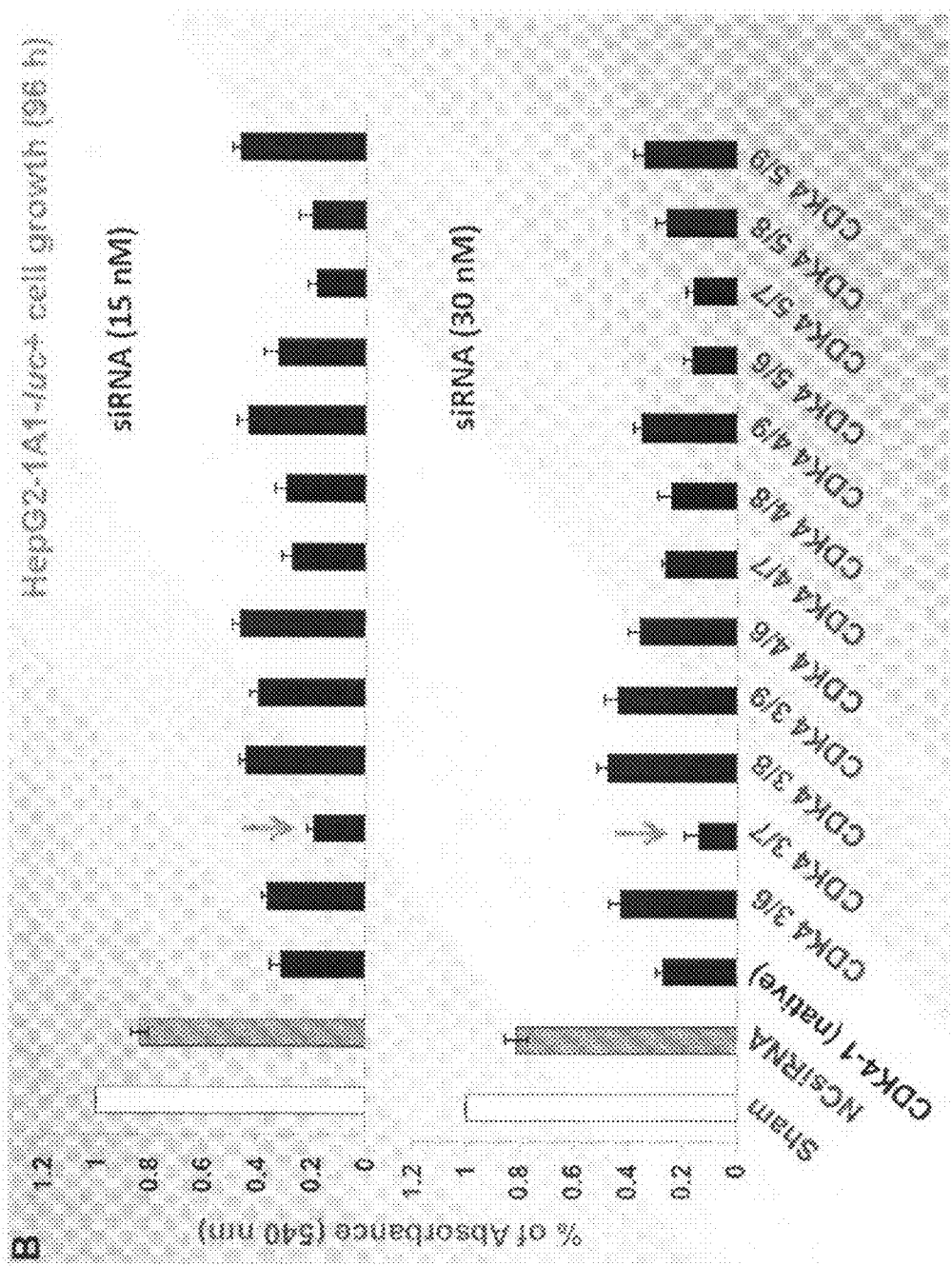

FIG. 27 illustrates the inhibition of (A) Huh7-luc$^+$ or (B) HepG2-luc$^+$ cell growth after transfection with 15 or 30 nM of SNALP-formulated unmodified or modified CDK4-1 siRNA. The cells were examined by an MTT assay 4 days after the treatment. Results are shown as the mean percentage of absorbance at 540 nm±s.d.

Figure 28:
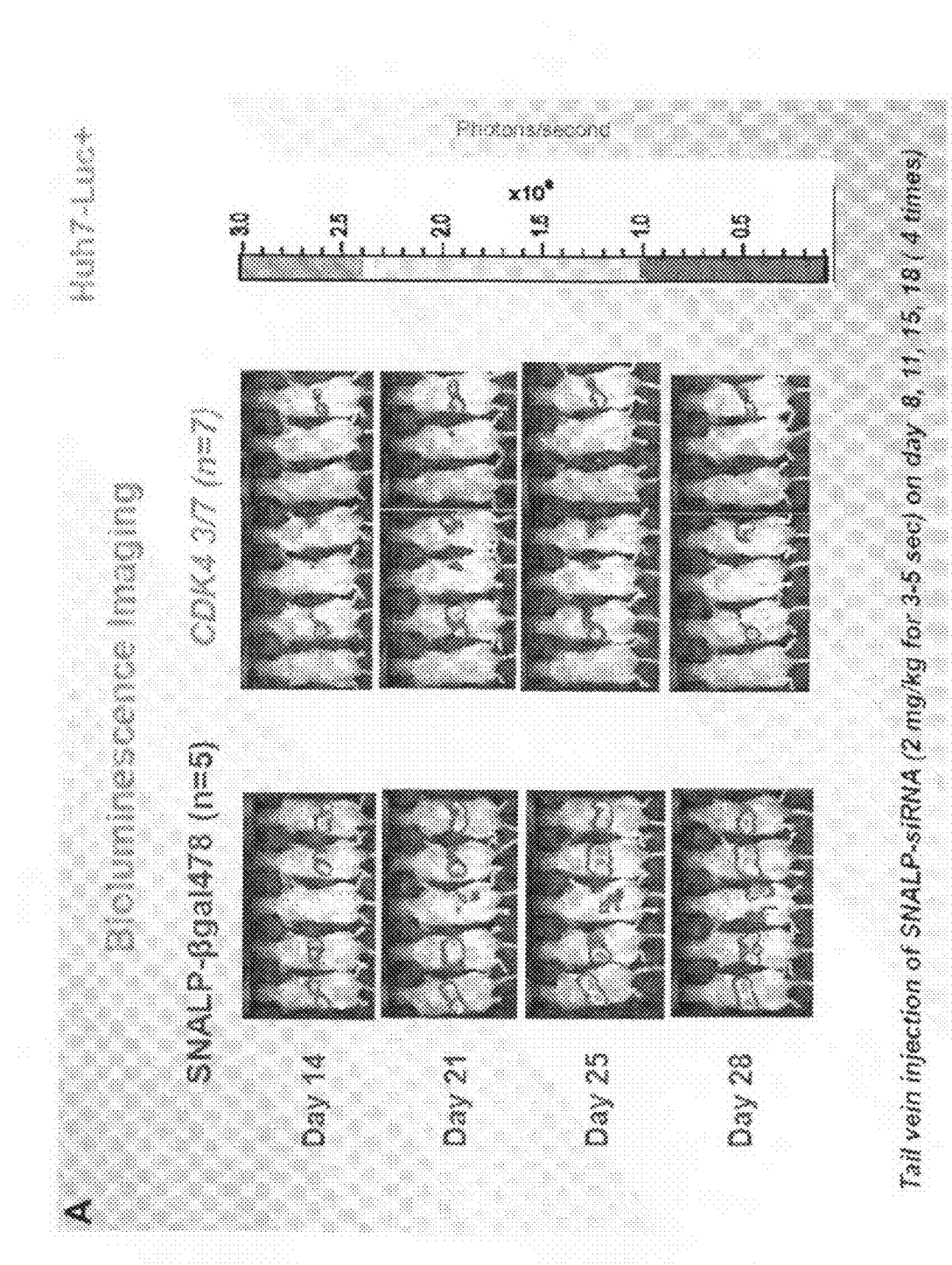
Figure 28:
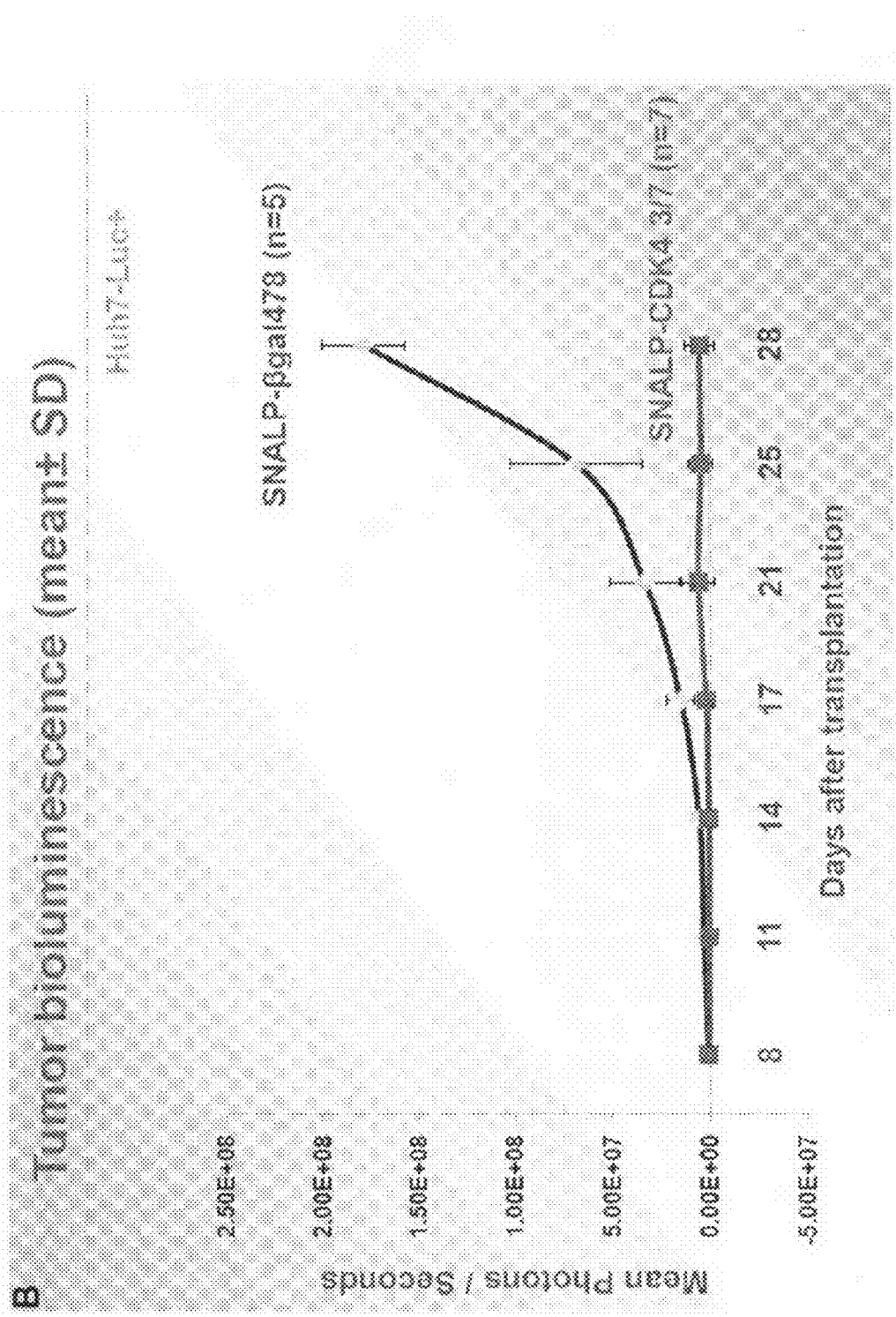
Figure 28:
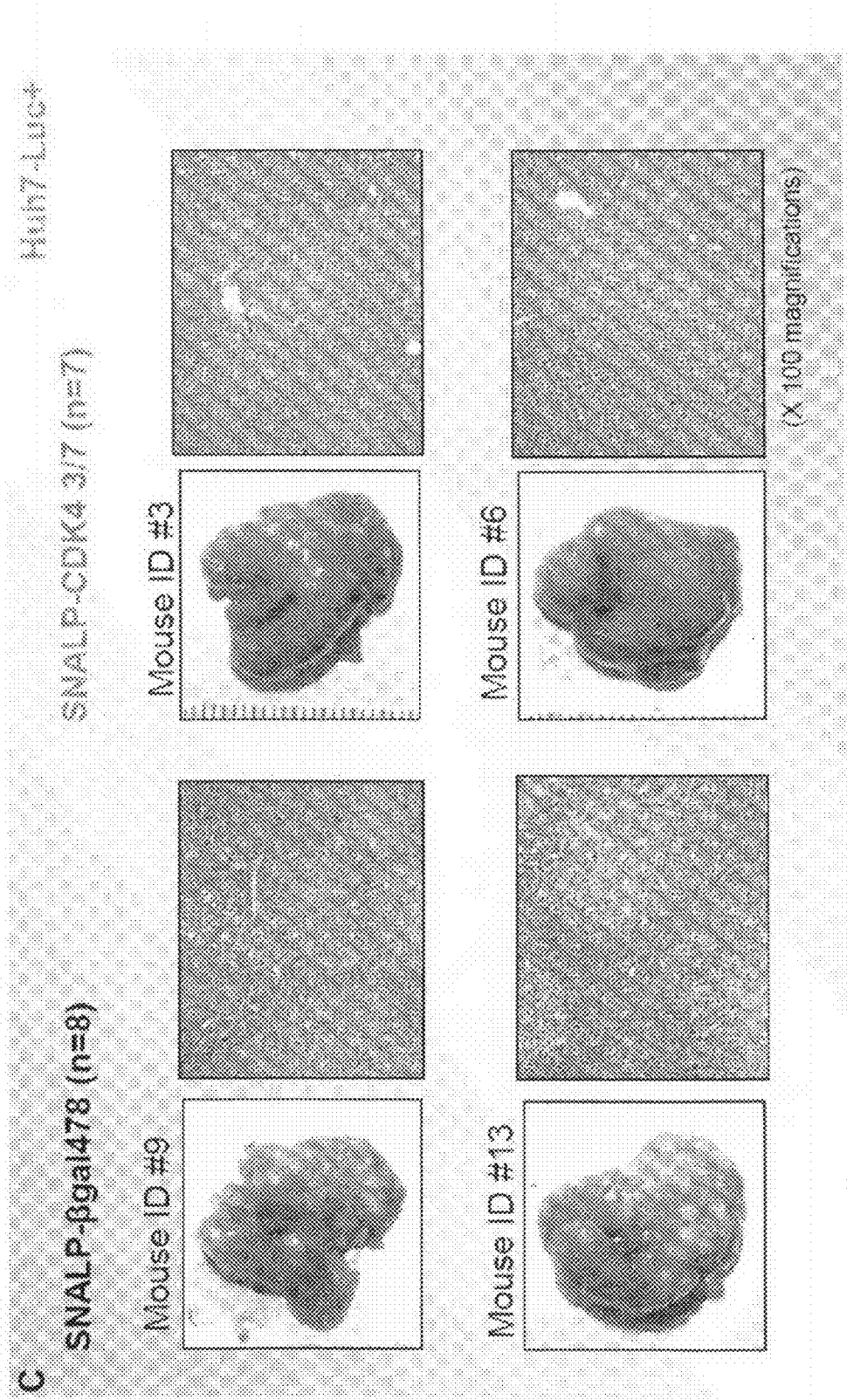

FIG. 28 illustrates that treatment with SNALP containing CDK4-3/7 siRNA effectively suppressed neoplastic growth in a mouse model of metastatic human liver cancer. (A) In vivo monitoring of tumor growth by BLI during and after treatments. On days 8, 11, 15, and 18 after transplantation, SNALP-formulated βgal478 or CDK4-3/7 siRNA was injected into the tail vein at a dosage of 2 mg/kg. Images were set at the same pseudocolor scale to show relative bioluminescent changes over time. (B) Measurement of mean in vivo tumor bioluminescence. Bioluminescent signals emitted from the liver tumors of Huh7-luc$^+$ cells were quantified in photons/second at each imaging time point, and mean tumor bioluminescence±s.d. was graphed over time for the mice treated with SNALP-formulated βgal478 or CDK4-3/7 siRNA. (C) This panel shows examples of the gross liver morphology and histological analysis of excised livers on day 28 after administration of SNALP-formulated βgal478 or CDK4-3/7 siRNA.

Figure 29:
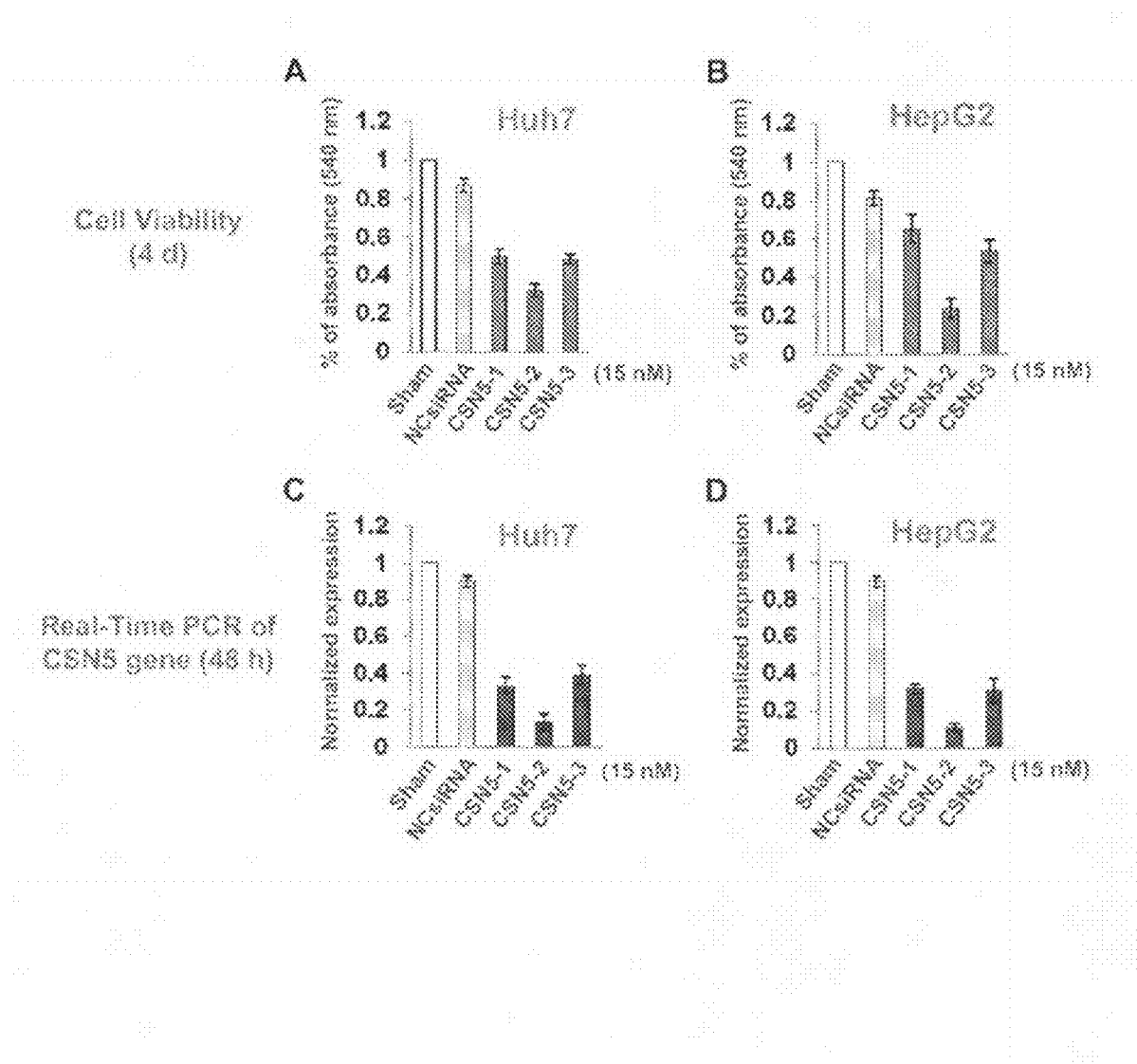

FIG. 29 illustrates that CSN5 gene silencing decreased HCC cell survival in a cell viability assay and reduced CSN5 mRNA levels in a quantitative real-time RT-PCR assay. (A, B) Growth inhibition of Huh7 (A) or HepG2 (B) cells after transfection with 15 nM of three CSN5-specific siRNA was examined by an MTT assay 4 d after the treatment. The cells that were untreated (sham) and treated with NC siRNA were assayed simultaneously. Results are presented as mean percentage of absorbance at 540 nm±s.d. (C, D) Real-time RT-PCR analysis of CSN5 gene expression in Huh7 (C) or HepG2 (D) cells treated with the CSN5-specific siRNA. Total RNA was extracted at 48 h after treatment with 15 nM of the siRNA. In all PCR experiments, expression was calculated relative to GAPDH and is normalized to untreated control. Each bar value represents the mean±s.d. of triplicate experiments. NCsiRNA=negative control siRNA.

Figure 30:
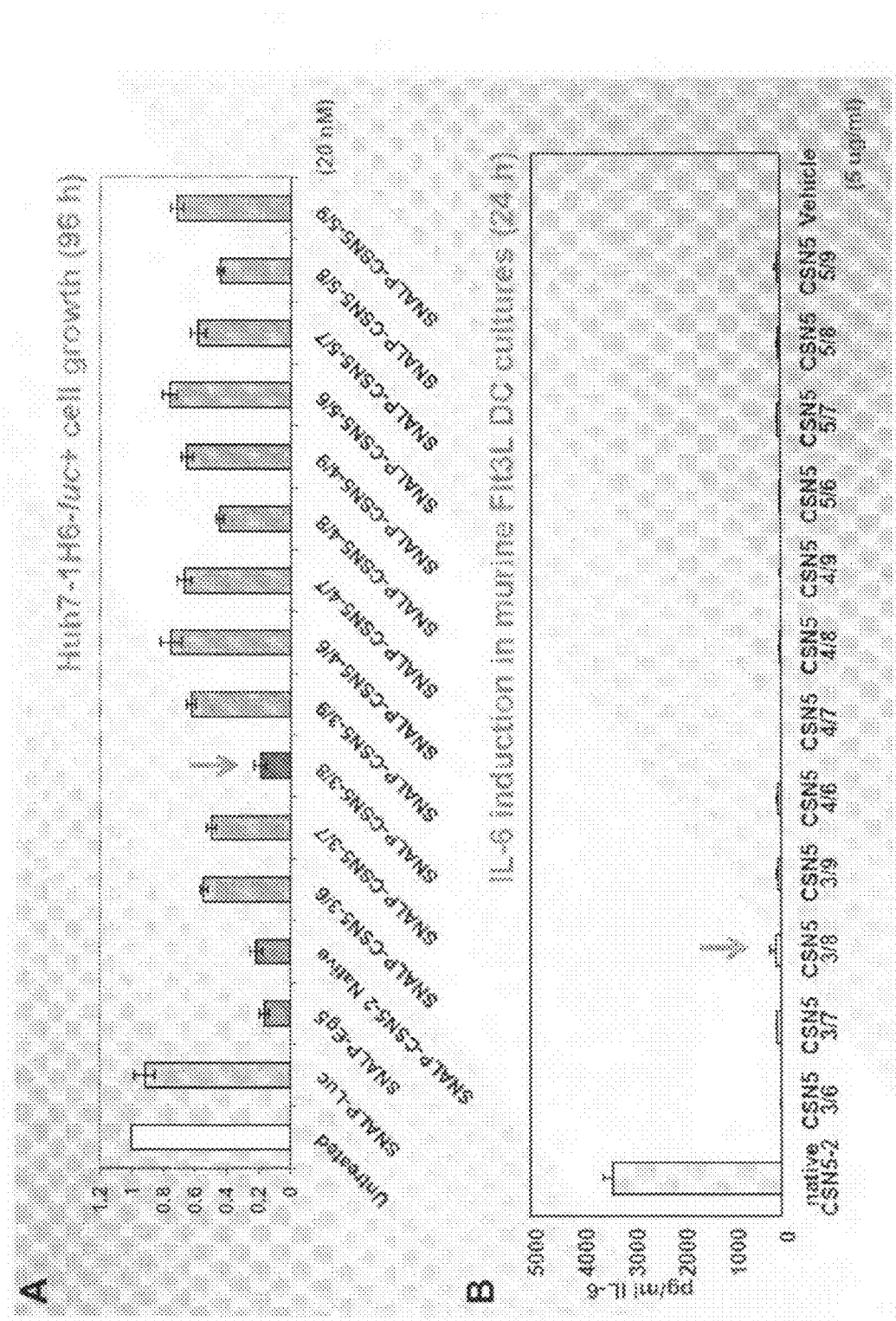

FIG. 30 illustrates the effect of SNALP containing CSN5 siRNA on Huh7-luc$^+$ cell growth and Flt3L DC cytokine response. (A) Inhibition of Huh7-luc$^+$ cell growth after transfection with 20 nM of SNALP-formulated unmodified CSN5-2 siRNA or its modified variants. The cells were examined by an MTT assay 4 days after the treatment. SNALP containing Luc siRNA was used as a negative control, and SNALP containing Eg5 siRNA was used as a positive control. Results are shown as the mean percentage of absorbance at 540 nm±s.d. (B) This panel shows the quantification of IL-6 levels after i.v. administration of SNALP-encapsulated unmodified or modified CSN5-2 siRNA into mice. After 24 h of siRNA treatment, culture supernatants of Flt3L-derived dendricytes isolated from mouse bone marrow were assayed for IL-6 by an ELISA method. Each value is the mean±s.d. of triplicate experiments.

Figure 31:
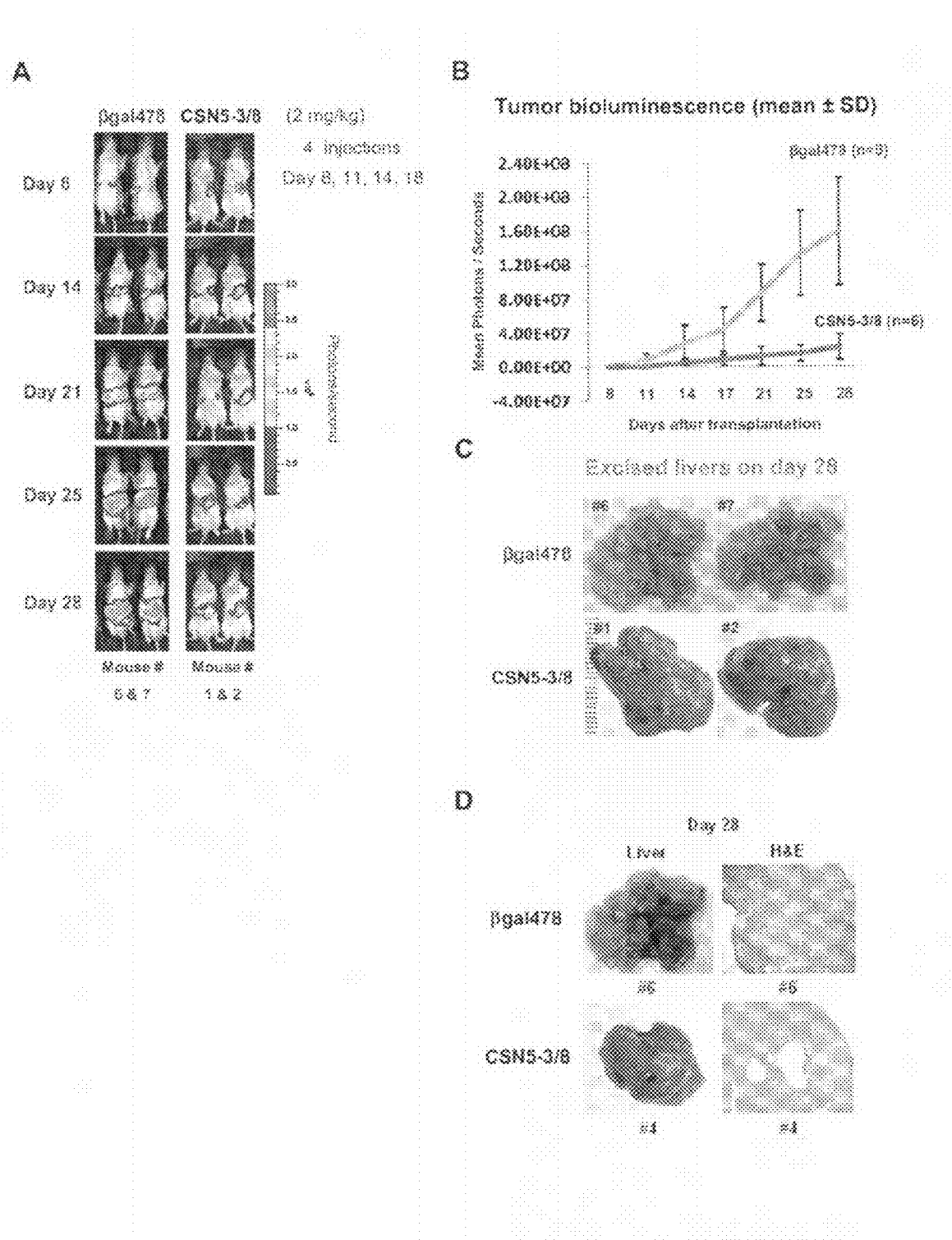

FIG. 31 illustrates that treatment with SNALP containing CSN5-3/8 siRNA effectively suppressed neoplastic growth in a mouse model of metastatic human liver cancer. (A) In vivo monitoring of tumor growth by BLI during and after treatments. Images of two representative mice from each treatment group are shown. On days 8, 11, 14, and 18 after transplantation, SNALP-formulated βgal478 or CSN5-3/8 siRNA was injected into the tail vein at a dosage of 2 mg/kg. Images were set at the same pseudocolor scale to show relative bioluminescent changes over time. (B) Measurement of mean in vivo tumor bioluminescence. Bioluminescent signals emitted from the liver tumors of Huh7-luc$^+$ cells were quantified in photons/second at each imaging time point, and mean tumor bioluminescence±s.d. was graphed over time for the mice treated with SNALP-formulated βgal478 or CSN5-3/8 siRNA. (C) This panel shows examples of the gross liver morphology of excised livers on day 28 after administration of SNALP-formulated βgal478 or CSN5-3/8 siRNA. (D) This panel shows the gross liver morphology and histological analysis of excised livers on day 28 after administration of SNALP-formulated βgal478 or CSN5-3/8 siRNA. Livers from all mice tested were sectioned and stained with H&E to observe the status of tumor growth within tissues. Both gross liver morphology and a microscopic image (100×) of a representative liver from each treatment group are shown.

FIG. 32 illustrates the effect of FOXM1 siRNA on Huh7-luc$^+$ cell growth and Flt3L DC cytokine response. (A) Inhibition of Huh7-luc$^+$ cell growth after transfection with 15 nM of unmodified or modified FOXM1-1 siRNA complexed with LF2000. The cells were examined by an MTT assay 3 days after the treatment. Results are shown as the mean percentage of absorbance at 540 nm±s.d. (B) This panel shows the quantification of IL-6 levels after i.v. administration of SNALP-encapsulated unmodified or modified FOXM1-1 siRNA into mice. After 24 h of siRNA treatment, culture supernatants of Flt3L-derived dendricytes isolated from mouse bone marrow were assayed for IL-6 by an ELISA method. Each value is the mean±s.d. of triplicate experiments.

FIG. 33 illustrates the effect of R1 siRNA on Huh7-luc+ cell growth and Flt3L DC cytokine response. (A) Inhibition of Huh7-luc+ cell growth after transfection with 15 nM of unmodified or modified R1-2 siRNA complexed with LF2000. The cells were examined by an MTT assay 3 days after the treatment. Results are shown as the mean percentage of absorbance at 540 nm±s.d. (B) This panel shows the quantification of IL-6 levels after i.v. administration of SNALP-encapsulated unmodified or modified R1-2 siRNA into mice. After 24 h of siRNA treatment, culture supernatants of Flt3L-derived dendricytes isolated from mouse bone marrow were assayed for IL-6 by an ELISA method. Each value is the mean±s.d. of triplicate experiments.

Figure 34:
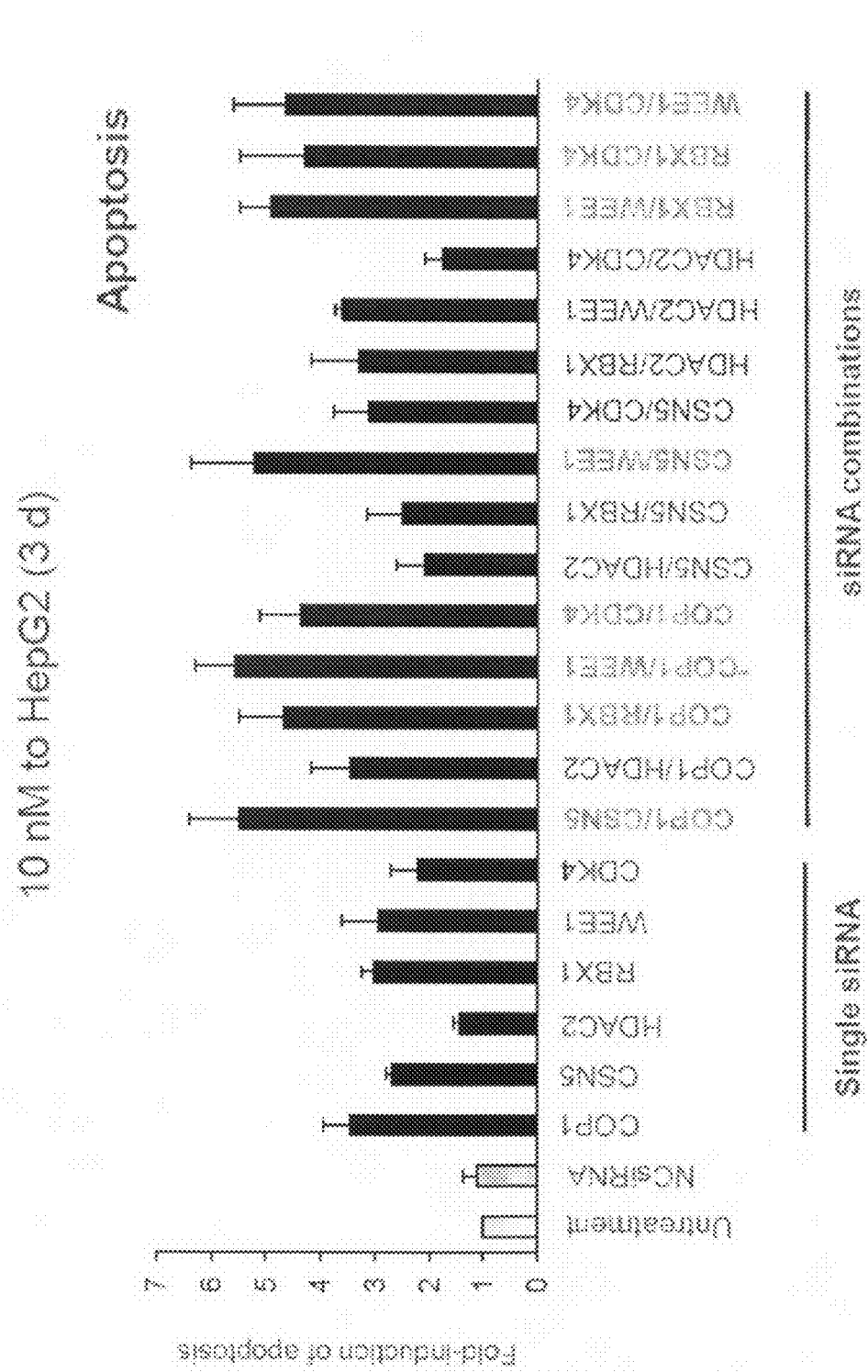

FIG. 34 illustrates that numerous combinations of siRNA sequences targeting COP1, WEE1, HDAC2, RBX1, CDK4, CSN5, FOXM1, and/or R1 (RAM2) gene expression were effective at inducing the apoptosis of cancer cells.

Figure 35:
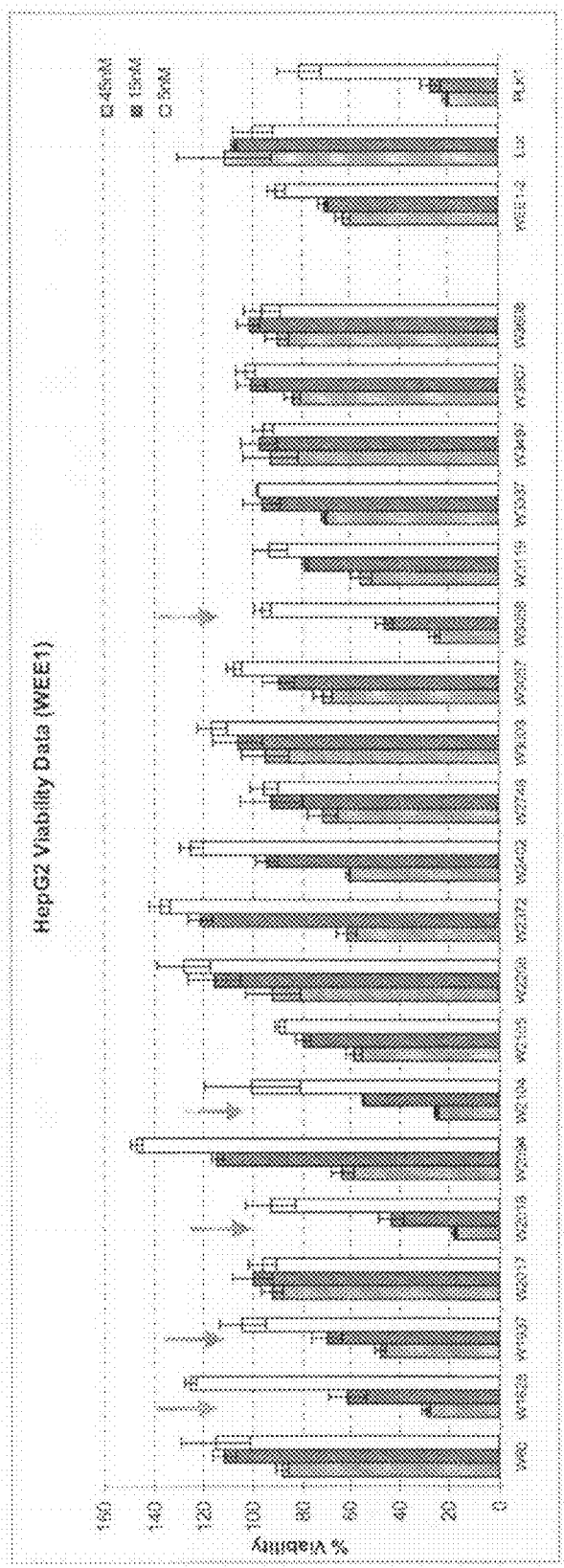

FIG. 35 illustrates that numerous additional WEE1 siRNAs were as effective as WEE1-2 siRNA or more efficacious than WEE1-2 siRNA at inhibiting the growth of HepG2 cells.

Figure 36:
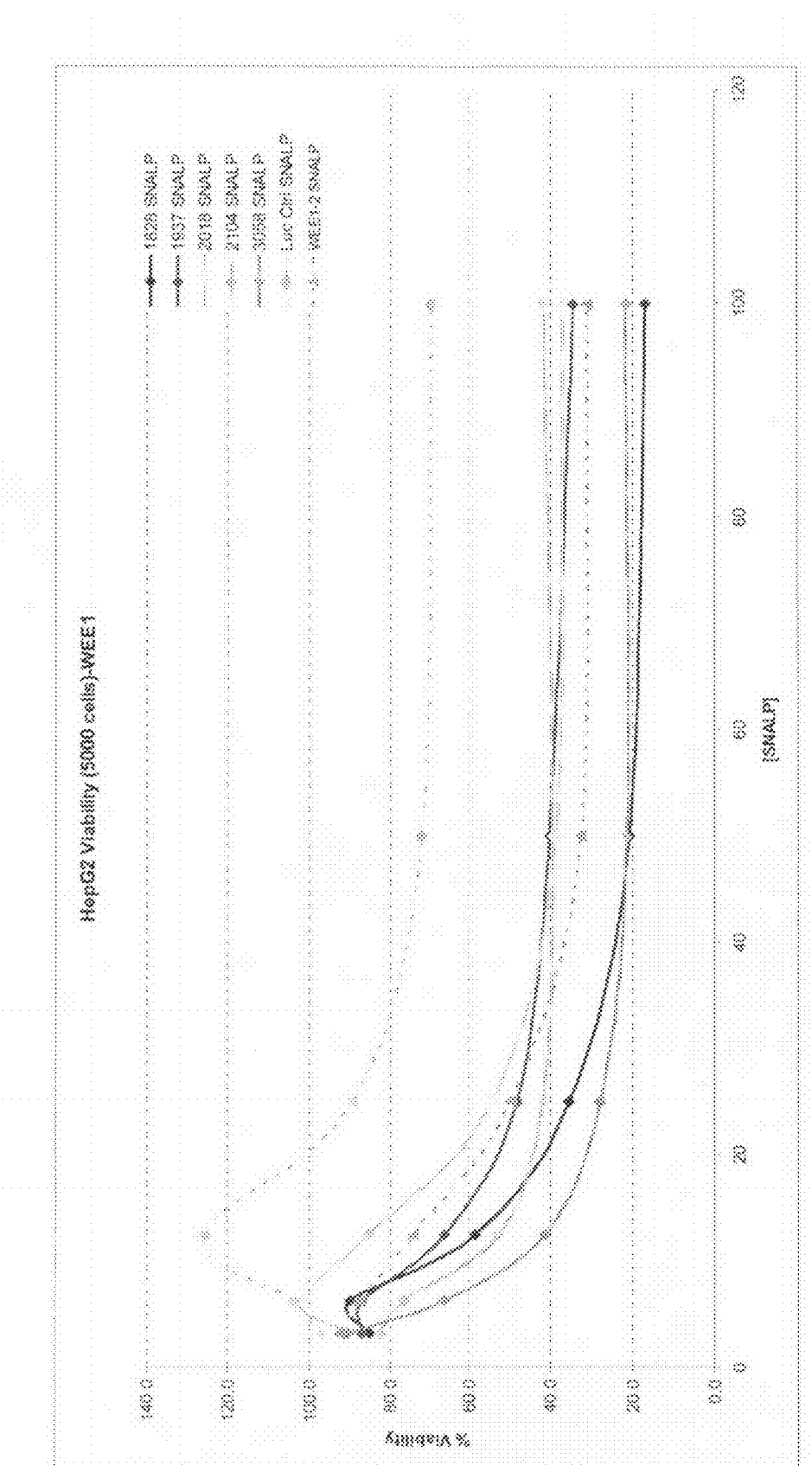

FIG. 36 illustrates a dose-response curve analysis for some of the additional WEE1 siRNA sequences.

Figure 37:
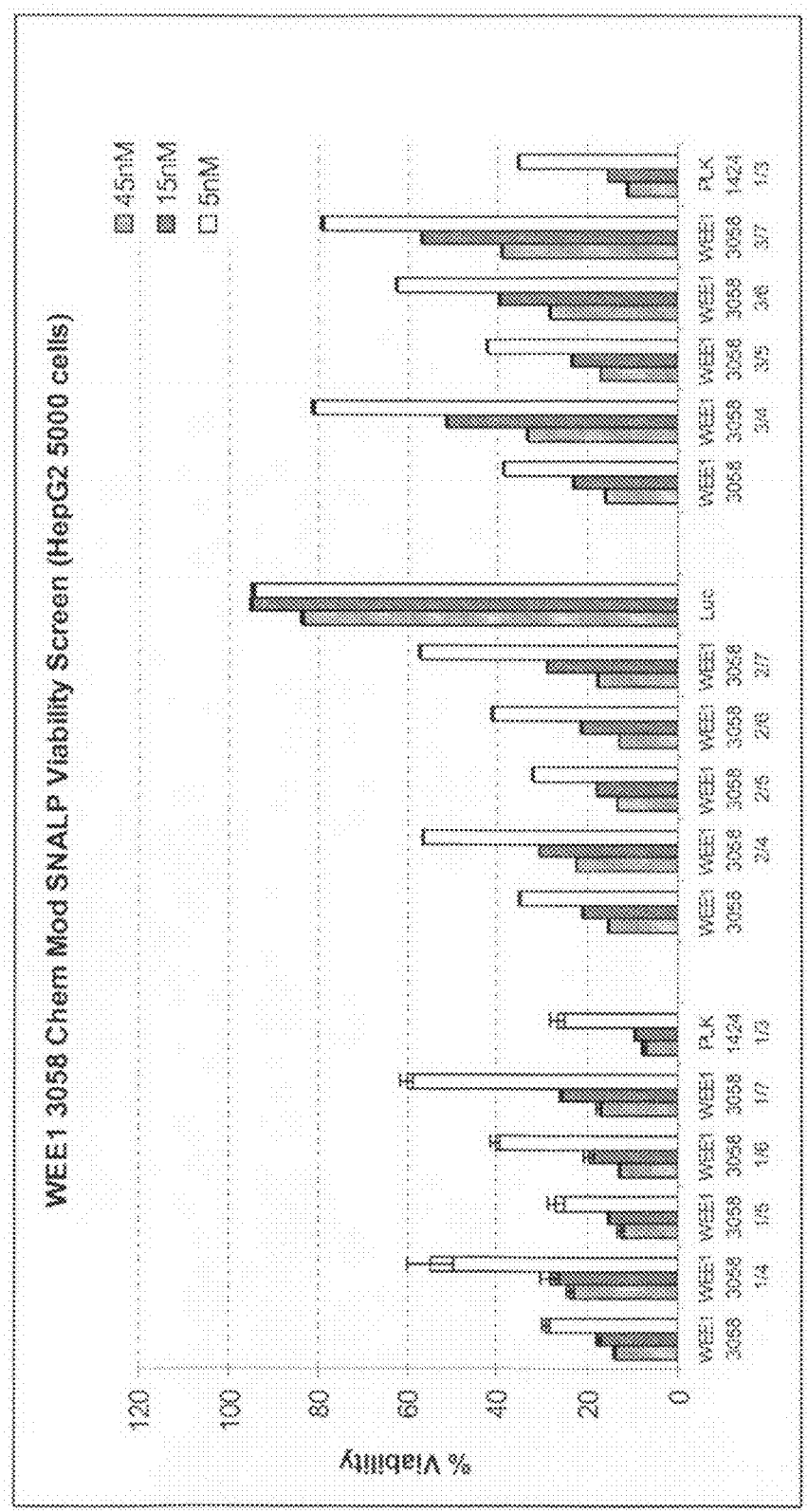

FIG. 37 illustrates that unmodified as well as 2'OMe-modified WEE1-3058 siRNA were effective at inhibiting the growth of HepG2 cells.

Figure 38:
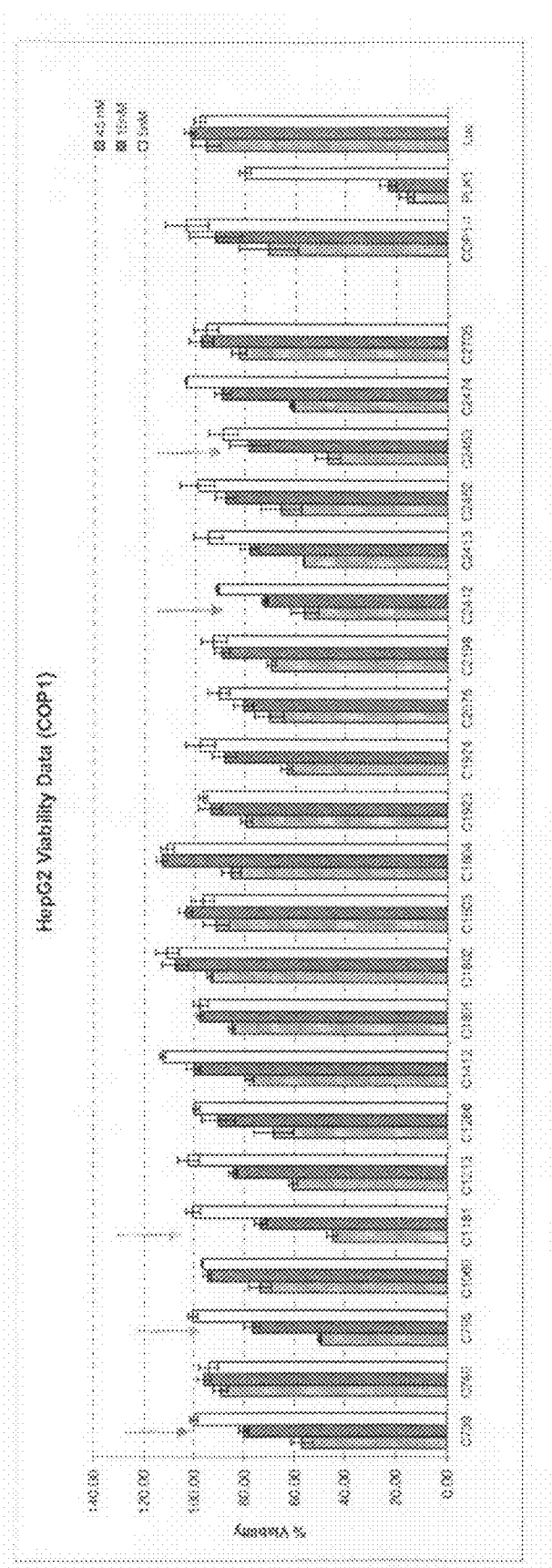

FIG. 38 illustrates that numerous COP1 siRNAs were as effective as COP1-1 siRNA or more efficacious than COP1-1 siRNA at inhibiting the growth of HepG2 cells.

Figure 39:
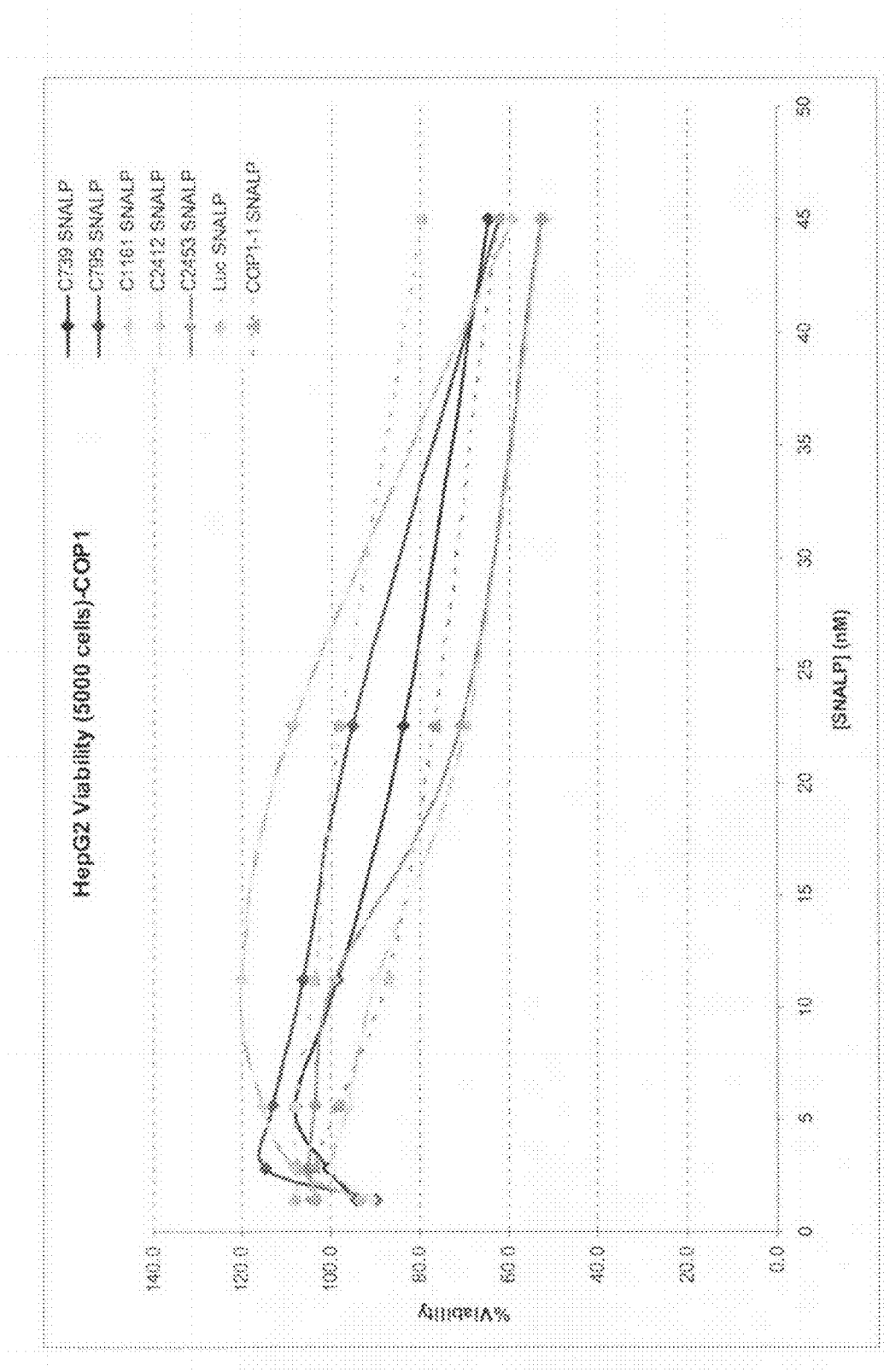

FIG. 39 illustrates a dose-response curve analysis for some of the additional COP1 siRNA sequences.

Figure 40:
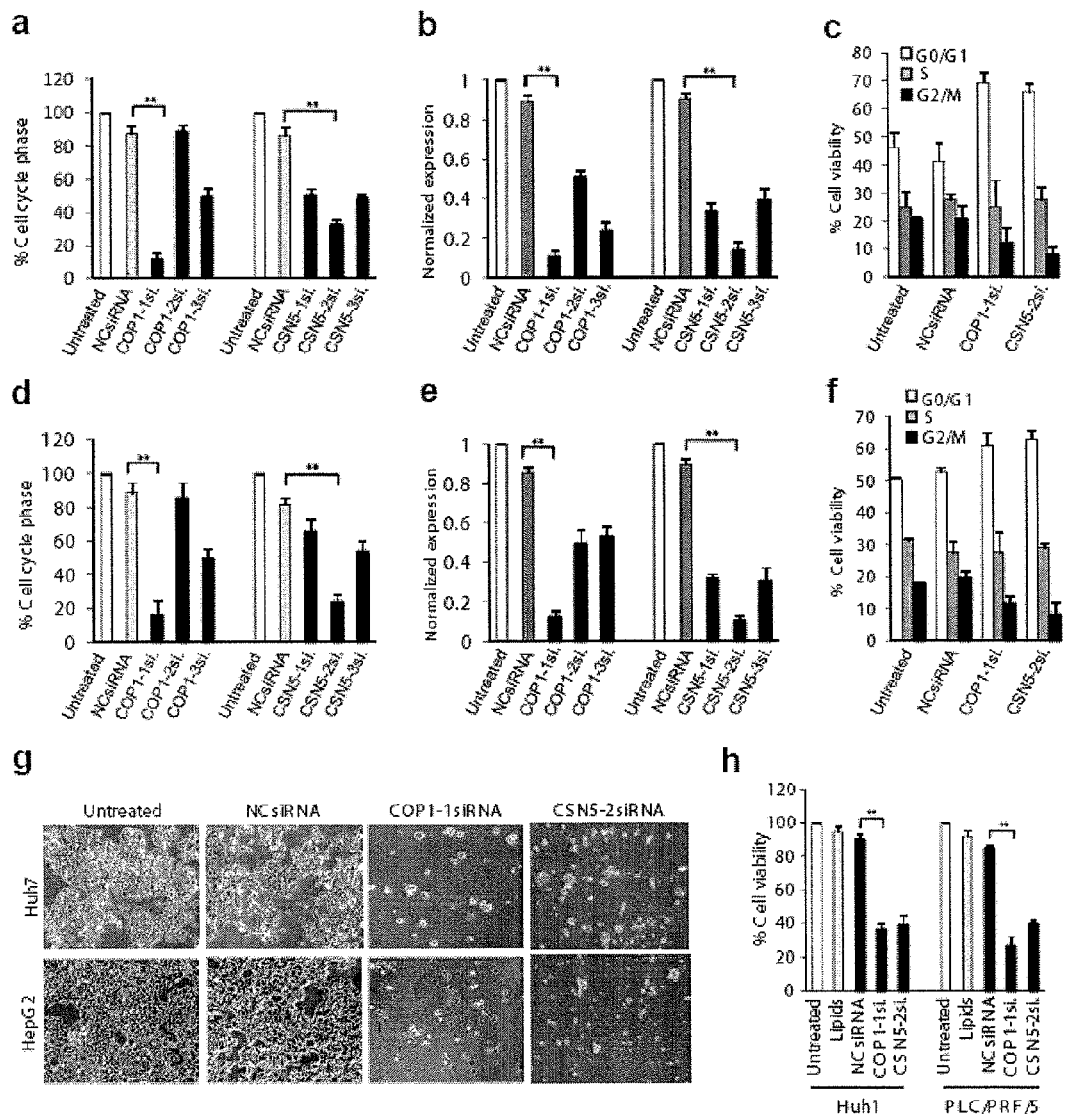

FIG. 40 illustrates that COP1-1 siRNA and CSN5-2 siRNA inhibit growth of HCC cells and silence target gene expression at the mRNA level. (a,d) Huh7 (a) and HepG2 (d) cells were transfected with 15 nM of COP1- or CSN5-specific siRNAs and examined by an MTT assay 4 d after the treatment. Results are presented as the mean percentage of absorbance at 540 nm±s.d. (P<0.01; n=3; Bootstrap Test). NCsiRNA, negative control siRNA; si., siRNA. (b,e) Real-Time RT-PCR analysis of COP1 and CSN5 gene expression in Huh7 (b) or HepG2 (e). Total RNA was extracted 48 h after transfection with 15 nM of the siRNAs. Expression was calculated relative to GAPDH and normalized to untreated control. Each bar represents the mean±s.d. of triplicate experiments (P<0.01; Bootstrap Test). (c,f) Cell cycle analysis in Huh7 (c) and HepG2 (0 cells treated with 15 nM of COP1-1siRNA or CSN5-2siRNA for 48 h. The analysis was performed in duplicate on an equal number of cells (10$^4$ events) by flow cytometry after staining of DNA with propium iodide. (g) Morphology of Huh7 or HepG2 cells treated with 15 nM of COP1-1siRNA or CSN5-2siRNA for 4 d (×100). (h) Huh1 and PLC/PRF/5 cells were treated with COP1-1 siRNA and CSN5-2 siRNA for 4 d. Results of MTT assay are presented as mean percentage of absorbance at 540 nm s.d. (**P<0.01; n=3; Bootstrap Test).

Figure 41:
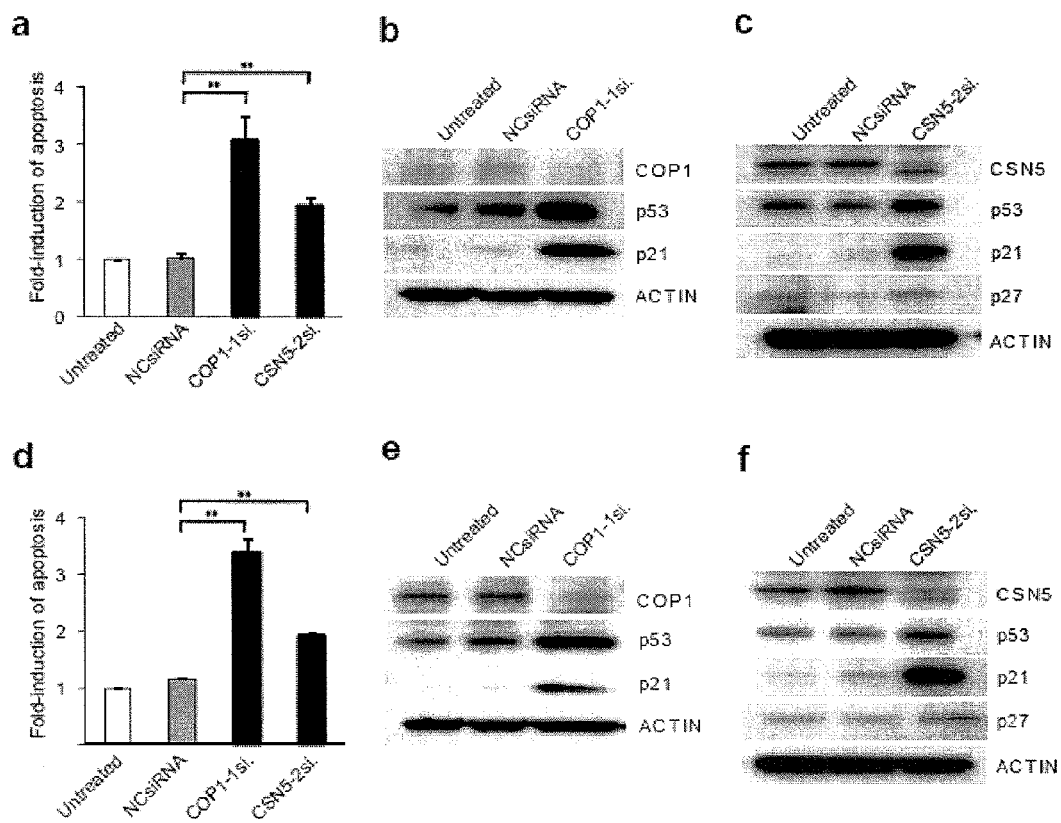

FIG. 41 illustrates that COP1 and CSN5 gene silencing results in induction of apoptosis through restoration of p53 activity. (a,d) Detection of apoptosis in Huh7 (a) and HepG2 (d) cells 3 d after transfection with 15 nM of COP1-1 siRNA and CSN5-2 siRNA. Results are shown as the mean fold-induction of apoptosis±s.d. of three independent experiments (**P<0.01; Bootstrap Test). (b,e) Western blot analysis of COP1, p53 and p21 protein expression in Huh7 (b) and HepG2 (e) cells that were untreated and treated with 15 nM of NCsiRNA or COP1-1 siRNA for 48 h. (c,f) Western blot analysis of COP1, p53, p21 and p27 protein expression in Huh7 (c) and HepG2 (f) cells that were untreated and treated with 15 nM of NCsiRNA or CSN5-2 siRNA for 48 h. NCsiRNA, negative control siRNA; si., siRNA.

Figure 42:
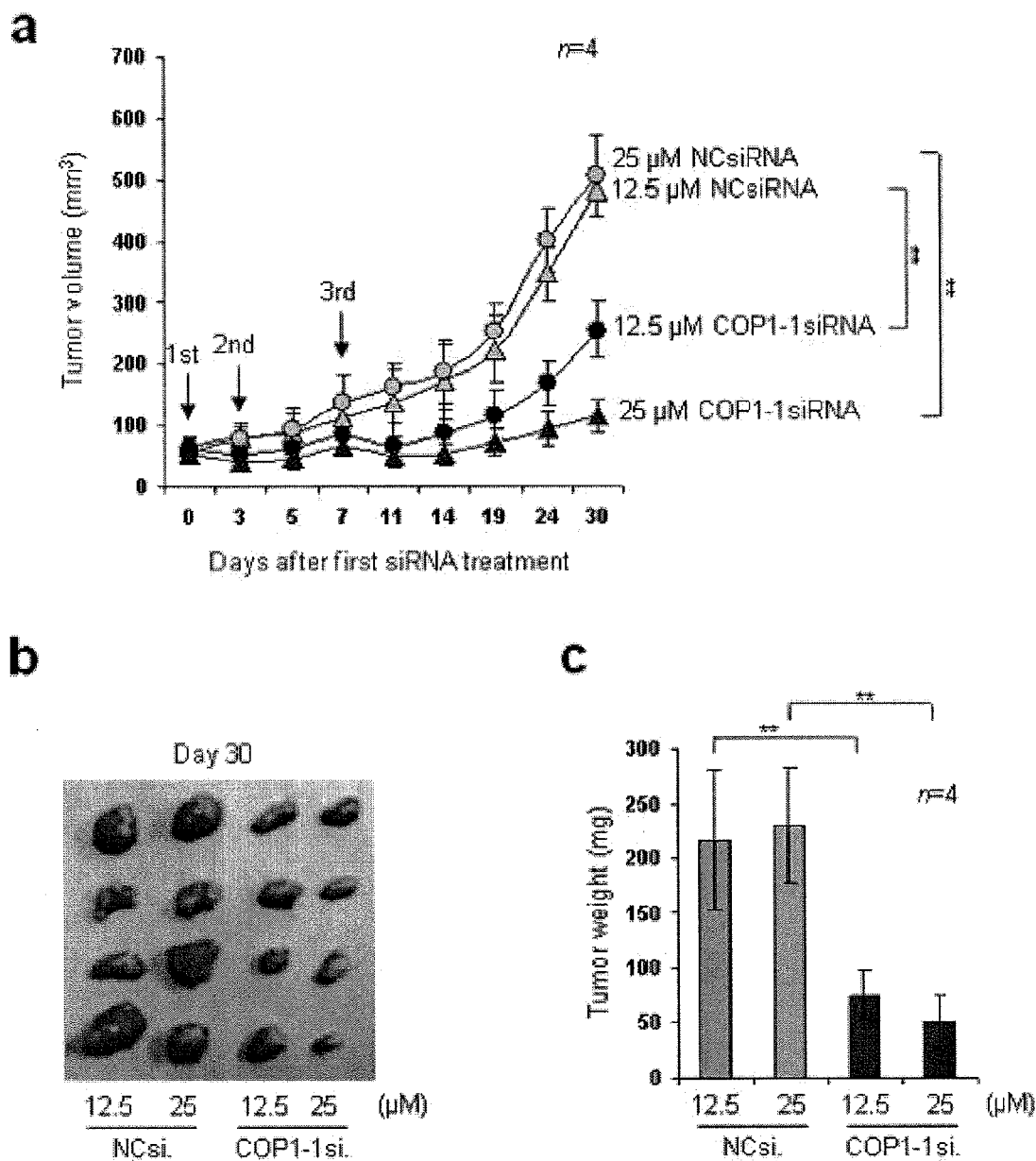

FIG. 42 illustrates the antitumor effect of native COP1-1 siRNA in a model of subcutaneous Huh7 growth. (a) Kinetics of tumor growth. 5×10$^5$ Huh7 cells were subcutaneously inoculated in 50 μl PBS buffer into lower flank of athynic male Balb/c nude mice. When tumors reached an average volume of ~50-60 mm$^3$, the tumor bearing mice were treated with native NCsiRNA or COP1-1 siRNA mixed with LF2000. Day 0 corresponds to 15 days after inoculations. Tumor diameters were measured with digital calipers. The mean tumor volume±s.d. is shown (P<0.01; n=4; t-test with Equal Variance). (b) Size of Huh7 xenografts on day 30. (c) Mean tumor weight. Each bar represents the mean±s.d (P<0.01; n=4; Two Samples t-test).

Figure 43:
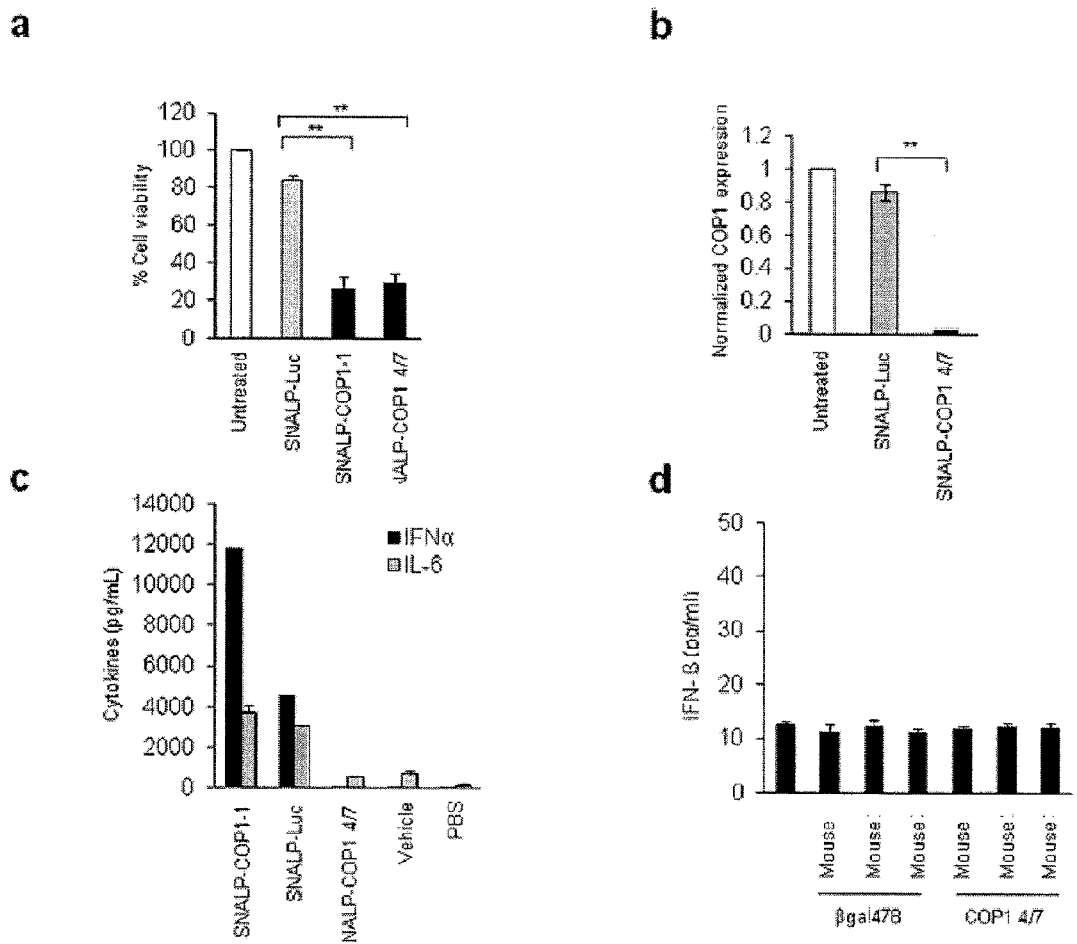

FIG. 43 illustrates the selection of COP1-4/7 siRNA for in vivo application. (a) Inhibition of Huh7-luc+ cell growth after transfection with 15 nM of SNALP-encapsulated COP1-1 (native) or COP1-4/7 siRNA (a modified variant). The siRNA transfectants were examined by an MTT assay 4 d after the treatment. Untreated cells and cells treated with luciferase-specific siRNA were assayed simultaneously. Results are shown as the mean percentage of absorbance at 540 nm±s.d. (P<0.01; n=3; Bootstrap Test). (b) Real-Time RT-PCR analysis of COP1 gene expression in Huh7-luc+ cells treated with the indicated siRNAs. P<0.01, n=3, Bootstrap Test. (c) Effect of encapsulated siRNA targeting luciferase (Luc) or COP1 on cytokines levels in vitro. Dendritic cells from mouse Flt3L-derived bone marrow cultures were treated with SNALP-encapsulated siRNA (5 μg/ml) targeting COP1 for 24 h. Culture supernatants were assayed for IFN-α and IL-6 by an ELISA method. As controls, cells treated with an immunostimulatory Luc siRNA (SNALP-Luc), empty lipid particles (vehicle) or PBS were assayed simultaneously. Each value is the mean±s.d. of triplicate cultures. (d) Serum IFN-β 48 h after i.v. administration of encapsulated siRNA targeting -galactosidase or COP1 into immunodeficient mice (n=3). Each bar represents the mean pg/ml of INF-+s.d. of duplicate experiments.

Figure 44:
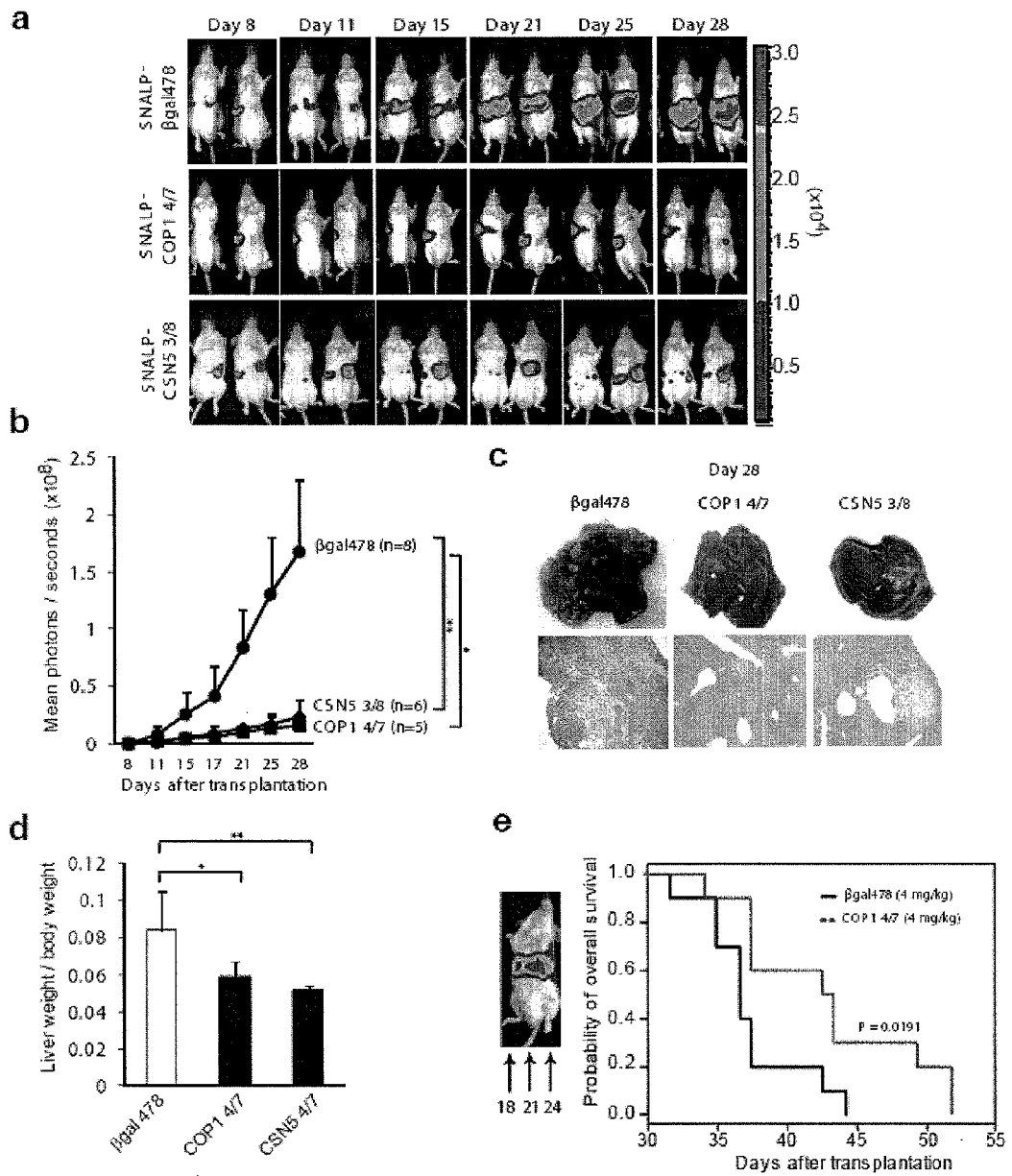

FIG. 44 illustrates that systemic SNALP siRNA targeting of COP1 and CSN5 suppresses growth of Huh7-luc+ xenografts in liver. (a) In vivo monitoring of tumor growth by bioluminescence imaging during and after treatment. Mice were randomly assigned either to control (SNALP-βgal478) or treatment group (SNALP-COP1-4/7 and SNALP-CSN5-3/8) based on the intensity of bioluminescence imaging before initiation of therapy. siRNAs were injected into tail vein at a dose of 2 mg/kg at 8, 11, 14 and 18 after Huh7-luc+ transplantation. Representative images of two mice from each treatment group are shown. Images were set at the same pseudocolor scale to show relative bioluminescent changes over time. (b) Quantification of bioluminescence. Bioluminescence signals from Huh7-luc+ xenografts were measured in photons/second, and mean tumor bioluminescence±s.d. was plotted over time. **P<0.01, n=8 vs n=6, Mann-Whitney U-test; *P<0.05, n=8 vs n=5, two Samples t-test. (c) Gross liver morphology and microscopy of Huh7-luc+ xenografts on day 28. H&E staining, ×100. (d) Liver to body weight ratios. Each bar represents the mean±s.d. **P<0.01, n=8 vs. n=6, Mann-Whitney U-test; *P<0.05, n=8 vs. n=5, t-test. (e) Effect of SNALP-COP1-4/7 on overall survival of Huh7-luc+ recipients. SNALP-βgal478 and SNALP-COP1-4/7 were injected on day 18, 21 and 24 after tumor implantation. Representative image of mouse taken at day 18 is shown on the left. The experiment was terminated on day 56 (*P<0.05, n=10, Log-rank test).

Figure 45:
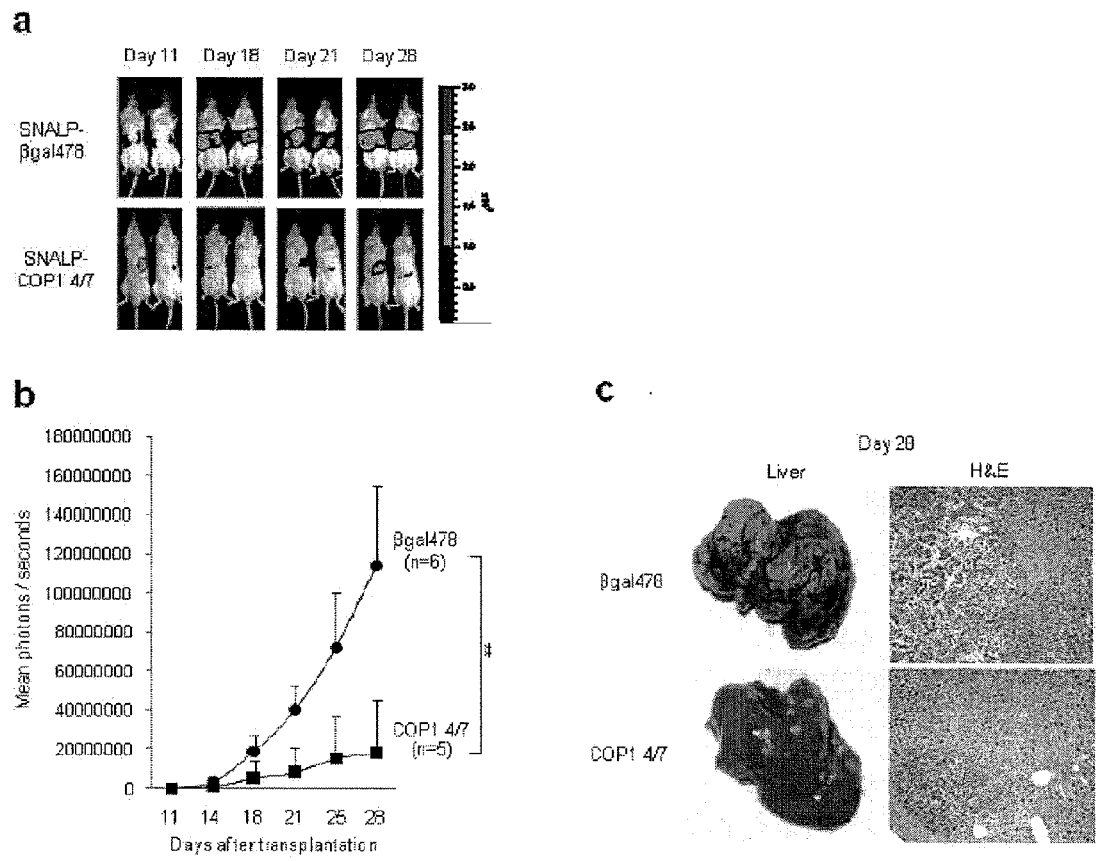

FIG. 45 illustrates that systemic delivery of SNALP-COP1-4/7 inhibits HepG2-luc+ orthotopic tumor growth. (a) In vivo monitoring of tumor growth by bioluminescence imaging. Representative images from each treatment group are shown. SNALP-βgal478 and SNALP-COP1-4/7 were injected at a dose of 2 mg/kg into the tail vein on day 11, 14, 17 and 21. (b) Quantification of in vivo tumor bioluminescence. Bioluminescence signals were expressed as photons/second and plotted as the mean tumor bioluminescence±s.d. **P<0.01, n=6 vs n=5, Mann-Whitney U-test. (c) Gross liver morphology and microscopy of liver tumors on day 28. H&E staining, original magnification, ×100.

Figure 46:
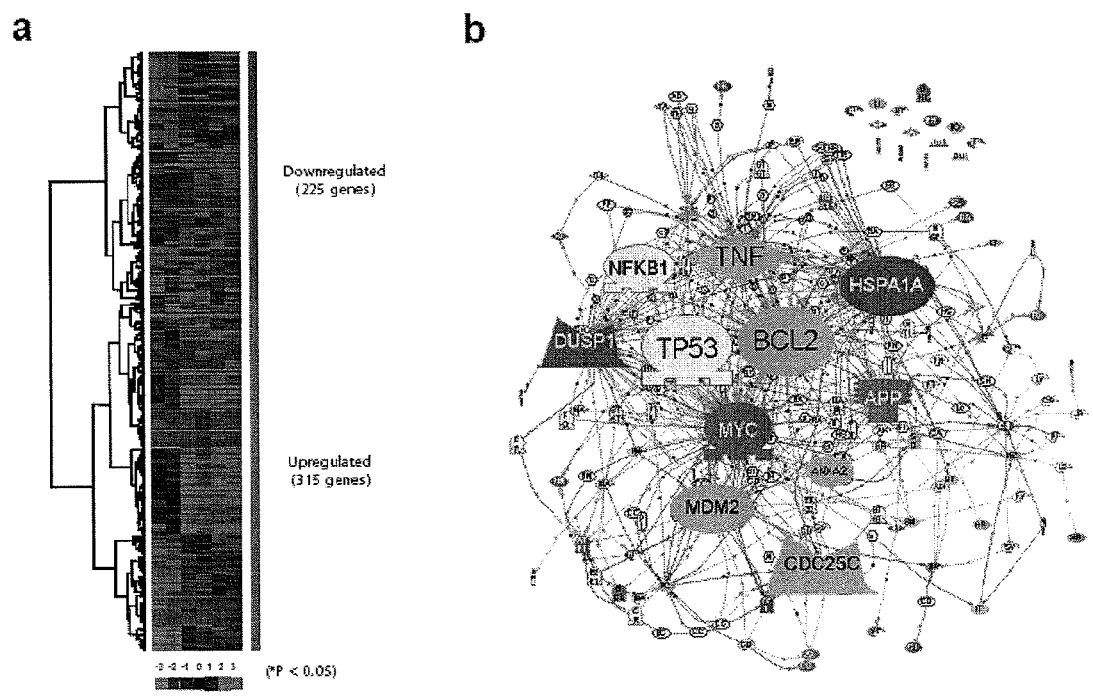

FIG. 46 illustrates that COP1 knockdown activates p53-dependent apoptosis in Huh7-luc+ xenografts. (a) A heat-map overview of up- and downregulated genes. Tumor-bearing mice received a single i.v. injection of 2 mg/kg of SNALP-COP1-4/7 or SNALP-βgal478 siRNA. Tumors (n=6 from 3 mice) were analyzed for changes in gene expression 48 h following treatment by illumina microarray. Each cell in the matrix represents the expression level of a gene feature in an individual sample. Columns represent individual samples and rows represent each gene. Red and green in cells reflect high and low expression levels, respectively, as indicated in the scale bar ($\log_2$-transformed scale). (b) Identification of key regulators of COP1 knockdown signature in tumors using Ingenuity pathway analysis. Up- and downregulated genes are shown in red and green, respectively. Genes in gray are associated with the regulated genes.

FIG. 47 provides a list of the representative genes and functional categories affected by COP1 knockdown in liver tumors.

FIG. 48 provides the top 5 gene networks from Ingenuity Pathway Analysis.

FIG. 49 provides a list of the representative genes that are deregulated by COP1 knockdown and functionally involved in p53, Wnt/β-catenin and death receptor signaling.

Figure 50:
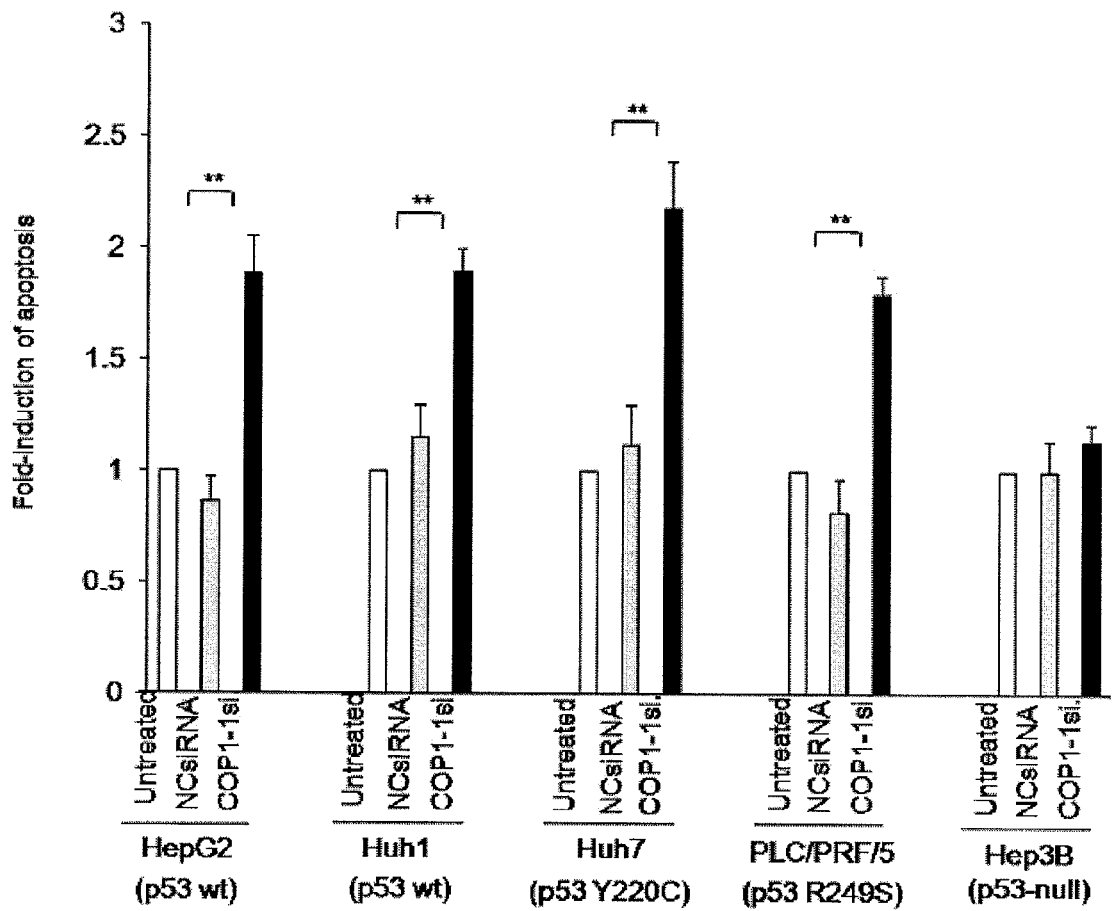

FIG. 50 illustrates that COP1 gene silencing induces apoptosis in p53 wild-type (HepG2, Huh1) and p53 mutant (Huh7, PLC/PRF/5) HCC cell lines. Three days after transfection with 15 nM of COP1-1 siRNA, the induction of apoptosis was measured by detecting the ratio of denatured DNA to single-stranded DNA formed in apoptotic cells. Untreated cells and cells treated with NCsiRNA were assayed simultaneously. Results are shown as the mean fold-induction of apoptosis±s.d. of three independent experiments (**P<0.01, *P<0.05, n=3, Bootstrap Test).

FIG. 51 provides a list of siRNA molecules (SEQ ID NOs: 51, 52, 238, 239, 240, 241, 352, 353, 191, 192, 354, 355, 236, 237, 58, 59, 200 and 201, respectively) used in the study described in Example 13.

FIG. 52 provides a list of siRNA molecules (SEQ ID NOs: 51, 52, 238, 239, 240, 241, 236, 237, 58 and 59, respectively) used in the study described in Example 14.

Figure 53:
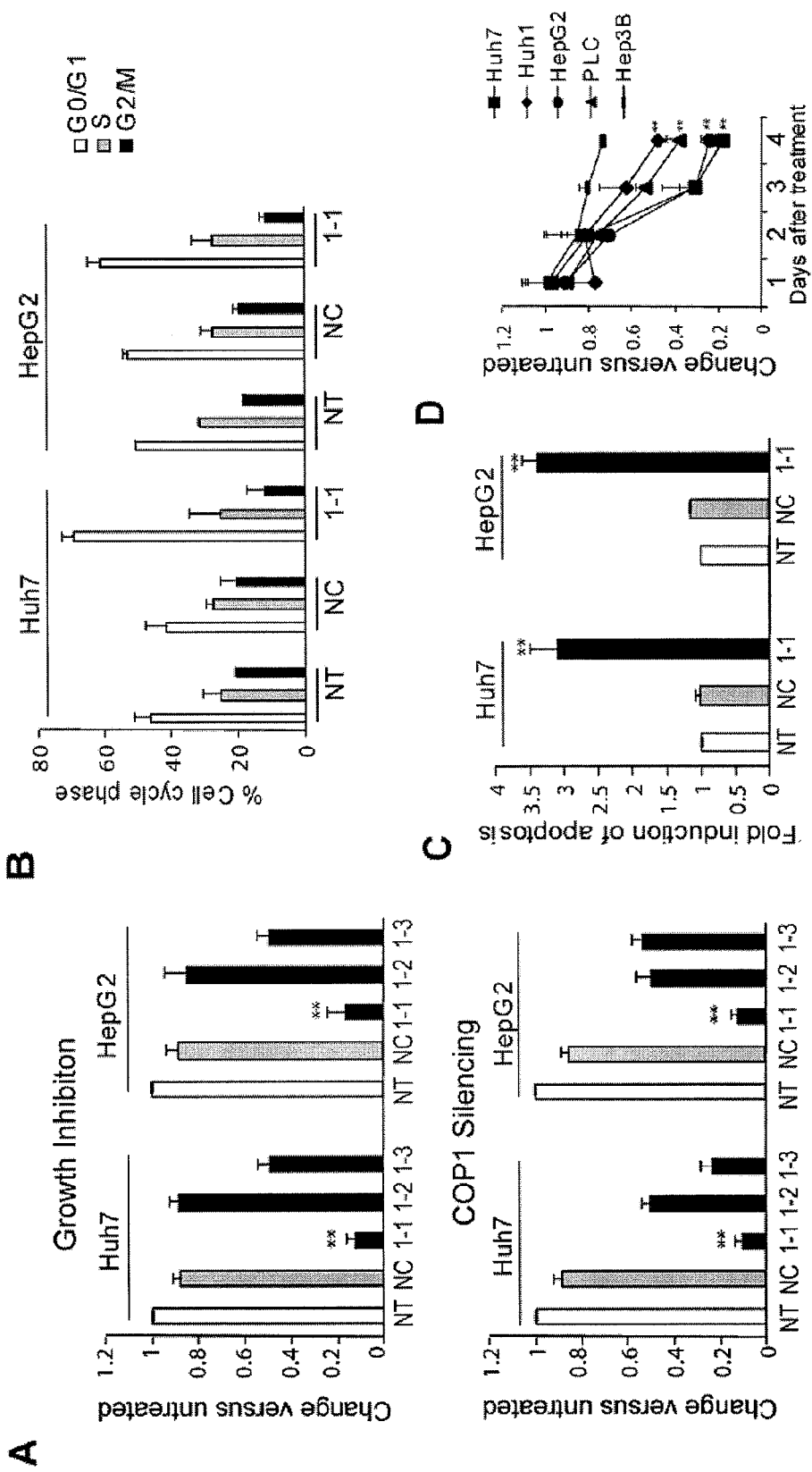

FIG. 53 illustrates that siRNA knockdown of COP1 inhibits growth of HCC cells in vitro. A, Huh7 and HepG2 cells were transfected with COP1-specific siRNAs and examined at 4 days by MTT assay (top) and at 2 days by real-time RT-PCR (bottom). B, Cell cycle analysis 2 days after transfection. C, Detection of apoptosis 3 days after transfection. D, Effect of COP1-1siRNA knockdown on survival of HCC cells. The data are calculated relative to the negative control siRNA (NC) and presented as the mean±SD of triplicate experiments. Statistical analysis was performed using Bootstrap t-test. NT, No treatment, COP1-1, COP1-2 and COP1-3 specific siRNA are shown as 1-1, 1-2, and 1-3. **, P<0.01.

Figure 54:
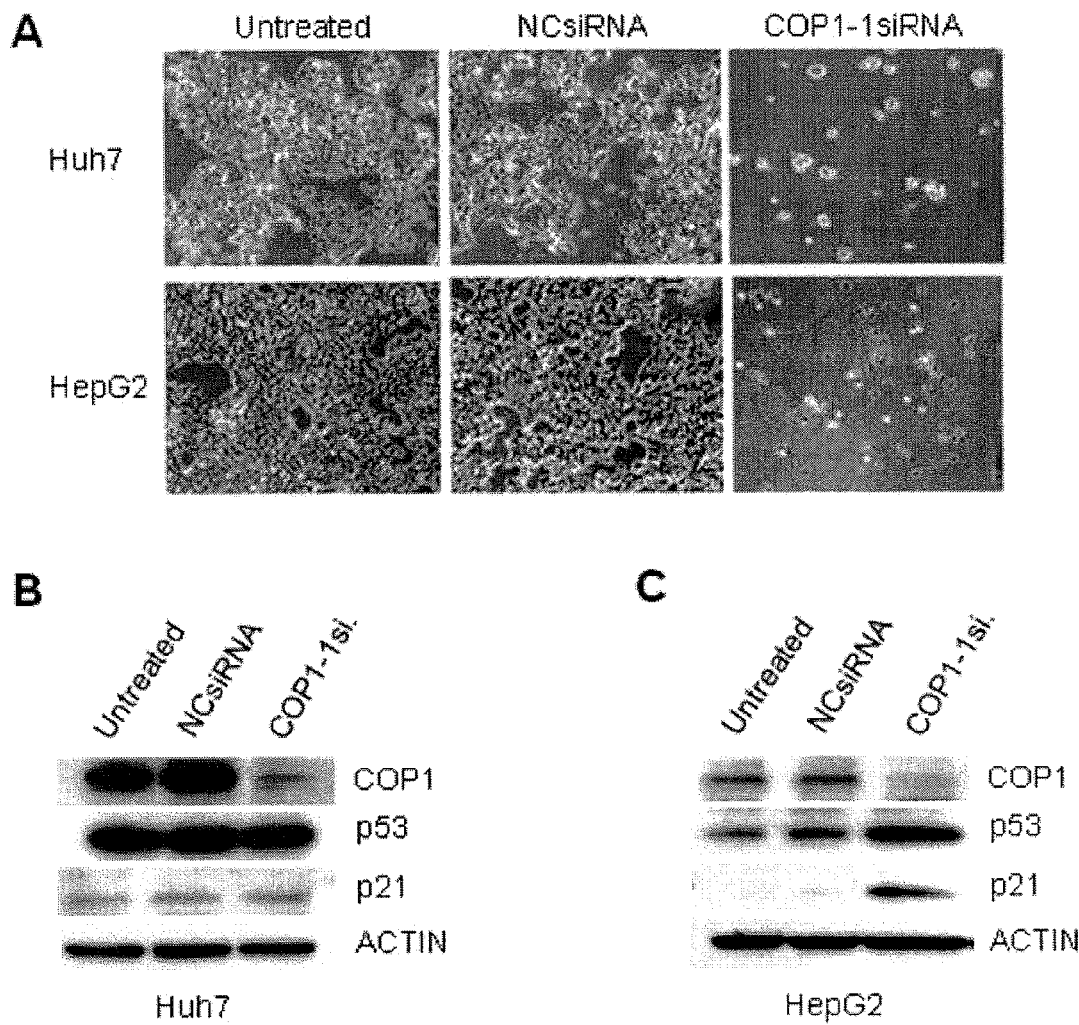

FIG. 54 illustrates the effect of COP1-1siRNA on morphology and protein expression in HCC cells. A, Microscopic observation of Huh7 or HepG2 cells treated with 15 nM of COP1-1siRNA for 4 days (Original magnification, ×100). B and C, Western blot analysis of COP1, p53 and p21 protein expression in Huh7 (B) or HepG2 (C) cells that were treated with 15 nM of NCsiRNA or COP1-1siRNA for 48 h. The ACTIN protein was included as a loading control.

Figure 55:
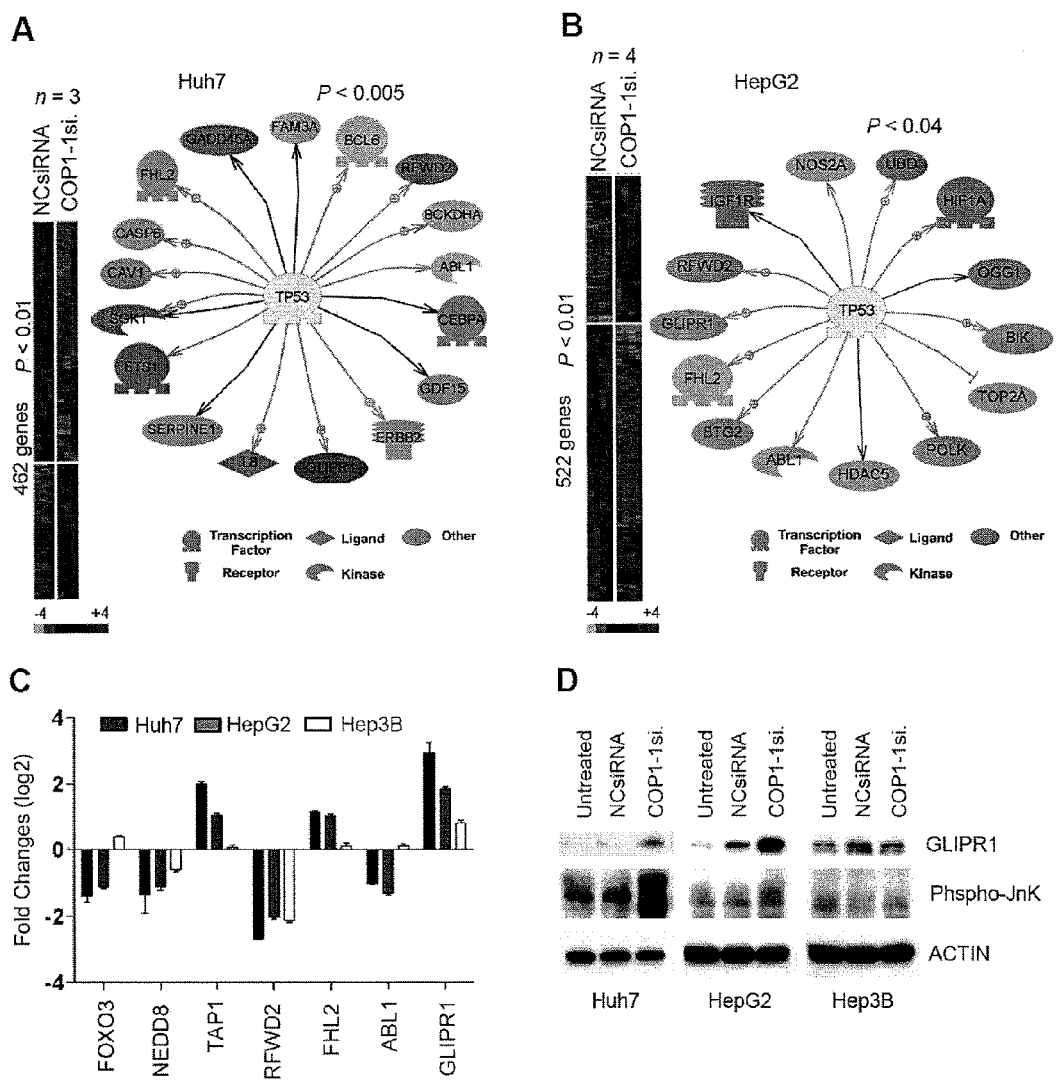

FIG. 55 illustrates the changes in gene expression following COP1 knockdown. A,B, Heat-map overview of genes up- and downregulated at 48 h after COP1 inactivation in Huh7 (A) and HepG2 (B) cells. The means of the intensity log ratios from COP1-1siRNA treated cells were calculated relative to the negative control siRNA-treated cells. P<0.01 by Bootstrap t-test. Expression targets of p53 are shown to the right. C, Fold-changes of genes commonly dysregulated and functionally associated with p53. D, Western blot analysis of GLIPR1 and phosphorylated JNK in Huh7, HepG2, and Hep3B cells that were untreated or treated with the indicated siRNA for 48 h. Actin was included as a loading control.

FIG. 56 provides a list of 78 genes commonly dysregulated in both Huh7 and HepG2 cells with COP1 depletion.

Figure 57:
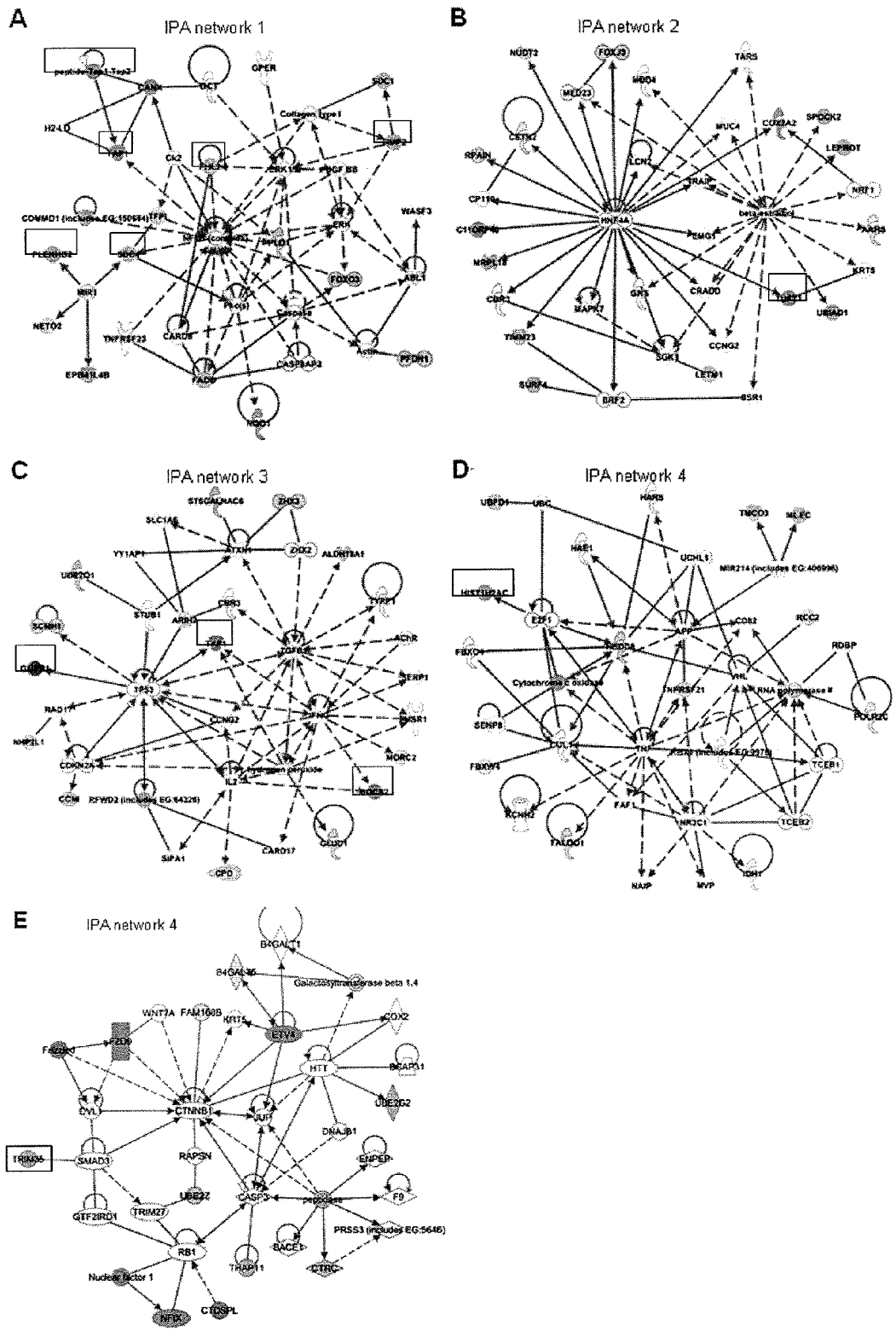

FIG. 57 illustrates the functional connectivity of 78 commonly dysregulated genes in Huh7 (mtp53: Y220C) and HepG2 (wtp53) cells treated with COP1-1siRNA for 48 hours. A-E, Five putative networks with high score (>19), which are strongly associated with NFκB, HNF4α, p53, TNF, etc. Upregulated genes are boxed, while downregulated genes are shown in gray. Other genes depicted are associated with the regulated genes.

FIG. 58 provides a list of the top 5 gene networks from Ingenuity Pathway Analysis.

Figure 59:
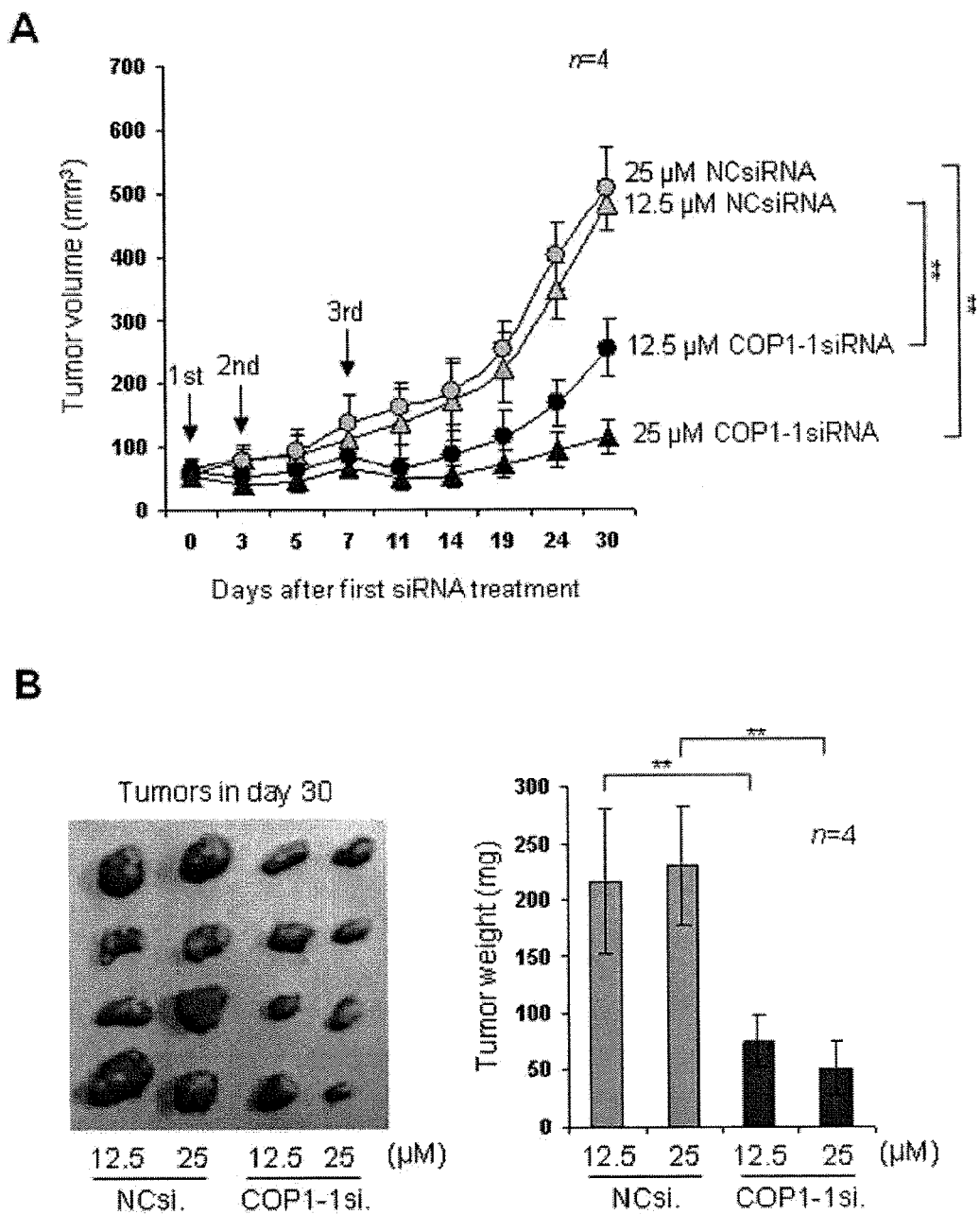

FIG. 59 illustrates the antitumor effect of native COP1-1siRNA on the subcutaneous growth of Huh7 xenografts. A, Kinetics of tumor growth. Native NCsiRNA and COP1-1siRNA were mixed with LF2000 and injected directly into tumors three times with a 3-day interval. Day 0 corresponds to 15 days after inoculations of 5×10$^5$ Huh7 cells, when tumors had reached an average volume of ~50-60 mm$^3$. Tumor diameters were measured at 3-day intervals with digital calipers, and the tumor volume in mm$^3$ was calculated by the formula: volume=(width)$^2$×length/2. Results are shown as the mean tumor volume±s.d. , P<0.01 (n=4) by Student's t-test with equal variance. B, Gross tumor morphology at 30 days after initiation of treatment (left panel) and tumor weigh (right panel). Results are shown as the mean±s.d. , P<0.01 (n=4) by Student's t-test. NCsi, negative control siRNA.

Figure 60:
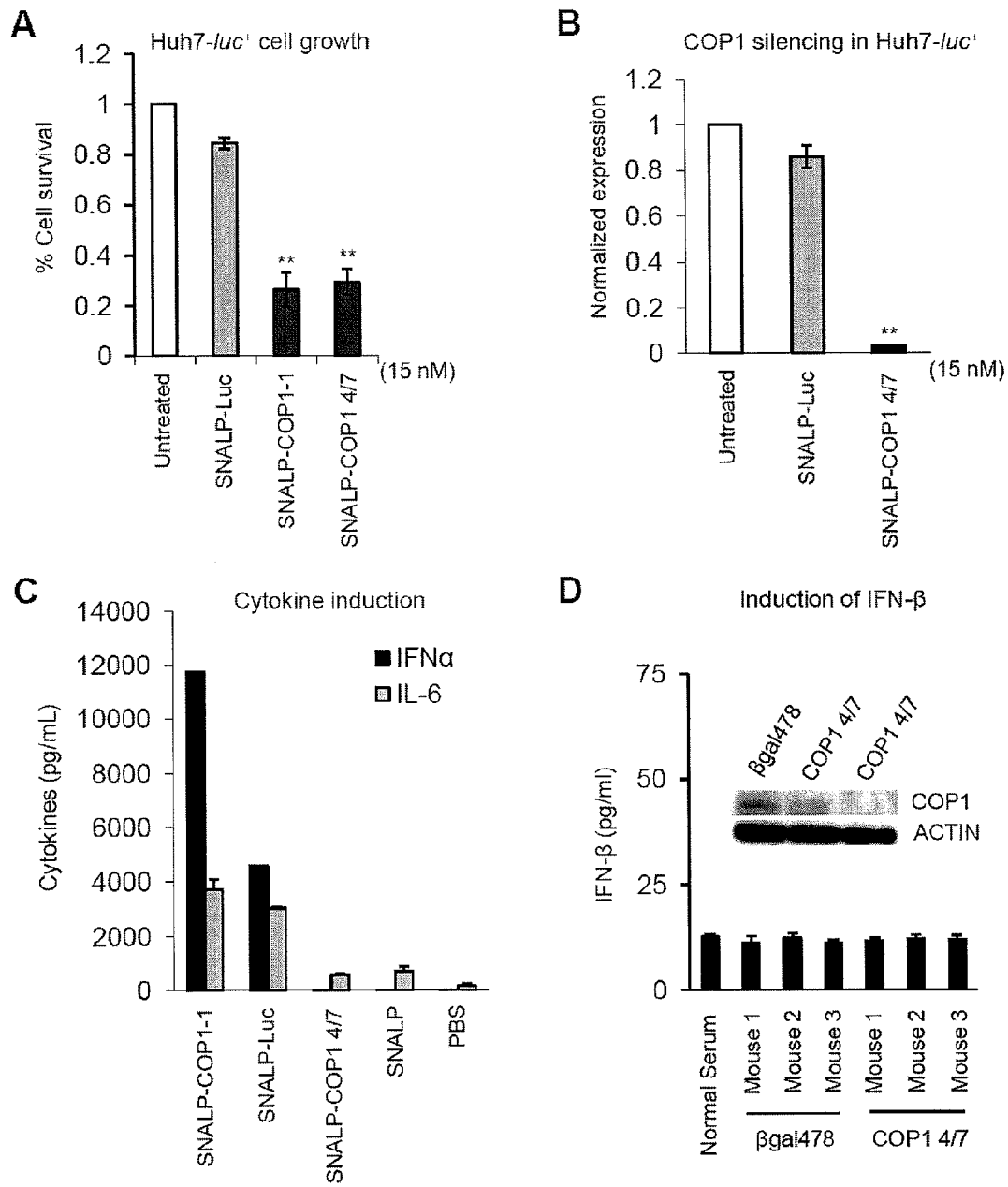

FIG. 60 illustrates the selection of COP1 4/7siRNA for in vivo application based on the inhibition of tumor cell growth and minimal cytokine induction. A, Inhibition of Huh7-luc+ cell growth after transfection of SNALP-formulated COP1-1 (native) or COP1 4/7 siRNA (a modified variant). The siRNA transfectants were examined by MTT assay at 4 days after treatment. B, Real-Time RT-PCR analysis of COP1 gene expression in Huh7-luc+ cells treated with the indicated siRNA. **, P<0.01 (n=3) by Bootstrap t-test. C, Quantification of cytokines after luciferase (LUC) or COP1 targeting. Culture supernatants of Flt3L-derived dendrocytes were assayed for IFN-α and IL-6 using ELISA at 24 h after siRNA treatment. Data are shown are the means±SD of triplicate experiments. D, Serum levels of IFN-β and downregulation of COP1 protein levels in Huh7-derived tumors (inset) 48 h after a single i.v. administration of encapsulated siRNA (2 mg/kg) targeting β-galactosidase (βgal) or COP1 into immunodeficient mice. Each bar represents the mean picogram of IFN-β±SD of duplicate experiments. NS, normal serum, S, SNALP.

Figure 61:
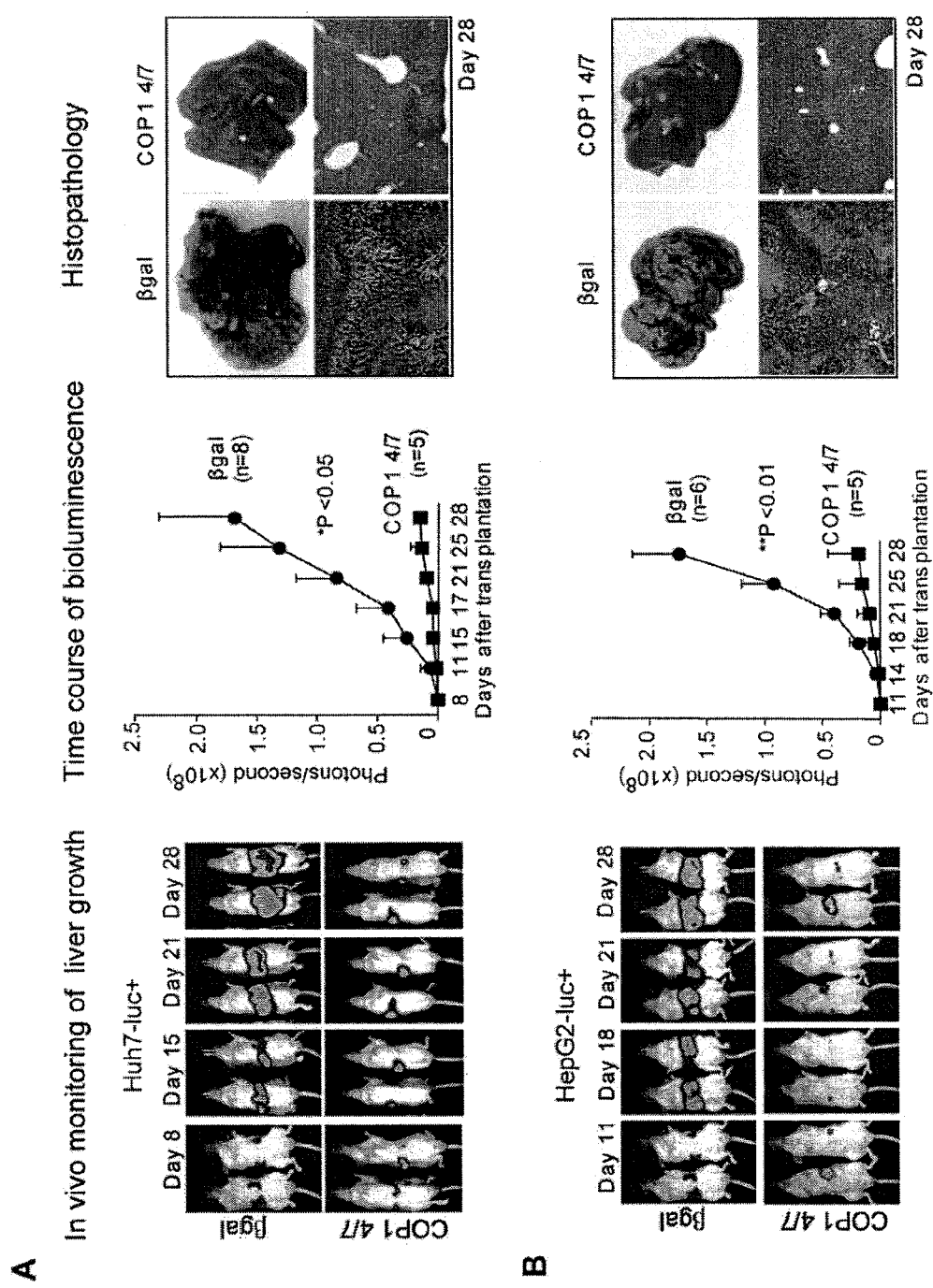

FIG. 61 illustrates that systemic delivery of COP1 4/7siRNA by SNALP suppresses human HCC growth in orthotopic xenograft model. SCID/beige mice received Huh7-luc+(A) and HepG2-luc+(B) cells through intrasplenic injection resulting in tumorous growth in the liver. Mice were randomly assigned either to control (SNALP-βgal478) or treatment (SNALP-COP1 4/7) group based on the intensity of bioluminescence before initiation of COP1 4/7siRNA therapy at day 8 for Huh7 and day 11 day for HepG2. Two mg/kg of SNALP-βgal478 and SNALP-COP1 4/7 were injected into tail vein at the time indicated. Representative in vivo bioluminescence imaging of Huh7- and HepG2-xenografts are shown on the left. Images were set at the same pseudocolor scale to show the relative bioluminescence changes over time. Quantification of bioluminescence (middle panels). The total flux is plotted as photon/second. *, $P<0.05$ (n=8 vs. n=5) by Student's t-test; **, $P<0.01$, (n=8 vs. n=6) by Mann-Whitney U-test. Histopathological evaluation (right panels). Representative photos of gross liver morphology at 28 days after transplantation are shown. H&E staining, original magnification X50.

DETAILED DESCRIPTION OF THE INVENTION

I. Introduction

Cancer is responsible for about 25% of all deaths in the U.S., and is a major public health problem in many parts of the world. According to the American Cancer Society, 7.6 million people died from cancer in the world during 2007. Once diagnosed, cancer is usually treated with a combination of surgery, chemotherapy, and radiotherapy. However, there is an unmet need in the art for novel therapeutic agents that target cancer cells such as cells of a solid tumor with high potency and specificity, without producing toxic side-effects associated with conventional therapies.

Figure 1:
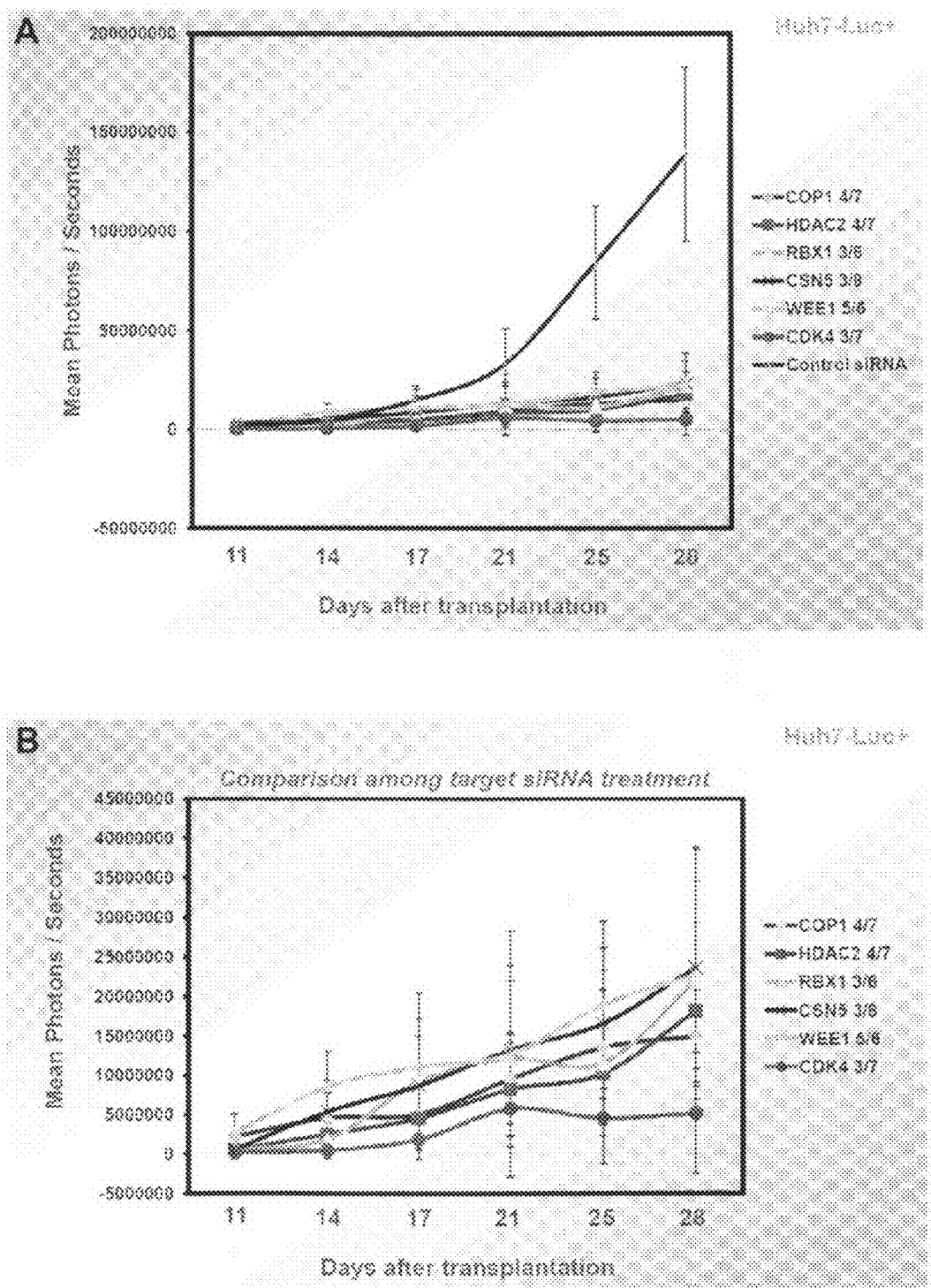
FIG. 1 illustrates that systemic delivery of SNALP-formulated COP1-4/7, WEE1-5/6, HDAC2-4/7, RBX1-3/6, CSN5-3/8, or CDK4-3/7 siRNA effectively prevented orthotopic tumor growth in the liver in a mouse model of metastatic human liver cancer.

The present invention is based in part on the discovery that silencing COP1, WEE1, HDAC2, RBX1, CDK4, CSN5, FOXM1, and/or R1 (RAM2) gene expression is an effective means to halt proliferation of rapidly dividing cells, e.g., cancer cells. As illustrated in the Examples provided herein, the potency of delivering interfering RNA such as siRNA that target one or more of these genes without overt toxicity is a clinically viable therapeutic modality for the treatment of cancers such as liver cancer (e.g., HCC) and other solid tumors. In particular, FIG. 1 shows that in vivo delivery of chemically modified COP1, WEE1, HDAC2, RBX1, CDK4, CSN5, FOXM1, or R1 (RAM2) siRNA in nucleic acid-lipid particle formulations (e.g., SNALP) effectively prevented orthotopic tumor growth in the liver in a mouse model of metastatic human liver cancer. Example 9 illustrates the increased potency obtained with numerous combinations of siRNAs targeting two of these genes as compared to the individual siRNA sequences.

Accordingly, the interfering RNA (e.g., siRNA) molecules of the present invention, when delivered using a safe and effective systemic delivery vehicle such as a nucleic acid-lipid particle, are able to affect therapeutic gene silencing through the confirmed mechanism of RNAi in the absence of unintended immune stimulation.

II. Definitions

As used herein, the following terms have the meanings ascribed to them unless specified otherwise.

The term "interfering RNA" or "RNAi" or "interfering RNA sequence" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), a DNA-RNA hybrid (see, e.g., PCT Publication No. WO 2004/078941), or a DNA-DNA hybrid (see, e.g., PCT Publication No. WO 2004/104199) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized. The disclosures of each of the above patent documents are herein incorporated by reference in their entirety for all purposes.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. As used herein, the term "siRNA" includes RNA-RNA duplexes as well as DNA-RNA hybrids (see, e.g., PCT Publication No. WO 2004/078941).

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA*, 99:9942-9947 (2002); Calegari et al., *Proc. Natl. Acad. Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "inhibiting expression of a target gene" refers to the ability of an interfering RNA (e.g., siRNA) of the invention to silence, reduce, or inhibit the expression of a target gene (e.g., COP1, WEE1, HDAC2, RBX1, CDK4, CSN5, FOXM1, R1 (RAM2), or combinations thereof). To examine the extent of gene silencing, a test sample (e.g., a sample of cells in culture expressing the target gene) or a test mammal (e.g., a mammal such as a human or an animal model such as a rodent (e.g., mouse) or a non-human primate (e.g., monkey) model) is contacted with an interfering RNA (e.g., siRNA) that silences, reduces, or inhibits expression of the target gene. Expression of the target gene in the test sample or test animal is compared to expression of the target gene in a control sample (e.g., a sample of cells in culture expressing the target gene) or a control mammal (e.g., a mammal such as a human or an animal model such as a rodent (e.g., mouse) or non-human primate (e.g., monkey) model) that is not contacted with or administered the interfering RNA (e.g., siRNA). The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the interfering RNAs (e.g., siRNAs) of the present invention are capable of silencing, reducing, or inhibiting the expression of a target gene (e.g., COP1, WEE1, HDAC2, RBX1, CDK4, CSN5, FOXM1, R1 (RAM2), or combinations thereof) by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the interfering RNA. Suitable assays for determining the level of target gene expression include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

An "effective amount" or "therapeutically effective amount" of a therapeutic nucleic acid such as an interfering RNA is an amount sufficient to produce the desired effect, e.g., an inhibition of expression of a target sequence in comparison to the normal expression level detected in the absence of an interfering RNA. Inhibition of expression of a target gene or target sequence is achieved when the value obtained with an interfering RNA relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFN$\gamma$, IFN$\alpha$, TNF$\alpha$, IL-6, IL-8, or IL-12) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-$\alpha$, IFN-$\alpha$, IFN-$\gamma$, IL-1, IL-2, IL-3, IL-4, IL-5, IL-6, IL-8, IL-10, IL-12, IL-13, TGF, and combinations thereof. Detectable immune responses also include, e.g., induction of interferon-induced protein with tetratricopeptide repeats 1 (IFIT1) mRNA.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

Non-limiting examples of algorithms that are suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/). Another example is a global alignment algorithm for determining percent sequence identity such as the Needleman-Wunsch algorithm for aligning protein or nucleotide (e.g., RNA) sequences.

The BLAST algorithm also performs a statistical analysis of the similarity between two sequences (see, e.g., Karlin and Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985);

Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver a therapeutic nucleic acid (e.g., interfering RNA) to a target site of interest (e.g., cell, tissue, organ, tumor, and the like). In preferred embodiments, the lipid particle of the invention is a nucleic acid-lipid particle, which is typically formed from a cationic lipid, a non-cationic lipid, and optionally a conjugated lipid that prevents aggregation of the particle. In other preferred embodiments, the therapeutic nucleic acid (e.g., interfering RNA) may be encapsulated in the lipid portion of the particle, thereby protecting it from enzymatic degradation.

As used herein, the term "SNALP" refers to a stable nucleic acid-lipid particle. A SNALP represents a particle made from lipids (e.g., a cationic lipid, a non-cationic lipid, and optionally a conjugated lipid that prevents aggregation of the particle), wherein the nucleic acid (e.g., an interfering RNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides a therapeutic nucleic acid, such as an interfering RNA (e.g., siRNA), with full encapsulation, partial encapsulation, or both. In a preferred embodiment, the nucleic acid (e.g., interfering RNA) is fully encapsulated in the lipid particle (e.g., to form a SNALP or other nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., U.S. Provisional Application No. 61/294,828, filed Jan. 13, 2010, and U.S. Provisional Application No. 61/295,140, filed Jan. 14, 2010), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an interfering RNA (e.g., siRNA) directly to a target site within an organism. For example, an agent can be locally delivered by direct injection into a disease site such as a tumor, other target site, or a target organ such as the liver, heart, pancreas, kidney, and the like.

The term "mammal" refers to any mammalian species such as a human, mouse, rat, dog, cat, hamster, guinea pig, rabbit, livestock, and the like.

The term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, liver cancer, lung cancer, colon cancer, rectal cancer, anal cancer, bile duct cancer, small intestine cancer, stomach (gastric) cancer, esophageal cancer; gallbladder cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma. As used herein, a "tumor" comprises one or more cancerous cells.

III. Description of the Embodiments

The present invention provides therapeutic nucleic acids such as interfering RNA that target the expression of genes associated with tumorigenesis or cell transformation, lipid particles comprising one or more (e.g., a cocktail) of the therapeutic nucleic acids, methods of making the lipid particles, and methods of delivering and/or administering the lipid particles (e.g., for the treatment of a cell proliferative disorder such as cancer).

In one aspect, the present invention provides interfering RNA molecules that target COP1, WEE1, HDAC2, RBX1, CDK4, CSN5, FOXM1, and/or R1 (RAM2) gene expression. Non-limiting examples of interfering RNA include siRNA, Dicer-substrate dsRNA, shRNA, aiRNA, miRNA, and mixtures thereof. In some embodiments, the present invention provides compositions comprising an siRNA that targets a gene expressed in cancer. In certain other embodiments, the present invention provides compositions comprising a combination (e.g., a cocktail, pool, or mixture) of siRNAs that target multiple genes (e.g., at least two, three, four, five, six, seven, or eight different genes) expressed in cancer. The interfering RNA (e.g., siRNA) molecules of the invention are capable of inhibiting the proliferation of cancer cells and/or inducing cancer cell apoptosis in vitro or in vivo.

In some embodiments, the interfering RNA (e.g., siRNA) comprises a sense strand and a complementary antisense strand. In certain embodiments, the sense strand comprises or consists of a sequence that is at least about 80%, 85%, 86%, 87%, 88%, 89%, 90%, 91%, 92%, 93%, 94%, 95%, 96%, 97%, 98%, 99%, or 100% identical to the target sequence or a portion thereof. In certain other embodiments, the sense strand comprises or consists of at least about 15 contiguous nucleotides (e.g., at least about 15, 16, 17, 18, or 19 contiguous nucleotides) of a sequence that is identical to the target sequence or a portion thereof. In preferred embodiments, the interfering RNA (e.g., siRNA) comprising such a sense strand sequence is capable of mediating target-specific RNAi (e.g., capable of silencing COP1, WEE1, HDAC2, RBX1, CDK4, CSN5, FOXM1, and/or R1 (RAM2) gene expression).

In other embodiments, the antisense strand comprises or consists of a sequence that is at least about 80%, 85%, 86%, 87%, 88%, 89%, 90%, 91%, 92%, 93%, 94%, 95%, 96%, 97%, 98%, 99%, or 100% complementary to the target sequence or a portion thereof. In certain other embodiments, the antisense strand comprises or consists of at least about 15 contiguous nucleotides (e.g., at least about 15, 16, 17, 18, or 19 contiguous nucleotides) of a sequence that is complementary to the target sequence or a portion thereof. In further embodiments, the antisense strand comprises or consists of a sequence that specifically hybridizes to the target sequence or a portion thereof. In preferred embodiments, the interfering RNA (e.g., siRNA) comprising such an antisense strand sequence is capable of mediating target-specific RNAi (e.g., capable of silencing COP1, WEE1, HDAC2, RBX1, CDK4, CSN5, FOXM1, and/or R1 (RAM2) gene expression).

In a first embodiment, the present invention provides a composition comprising an interfering RNA (e.g., siRNA) that silences constitutive photomorphogenic protein ("COP1") gene expression, wherein the interfering RNA comprises a sense strand and a complementary antisense strand, and wherein the antisense strand comprises one of the antisense strand sequences set forth in Tables 1 and 2. In some embodiments, the sense strand comprises one of the sense strand sequences set forth in Tables 1 and 2. In particular embodiments, the COP1 interfering RNA (e.g., siRNA) of the present invention comprises: a sense strand comprising nucleotides 1-19 of any one of the sense strand sequences set forth in Tables 11, 13, and 29-30; and an antisense strand comprising nucleotides 1-19 of any one of the antisense strand sequences set forth in Tables 11, 13, and 29-30. In other particular embodiments, the COP1 interfering RNA (e.g., siRNA) of the present invention comprises: a sense strand selected from any one of the sense strand sequences set forth in Tables 11, 13, and 29-30; and an antisense strand selected from any one of the antisense strand sequences set forth in Tables 11, 13, and 29-30. "COP1" is also known as ring finger and WD repeat domain 2 (RFWD2), RNF200, FLJ10416, and RP11-318C24.3.

TABLE 1 siRNA sequences that target human COP1 gene expression.

| siRNA | Target or Sense Strand Sequence (5' → 3') | Antisense Strand Sequence (5' → 3') |
|---|---|---|
| COP1-1 | GGACACCGUAAAGCAGUCU (SEQ ID NO: 1) | AGACUGCUUUACGGUGUCC (SEQ ID NO: 2) |
| COP1-2 | GGAAUGCUUGUCCAAGUUU (SEQ ID NO: 3) | AAACUUGGACAAGCAUUCC (SEQ ID NO: 4) |
| COP1-3 | GCAACGACUUCGUAUGCCC (SEQ ID NO: 5) | GGGCAUACGAAGUCGUUGC (SEQ ID NO: 6) |

TABLE 2

Additional siRNA sequences that target human COP1 gene expression.

| siRNA | Target or Sense Strand Sequence (5' → 3') | Antisense Strand Sequence (5' → 3') |
|---|---|---|
| COP1-739 | AGAGUUUGGAGGACAAUAA (SEQ ID NO: 7) | UUAUUGUCCUCCAAACUCU (SEQ ID NO: 8) |
| COP1-740 | GAGUUUGGAGGACAAUAAU (SEQ ID NO: 9) | AUUAUUGUCCUCCAAACUC (SEQ ID NO: 10) |
| COP1-795 | GACCAUCUGUAUCCUAAUU (SEQ ID NO: 11) | AAUUAGGAUACAGAUGGUC (SEQ ID NO: 12) |
| COP1-1060 | AGGUUGCAAGAAGAAAUAA (SEQ ID NO: 13) | UUAUUUCUUCUUGCAACCU (SEQ ID NO: 14) |
| COP1-1181 | UAGCACAGUGCCUCAAUUU (SEQ ID NO: 15) | AAAUUGAGGCACUGUGCUA (SEQ ID NO: 16) |

TABLE 2-continued

Additional siRNA sequences that target human COP1 gene expression.

| siRNA | Target or Sense Strand Sequence (5' → 3') | Antisense Strand Sequence (5' → 3') |
|---|---|---|
| COP1-1213 | CAUCACACAGUAGUAUUAU (SEQ ID NO: 17) | AUAAUACUACUGUGUGAUG (SEQ ID NO: 18) |
| COP1-1286 | GAAACAGCCUUGGUAUAAU (SEQ ID NO: 19) | AUUAUACCAAGGCUGUUUC (SEQ ID NO: 20) |
| COP1-1412 | AAGCCAGUUGGAUGAAUUU (SEQ ID NO: 21) | AAAUUCAUCCAACUGGCUU (SEQ ID NO: 22) |
| COP1-1801 | GUUGGAGUGUUGACUUUAA (SEQ ID NO: 23) | UUAAAGUCAACACUCCAAC (SEQ ID NO: 24) |
| COP1-1802 | UUGGAGUGUUGACUUUAAU (SEQ ID NO: 25) | AUUAAAGUCAACACUCCAA (SEQ ID NO: 26) |
| COP1-1803 | UGGAGUGUUGACUUUAAUU (SEQ ID NO: 27) | AAUUAAAGUCAACACUCCA (SEQ ID NO: 28) |
| COP1-1804 | GGAGUGUUGACUUUAAUUU (SEQ ID NO: 29) | AAAUUAAAGUCAACACUCC (SEQ ID NO: 30) |
| COP1-1923 | AAUGUGUGCUGUGUUAAAU (SEQ ID NO: 31) | AUUUAACACAGCACACAUU (SEQ ID NO: 32) |
| COP1-1924 | AUGUGUGCUGUGUUAAAUU (SEQ ID NO: 33) | AAUUUAACACAGCACACAU (SEQ ID NO: 34) |
| COP1-2075 | UGUGAGUGGUGAGGAAAUU (SEQ ID NO: 35) | AAUUCCUCACCACUCACA (SEQ ID NO: 36) |
| COP1-2198 | GGCUUCCAAUGGAGAUUAU (SEQ ID NO: 37) | AUAAUCUCCAUUGGAAGCC (SEQ ID NO: 38) |
| COP1-2412 | AACAGUCAGGGUACAAUUA (SEQ ID NO: 39) | UAAUUGUACCCUGACUGUU (SEQ ID NO: 40) |
| COP1-2413 | ACAGUCAGGGUACAAUUAA (SEQ ID NO: 41) | UUAAUUGUACCCUGACUGU (SEQ ID NO: 42) |
| COP1-2452 | GGGUUAACUCAAGUCAAAU (SEQ ID NO: 43) | AUUUGACUUGAGUUAACCC (SEQ ID NO: 44) |
| COP1-2453 | GGUUAACUCAAGUCAAAUU (SEQ ID NO: 45) | AAUUUGACUUGAGUUAACC (SEQ ID NO: 46) |
| COP1-2474 | ACUUGAUCCUGCUGAAAUA (SEQ ID NO: 47) | UAUUUCAGCAGGAUCAAGU (SEQ ID NO: 48) |
| COP1-2705 | UGUGAUAGGGAAACAAAUU (SEQ ID NO: 49) | AAUUUGUUUCCCUAUCACA (SEQ ID NO: 50) |

In some embodiments, the COP1 interfering RNA (e.g., siRNA) comprises a sense strand, a complementary antisense strand, and a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In other embodiments, the COP1 interfering RNA is chemically synthesized.

In certain embodiments, the COP1 interfering RNA (e.g., siRNA) may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the COP1 interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the COP1 interfering RNA (e.g., siRNA) comprise modified nucleotides such as, e.g., 2'OMe nucleotides (e.g., 2'OMe-guanosine and/or 2'OMe-uridine nucleotides).

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the COP1 interfering RNA molecule strikes a balance between reduction or abrogation of the immunostimulatory properties of the interfering RNA and retention of RNAi activity.

In particular embodiments, the COP1 interfering RNA (e.g., siRNA) may comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA (e.g., siRNA) may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target COP1 sequence (3' overhang in antisense strand) or the complementary strand thereof (3' overhang in sense strand).

In one preferred embodiment, the COP1 interfering RNA (e.g., siRNA) comprises an antisense strand comprising the following sequence: 5'-AGACUGCUUUACGGUGUCC-3' (SEQ ID NO: 2). In certain instances, the antisense strand further comprises a 5'-tt-3' (i.e., 5'-dTdT-3') or 5'-UU-3' overhang. In other embodiments, the COP1 interfering RNA (e.g., siRNA) comprises a sense strand comprising the following sequence: 5'-GGACACCGUAAAGCAGUCU-3' (SEQ ID NO: 1). In certain instances, the sense strand further comprises a 5'-tt-3' (5'-dTdT-3') or 5'-UU-3' overhang. In some aspects of these embodiments, the COP1 interfering RNA (e.g., siRNA) comprises at least one 2'OMe nucleotide, e.g., at least one 2'OMe-guanosine and/or 2'OMe-uridine nucleotide. In certain instances, the COP1 interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the COP1 interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In one particular embodiment, the COP1 interfering RNA comprises an siRNA that consists of the following sense and antisense sequences:

```
5'-GGACACCGUAAAGCAGUCUtt-3'    (SEQ ID NO: 51)

3'-ttCCUGUGGCAUUUCGUCAGA-5'    (SEQ ID NO: 52)
COP1-1 siRNA.
```

In certain embodiments, the COP1-1 siRNA comprises at least one, two, three, four, five, six, seven, eight, nine, ten, or more modified nucleotides such as 2'OMe nucleotides (e.g., in the sense and/or antisense strand of the double-stranded region) in accordance with the selective modification patterns described herein.

In some embodiments, the COP1 interfering RNA (e.g., siRNA) comprises an antisense strand comprising the following sequence: 5'-AGACUGCUUUACGGUGUCC-3' (SEQ ID NO: 53), wherein the bolded and underlined nucleotides are 2'OMe nucleotides. In alternative embodiments, the COP1 interfering RNA (e.g., siRNA) may comprise an antisense strand having any combination of 2'OMe-uridine and/or 2'OMe-guanosine nucleotides. In certain instances, the antisense strand may further comprise 2'OMe-adenosine and/or 2'OMe-cytosine nucleotides. As non-limiting examples, the antisense strand may alternatively comprise one of the following 2'OMe-modified sequences: 5'-AGACUGCUUUACGGUGUCC-3' (SEQ ID NO: 54) or 5'-AGACUGCUUUACGGUGUCC-3' (SEQ ID NO: 55), wherein the bolded and underlined nucleotides are 2'OMe nucleotides. In certain instances, the antisense strand further comprises a 5'-tt-3' or 5'-UU-3' overhang.

In other embodiments, the COP1 interfering RNA (e.g., siRNA) comprises a sense strand comprising the following sequence: 5'-GGACACCGUAAAGCAGUCU-3' (SEQ ID NO: 56), wherein the bolded and underlined nucleotides are 2'OMe nucleotides. In alternative embodiments, the COP1 interfering RNA (e.g., siRNA) may comprise a sense strand having any combination of 2'OMe-uridine and/or 2'OMe-guanosine nucleotides. In certain instances, the sense strand may further comprise 2'OMe-adenosine and/or 2'OMe-cytosine nucleotides. As non-limiting examples, the sense strand may alternatively comprise the following 2'OMe-modified sequence: 5'-GGACACCGUAAAGCAGUCU-3' (SEQ ID NO: 57), wherein the bolded and underlined nucleotides are 2'OMe nucleotides. In certain instances, the sense strand further comprises a 5'-tt-3' or 5'-UU-3' overhang.

In a particularly preferred embodiment, the COP1 interfering RNA comprises an siRNA that consists of the following sense and antisense sequences:

```
5'-GGACACCGUAAAGCAGUCUtt-3'    (SEQ ID NO: 58)

3'-ttCCUGUGGCAUUUCGUCAGA-5'    (SEQ ID NO: 59)
COP1-4/7 siRNA,
``` wherein the bolded and underlined nucleotides are 2'OMe nucleotides.

In another embodiment, the COP1 interfering RNA (e.g., siRNA) comprises an antisense strand comprising the following sequence: 5'-AAAUUGAGGCACUGUGCUA-3' (SEQ ID NO: 16). In certain instances, the antisense strand further comprises a 5'-UC-3' overhang. In other embodiments, the COP1 interfering RNA (e.g., siRNA) comprises a sense strand comprising the following sequence: 5'-UAGCACAGUGCCUCAAUUU-3' (SEQ ID NO: 15). In certain instances, the sense strand further comprises a 5'-GA-3' overhang. In some aspects of these embodiments, the COP1 interfering RNA (e.g., siRNA) comprises at least one 2'OMe nucleotide, e.g., at least one 2'OMe-guanosine and/or 2'OMe-uridine nucleotide. In certain instances, the COP1 interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the COP1 interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In one particular embodiment, the COP1 interfering RNA comprises an siRNA that consists of the following sense and antisense sequences:

```
5'-UAGCACAGUGCCUCAAUUUGA-3'     (SEQ ID NO: 60)

3'-CUAUCGUGUCACGGAGUUAAA-5'     (SEQ ID NO: 61)
COP1-1181 siRNA.
```

In certain embodiments, the COP1-1 siRNA comprises at least one, two, three, four, five, six, seven, eight, nine, ten, or more modified nucleotides such as 2'OMe nucleotides (e.g., in the sense and/or antisense strand of the double-stranded region) in accordance with the selective modification patterns described herein.

As non-limiting examples, the antisense strand may comprise one of the following 2'OMe-modified sequences: 5'-AAAUUGAGGCACUGUGCUA-3' (SEQ ID NO: 62), 5'-AAAUUGAGGCACUGUGCUA-3' (SEQ ID NO: 63), 5'-AAAUUGAGGCACUGUGCUA-3' (SEQ ID NO: 64), or 5'-AAAUUGAGGCACUGUGCUA-3' (SEQ ID NO: 65), wherein the bolded and underlined nucleotides are 2'OMe nucleotides. In certain instances, the antisense strand further comprises a 5'-UC-3' or 5'-mUC-3' overhang, wherein "mU"=2'OMe-uridine.

As non-limiting examples, the sense strand may comprise one of the following 2'OMe-modified sequences: 5'-UAGCACAGUGCCUCAAUUU-3' (SEQ ID NO: 66), 5'-UAGCACAGUGCCUCAAUUU-3' (SEQ ID NO: 67), or 5'-UAGGCACAGUGCCUCAAUUU-3' (SEQ ID NO: 68), wherein the bolded and underlined nucleotides are 2'OMe nucleotides. In certain instances, the sense strand further comprises a 5'-GA-3' or 5'-mGA-3' overhang, wherein "mG"=2'OMe-guanosine.

In certain embodiments, the COP1 interfering RNA (e.g., siRNA) composition further comprises one or more interfering RNAs targeting the WEE1, HDAC2, RBX1, CDK4, CSN5, FOXM1, and/or R1 (RAM2) genes. In some embodiments, the antisense strand of each additional interfering RNA comprises a sequence that is complementary to one of the target sequences set forth in FIGS. 42-47 from U.S. Provisional Application No. 61/377,439. In other embodiments, the sense strand of each additional interfering RNA comprises one of the target sequences set forth in FIGS. 42-47 from U.S. Provisional Application No. 61/377,439. In certain embodiments, the antisense strand of each additional interfering RNA comprises one of the antisense strand sequences set forth in Tables 3-10, and/or the sense strand of each additional interfering RNA comprises one of the sense strand sequences set forth in Tables 3-10. In particular embodiments, the antisense strand of each additional interfering RNA (e.g., siRNA) comprises one of the antisense strand sequences set forth in Tables 12 and 14-28 (or nucleotides 1-19 thereof), and/or the sense strand of each additional interfering RNA comprises one of the sense strand sequences set forth in Tables 12 and 14-28 (or nucleotides 1-19 thereof). The sense and/or antisense strand of each additional interfering RNA may contain modified nucleotides and/or 3' overhangs as described herein.

In one particular embodiment, the COP1 interfering RNA composition further comprises an interfering RNA (e.g., siRNA) that silences WEE1 gene expression. In certain embodiments, the antisense strand of the WEE1 interfering RNA comprises one of the antisense strand sequences set forth in Tables 3 and 4 below, and/or the sense strand of the WEE1 interfering RNA comprises one of the sense strand sequences set forth in Tables 3 and 4. The sense and/or antisense strand of the WEE1 interfering RNA may contain modified nucleotides and/or 3' overhangs as described herein.

In a preferred embodiment, the invention provides a composition comprising the following cocktail of interfering RNAs (e.g., siRNAs):
  (a) a first interfering RNA (e.g., siRNA) that silences COP1 gene expression, wherein the first interfering RNA comprises a sense strand and a complementary antisense strand, and wherein the antisense strand comprises one of the following antisense strand sequences: 5'-AGACUGCUUUACGGUGUCC-3 (SEQ ID NO: 2)_ or 5'-AAAUUGAGGCACUGUGCUA-3' (SEQ ID NO: 16); and
  (b) a second interfering RNA (e.g., siRNA) that silences WEE1 gene expression, wherein the second interfering RNA comprises a sense strand and a complementary antisense strand, and wherein the antisense strand comprises one of the following antisense strand sequences: 5'-UAAAUGCAUCCAUCCAGCC-3' (SEQ ID NO: 69) or 5'-UAUAUAGUAAGGCUGACAG-3' (SEQ ID NO 70).
The sense and/or antisense strands of the COP1 and WEE1 interfering RNAs (e.g., siRNAs) may each independently contain modified nucleotides and/or 3' overhangs as described herein.

In another particular embodiment, the COP1 interfering RNA composition further comprises an interfering RNA (e.g., siRNA) that silences CSN5 gene expression. In some embodiments, the antisense strand of the CSN5 interfering RNA comprises a sequence that is complementary to one of the target sequences set forth in FIG. 45 from U.S. Provisional Application No. 61/377,439. In other embodiments, the sense strand of the CSN5 interfering RNA comprises one of the target sequences set forth in FIG. 45 from U.S. Provisional Application No. 61/377,439. In certain embodiments, the antisense strand of the CSN5 interfering RNA comprises one of the antisense strand sequences set forth in Table 8 below, and/or the sense strand of the CSN5 interfering RNA comprises one of the sense strand sequences set forth in Table 8.

The sense and/or antisense strand of the CSN5 interfering RNA may contain modified nucleotides and/or 3' overhangs as described herein.

In a preferred embodiment, the invention provides a composition comprising the following cocktail of interfering RNAs (e.g., siRNAs):

(a) a first interfering RNA (e.g., siRNA) that silences COP1 gene expression, wherein the first interfering RNA comprises a sense strand and a complementary antisense strand, and wherein the antisense strand comprises one of the following antisense strand sequences: 5'-AGACUGCUUUACGGUGUCC-3' (SEQ ID NO: 2) or 5'-AAAUUGAGGCACUGUGCUA-3' (SEQ ID NO: 16); and (b) a second interfering RNA (e.g., siRNA) that silences CSN5 gene expression, wherein the second interfering RNA comprises a sense strand and a complementary antisense strand, and wherein the antisense strand comprises the following sequence: 5'-CUUAAAGUAAUG-GUGAUCC-3' (SEQ ID NO: 71).

The sense and/or antisense strands of the COP1 and CSN5 interfering RNAs (e.g., siRNAs) may each independently contain modified nucleotides and/or 3' overhangs as described herein.

In a second embodiment, the present invention provides a composition comprising an interfering RNA (e.g., siRNA) that silences WEE1 homolog (S. pombe) ("WEE1") gene expression, wherein the interfering RNA comprises a sense strand and a complementary antisense strand, and wherein the antisense strand comprises one of the antisense strand sequences set forth in Tables 3 and 4. In some embodiments, the sense strand comprises one of the sense strand sequences set forth in Tables 3 and 4. In particular embodiments, the WEE1 interfering RNA (e.g., siRNA) of the present invention comprises: a sense strand comprising nucleotides 1-19 of any one of the sense strand sequences set forth in Tables 12, 14, and 27-28; and an antisense strand comprising nucleotides 1-19 of any one of the antisense strand sequences set forth in Tables 12, 14, and 27-28. In other particular embodiments, the WEE1 interfering RNA (e.g., siRNA) of the present invention comprises: a sense strand selected from any one of the sense strand sequences set forth in Tables 12, 14, and 27-28; and an antisense strand selected from any one of the antisense strand sequences set forth in Tables 12, 14, and 27-28. "WEE1" is also known as WEE1A, WEE1hu, FLJ16446, and DKFZp686118166.

TABLE 3 siRNA sequences that target human WEE1 gene expression.

| siRNA | Target or Sense Strand Sequence (5' → 3') | Antisense Strand Sequence (5' → 3') |
|---|---|---|
| WEE1-1 | GGUAUAUUCAUUCAAUGUC (SEQ ID NO: 72) | GACAUUGAAUGAAUAUACC (SEQ ID NO: 73) |
| WEE1-2 | GGCUGGAUGGAUGCAUUUA (SEQ ID NO: 74) | UAAAUGCAUCCAUCCAGCC (SEQ ID NO: 69) |
| WEE1-3 | GGACAGUGUCGUCGUAGAA (SEQ ID NO: 75) | UUCUACGACGACACUGUCC (SEQ ID NO: 76) |

TABLE 4

Additional siRNA sequences that target human WEE1 gene expression.

| siRNA | Target or Sense Strand Sequence (5' → 3') | Antisense Strand Sequence (5' → 3') |
|---|---|---|
| WEE1-60 | GCUGGCGAACAAAUGUAAA (SEQ ID NO: 77) | UUUACAUUUGUUCGCCAGC (SEQ ID NO: 78) |
| WEE1-1828 | CUCCUCAAGUGAAUAUUAA (SEQ ID NO: 79) | UUAAUAUUCACUUGAGGAG (SEQ ID NO: 80) |
| WEE1-1937 | CAUGGAAGCCAGUGAUUAU (SEQ ID NO: 81) | AUAAUCACUGGCUUCCAUG (SEQ ID NO: 82) |
| WEE1-2017 | CCCGGUAUACAACAGAAUU (SEQ ID NO: 83) | AAUUCUGUUGUAUACCGGG (SEQ ID NO: 84) |
| WEE1-2018 | CCGGUAUACAACAGAAUUU (SEQ ID NO: 85) | AAAUUCUGUUGUAUACCGG (SEQ ID NO: 86) |
| WEE1-2094 | AGGCUGGAUGGAUGCAUUU (SEQ ID NO: 87) | AAAUGCAUCCAUCCAGCCU (SEQ ID NO: 88) |
| WEE1-2104 | GAUGCAUUUAUGCCAUUAA (SEQ ID NO: 89) | UUAAUGGCAUAAAUGCAUC (SEQ ID NO: 90) |
| WEE1-2105 | AUGCAUUUAUGCCAUUAAG (SEQ ID NO: 91) | CUUAAUGGCAUAAAUGCAU (SEQ ID NO: 92) |
| WEE1-2208 | UCUCAUGUAGUUCGAUAUU (SEQ ID NO: 93) | AAUAUCGAACUACAUGAGA (SEQ ID NO: 94) |
| WEE1-2372 | CCGAGGCUUGAGGUAUAUU (SEQ ID NO: 95) | AAUAUACCUCAAGCCUCGG (SEQ ID NO: 96) |
| WEE1-2402 | UUUGGUUCACAUGGAUAUA (SEQ ID NO: 97) | UAUAUCCAUGUGAACCAAA (SEQ ID NO: 98) |
| WEE1-2748 | GUGCUUUCCCAAGAAUUUA (SEQ ID NO: 99) | UAAAUUCUUGGGAAAGCAC (SEQ ID NO: 100) |
| WEE1-3003 | UCCACCACCCAGAGUAAUA (SEQ ID NO: 101) | UAUUACUCUGGGUGGUGGA (SEQ ID NO: 102) |
| WEE1-3057 | UCUGUCAGCCUUACUAUAU (SEQ ID NO: 103) | AUAUAGUAAGGCUGACAGA (SEQ ID NO: 104) |
| WEE1-3058 | CUGUCAGCCUUACUAUAUA (SEQ ID NO: 105) | UAUAUAGUAAGGCUGACAG (SEQ ID NO: 70) |
| WEE1-3119 | GAGGAAGCUAGGUUGAAAU (SEQ ID NO: 106) | AUUUCAACCUAGCUUCCUC (SEQ ID NO: 107) |
| WEE1-3337 | UGGUGGUGUGCUGCUUAUA (SEQ ID NO: 108) | UAUAAGCAGCACACCACCA (SEQ ID NO: 109) |
| WEE1-3497 | GUGUGUCCAUCUUAUAUUU (SEQ ID NO: 110) | AAAUAUAAGAUGGACACAC (SEQ ID NO: 111) |
| WEE1-3607 | AGGUAUUGCCUUGUGAAUU (SEQ ID NO: 112) | AAUUCACAAGGCAAUACCU (SEQ ID NO: 113) |
| WEE1-3608 | GGUAUUGCCUUGUGAAUUU (SEQ ID NO: 114) | AAAUUCACAAGGCAAUACC (SEQ ID NO: 115) |

In some embodiments, the WEE1 interfering RNA (e.g., siRNA) comprises a sense strand, a complementary antisense strand, and a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In other embodiments, the WEE1 interfering RNA is chemically synthesized.

In certain embodiments, the WEE1 interfering RNA (e.g., siRNA) may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the WEE1 interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the WEE1 interfering RNA (e.g., siRNA) comprise modified nucleotides such as, e.g., 2'OMe nucleotides (e.g., 2'OMe-guanosine and/or 2'OMe-uridine nucleotides).

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the WEE1 interfering RNA molecule strikes a balance between reduction or abrogation of the immunostimulatory properties of the interfering RNA and retention of RNAi activity.

In particular embodiments, the WEE1 interfering RNA (e.g., siRNA) may comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA (e.g., siRNA) may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target WEE1 sequence (3' overhang in antisense strand) or the complementary strand thereof (3' overhang in sense strand).

In one preferred embodiment, the WEE1 interfering RNA (e.g., siRNA) comprises an antisense strand comprising the following sequence: 5'-UAAAUGCAUCCAUCCAGCC-3' (SEQ ID NO: 69). In certain instances, the antisense strand further comprises a 5'-tc-3' or 5'-UC-3' overhang. In other embodiments, the WEE1 interfering RNA (e.g., siRNA) comprises a sense strand comprising the following sequence: 5'-GGCUGGAUGGAUGCAUUUA-3' (SEQ ID NO: 74). In certain instances, the sense strand further comprises a 5'-tt-3' or 5'-UU-3' overhang. In some aspects of these embodiments, the WEE1 interfering RNA (e.g., siRNA) comprises at least one 2'OMe nucleotide, e.g., at least one 2'OMe-guanosine and/or 2'OMe-uridine nucleotide. In certain instances, the WEE1 interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the WEE1 interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In one particular embodiment, the WEE1 interfering RNA comprises an siRNA that consists of the following sense and antisense sequences:

```
5'-GGCUGGAUGGAUGCAUUUAtt-3'     (SEQ ID NO: 116)

3'-ctCCGACCUACCUACGUAAAU-5'     (SEQ ID NO: 117)
WEE1-2 siRNA.
```

In certain embodiments, the WEE1-2 siRNA comprises at least one, two, three, four, five, six, seven, eight, nine, ten, or more modified nucleotides such as 2'OMe nucleotides (e.g., in the sense and/or antisense strand of the double-stranded region) in accordance with the selective modification patterns described herein.

In some embodiments, the WEE1 interfering RNA (e.g., siRNA) comprises an antisense strand comprising the following sequence: 5'-UAAAUGCAUCCAUCCAGCC-3' (SEQ ID NO: 118), wherein the bolded and underlined nucleotides are 2'OMe nucleotides. In alternative embodiments, the WEE1 interfering RNA (e.g., siRNA) may comprise an antisense strand having any combination of 2'OMe-uridine and/or 2'OMe-guanosine nucleotides. In certain instances, the antisense strand may further comprise 2'OMe-adenosine and/or 2'OMe-cytosine nucleotides. As non-limiting examples, the antisense strand may alternatively comprise one of the following 2'OMe-modified sequences: 5'-UAAA UGCAUCCAUCCAGCC-3' (SEQ ID NO: 119), 5'-UAAAUGCAUCCAUCCAGCC-3' (SEQ ID NO: 120), or 5'-UAAAUGCAUCCAUCCAGCC-3' (SEQ ID NO: 121), wherein the bolded and underlined nucleotides are 2'OMe nucleotides. In certain instances, the antisense strand further comprises a 5'-tc-3' or 5'-UC-3' overhang.

In other embodiments, the WEE1 interfering RNA (e.g., siRNA) comprises a sense strand comprising the following sequence: 5'-GGCUGGAUGGAUGCAUUUA-3' (SEQ ID NO: 122), wherein the bolded and underlined nucleotides are 2'OMe nucleotides. In alternative embodiments, the WEE1 interfering RNA (e.g., siRNA) may comprise a sense strand having any combination of 2'OMe-uridine and/or 2'OMe-guanosine nucleotides. In certain instances, the sense strand may further comprise 2'OMe-adenosine and/or 2'OMe-cytosine nucleotides. As non-limiting examples, the sense strand may alternatively comprise one of the following 2'OMe-modified sequences: 5'-GGCUGGAUGGAUGCA UUUA-3' (SEQ ID NO: 123) or 5'-GGC UGGAUGGAUGCAUUUA-3' (SEQ ID NO: 124), wherein the bolded and underlined nucleotides are 2'OMe nucleotides. In certain instances, the sense strand further comprises a 5'-tt-3' or 5'-UU-3' overhang.

In a particularly preferred embodiment, the WEE1 interfering RNA comprises an siRNA that consists of the following sense and antisense sequences:

```
5'-GGCUGGAUGGAUGCAUUUAUU-3'      (SEQ ID NO: 125)

3'-CUCCGACCUACCUACGUAAAU-5'      (SEQ ID NO: 126)
WEE1-5/6 siRNA,
``` wherein the bolded and underlined nucleotides are 2'OMe nucleotides.

In another embodiment, the WEE1 interfering RNA (e.g., siRNA) comprises an antisense strand comprising the following sequence: 5'-UAUAUAGUAAGGCUGACAG-3' (SEQ ID NO: 70_). In certain instances, the antisense strand further comprises a 5'-AG-3' overhang. In other embodiments, the WEE1 interfering RNA (e.g., siRNA) comprises a sense strand comprising the following sequence: 5'-CUGUCAGCCUUACUAUAUA-3' (SEQ ID NO: 105). In certain instances, the sense strand further comprises a 5'-CU-3' overhang. In some aspects of these embodiments, the WEE1 interfering RNA (e.g., siRNA) comprises at least one 2'OMe nucleotide, e.g., at least one 2'OMe-guanosine and/or 2'OMe-uridine nucleotide. In certain instances, the WEE1 interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the WEE1 interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In one particular embodiment, the WEE1 interfering RNA comprises an siRNA that consists of the following sense and antisense sequences:

```
5'-CUGUCAGCCUUACUAUAUACU-3'      (SEQ ID NO: 127)

3'-GAGACAGUCGGAAUGAUAUAU-5'      (SEQ ID NO: 128)
WEE1-3058 siRNA.
```

In some embodiments, the WEE1 interfering RNA (e.g., siRNA) comprises an antisense strand comprising the following sequence: 5'-UAUAUAGUAAGGCUGACAG-3' (SEQ ID NO: 129), wherein the bolded and underlined nucleotides are 2'OMe nucleotides. In alternative embodiments, the WEE1 interfering RNA (e.g., siRNA) may comprise an antisense strand having any combination of 2'OMe-uridine and/or 2'OMe-guanosine nucleotides. In certain instances, the antisense strand may further comprise 2'OMe-adenosine and/or 2'OMe-cytosine nucleotides. As non-limiting examples, the antisense strand may alternatively comprise one of the following 2'OMe-modified sequences: 5'-UAUAUAGUAAGGCUGACAG-3 (SEQ ID NO: 130), 5'-UAUAUAGUAAGGCUGACAG-3' (SEQ ID NO: 131), or 5'-UAUAUAGUAAGGCUGACAG-3' (SEQ ID NO: 132), wherein the bolded and underlined nucleotides are 2'OMe nucleotides. In certain instances, the antisense strand further comprises a 5'-AG-3' overhang.

In other embodiments, the WEE1 interfering RNA (e.g., siRNA) comprises a sense strand comprising the following sequence: 5'-CUGUCAGCCUUACUAUAUA-3' (SEQ ID NO: 133), wherein the bolded and underlined nucleotides are 2'OMe nucleotides. In alternative embodiments, the WEE1 interfering RNA (e.g., siRNA) may comprise a sense strand having any combination of 2'OMe-uridine and/or 2'OMe-guanosine nucleotides. In certain instances, the sense strand may further comprise 2'OMe-adenosine and/or 2'OMe-cytosine nucleotides. As non-limiting examples, the sense strand may alternatively comprise one of the following 2'OMe-modified sequences: 5'-CUGUCAGCCUUACUAUAUA-3' (SEQ ID NO: 134) or 5'-CUGUCAGCCUUACUAUAUA-3' (SEQ ID NO: 135), wherein the bolded and underlined nucleotides are 2'OMe nucleotides. In certain instances, the sense strand further comprises a 5'-CU-3' overhang.

In a particularly preferred embodiment, the WEE1 interfering RNA comprises an siRNA that consists of the following sense and antisense sequences:

```
                                 (SEQ ID NO: 136)
5'-CUGUCAGCCUUACUAUAUACU-3'

(SEQ ID NO: 137)
3'-GAGACAGUCGGAAUGAUAUAU-5'
WEE1-3058-1/5 siRNA,
``` wherein the bolded and underlined nucleotides are 2'OMe nucleotides.

In certain embodiments, the WEE1 interfering RNA (e.g., siRNA) composition further comprises one or more interfering RNAs (e.g., siRNAs) targeting the COP1, HDAC2, RBX1, CDK4, CSN5, FOXM1, and/or R1 genes. In some embodiments, the antisense strand of each additional interfering RNA comprises a sequence that is complementary to one of the target sequences set forth in FIGS. 42-47 from U.S. Provisional Application No. 61/377,439. In other embodiments, the sense strand of each additional interfering RNA comprises one of the target sequences set forth in FIGS. 42-47 from U.S. Provisional Application No. 61/377,439. In certain embodiments, the antisense strand of each additional interfering RNA comprises one of the antisense strand sequences set forth in Tables 1-2 and 5-10, and/or the sense strand of each additional interfering RNA comprises one of the sense strand sequences set forth in Tables 1-2 and 5-10. In particular embodiments, the antisense strand of each additional interfering RNA (e.g., siRNA) comprises one of the antisense strand sequences set forth in Tables 11, 13, 16-26, and 29-30 (or nucleotides 1-19 thereof), and/or the sense strand of each additional interfering RNA comprises one of the sense strand sequences set forth in Tables 11, 13, 16-26, and 29-30 (or nucleotides 1-19 thereof). The sense and/or antisense strand of each additional interfering RNA (e.g., siRNA) may contain modified nucleotides and/or 3' overhangs as described herein.

In a third embodiment, the present invention provides a composition comprising an interfering RNA (e.g., siRNA) that silences histone deacetylase 2 ("HDAC2") gene expression, wherein the interfering RNA comprises a sense strand and a complementary antisense strand, and wherein the antisense strand comprises one of the antisense strand sequences set forth in Table 5. In some embodiments, the sense strand comprises one of the sense strand sequences set forth in Table 5. In other embodiments, the antisense strand comprises a sequence that is complementary to one of the target sequences set forth in FIG. 42 from U.S. Provisional Application No. 61/377,439, and/or the sense strand comprises one of the target sequences set forth in FIG. 42 from U.S. Provisional Application No. 61/377,439. In particular embodiments, the HDAC2 interfering RNA (e.g., siRNA) of the present invention comprises: a sense strand comprising nucleotides 1-19 of any one of the sense strand sequences set forth in Tables 15-16; and an antisense strand comprising nucleotides 1-19 of any one of the antisense strand sequences set forth in Tables 15-16. In other particular embodiments, the HDAC2 interfering RNA (e.g., siRNA) of the present invention comprises: a sense strand selected from any one of the sense strand sequences set forth in Tables 15-16; and an antisense strand selected from any one of the antisense strand sequences set forth in Tables 15-16. "HDAC2" is also known as RPD3 and YAF1.

TABLE 5 siRNA sequences that target human HDAC2 gene expression.

| siRNA | Target or Sense Strand Sequence (5' → 3') | Antisense Strand Sequence (5' → 3') |
| --- | --- | --- |
| HDAC2-1 | GCCACUGCCGAAGAAAUGA (SEQ ID NO: 138) | UCAUUUCUUCGGCAGUGGC (SEQ ID NO: 139) |
| HDAC2-2 | GCUGUGAAGUUAAACCGAC (SEQ ID NO: 140) | GUCGGUUUAACUUCACAGC (SEQ ID NO: 141) |
| HDAC2-3 | GCCUAUUAUCUCAAAGGUG (SEQ ID NO: 142) | CACCUUUGAGAUAAUAGGC (SEQ ID NO: 143) |

In some embodiments, the HDAC2 interfering RNA (e.g., siRNA) comprises a sense strand, a complementary antisense strand, and a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In other embodiments, the HDAC2 interfering RNA is chemically synthesized.

In certain embodiments, the HDAC2 interfering RNA (e.g., siRNA) may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the HDAC2 interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the HDAC2 interfering RNA (e.g., siRNA) comprise modified nucleotides such as, e.g., 2'OMe nucleotides (e.g., 2'OMe-guanosine and/or 2'OMe-uridine nucleotides).

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the HDAC2 interfering RNA molecule strikes a balance between reduction or abrogation of the immunostimulatory properties of the interfering RNA and retention of RNAi activity.

In particular embodiments, the HDAC2 interfering RNA (e.g., siRNA) may comprise a 3' overhang of 1, 2, 3, or 4 nucleotides in one or both strands. In certain instances, the HDAC2 interfering RNA may contain at least one blunt end. In particular embodiments, the 3' overhangs in one or both strands of the interfering RNA (e.g., siRNA) may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target HDAC2 sequence (3' overhang in antisense strand) or the complementary strand thereof (3' overhang in sense strand).

In one preferred embodiment, the HDAC2 interfering RNA (e.g., siRNA) comprises an antisense strand comprising the following sequence: 5'-UCAUUUCUUCG-GCAGUGGC-3' (SEQ ID NO: 139). In certain instances, the antisense strand further comprises a 5'-tt-3' or 5'-UU-3' overhang. In other embodiments, the HDAC2 interfering RNA (e.g., siRNA) comprises a sense strand comprising the following sequence: 5'-GCCACUGCCGAAGAAAUGA-3' (SEQ ID NO: 138). In certain instances, the sense strand further comprises a 5'-tt-3' or 5'-UU-3' overhang. In some aspects of these embodiments, the HDAC2 interfering RNA (e.g., siRNA) comprises at least one 2'OMe nucleotide, e.g., at least one 2'OMe-guanosine and/or 2'OMe-uridine nucleotide. In certain instances, the HDAC2 interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the HDAC2 interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In one particular embodiment, the HDAC2 interfering RNA comprises an siRNA that consists of the following sense and antisense sequences:

5'-GCCACUGCCGAAGAAAUGAtt-3' (SEQ ID NO: 144)

3'-ttCGGUGACGGCUUCUUUACU-5' (SEQ ID NO: 145)
HDAC2-1 siRNA.

In certain embodiments, the HDAC2-1 siRNA comprises at least one, two, three, four, five, six, seven, eight, nine, ten, or more modified nucleotides such as 2'OMe nucleotides (e.g., in the sense and/or antisense strand of the double-stranded region) in accordance with the selective modification patterns described herein.

In some embodiments, the HDAC2 interfering RNA (e.g., siRNA) comprises an antisense strand comprising the following sequence: 5'-UCAUUUCUUCGGCAGUGGC-3' (SEQ ID NO: 146), wherein the bolded and underlined nucleotides are 2'OMe nucleotides. In alternative embodiments, the HDAC2 interfering RNA (e.g., siRNA) may comprise an antisense strand having any combination of 2'OMe-uridine and/or 2'OMe-guanosine nucleotides. In certain instances, the antisense strand may further comprise 2'OMe-adenosine and/or 2'OMe-cytosine nucleotides. As non-limiting examples, the antisense strand may alternatively comprise one of the following 2'OMe-modified sequences: 5'-UCAUUUCUUCGGCAGUGGC-3' (SEQ ID NO: 147) or 5'-UCAUUUCUUCGGCAGUGGC-3' (SEQ ID NO: 148), wherein the bolded and underlined nucleotides are 2'OMe nucleotides. In certain instances, the antisense strand further comprises a 5'-tt-3' or 5'-UU-3' overhang.

In other embodiments, the HDAC2 interfering RNA (e.g., siRNA) comprises a sense strand comprising the following sequence: 5'-GCCACUGCCGAAGAAAUGA-3' (SEQ ID NO: 149), wherein the bolded and underlined nucleotides are 2'OMe nucleotides. In alternative embodiments, the HDAC2 interfering RNA (e.g., siRNA) may comprise a sense strand having any combination of 2'OMe-uridine and/or 2'OMe-guanosine nucleotides. In certain instances, the sense strand may further comprise 2'OMe-adenosine and/or 2'OMe-cytosine nucleotides. As non-limiting examples, the sense strand may alternatively comprise one of the following 2'OMe-modified sequences: 5'-GCCACUGCCGAAGAAAUGA-3' (SEQ ID NO: 150) or 5'-GCCACUGCCGAAGAAAUGA-3' (SEQ ID NO: 151), wherein the bolded and underlined nucleotides are 2'OMe nucleotides. In certain instances, the sense strand further comprises a 5'-tt-3' or 5'-UU-3' overhang.

In a particularly preferred embodiment, the HDAC2 interfering RNA comprises an siRNA that consists of the following sense and antisense sequences:

5'-GCCACUGCCGAAGAAAUGAtt-3' (SEQ ID NO: 152)

3'-ttCGGUGACGGCUUCUUUACU-5' (SEQ ID NO: 153)
HDAC2-3/7 siRNA, wherein the bolded and underlined nucleotides are 2'OMe nucleotides.

In certain embodiments, the HDAC2 interfering RNA (e.g., siRNA) composition further comprises one or more interfering RNAs (e.g., siRNAs) targeting the COP1, WEE1, RBX1, CDK4, CSN5, FOXM1, and/or R1 genes. In some embodiments, the antisense strand of each additional interfering RNA comprises a sequence that is complementary to one of the target sequences set forth in FIGS. 43-47 from U.S. Provisional Application No. 61/377,439. In other embodiments, the sense strand of each additional interfering RNA comprises one of the target sequences set forth in FIGS. 43-47 from U.S. Provisional Application No. 61/377,439. In certain embodiments, the antisense strand of each additional interfering RNA comprises one of the antisense strand sequences set forth in Tables 1-4 and 6-10, and/or the sense strand of each additional interfering RNA comprises one of the sense strand sequences set forth in Tables 1-4 and 6-10. In particular embodiments, the antisense strand of each additional interfering RNA (e.g., siRNA) comprises one of the antisense strand sequences set forth in Tables 11-14 and 17-30 (or nucleotides 1-19 thereof), and/or the sense strand of each additional interfering RNA comprises one of the sense strand sequences set forth in Tables 11-14 and 17-30 (or nucleotides 1-19 thereof). The sense and/or antisense strand of each additional interfering RNA (e.g., siRNA) may contain modified nucleotides and/or 3' overhangs as described herein.

In a fourth embodiment, the present invention provides a composition comprising an interfering RNA (e.g., siRNA) that silences ring-box 1 ("RBX1") gene expression, wherein the interfering RNA comprises a sense strand and a complementary antisense strand, and wherein the antisense strand comprises one of the antisense strand sequences set forth in Table 6. In some embodiments, the sense strand comprises one of the sense strand sequences set forth in Table 6. In other embodiments, the antisense strand comprises a sequence that is complementary to one of the target sequences set forth in FIG. 43 from U.S. Provisional Application No. 61/377,439, and/or the sense strand comprises one of the target sequences set forth in FIG. 43 from U.S. Provisional Application No. 61/377,439. In particular embodiments, the RBX1 interfering RNA (e.g., siRNA) of the present invention comprises: a sense strand comprising nucleotides 1-19 of any one of the sense strand sequences set forth in Tables 17-18; and an antisense strand comprising nucleotides 1-19 of any one of the antisense strand sequences set forth in Tables 17-18. In other particular embodiments, the RBX1 interfering RNA (e.g., siRNA) of the present invention comprises: a sense strand selected from any one of the sense strand sequences set forth in Tables 17-18; and an antisense strand selected from any one of the antisense strand sequences set forth in Tables 17-18. "RBX1" is also known as ROC1, RNF75, MGC1481, MGC13357, and BA554C12.1.

TABLE 6 siRNA sequences that target human RBX1 gene expression.

| siRNA | Target or Sense Strand Sequence (5' → 3') | Antisense Strand Sequence (5' → 3') |
|---|---|---|
| RBX1-1 | GGUGUGUCCAUUGGACAAC (SEQ ID NO: 154) | GUUGUCCAAUGGACACACC (SEQ ID NO: 155) |
| RBX1-2 | GGAACCACAUUAUGGAUCU (SEQ ID NO: 156) | AGAUCCAUAAUGUGGUUCC (SEQ ID NO: 157) |
| RBX1-3 | GUGAAAAGUGGAAUGCAG (SEQ ID NO: 158) | CUGCAUUCCACUUUUUCAC (SEQ ID NO: 159) |

In some embodiments, the RBX1 interfering RNA (e.g., siRNA) comprises a sense strand, a complementary antisense strand, and a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In other embodiments, the RBX1 interfering RNA is chemically synthesized.

In certain embodiments, the RBX1 interfering RNA (e.g., siRNA) may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the RBX1 interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the RBX1 interfering RNA (e.g., siRNA) comprise modified nucleotides such as, e.g., 2'OMe nucleotides (e.g., 2'OMe-guanosine and/or 2'OMe-uridine nucleotides).

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the RBX1 interfering RNA molecule strikes a balance between reduction or abrogation of the immunostimulatory properties of the interfering RNA and retention of RNAi activity.

In particular embodiments, the RBX1 interfering RNA (e.g., siRNA) may comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA (e.g., siRNA) may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target RBX1 sequence (3' overhang in antisense strand) or the complementary strand thereof (3' overhang in sense strand).

In one preferred embodiment, the RBX1 interfering RNA (e.g., siRNA) comprises an antisense strand comprising the following sequence: 5'-AGAUCCAUAAUGUGGUUCC-3' (SEQ ID NO: 157). In certain instances, the antisense strand further comprises a 5'-tg-3' or 5'-UG-3' overhang. In other embodiments, the RBX1 interfering RNA (e.g., siRNA) comprises a sense strand comprising the following sequence: 5'-GGAACCACAUUAUGGAUCU-3' (SEQ ID NO: 156). In certain instances, the sense strand further comprises a 5'-tt-3' or 5'-UU-3' overhang. In some aspects of these embodiments, the RBX1 interfering RNA (e.g., siRNA) comprises at least one 2'OMe nucleotide, e.g., at least one 2'OMe-guanosine and/or 2'OMe-uridine nucleotide. In certain instances, the RBX1 interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the RBX1 interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In one particular embodiment, the RBX1 interfering RNA comprises an siRNA that consists of the following sense and antisense sequences:

```
                                        (SEQ ID NO: 160)
     5'-GGAACCACAUUAUGGAUCUtt-3'

(SEQ ID NO: 161)
     3'-gtCCUUGGUGUAAUACCUAGA-5'
     RBX1-2 siRNA.
```

In certain embodiments, the RBX1-2 siRNA comprises at least one, two, three, four, five, six, seven, eight, nine, ten, or more modified nucleotides such as 2'OMe nucleotides (e.g., in the sense and/or antisense strand of the double-stranded region) in accordance with the selective modification patterns described herein.

In some embodiments, the RBX1 interfering RNA (e.g., siRNA) comprises an antisense strand comprising the following sequence: 5'-AGAUCCAUAAUGUGGUUCC-3' (SEQ ID NO: 162), wherein the bolded and underlined nucleotides are 2'OMe nucleotides. In alternative embodiments, the RBX1 interfering RNA (e.g., siRNA) may comprise an antisense strand having any combination of 2'OMe-uridine and/or 2'OMe-guanosine nucleotides. In certain instances, the antisense strand may further comprise 2'OMe-adenosine and/or 2'OMe-cytosine nucleotides. As non-limiting examples, the antisense strand may alternatively comprise one of the following 2'OMe-modified sequences: 5'-AGAUCCAUAAUGUGGUUCC-3' (SEQ ID NO: 163) or 5'-AGAUCCAUAAUGUGGUUCC-3' (SEQ ID NO: 164), wherein the bolded and underlined nucleotides are 2'OMe nucleotides. In certain instances, the antisense strand further comprises a 5'-tg-3' or 5'-UG-3' overhang.

In other embodiments, the RBX1 interfering RNA (e.g., siRNA) comprises a sense strand comprising the following sequence: 5'-GGAACCACAUUAUGGAUCU-3' (SEQ ID NO: 165), wherein the bolded and underlined nucleotides are 2'OMe nucleotides. In alternative embodiments, the RBX1 interfering RNA (e.g., siRNA) may comprise a sense strand having any combination of 2'OMe-uridine and/or 2'OMe-guanosine nucleotides. In certain instances, the sense strand may further comprise 2'OMe-adenosine and/or 2'OMe-cytosine nucleotides. As non-limiting examples, the sense strand may alternatively comprise the following 2'OMe-modified sequence: 5'-GGAACCACAUUAUGGAUCU-3' (SEQ ID NO: 166), wherein the bolded and underlined nucleotides are 2'OMe nucleotides. In certain instances, the sense strand further comprises a 5'-tt-3' or 5'-UU-3' overhang.

In a particularly preferred embodiment, the RBX1 interfering RNA comprises an siRNA that consists of the following sense and antisense sequences:

```
                                         (SEQ ID NO: 167)
5'-GGAACCACAUUAUGGAUCUtt-3'

(SEQ ID NO: 168)
3'-gtCCUUGGUGUAAUACCUAGA-5'
RBX1-3/6 siRNA,
``` wherein the bolded and underlined nucleotides are 2'OMe nucleotides.

In certain embodiments, the RBX1 interfering RNA (e.g., siRNA) composition further comprises one or more interfering RNAs (e.g., siRNAs) targeting the COP1, WEE1, HDAC2, CDK4, CSN5, FOXM1, and/or R1 genes. In some embodiments, the antisense strand of each additional interfering RNA comprises a sequence that is complementary to one of the target sequences set forth in FIGS. 42 and 44-47 from U.S. Provisional Application No. 61/377,439. In other embodiments, the sense strand of each additional interfering RNA comprises one of the target sequences set forth in FIGS. 42 and 44-47 from U.S. Provisional Application No. 61/377,439. In certain embodiments, the antisense strand of each additional interfering RNA comprises one of the antisense strand sequences set forth in Tables 1-5 and 7-10, and/or the sense strand of each additional interfering RNA comprises one of the sense strand sequences set forth in Tables 1-5 and 7-10. In particular embodiments, the antisense strand of each additional interfering RNA (e.g., siRNA) comprises one of the antisense strand sequences set forth in Tables 11-16 and 19-30 (or nucleotides 1-19 thereof), and/or the sense strand of each additional interfering RNA comprises one of the sense strand sequences set forth in Tables 11-16 and 19-30 (or nucleotides 1-19 thereof). The sense and/or antisense strand of each additional interfering RNA (e.g., siRNA) may contain modified nucleotides and/or 3' overhangs as described herein.

In a fifth embodiment, the present invention provides a composition comprising an interfering RNA (e.g., siRNA) that silences cyclin-dependent kinase 4 ("CDK4") gene expression, wherein the interfering RNA comprises a sense strand and a complementary antisense strand, and wherein the antisense strand comprises one of the antisense strand sequences set forth in Table 7. In some embodiments, the sense strand comprises one of the sense strand sequences set forth in Table 7. In other embodiments, the antisense strand comprises a sequence that is complementary to one of the target sequences set forth in FIG. 44 from U.S. Provisional Application No. 61/377,439, and/or the sense strand comprises one of the target sequences set forth in FIG. 44 from U.S. Provisional Application No. 61/377,439. In particular embodiments, the CDK4 interfering RNA (e.g., siRNA) of the present invention comprises: a sense strand comprising nucleotides 1-19 of any one of the sense strand sequences set forth in Tables 19-20; and an antisense strand comprising nucleotides 1-19 of any one of the antisense strand sequences set forth in Tables 19-20. In other particular embodiments, the CDK4 interfering RNA (e.g., siRNA) of the present invention comprises: a sense strand selected from any one of the sense strand sequences set forth in Tables 19-20; and an antisense strand selected from any one of the antisense strand sequences set forth in Tables 19-20. "CDK4" is also known as CMM3, PSK-J3, and MGC14458.

TABLE 7 siRNA sequences that target human CDK4 gene expression.

| siRNA | Target or Sense Strand Sequence (5' → 3') | Antisense Strand Sequence (5' → 3') |
|---|---|---|
| CDK4-1 | GGCUUUUGAGCAUCCCAAU (SEQ ID NO: 169) | AUUGGGAUGCUCAAAAGCC (SEQ ID NO: 170) |
| CDK4-2 | GCCGAAACGAUCAAGGAUC (SEQ ID NO: 171) | GAUCCUUGAUCGUUUCGGC (SEQ ID NO: 172) |
| CDK4-3 | GCACUCUUAUCUACAUAAG (SEQ ID NO: 173) | CUUAUGUAGAUAAGAGUGC (SEQ ID NO: 174) |

In some embodiments, the CDK4 interfering RNA (e.g., siRNA) comprises a sense strand, a complementary antisense strand, and a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In other embodiments, the CDK4 interfering RNA is chemically synthesized.

In certain embodiments, the CDK4 interfering RNA (e.g., siRNA) may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the CDK4 interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the CDK4 interfering RNA (e.g., siRNA) comprise modified nucleotides such as, e.g., 2'OMe nucleotides (e.g., 2'OMe-guanosine and/or 2'OMe-uridine nucleotides).

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the CDK4 interfering RNA molecule strikes a balance between reduction or abrogation of the immunostimulatory properties of the interfering RNA and retention of RNAi activity.

In particular embodiments, the CDK4 interfering RNA (e.g., siRNA) may comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA (e.g., siRNA) may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target CDK4 sequence (3' overhang in antisense strand) or the complementary strand thereof (3' overhang in sense strand).

In one preferred embodiment, the CDK4 interfering RNA (e.g., siRNA) comprises an antisense strand comprising the following sequence: 5'-AUUGGGAUGCUCAAAAGCC-3' (SEQ ID NO: 170). In certain instances, the antisense strand further comprises a 5'-tc-3' or 5'-UC-3' overhang. In other embodiments, the CDK4 interfering RNA (e.g., siRNA) comprises a sense strand comprising the following sequence: 5'-GGCUUUUGAGCAUCCCAAU-3' (SEQ ID NO: 169). In certain instances, the sense strand further comprises a 5'-tt-3' or 5'-UU-3' overhang. In some aspects of these embodiments, the CDK4 interfering RNA (e.g., siRNA) comprises at least one 2'OMe nucleotide, e.g., at least one 2'OMe-guanosine and/or 2'OMe-uridine nucleotide. In certain instances, the CDK4 interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the CDK4 interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In one particular embodiment, the CDK4 interfering RNA comprises an siRNA that consists of the following sense and antisense sequences:

```
                                    (SEQ ID NO: 175)
5'-GGCUUUUGAGCAUCCCAAUtt-3'

(SEQ ID NO: 176)
3'-ctCCGAAAACUCGUAGGGUUA-5'
CDK4-1 siRNA.
```

In certain embodiments, the CDK4-1 siRNA comprises at least one, two, three, four, five, six, seven, eight, nine, ten, or more modified nucleotides such as 2'OMe nucleotides (e.g., in the sense and/or antisense strand of the double-stranded region) in accordance with the selective modification patterns described herein.

In some embodiments, the CDK4 interfering RNA (e.g., siRNA) comprises an antisense strand comprising the following sequence: 5'-AUUGGGAUGCUCAAAAGCC-3' (SEQ ID NO: 177), wherein the bolded and underlined nucleotides are 2'OMe nucleotides. In alternative embodiments, the CDK4 interfering RNA (e.g., siRNA) may comprise an antisense strand having any combination of 2'OMe-uridine and/or 2'OMe-guanosine nucleotides. In certain instances, the antisense strand may further comprise 2'OMe-adenosine and/or 2'OMe-cytosine nucleotides. As non-limiting examples, the antisense strand may alternatively comprise one of the following 2'OMe-modified sequences: 5'-AUUGGGAU GCUCAAAAGCC-3' (SEQ ID NO: 178), 5'-AUUG GGAUGCUCAAAAGCC-3' (SEQ ID NO: 179), or 5'-AUU GGGAUGCUCAAAAGCC-3' (SEQ ID NO: 180), wherein the bolded and underlined nucleotides are 2'OMe nucleotides. In certain instances, the antisense strand further comprises a 5'-UC-3' or 5'-mUC-3' overhang, wherein "mU"=2'OMe-uridine.

In other embodiments, the CDK4 interfering RNA (e.g., siRNA) comprises a sense strand comprising the following sequence: 5'-GGCUUUUGAGCAUCCCAAU-3' (SEQ ID NO: 181), wherein the bolded and underlined nucleotides are 2'OMe nucleotides. In alternative embodiments, the CDK4 interfering RNA (e.g., siRNA) may comprise a sense strand having any combination of 2'OMe-uridine and/or 2'OMe-guanosine nucleotides. In certain instances, the sense strand may further comprise 2'OMe-adenosine and/or 2'OMe-cytosine nucleotides. As non-limiting examples, the sense strand may alternatively comprise one of the following 2'OMe-modified sequences: 5'-GGCUU UUGAGCAUCCCAAU-3' (SEQ ID NO: 182) or 5'-GGCU UUUGAGCAUCCCAAU-3' (SEQ ID NO: 183), wherein the bolded and underlined nucleotides are 2'OMe nucleotides. In certain instances, the sense strand further comprises a 5'-UU-3' overhang.

In a particularly preferred embodiment, the CDK4 interfering RNA comprises an siRNA that consists of the following sense and antisense sequences:

```
                                    (SEQ ID NO: 184)
5'-GGCUUUUGAGCAUCCCAAUUU-3'

(SEQ ID NO: 185)
3'-CUCCGAAAACUCGUAGGGUUA-5'
CDK4-3/7 siRNA,
``` wherein the bolded and underlined nucleotides are 2'OMe nucleotides.

In certain embodiments, the CDK4 interfering RNA (e.g., siRNA) composition further comprises one or more interfering RNAs (e.g., siRNAs) targeting the COP1, WEE1, HDAC2, RBX1, CSN5, FOXM1, and/or R1 genes. In some embodiments, the antisense strand of each additional interfering RNA comprises a sequence that is complementary to one of the target sequences set forth in FIGS. 43 and 45-47 from U.S. Provisional Application No. 61/377,439. In other embodiments, the sense strand of each additional interfering RNA comprises one of the target sequences set forth in FIGS. 43 and 45-47 from U.S. Provisional Application No. 61/377, 439. In certain embodiments, the antisense strand of each additional interfering RNA comprises one of the antisense strand sequences set forth in Tables 1-6 and 8-10, and/or the sense strand of each additional siRNA comprises one of the sense strand sequences set forth in Tables 1-6 and 8-10. In particular embodiments, the antisense strand of each additional interfering RNA (e.g., siRNA) comprises one of the antisense strand sequences set forth in Tables 11-18 and 21-30 (or nucleotides 1-19 thereof), and/or the sense strand of each additional interfering RNA comprises one of the sense strand sequences set forth in Tables 11-18 and 21-30 (or nucleotides 1-19 thereof). The sense and/or antisense strand of each additional interfering RNA (e.g., siRNA) may contain modified nucleotides and/or 3' overhangs as described herein.

In a sixth embodiment, the present invention provides a composition comprising an interfering RNA (e.g., siRNA) that silences COP9 signalosome subunit 5 ("CSN5") gene expression, wherein the interfering RNA comprises a sense strand and a complementary antisense strand, and wherein the antisense strand comprises one of the antisense strand sequences set forth in Table 8. In some embodiments, the sense strand comprises one of the sense strand sequences set forth in Table 8. In other embodiments, the antisense strand comprises a sequence that is complementary to one of the target sequences set forth in FIG. 45 from U.S. Provisional Application No. 61/377,439, and/or the sense strand comprises one of the target sequences set forth in FIG. 45 from U.S. Provisional Application No. 61/377,439. In particular embodiments, the CSN5 interfering RNA (e.g., siRNA) of the present invention comprises: a sense strand comprising nucleotides 1-19 of any one of the sense strand sequences set forth in Tables 21-22; and an antisense strand comprising nucleotides 1-19 of any one of the antisense strand sequences set forth in Tables 21-22. In other particular embodiments, the CSN5 interfering RNA (e.g., siRNA) of the present invention comprises: a sense strand selected from any one of the sense strand sequences set forth in Tables 21-22; and an antisense strand selected from any one of the antisense strand sequences set forth in Tables 21-22. "CSN5" is also known as Jun activating binding protein (Jab1), COPS5, SGN5, MOV-34, and MGC3149.

TABLE 8 siRNA sequences that target human CSN5 gene expression.

| siRNA | Target or Sense Strand Sequence (5' → 3') | Antisense Strand Sequence (5' → 3') |
|---|---|---|
| CSN5-1 | CCAUUACUUUAAGUACUGC (SEQ ID NO: 186) | GCAGUACUUAAAGUAAUGG (SEQ ID NO: 187) |
| CSN5-2 | GGAUCACCAUUACUUUAAG (SEQ ID NO: 188) | CUUAAAGUAAUGGUGAUCC (SEQ ID NO: 71) |
| CSN5-3 | CCGAAAAUCAGAAGACAAA (SEQ ID NO: 189) | UUUGUCUUCUGAUUUUCGG (SEQ ID NO: 190) |

In some embodiments, the CSN5 interfering RNA (e.g., siRNA) comprises a sense strand, a complementary antisense strand, and a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In other embodiments, the CSN5 interfering RNA is chemically synthesized.

In certain embodiments, the CSN5 interfering RNA (e.g., siRNA) may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the CSN5 interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the CSN5 interfering RNA (e.g., siRNA) comprise modified nucleotides such as, e.g., 2'OMe nucleotides (e.g., 2'OMe-guanosine and/or 2'OMe-uridine nucleotides).

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the CSN5 interfering RNA molecule strikes a balance between reduction or abrogation of the immunostimulatory properties of the interfering RNA and retention of RNAi activity.

In particular embodiments, the CSN5 interfering RNA (e.g., siRNA) may comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA (e.g., siRNA) may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target CSN5 sequence (3' overhang in antisense strand) or the complementary strand thereof (3' overhang in sense strand).

In one preferred embodiment, the CSN5 interfering RNA (e.g., siRNA) comprises an antisense strand comprising the following sequence: 5'-CUUAAAGUAAUGGUGAUCC-3' (SEQ ID NO: 71). In certain instances, the antisense strand further comprises a 5'-tt-3' or 5'-UU-3' overhang. In other embodiments, the CSN5 interfering RNA (e.g., siRNA) comprises a sense strand comprising the following sequence: 5'-GGAUCACCAUUACUUUAAG-3' (SEQ ID NO: 188). In certain instances, the sense strand further comprises a 5'-tt-3' or 5'-UU-3' overhang. In some aspects of these embodiments, the CSN5 interfering RNA (e.g., siRNA) comprises at least one 2'OMe nucleotide, e.g., at least one 2'OMe-guanosine and/or 2'OMe-uridine nucleotide. In certain instances, the CSN5 interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the CSN5 interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In one particular embodiment, the CSN5 interfering RNA comprises an siRNA that consists of the following sense and antisense sequences:

(SEQ ID NO: 191)
5'-GGAUCACCAUUACUUUAAGtt-3'

(SEQ ID NO: 192)
3'-ttCCUAGUGGUAAUGAAAUUC-5'
CSN5-2 siRNA.

In certain embodiments, the CSN5-2 siRNA comprises at least one, two, three, four, five, six, seven, eight, nine, ten, or more modified nucleotides such as 2'OMe nucleotides (e.g., in the sense and/or antisense strand of the double-stranded region) in accordance with the selective modification patterns described herein.

In some embodiments, the CSN5 interfering RNA (e.g., siRNA) comprises an antisense strand comprising the following sequence: 5'-CUUAAAGUAAUGGUGAUCC-3' (SEQ ID NO: 193), wherein the bolded and underlined nucleotides are 2'OMe nucleotides. In alternative embodiments, the CSN5 interfering RNA (e.g., siRNA) may comprise an antisense strand having any combination of 2'OMe-uridine and/or 2'OMe-guanosine nucleotides. In certain instances, the antisense strand may further comprise 2'OMe-adenosine and/or 2'OMe-cytosine nucleotides. As non-limiting examples, the antisense strand may alternatively comprise one of the following 2'OMe-modified sequences: 5'-CUUAAAGUAAUGGUGAUCC-3 (SEQ ID NO: 194), 5'-CUUAAAGUAAUGGUGAUCC-3' (SEQ ID NO: 195), or 5'-CUUAAAGUAAUGGUGAUCC-3' (SEQ ID NO: 196), wherein the bolded and underlined nucleotides are 2'OMe nucleotides. In certain instances, the antisense strand further comprises a 5'-UU-3' overhang.

In other embodiments, the CSN5 interfering RNA (e.g., siRNA) comprises a sense strand comprising the following sequence: 5'-GGAUCACCAUUACUUUAAG-3' (SEQ ID NO: 197), wherein the bolded and underlined nucleotides are 2'OMe nucleotides. In alternative embodiments, the CSN5 interfering RNA (e.g., siRNA) may comprise a sense strand having any combination of 2'OMe-uridine and/or 2'OMe-guanosine nucleotides. In certain instances, the sense strand may further comprise 2'OMe-adenosine and/or 2'OMe-cytosine nucleotides. As non-limiting examples, the sense strand may alternatively comprise one of the following 2'OMe-modified sequences: 5'-GGAUCACCAUUACUUUAAG-3' (SEQ ID NO: 198) or 5'-GGAUCACCAUUACUUUAAG-3' (SEQ ID NO: 199), wherein the bolded and underlined nucleotides are 2'OMe nucleotides. In certain instances, the sense strand further comprises a 5'-UU-3' overhang.

In a particularly preferred embodiment, the CSN5 interfering RNA comprises an siRNA that consists of the following sense and antisense sequences:

(SEQ ID NO: 200)
5'-GGAUCACCAUUACUUUAAGUU-3'

(SEQ ID NO: 201)
3'-UUCCUAGUGGUAAUGAAAUUC-5'
CSN5-3/8 siRNA, wherein the bolded and underlined nucleotides are 2'OMe nucleotides.

In certain embodiments, the CSN5 interfering RNA (e.g., siRNA) composition further comprises one or more interfering RNAs (e.g., siRNAs) targeting the COP1, WEE1, HDAC2, RBX1, CDK4, FOXM1, and/or R1 genes. In some embodiments, the antisense strand of each additional interfering RNA comprises a sequence that is complementary to one of the target sequences set forth in FIGS. 44 and 46-47 from U.S. Provisional Application No. 61/377,439. In other embodiments, the sense strand of each additional interfering RNA comprises one of the target sequences set forth in FIGS. 44 and 46-47 from U.S. Provisional Application No. 61/377,439. In certain embodiments, the antisense strand of each additional interfering RNA comprises one of the antisense strand sequences set forth in Tables 1-7 and 9-10, and/or the sense strand of each additional interfering RNA comprises one of the sense strand sequences set forth in Tables 1-7 and 9-10. In particular embodiments, the antisense strand of each additional interfering RNA (e.g., siRNA) comprises one of the antisense strand sequences set forth in Tables 11-20 and 23-30 (or nucleotides 1-19 thereof), and/or the sense strand of each additional interfering RNA comprises one of the sense strand sequences set forth in Tables 11-20 and 23-30 (or nucleotides 1-19 thereof). The sense and/or antisense strand of each additional interfering RNA (e.g., siRNA) may contain modified nucleotides and/or 3' overhangs as described herein.

In a seventh embodiment, the present invention provides a composition comprising an interfering RNA (e.g., siRNA) that silences forkhead box M1 ("FOXM1") gene expression, wherein the interfering RNA comprises a sense strand and a complementary antisense strand, and wherein the antisense strand comprises one of the antisense strand sequences set forth in Table 9. In some embodiments, the sense strand comprises one of the sense strand sequences set forth in Table 9. In other embodiments, the antisense strand comprises a sequence that is complementary to one of the target sequences set forth in FIG. 46 from U.S. Provisional Application No. 61/377,439, and/or the sense strand comprises one of the target sequences set forth in FIG. 46 from U.S. Provisional Application No. 61/377,439. In particular embodiments, the FOXM1 interfering RNA (e.g., siRNA) of the present invention comprises: a sense strand comprising nucleotides 1-19 of any one of the sense strand sequences set forth in Tables 23-24; and an antisense strand comprising nucleotides 1-19 of any one of the antisense strand sequences set forth in Tables 23-24. In other particular embodiments, the FOXM1 interfering RNA (e.g., siRNA) of the present invention comprises: a sense strand selected from any one of the sense strand sequences set forth in Tables 23-24; and an antisense strand selected from any one of the antisense strand sequences set forth in Tables 23-24. "FOXM1" is also known as MPP2, TGT3, HFH11, HNF-3, INS-1, MPP-2, PIG29, FKHL16, FOXM1B, HFH-11, TRIDENT, and MPHOSPH2.

TABLE 9 siRNA sequences that target human FOXM1 gene expression.

| siRNA | Target or Sense Strand Sequence (5' → 3') | Antisense Strand Sequence (5' → 3') |
|---|---|---|
| FOXM1-1 | GGACCUUUUAAGACACCCA (SEQ ID NO: 202) | UGGGUGUCUUAAAAGGUCC (SEQ ID NO: 203) |
| FOXM1-2 | GGAAAUGCCACACUUAGCG (SEQ ID NO: 204) | CGCUAAGUGUGGCAUUUCC (SEQ ID NO: 205) |
| FOXM1-3 | GGCUGCACUAUCAACAAUA (SEQ ID NO: 206) | UAUUGUUGAUAGUGCAGCC (SEQ ID NO: 207) |

In some embodiments, the FOXM1 interfering RNA (e.g., siRNA) comprises a sense strand, a complementary antisense strand, and a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In other embodiments, the FOXM1 interfering RNA is chemically synthesized.

In certain embodiments, the FOXM1 interfering RNA (e.g., siRNA) may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the FOXM1 interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the FOXM1 interfering RNA (e.g., siRNA) comprise modified nucleotides such as, e.g., 2'OMe nucleotides (e.g., 2'OMe-guanosine and/or 2'OMe-uridine nucleotides).

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the FOXM1 interfering RNA molecule strikes a balance between reduction or abrogation of the immunostimulatory properties of the interfering RNA and retention of RNAi activity.

In particular embodiments, the FOXM1 interfering RNA (e.g., siRNA) may comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA (e.g., siRNA) may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target FOXM1 sequence (3' overhang in antisense strand) or the complementary strand thereof (3' overhang in sense strand).

In one preferred embodiment, the FOXM1 interfering RNA (e.g., siRNA) comprises an antisense strand comprising the following sequence: 5'-UGGGUGUCUUAAAAG-GUCC-3' (SEQ ID NO: 203). In certain instances, the antisense strand further comprises a 5'-tc-3' or 5'-UC-3' overhang. In other embodiments, the FOXM1 interfering RNA (e.g., siRNA) comprises a sense strand comprising the following sequence: 5'-GGACCUUUUAAGACACCCA-3' (SEQ ID NO: 202). In certain instances, the sense strand further comprises a 5'-tt-3' or 5'-UU-3' overhang. In some aspects of these embodiments, the FOXM1 interfering RNA (e.g., siRNA) comprises at least one 2'OMe nucleotide, e.g., at least one 2'OMe-guanosine and/or 2'OMe-uridine nucleotide. In certain instances, the FOXM1 interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the FOXM1 interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In one particular embodiment, the FOXM1 interfering RNA comprises an siRNA that consists of the following sense and antisense sequences:

```
                                         (SEQ ID NO: 208)
5'-GGACCUUUUAAGACACCCAtt-3'

(SEQ ID NO: 209)
3'-ctCCUGGAAAAUUCUGUGGGU-5'
FOXM1-1 siRNA.
```

In certain embodiments, the FOXM1-1 siRNA comprises at least one, two, three, four, five, six, seven, eight, nine, ten, or more modified nucleotides such as 2'OMe nucleotides (e.g., in the sense and/or antisense strand of the double-stranded region) in accordance with the selective modification patterns described herein.

In some embodiments, the FOXM1 interfering RNA (e.g., siRNA) comprises an antisense strand comprising the following sequence: 5'-UGGGUGUCUUAAAAGGUCC-3' (SEQ ID NO: 210), wherein the bolded and underlined nucleotides are 2'OMe nucleotides. In alternative embodiments, the FOXM1 interfering RNA (e.g., siRNA) may comprise an antisense strand having any combination of 2'OMe-uridine and/or 2'OMe-guanosine nucleotides. In certain instances, the antisense strand may further comprise 2'OMe-adenosine and/or 2'OMe-cytosine nucleotides. As non-limiting examples, the antisense strand may alternatively comprise one of the following 2'OMe-modified sequences: 5'-UGGGUGUCUUAAAAGGUCC-3' (SEQ ID NO: 211), 5'-UGGGUGUCUUAAAAGGUCC-3' (SEQ ID NO: 212), or 5'-UGGGUGUCUUAAAAGGUCC-3' (SEQ ID NO: 213), wherein the bolded and underlined nucleotides are 2'OMe nucleotides. In certain instances, the antisense strand further comprises a 5'-UC-3' overhang.

In other embodiments, the FOXM1 interfering RNA (e.g., siRNA) comprises a sense strand comprising the following sequence: 5'-GGACCUUUUAAGACACCCA-3' (SEQ ID NO: 214), wherein the bolded and underlined nucleotides are 2'OMe nucleotides. In alternative embodiments, the FOXM1 interfering RNA (e.g., siRNA) may comprise a sense strand having any combination of 2'OMe-uridine and/or 2'OMe-guanosine nucleotides. In certain instances, the sense strand may further comprise 2'OMe-adenosine and/or 2'OMe-cytosine nucleotides. As non-limiting examples, the sense strand may alternatively comprise one of the following 2'OMe-modified sequences: 5'-GGACCUUUUAAGACACCCA-3' (SEQ ID NO: 215) or 5'-GGACCUUUUAAGACACCCA-3' (SEQ ID NO: 216), wherein the bolded and underlined nucleotides are 2'OMe nucleotides. In certain instances, the sense strand further comprises a 5'-UU-3' overhang.

In a particularly preferred embodiment, the FOXM1 interfering RNA comprises an siRNA that consists of the following sense and antisense sequences:

(SEQ ID NO: 217)
5'-GGACCUUUUAAGACACCCAUU-3'

(SEQ ID NO: 218)
3'-CUCCUGGAAAAUUCUGUGGGU-5'
FOXM1-5/6 siRNA, wherein the bolded and underlined nucleotides are 2'OMe nucleotides.

In certain embodiments, the FOXM1 interfering RNA (e.g., siRNA) composition further comprises one or more interfering RNAs (e.g., siRNAs) targeting the COP1, WEE1, HDAC2, RBX1, CDK4, CSN5, and/or R1 genes. In some embodiments, the antisense strand of each additional interfering RNA comprises a sequence that is complementary to one of the target sequences set forth in FIGS. 45 and 47 from U.S. Provisional Application No. 61/377,439. In other embodiments, the sense strand of each additional interfering RNA comprises one of the target sequences set forth in FIGS. 45 and 47 from U.S. Provisional Application No. 61/377,439. In certain embodiments, the antisense strand of each additional interfering RNA comprises one of the antisense strand sequences set forth in Tables 1-8 and 10, and/or the sense strand of each additional interfering RNA comprises one of the sense strand sequences set forth in Tables 1-8 and 10. In particular embodiments, the antisense strand of each additional interfering RNA (e.g., siRNA) comprises one of the antisense strand sequences set forth in Tables 11-22 and 25-30 (or nucleotides 1-19 thereof), and/or the sense strand of each additional interfering RNA comprises one of the sense strand sequences set forth in Tables 11-22 and 25-30 (or nucleotides 1-19 thereof). The sense and/or antisense strand of each additional interfering RNA (e.g., siRNA) may contain modified nucleotides and/or 3' overhangs as described herein.

In an eighth embodiment, the present invention provides a composition comprising an interfering RNA (e.g., siRNA) that silences R1 gene expression, wherein the interfering RNA comprises a sense strand and a complementary antisense strand, and wherein the antisense strand comprises one of the antisense strand sequences set forth in Table 10. In some embodiments, the sense strand comprises one of the sense strand sequences set forth in Table 10. In other embodiments, the antisense strand comprises a sequence that is complementary to one of the target sequences set forth in FIG. 47 from U.S. Provisional Application No. 61/377,439, and/or the sense strand comprises one of the target sequences set forth in FIG. 47 from U.S. Provisional Application No. 61/377,439. In particular embodiments, the R1 interfering RNA (e.g., siRNA) of the present invention comprises: a sense strand comprising nucleotides 1-19 of any one of the sense strand sequences set forth in Tables 25-26; and an antisense strand comprising nucleotides 1-19 of any one of the antisense strand sequences set forth in Tables 25-26. In other particular embodiments, the R1 interfering RNA (e.g., siRNA) of the present invention comprises: a sense strand selected from any one of the sense strand sequences set forth in Tables 25-26; and an antisense strand selected from any one of the antisense strand sequences set forth in Tables 25-26. "R1" is also known as RAM2, cell division cycle associated 7-like (CDCA7L), JPO2, and DKFZp762L0311.

TABLE 10 siRNA sequences that target human R1 gene expression.

| siRNA | Target or Sense Strand Sequence (5' → 3') | Antisense Strand Sequence (5' → 3') |
|---|---|---|
| R1-1 | GCAGUUGUUUUCUAGCGCA (SEQ ID NO: 219) | UGCGCUAGAAAACAACUGC (SEQ ID NO: 220) |
| R1-2 | GGAUGUCAGAUCGGCAUUG (SEQ ID NO: 221) | CAAUGCCGAUCUGACAUCC (SEQ ID NO: 222) |
| R1-3 | GGAUUUACGCAGAGUGAUC (SEQ ID NO: 223) | GAUCACUCUGCGUAAAUCC (SEQ ID NO: 224) |

In some embodiments, the R1 interfering RNA (e.g., siRNA) comprises a sense strand, a complementary antisense strand, and a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In other embodiments, the R1 interfering RNA is chemically synthesized.

In certain embodiments, the R1 interfering RNA (e.g., siRNA) may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the R1 interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

In particular embodiments, from about 20%-40%, 25%-40%, 30%-40%, 20%-35%, 25%-35%, 20%-30%, 25%-30%, 26%-34%, 27%-33%, 28%-32%, or about 20%, 21%, 22%, 23%, 24%, 25%, 26%, 27%, 28%, 29%, 30%, 31%, 32%, 33%, 34%, 35%, 36%, 37%, 38%, 39%, or 40% of the nucleotides in the double-stranded region of the R1 interfering RNA (e.g., siRNA) comprise modified nucleotides such as, e.g., 2'OMe nucleotides (e.g., 2'OMe-guanosine and/or 2'OMe-uridine nucleotides).

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the R1 interfering RNA molecule strikes a balance between reduction or abrogation of the immunostimulatory properties of the interfering RNA and retention of RNAi activity.

In particular embodiments, the R1 interfering RNA (e.g., siRNA) may comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA (e.g., siRNA) may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target R1 sequence (3' overhang in antisense strand) or the complementary strand thereof (3' overhang in sense strand).

In one preferred embodiment, the R1 interfering RNA (e.g., siRNA) comprises an antisense strand comprising the following sequence: 5'-CAAUGCCGAUCUGACAUCC-3' (SEQ ID NO: 222). In certain instances, the antisense strand further comprises a 5'-tc-3' or 5'-UC-3' overhang. In other embodiments, the R1 interfering RNA (e.g., siRNA) comprises a sense strand comprising the following sequence: 5'-GGAUGUCAGAUCGGCAUUG-3' (SEQ ID NO: 221). In certain instances, the sense strand further comprises a 5'-tt-3' or 5'-UU-3' overhang. In some aspects of these embodiments, the R1 interfering RNA (e.g., siRNA) comprises at least one 2'OMe nucleotide, e.g., at least one 2'OMe-guanosine and/or 2'OMe-uridine nucleotide. In certain instances, the R1 interfering RNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the R1 interfering RNA comprises a sense strand comprising at least one, at least two, at least three, at least four, at least five, at least six, at least seven, or more 2'OMe nucleotides, e.g., 2'OMe-guanosine and/or 2'OMe-uridine nucleotides. In further instances, the antisense strand and/or sense strand may further comprise at least one, at least two, at least three, at least four, at least five, at least six, at least seven, or more 2'OMe-adenosine and/or 2'OMe-cytosine nucleotides.

In one particular embodiment, the R1 interfering RNA comprises an siRNA that consists of the following sense and antisense sequences:

```
                                      (SEQ ID NO: 225)
         5'-GGAUGUCAGAUCGGCAUUGtt-3'

(SEQ ID NO: 226)
         3'-ctCCUACAGUCUAGCCGUAAC-5'
         R1-2 siRNA.
```

In certain embodiments, the R1-2 siRNA comprises at least one, two, three, four, five, six, seven, eight, nine, ten, or more modified nucleotides such as 2'OMe nucleotides (e.g., in the sense and/or antisense strand of the double-stranded region) in accordance with the selective modification patterns described herein.

In some embodiments, the R1 interfering RNA (e.g., siRNA) comprises an antisense strand comprising the following sequence: 5'-CAAUGCCGAUCUGACAUCC-3' (SEQ ID NO: 227), wherein the bolded and underlined nucleotides are 2'OMe nucleotides. In alternative embodiments, the R1 interfering RNA (e.g., siRNA) may comprise an antisense strand having any combination of 2'OMe-uridine and/or 2'OMe-guanosine nucleotides. In certain instances, the antisense strand may further comprise 2'OMe-adenosine and/or 2'OMe-cytosine nucleotides. As non-limiting examples, the antisense strand may alternatively comprise one of the following 2'OMe-modified sequences: 5'-CAAUGCCGAUCUGACAUCC-3' (SEQ ID NO: 228), 5'-CAAUGCCGAUCUGACAUCC-3' (SEQ ID NO: 229), or 5'-CAAUGCCGAUCUGACAUCC-3' (SEQ ID NO: 230), wherein the bolded and underlined nucleotides are 2'OMe nucleotides. In certain instances, the antisense strand further comprises a 5'-UC-3' or 5'-mUC-3' overhang, wherein "mU"=2'OMe-uridine.

In other embodiments, the R1 interfering RNA (e.g., siRNA) comprises a sense strand comprising the following sequence: 5'-GGAUGUCAGAUCGGCAUUG-3' (SEQ ID NO: 231), wherein the bolded and underlined nucleotides are 2'OMe nucleotides. In alternative embodiments, the R1 interfering RNA (e.g., siRNA) may comprise a sense strand having any combination of 2'OMe-uridine and/or 2'OMe-guanosine nucleotides. In certain instances, the sense strand may further comprise 2'OMe-adenosine and/or 2'OMe-cytosine nucleotides. As non-limiting examples, the sense strand may alternatively comprise one of the following 2'OMe-modified sequences: 5'-GGAUGUCAGAUCGGCAUUG-3' (SEQ ID NO: 232) or 5'-GGAUGUCAGAUCGGCAUUG-3' (SEQ ID NO: 233), wherein the bolded and underlined nucleotides are 2'OMe nucleotides. In certain instances, the sense strand further comprises a 5'-UU-3' overhang.

In a particularly preferred embodiment, the R1 interfering RNA comprises an siRNA that consists of the following sense and antisense sequences:

```
                                      (SEQ ID NO: 234)
         5'-GGAUGUCAGAUCGGCAUUGUU-3'

(SEQ ID NO: 235)
         3'-CUCCUACAGUCUAGCCGUAAC-5'
         R1-5/8 siRNA,
``` wherein the bolded and underlined nucleotides are 2'OMe nucleotides.

In certain embodiments, the R1 interfering RNA (e.g., siRNA) composition further comprises one or more interfering RNAs (e.g., siRNAs) targeting the COP1, WEE1, HDAC2, RBX1, CDK4, CSN5, and/or FOXM1 genes. In some embodiments, the antisense strand of each additional interfering RNA comprises a sequence that is complementary to one of the target sequences set forth in FIGS. 42-46 from U.S. Provisional Application No. 61/377,439. In other embodiments, the sense strand of each additional interfering RNA comprises one of the target sequences set forth in FIGS. 42-46 from U.S. Provisional Application No. 61/377,439. In certain embodiments, the antisense strand of each additional interfering RNA comprises one of the antisense strand sequences set forth in Tables 1-9, and/or the sense strand of each additional interfering RNA comprises one of the sense strand sequences set forth in Tables 1-9. In particular embodiments, the antisense strand of each additional interfering RNA (e.g., siRNA) comprises one of the antisense strand sequences set forth in Tables 11-24 and 27-30 (or nucleotides 1-19 thereof), and/or the sense strand of each additional interfering RNA comprises one of the sense strand sequences set forth in Tables 11-24 and 27-30 (or nucleotides 1-19 thereof). The sense and/or antisense strand of each additional interfering RNA may contain modified nucleotides and/or 3' overhangs as described herein.

In a ninth embodiment, the present invention provides a composition comprising a cocktail (e.g., at least 2, 3, 4, 5, 6, 7, 8, 9, 10, 11, 12, 13, 14, 15, 16, 17, 18, 19, 20, or more) of the unmodified and/or modified interfering RNA (e.g., siRNA) sequences set forth in Tables 1-30 herein and/or in FIGS. 42-47 from U.S. Provisional Application No. 61/377,439. In particular embodiments, the present invention provides a composition comprising a cocktail of the interfering RNA (e.g., siRNA) sequences set forth in Tables 1-10. In certain embodiments, at least 1, 2, 3, 4, 5, 6, 7, 8, 9, 10, or more (e.g., all) of these interfering RNA (e.g., siRNA) sequences are chemically modified (e.g., 2'OMe-modified) as described herein. In preferred embodiments, the present invention provides a composition comprising a cocktail of the interfering RNA (e.g., siRNA) sequences set forth in Tables 13, 14, 16, 18, 20, 22, 24, 26, 28, and 30. In particularly preferred embodiments, the cocktail of interfering RNA molecules comprises at least 1, 2, 3, 4, 5, 6, 7, or all 8 of the following siRNAs: (1) COP1-1 siRNA, COP1-1181 siRNA, or a 2'OMe-modified variant thereof such as COP1-4/7 siRNA; (2) WEE1-2 siRNA, WEE1-3058 siRNA, or a 2'OMe-modified variant thereof such as WEE1-5/6 siRNA or WEE1-3058-1/5 siRNA; (3) HDAC2-1 siRNA or a 2'OMe-modified variant thereof such as HDAC2-3/7 siRNA; (4) RBX1-2 siRNA or a 2'OMe-modified variant thereof such as RBX1-3/6 siRNA; (5) CDK4-1 siRNA or a 2'OMe-modified variant thereof such as CDK4-3/7 siRNA; (6) CSN5-2 siRNA or a 2'OMe-modified variant thereof such as CSN5-3/8 siRNA; (7) FOXM1-1 siRNA or a 2'OMe-modified variant thereof such as FOXM1-5/6 siRNA; and (8) R1-2 siRNA or a 2'OMe-modified variant thereof such as R1-5/8 siRNA. In one particular embodiment, the cocktail of interfering RNAs comprises at least 1, 2, 3, or 4 of the following siRNAs: (1) COP1-1 siRNA and/or COP1-1181 siRNA, and/or a 2'OMe-modified variant thereof such as COP1-4/7 siRNA; and (2) WEE1-2 siRNA and/or WEE1-3058 siRNA, and/or a 2'OMe-modified variant thereof such as WEE1-5/6 siRNA and/or WEE1-3058-1/5 siRNA.

The present invention also provides a pharmaceutical composition comprising one or more (e.g., a cocktail) of the interfering RNA (e.g., siRNA) molecules described herein and a pharmaceutically acceptable carrier.

In another aspect, the present invention provides a nucleic acid-lipid particle (e.g., SNALP formulation) that targets one or more genes expressed in cancer (e.g., silences COP1, WEE1, HDAC2, RBX1, CDK4, CSN5, FOXM1, and/or R1 gene expression). The nucleic acid-lipid particles (e.g., SNALP) typically comprise one or more (e.g., a cocktail) of the interfering RNAs (e.g., siRNAs) described herein, a cationic lipid, and a non-cationic lipid. In certain embodiments, the nucleic acid-lipid particle (e.g., SNALP) further comprises a conjugated lipid that inhibits aggregation of particles. In some embodiments, the nucleic acid-lipid particles comprise one or more (e.g., a cocktail) of the interfering RNA (e.g., siRNA) molecules described herein, a cationic lipid, a non-cationic lipid, and a conjugated lipid that inhibits aggregation of particles. In particular embodiments, the nucleic acid-lipid particles (e.g., SNALP) comprise 1, 2, 3, 4, 5, 6, 7, 8, or more of the unmodified and/or modified interfering RNA (e.g., siRNA) molecules described herein that silence 1, 2, 3, 4, 5, 6, 7, 8, or more different genes expressed in cancer (e.g., COP1, WEE1, HDAC2, RBX1, CDK4, CSN5, FOXM1, and/or R1), a cationic lipid, a non-cationic lipid, and a conjugated lipid that inhibits aggregation of particles.

In some embodiments, the interfering RNAs (e.g., siRNAs) are fully encapsulated in the nucleic acid-lipid particle (e.g., SNALP). With respect to formulations comprising an interfering RNA cocktail, the different types of interfering RNA species present in the cocktail (e.g., interfering RNA compounds with different sequences) may be co-encapsulated in the same particle, or each type of interfering RNA species present in the cocktail may be encapsulated in a separate particle. The interfering RNA cocktail may be formulated in the particles described herein using a mixture of two or more individual interfering RNAs (each having a unique sequence) at identical, similar, or different concentrations or molar ratios. In one embodiment, a cocktail of interfering RNAs (corresponding to a plurality of interfering RNAs with different sequences) is formulated using identical, similar, or different concentrations or molar ratios of each interfering RNA species, and the different types of interfering RNAs are co-encapsulated in the same particle. In another embodiment, each type of interfering RNA species present in the cocktail is encapsulated in different particles at identical, similar, or different interfering RNA concentrations or molar ratios, and the particles thus formed (each containing a different interfering RNA payload) are administered separately (e.g., at different times in accordance with a therapeutic regimen), or are combined and administered together as a single unit dose (e.g., with a pharmaceutically acceptable carrier). In one particular embodiment, a cocktail of two interfering RNAs (e.g., siRNAs) may be formulated as a 1:1 mixture of each interfering RNA species. In another particular embodiment, a cocktail of three interfering RNAs (e.g., siRNAs) may be formulated as a 1:1:1 mixture of each interfering RNA species. The lipid particles described herein are serum-stable, are resistant to nuclease degradation, and are substantially non-toxic to mammals such as humans.

The cationic lipid in the nucleic acid-lipid particles of the present invention (e.g., SNALP) may comprise, e.g., one or more cationic lipids of Formula I-XVI described herein or any other cationic lipid species. In one particular embodiment, the cationic lipid comprises 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)[1,3]-dioxolane (DLin-K-C2-DMA), 2,2-dilinoleyl-4-dimethylaminomethyl [1,3]-dioxolane (DLin-K-DMA), salts thereof, or a mixture thereof.

The non-cationic lipid in the nucleic acid-lipid particles of the present invention (e.g., SNALP) may comprise, e.g., one or more anionic lipids and/or neutral lipids. In some embodiments, the non-cationic lipid comprises one of the following neutral lipid components: (1) a mixture of a phospholipid and cholesterol or a derivative thereof; (2) cholesterol or a derivative thereof; or (3) a phospholipid. In certain preferred embodiments, the phospholipid comprises dipalmitoylphosphatidylcholine (DPPC), distearoylphosphatidylcholine (DSPC), or a mixture thereof. In a particularly preferred embodiment, the non-cationic lipid is a mixture of DPPC and cholesterol.

The lipid conjugate in the nucleic acid-lipid particles of the invention (e.g., SNALP) inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, or mixtures thereof. In another embodiment, the lipid conjugate comprises a POZ-lipid conjugate such as a POZ-DAA conjugate.

In some embodiments, the present invention provides nucleic acid-lipid particles (e.g., SNALP) comprising: (a) one or more (e.g., a cocktail) of the interfering RNAs (e.g., siRNAs) described herein that target COP1, WEE1, HDAC2, RBX1, CDK4, CSN5, FOXM1, and/or R1 gene expression; (b) one or more cationic lipids (e.g., cationic lipids of Formula I-XVI) or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the nucleic acid-lipid particle comprises: (a) one or more (e.g., a cocktail) of the interfering RNAs (e.g., siRNAs) described herein that target COP1, WEE1, HDAC2, RBX1, CDK4, CSN5, FOXM1, and/or R1 gene expression; (b) a cationic lipid (e.g., cationic lipid of Formula I-XVI) or a salt thereof comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:57" formulation. In one particular embodiment, the 1:57 formulation is a four-component system comprising about 1.4 mol % PEG-lipid conjugate (e.g., PEG2000-C-DMA), about 57.1 mol % cationic lipid (e.g., cationic lipid of Formula I-XVI) or a salt thereof, about 7.1 mol % DPPC (or DSPC), and about 34.3 mol % cholesterol (or derivative thereof).

In another aspect of this embodiment, the nucleic acid-lipid particle comprises: (a) one or more (e.g., a cocktail) of the interfering RNAs (e.g., siRNAs) described herein that target COP1, WEE1, HDAC2, RBX1, CDK4, CSN5, FOXM1, and/or R1 gene expression; (b) a cationic lipid (e.g., cationic lipid of Formula I-XVI) or a salt thereof comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:62" formulation. In one particular embodiment, the 1:62 formulation is a three-component system which is phospholipid-free and comprises about 1.5 mol % PEG-lipid conjugate (e.g., PEG2000-C-DMA), about 61.5 mol % cationic lipid (e.g., cationic lipid of Formula I-XVI) or a salt thereof, and about 36.9 mol % cholesterol (or derivative thereof).

Additional embodiments related to the 1:57 and 1:62 formulations are described in PCT Publication No. WO 09/127, 060 and U.S. application Ser. No. 12/794,701, filed Jun. 4, 2010, the disclosures of which are herein incorporated by reference in their entirety for all purposes.

In other embodiments, the present invention provides nucleic acid-lipid particles (e.g., SNALP) comprising: (a) one or more (e.g., a cocktail) of the interfering RNAs (e.g., siRNAs) described herein that target COP1, WEE1, HDAC2, RBX1, CDK4, CSN5, FOXM1, and/or R1 gene expression; (b) one or more cationic lipids (e.g., cationic lipids of Formula I-XVI) or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) one or more (e.g., a cocktail) of the interfering RNAs (e.g., siRNAs) described herein that target COP1, WEE1, HDAC2, RBX1, CDK4, CSN5, FOXM1, and/or R1 gene expression; (b) a cationic lipid (e.g., cationic lipid of Formula I-XVI) or a salt thereof comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. This embodiment of nucleic acid-lipid particle is generally referred to herein as the "2:40" formulation. In one particular embodiment, the 2:40 formulation is a four-component system which comprises about 2 mol % PEG-lipid conjugate (e.g., PEG2000-C-DMA), about 40 mol % cationic lipid (e.g., cationic lipid of Formula I-XVI) or a salt thereof, about 10 mol % DPPC (or DSPC), and about 48 mol % cholesterol (or derivative thereof).

In further embodiments, the present invention provides nucleic acid-lipid particles (e.g., SNALP) comprising: (a) one or more (e.g., a cocktail) of the interfering RNAs (e.g., siRNAs) described herein that target COP1, WEE1, HDAC2, RBX1, CDK4, CSN5, FOXM1, and/or R1 gene expression; (b) one or more cationic lipids (e.g., cationic lipids of Formula I-XVI) or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In one aspect of this embodiment, the nucleic acid-lipid particle comprises: (a) one or more (e.g., a cocktail) of the interfering RNAs (e.g., siRNAs) described herein that target COP1, WEE1, HDAC2, RBX1, CDK4, CSN5, FOXM1, and/ or R1 gene expression; (b) a cationic lipid (e.g., cationic lipid of Formula I-XVI) or a salt thereof comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:54" formulation. In certain instances, the non-cationic lipid mixture in the 7:54 formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the 7:54 formulation is a four-component system comprising about 7 mol % PEG-lipid conjugate (e.g., PEG750-C-DMA), about 54 mol % cationic lipid (e.g., cationic lipid of Formula I-XVI) or a salt thereof, about 7 mol % DPPC (or DSPC), and about 32 mol % cholesterol (or derivative thereof).

In another aspect of this embodiment, the nucleic acid-lipid particle comprises: (a) one or more (e.g., a cocktail) of the interfering RNAs (e.g., siRNAs) described herein that target COP1, WEE1, HDAC2, RBX1, CDK4, CSN5, FOXM1, and/or R1 gene expression; (b) a cationic lipid (e.g., cationic lipid of Formula I-XVI) or a salt thereof comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:58" formulation. In one particular embodiment, the 7:58 formulation is a three-component system which is phospholipid-free and comprises about 7 mol % PEG-lipid conjugate (e.g., PEG750-C-DMA), about 58 mol % cationic lipid (e.g., cationic lipid of Formula I-XVI) or a salt thereof, and about 35 mol % cholesterol (or derivative thereof).

Additional embodiments related to the 7:54 and 7:58 formulations are described in U.S. application Ser. No. 12/828,189, filed Jun. 30, 2010, the disclosure of which is herein incorporated by reference in its entirety for all purposes.

The present invention also provides pharmaceutical compositions comprising a nucleic acid-lipid particle such as a SNALP and a pharmaceutically acceptable carrier.

In another aspect, the present invention provides methods for introducing one or more of the interfering RNA (e.g., siRNA) molecules described herein into a cell, the method comprising contacting the cell with a nucleic acid-lipid particle (e.g., SNALP). In one particular embodiment, the cell is a tumor cell such as, e.g., a cell present in a solid tumor of a mammal (e.g., a human). In some instances, the solid tumor is a liver tumor such as, e.g., hepatocellular carcinoma. In other instances, the solid tumor is located outside of the liver. In particular embodiments, the interfering RNA (e.g., siRNA) molecule is preferentially introduced into the tumor cell as compared to other cells. In certain embodiments, the cell is a non-tumor cell present in a mammal that produces one or more angiogenic and/or growth factors associated with cell proliferation, tumorigenesis, or cell transformation.

In yet another aspect, the present invention provides methods for the in vivo delivery of one or more of the interfering RNA (e.g., siRNA) molecules described herein to a tumor such as a solid tumor, the method comprising administering to a mammal (e.g., human) a nucleic acid-lipid particle described herein (e.g., SNALP).

In still yet another aspect, the present invention provides methods for treating a cell proliferative disorder such as cancer in a mammal (e.g., human) in need thereof, the method comprising administering to the mammal a therapeutically effective amount of a nucleic acid-lipid particle (e.g., SNALP) comprising one or more of the interfering RNA (e.g., siRNA) molecules described herein.

Non-limiting examples of cell proliferative disorders suitable for treatment with the nucleic acid-lipid particles of the invention include neoplasia (e.g., cancer), hyperplasia, restenosis, cardiac hypertrophy, immune disorders, and inflammation. Preferably, the cell proliferative disorder is a neoplastic disorder such as cancer. In some embodiments, the cancer includes, but is not limited to, liver cancer (e.g., hepatocellular carcinoma, secondary liver cancer, and hepatoblastoma), papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, lung cancer, colorectal cancer, thyroid cancer, pancreatic cancer, gastric cancer, leukemia, lymphoma, Hodgkin's disease, osteosarcoma, testicular cancer, and Burkitt's disease.

In one particular aspect, the present invention provides methods for introducing an interfering RNA such as an siRNA that silences the expression of a gene associated with cell proliferation, tumorigenesis, or cell transformation into a tumor cell of a mammal, the method comprising administering to the mammal a nucleic acid-lipid particle described herein (e.g., SNALP), wherein the siRNA is preferentially introduced into the tumor cell as compared to other cells. In certain embodiments, the tumor cell is present in a solid tumor of a mammal such as a human. In some instances, the solid tumor is a liver tumor. In other instances, the solid tumor is located outside of the liver. In certain other embodiments, the siRNA can also be introduced (e.g., preferentially) into non-tumor cells present in a mammal that produce one or more angiogenic and/or growth factors associated with cell proliferation, tumorigenesis, or cell transformation.

In a related aspect, the present invention provides methods for treating a cell proliferative disorder such as cancer by administering one or more of the interfering RNA (e.g., siRNA) molecules described herein in a nucleic acid-lipid particle (e.g., SNALP), alone or in combination with a chemotherapy drug. The methods can be carried out in vitro using standard tissue culture techniques or in vivo by administering the interfering RNA using any means known in the art. In preferred embodiments, the interfering RNA is delivered to a cancer cell in a mammal such as a human, alone or in combination with a chemotherapy drug. The nucleic acid-lipid particles and/or chemotherapy drugs may also be co-administered with conventional hormonal, immunotherapeutic, and/or radiotherapeutic agents.

In some embodiments, the nucleic acid-lipid particles of the present invention (e.g., SNALP) are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles are administered systemically, e.g., via enteral or parenteral routes of administration.

The nucleic acid-lipid particles of the invention (e.g., SNALP) are useful for the therapeutic delivery of interfering RNAs (e.g., siRNAs) that silence the expression of one or more genes associated with cell proliferation, tumorigenesis, or cell transformation (e.g., COP1, WEE1, HDAC2, RBX1, CDK4, CSN5, FOXM1, and/or R1). In some embodiments, a cocktail of siRNAs that target one or more genes expressed in tumor cells is formulated into the same or different nucleic acid-lipid particles (e.g., SNALP), and the particles are administered to a mammal (e.g., a human) requiring such treatment. In certain instances, a therapeutically effective amount of the nucleic acid-lipid particles (e.g., SNALP) can be administered to the mammal, e.g., for treating, preventing, reducing the risk of developing, or delaying the onset of cancer, e.g., by preferentially targeting a solid tumor.

In particular embodiments, the present invention provides in vitro and in vivo methods for treating a cell proliferative disorder such as cancer in a mammal (e.g., human) in need thereof by downregulating or silencing the transcription and/or translation of multiple (e.g., 2, 3, 4, 5, 6, 7, 8, or more) genes expressed in cancer (e.g., COP1, WEE1, HDAC2, RBX1, CDK4, CSN5, FOXM1, and/or R1). In certain embodiments, the invention provides a method for introducing a cocktail of siRNAs capable of silencing the expression of multiple genes expressed in cancer into a cell by contacting the cell with a nucleic acid-lipid particle described herein or a plurality of such particles comprising the siRNA cocktail (e.g., wherein each type of siRNA present in the cocktail is either co-encapsulated in the same particle or encapsulated in separate particles). In another embodiment, the invention provides a method for in vivo delivery of a cocktail of siRNA molecules capable of silencing the expression of multiple genes expressed in cancer by administering to a mammal a nucleic acid-lipid particle described herein or a plurality of such particles comprising the siRNA cocktail.

As described in the Examples below, it has surprisingly been found that the SNALP formulations of the present invention containing at least one cationic lipid of Formulas I-XVI (either alone or in combination with other cationic lipids) and at least one interfering RNA as described herein (e.g., one or more (e.g., a cocktail of) siRNA molecules that target COP1, WEE1, HDAC2, RBX1, CDK4, CSN5, FOXM1, and/or R1 gene expression) show increased potency (i.e., increased silencing activity) and/or increased tolerability (e.g., a more favorable toxicity profile) when targeting a gene of interest in a tumor cell, e.g., when compared to other SNALP formulations. Thus, in certain embodiments, the present invention provides methods for treating a disease or disorder associated with overexpression of COP1, WEE1, HDAC2, RBX1, CDK4, CSN5, FOXM1, and/or R1 in a mammal (e.g., human) in need thereof, the method comprising administering to the mammal a therapeutically effective amount of a nucleic acid-lipid particle (e.g., SNALP) comprising one or more interfering RNA molecules that silence the overexpressed gene or genes. Diseases and disorders associated with overexpression of COP1, WEE1, HDAC2, RBX1, CDK4, CSN5, FOXM1, and/or R1 are described herein and include, but are not limited to, cell proliferative disorders such as cancer.

In certain instances, a subsequent dose of a nucleic acid-lipid particle formulation described herein (e.g., a SNALP formulation) can be administered about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, or 24 hours, or about 1, 2, 3, 4, 5, 6, 7, 8, 9, 10, 11, 12, 13, or 14 days, or about 1, 2, 3, 4, 5, 6, 7, 8, 9, or 10 weeks, or about 1, 2, 3, 4, 5, or 6 months, or any interval thereof, after the initial dose of the same or different nucleic acid-lipid particle formulation. In one particular embodiment, more than one dose of nucleic acid-lipid particles containing one or a cocktail of the interfering RNAs (e.g., siRNAs) described herein can be administered at different times in accordance with a cancer therapy regimen. In certain instances, a mammal (e.g., human) diagnosed with a cell proliferative disorder such as cancer can be treated with a second, third, fourth, fifth, sixth, seventh, eighth, ninth, tenth, or more dose of the same or different nucleic acid-lipid particles containing one or a cocktail of the interfering RNAs (e.g., siRNAs) described herein. In another embodiment, a mammal (e.g., human) diagnosed with a cell proliferative disorder such as cancer can be treated with a daily dose of the same or different particles containing one or a cocktail of the interfering RNAs (e.g., siRNAs) described herein and assessed for a reduction in cell proliferation (e.g., decrease in tumor size) and/or a reduction in the severity of clinical symptoms associated with the cell proliferative disorder. In some embodiments, a mammal (e.g., human) susceptible to developing a cell proliferative disorder such as cancer may be pretreated with one or more doses of nucleic acid-lipid particles containing one or a cocktail of the interfering RNAs (e.g., siRNAs) described herein as a prophylactic measure for preventing the cell proliferative disorder.

In certain aspects, the present invention provides methods for silencing COP1, WEE1, HDAC2, RBX1, CDK4, CSN5, FOXM1, and/or R1 gene expression in a mammal (e.g., human) in need thereof, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting COP1, WEE1, HDAC2, RBX1, CDK4, CSN5, FOXM1, and/or R1). In some embodiments, administration of nucleic acid-lipid particles comprising one or more siRNAs described herein reduces mRNA levels of each target gene (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to mRNA levels of that target gene detected in the absence of the siRNA (e.g., buffer control or irrelevant siRNA control). In other embodiments, administration of nucleic acid-lipid particles comprising one or more siRNAs described herein reduces mRNA levels of each target gene (e.g., in a human or in an animal model such as a mouse model or monkey model) for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant siRNA control.

In certain other aspects, the present invention provides methods for treating, preventing, reducing the risk or likelihood of developing (e.g., reducing the susceptibility to), delaying the onset of, and/or ameliorating one or more symptoms associated with a cell proliferative disorder in a mammal (e.g., human) in need thereof, the method comprising administering to the mammal a therapeutically effective amount of a nucleic acid-lipid particle (e.g., a SNALP formulation) comprising one or more interfering RNA molecules (e.g., siRNAs) described herein (e.g., one or more siRNAs targeting the COP1, WEE1, HDAC2, RBX1, CDK4, CSN5, FOXM1, and/or R1 gene).

In a related aspect, the present invention provides a method for treating and/or ameliorating one or more symptoms associated with a cell proliferative disorder such as cancer in a mammal (e.g., human) in need thereof, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the COP1, WEE1, HDAC2, RBX1, CDK4, CSN5, FOXM1, and/or R1 gene). In some embodiments, administration of nucleic acid-lipid particles (e.g., SNALP) comprising one or more siRNA molecules described herein reduces tumor size and/or volume (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to the tumor size and/or volume detected in the absence of the siRNA (e.g., buffer control or irrelevant siRNA control).

In another related aspect, the present invention provides a method for reducing the risk or likelihood of developing (e.g., reducing the susceptibility to) a cell proliferative disorder such as cancer in a mammal (e.g., human) at risk of developing the cell proliferative disorder, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the COP1, WEE1, HDAC2, RBX1, CDK4, CSN5, FOXM1, and/or R1 gene). In some embodiments, administration of nucleic acid-lipid particles comprising one or more siRNA molecules described herein reduces the risk or likelihood of developing a cell proliferative disorder (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to the risk or likelihood of developing the cell proliferative disorder in the absence of the siRNA (e.g., buffer control or irrelevant siRNA control).

In yet another related aspect, the present invention provides a method for preventing or delaying the onset of a cell proliferative disorder such as cancer in a mammal (e.g., human) at risk of developing the cell proliferative disorder, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting COP1, WEE1, HDAC2, RBX1, CDK4, CSN5, FOXM1, and/or R1).

IV. Therapeutic Nucleic Acids

The term "nucleic acid" includes any oligonucleotide or polynucleotide, with fragments containing up to 60 nucleotides generally termed oligonucleotides, and longer fragments termed polynucleotides. In particular embodiments, oligonucleotides of the invention are from about 15 to about 60 nucleotides in length. In some embodiments, nucleic acid is associated with a carrier system such as the lipid particles described herein. In certain embodiments, the nucleic acid is fully encapsulated in the lipid particle. Nucleic acid may be administered alone in the lipid particles of the invention, or in combination (e.g., co-administered) with lipid particles comprising peptides, polypeptides, or small molecules such as conventional drugs.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid according to this invention includes any form of nucleic acid that is known. The nucleic acids used herein can be single-stranded DNA or RNA, or double-stranded DNA or RNA, or DNA-RNA hybrids. Examples of double-stranded DNA are described herein and include, e.g., structural genes, genes including control and termination regions, and self-replicating systems such as viral or plasmid DNA. Examples of double-stranded RNA are described herein and include, e.g., siRNA and other RNAi agents such as Dicer-substrate dsRNA, shRNA, aiRNA, and pre-miRNA. Single-stranded nucleic acids include, e.g., antisense oligonucleotides, ribozymes, mature miRNA, and triplex-forming oligonucleotides. In further embodiments, the nucleic acids are double-stranded DNA. Examples of double-stranded DNA include, e.g., DNA-DNA hybrids comprising a DNA sense strand and a DNA antisense strand as described in PCT Publication No. WO 2004/104199, the disclosure of which is herein incorporated by reference in its entirety for all purposes.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

A. siRNA

The unmodified and modified siRNA molecules of the invention are capable of silencing the expression of a gene associated with tumorigenesis or cell transformation such as a gene expressed in cancer, e.g., to inhibit the proliferation and/or to induce apoptosis of cancer cells. Each strand of the siRNA duplex is typically about 15 to about 60 nucleotides in length, preferably about 15 to about 30 nucleotides in length. In certain embodiments, the siRNA comprises at least one modified nucleotide. The modified siRNA is generally less immunostimulatory than a corresponding unmodified siRNA sequence and retains RNAi activity against the target gene of interest. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. The modified nucleotides can be present in one strand (i.e., sense or antisense) or both strands of the siRNA. In some preferred embodiments, one or more of the uridine and/or guanosine nucleotides are modified (e.g., 2'OMe-modified) in one strand (i.e., sense or antisense) or both strands of the siRNA. In these embodiments, the modified siRNA can further comprise one or more modified (e.g., 2'OMe-modified) adenosine and/or modified (e.g., 2'OMe-modified) cytosine nucleotides. In other preferred embodiments, only uridine and/or guanosine nucleotides are modified (e.g., 2'OMe-modified) in one strand (i.e., sense or antisense) or both strands of the siRNA. The siRNA sequences may have overhangs (e.g., 3' or 5' overhangs as described in Elbashir et al., *Genes Dev.*, 15:188 (2001) or Nykänen et al., *Cell*, 107:309 (2001)), or may lack overhangs (i.e., have blunt ends).

In particular embodiments, the selective incorporation of modified nucleotides such as 2'OMe uridine and/or guanosine nucleotides into the double-stranded region of either or both strands of the siRNA reduces or completely abrogates the immune response to that siRNA molecule. In certain instances, the immunostimulatory properties of specific siRNA sequences and their ability to silence gene expression can be balanced or optimized by the introduction of minimal and selective 2'OMe modifications within the double-stranded region of the siRNA duplex. This can be achieved at therapeutically viable siRNA doses without cytokine induction, toxicity, and off-target effects associated with the use of unmodified siRNA.

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides. In certain other embodiments, some or all of the modified nucleotides in the double-stranded region of the siRNA are 1, 2, 3, 4, 5, 6, 7, 8, 9, 10, or more nucleotides apart from each other. In one preferred embodiment, none of the modified nucleotides in the double-stranded region of the siRNA are adjacent to each other (e.g., there is a gap of at least 1, 2, 3, 4, 5, 6, 7, 8, 9, or 10 unmodified nucleotides between each modified nucleotide).

In some embodiments, less than about 50% (e.g., less than about 49%, 48%, 47%, 46%, 45%, 44%, 43%, 42%, 41%, 40%, 39%, 38%, 37%, or 36%, preferably less than about 35%, 34%, 33%, 32%, 31%, or 30%) of the nucleotides in the double-stranded region of the siRNA comprise modified (e.g., 2'OMe) nucleotides. In one aspect of these embodiments, less than about 50% of the uridine and/or guanosine nucleotides in the double-stranded region of one or both strands of the siRNA are selectively (e.g., only) modified. In another aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In other embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 25%-39%, 25%-38%, 25%-37%, 25%-36%, 26%-39%, 26%-38%, 26%-37%, 26%-36%, 27%-39%, 27%-38%, 27%-37%, 27%-36%, 28%-39%, 28%-38%, 28%-37%, 28%-36%, 29%-39%, 29%-38%, 29%-37%, 29%-36%, 30%-40%, 30%-39%, 30%-38%, 30%-37%, 30%-36%, 31%-39%, 31%-38%, 31%-37%, 31%-36%, 32%-39%, 32%-38%, 32%-37%, 32%-36%, 33%-39%, 33%-38%, 33%-37%, 33%-36%, 34%-39%, 34%-38%, 34%-37%, 34%-36%, 35%-40%, 5%-35%, 10%-35%, 15%-35%, 20%-35%, 21%-35%, 22%-35%, 23%-35%, 24%-35%, 25%-35%, 26%-35%, 27%-35%, 28%-35%, 29%-35%, 30%-35%, 31%-35%, 32%-35%, 33%-35%, 34%-35%, 30%-34%, 31%-34%, 32%-34%, 33%-34%, 30%-33%, 31%-33%, 32%-33%, 30%-32%, 31%-32%, 25%-34%, 25%-33%, 25%-32%, 25%-31%, 26%-34%, 26%-33%, 26%-32%, 26%-31%, 27%-34%, 27%-33%, 27%-32%, 27%-31%, 28%-34%, 28%-33%, 28%-32%, 28%-31%, 29%-34%, 29%-33%, 29%-32%, 29%-31%, 5%-30%, 10%-30%, 15%-30%, 20%-34%, 20%-33%, 20%-32%, 20%-31%, 20%-30%, 21%-30%, 22%-30%, 23%-30%, 24%-30%, 25%-30%, 25%-29%, 25%-28%, 25%-27%, 25%-26%, 26%-30%, 26%-29%, 26%-28%, 26%-27%, 27%-30%, 27%-29%, 27%-28%, 28%-30%, 28%-29%, 29%-30%, 5%-25%, 10%-25%, 15%-25%, 20%-25%, 20%-29%, 20%-28%, 20%-27%, 20%-26%, 20%-25%, 5%-20%, 10%-20%, 15%-20%, 5%-15%, 10%-15%, or 5%-10%) of the nucleotides in the double-stranded region of the siRNA comprise modified nucleotides. In one aspect of these embodiments, from about 1% to about 50% of the uridine and/or guanosine nucleotides in the double-stranded region of one or both strands of the siRNA are selectively (e.g., only) modified. In another aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In certain embodiments, the siRNA molecules of the present invention comprise an asymmetric siRNA duplex as described in PCT Publication No. WO 2004/078941, which comprises a double-stranded region consisting of a DNA sense strand and an RNA antisense strand (e.g., a DNA-RNA hybrid), wherein a blocking agent is located on the siRNA duplex. In some instances, the asymmetric siRNA duplex can be chemically modified as described herein. Other non-limiting examples of asymmetric siRNA duplexes are described in PCT Publication No. WO 2006/074108, which discloses self-protected oligonucleotides comprising a region having a sequence complementary to one, two, three, or more same or different target mRNA sequences (e.g., multivalent siRNAs) and one or more self-complementary regions. Yet other non-limiting examples of asymmetric siRNA duplexes are described in PCT Publication No. WO 2009/076321, which discloses self-forming asymmetric precursor polynucleotides comprising a targeting region comprising a polynucleotide sequence complementary to a region of one, two, three, or more same or different target mRNA sequences (e.g., multivalent siRNAs); a first self-complementary region; and a second self-complementary region, wherein the first and second self-complementary regions are located one at each end of the targeting region and both self-complementary regions form stem-loop structures, wherein the first self-complementary region is capable of being cleaved by a RNase III endoribonuclease that is not a class IV DICER endoribonuclease, and wherein both self-complementary regions comprise a nucleotide sequence that is complementary to a region of the target gene sequence, but wherein a portion of the target sequence present in the targeting region does not have a complementary sequence in either of the self-complementary regions. The disclosures of each of the above patent documents are herein incorporated by reference in their entirety for all purposes.

Additional ranges, percentages, and patterns of modifications that may be introduced into siRNA are described in U.S. Patent Publication No. 20070135372, the disclosure of which is herein incorporated by reference in its entirety for all purposes.

1. Selection of siRNA Sequences

Suitable siRNA sequences can be identified using any means known in the art. Typically, the methods described in Elbashir et al., *Nature*, 411:494-498 (2001) and Elbashir et al., *EMBO J.*, 20:6877-6888 (2001) are combined with rational design rules set forth in Reynolds et al., *Nature Biotech.*, 22(3):326-330 (2004).

As a non-limiting example, the nucleotide sequence 3' of the AUG start codon of a transcript from the target gene of interest may be scanned for dinucleotide sequences (e.g., AA, NA, CC, GG, or UU, wherein N=C, G, or U) (see, e.g., Elbashir et al., *EMBO J.*, 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://ihome.ust.hk/~bokcmho/siRNA/siRNA.html. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., *Cell*, 115:209-216 (2003); and Schwarz et al., *Cell*, 115:199-208 (2003). In other embodiments, potential siRNA sequences may be further analyzed based on secondary structure at the target site as described in, e.g., Luo et al., *Biophys. Res. Commun.*, 318: 303-310 (2004). For example, secondary structure at the target site can be modeled using the Mfold algorithm (available at http://mfold.burnet.edu.au/rna_form) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-8, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.*, 255:4980-4983 (1980)); enzyme-linked immunosorbent assays (ELISA) as described, for example, by Raines et al., *J. Biol. Chem.*, 257:5154-5160 (1982); immunocytochemical techniques, including the use of fluorochromes (Brooks et al., *Clin. Exp. Immunol.*, 39:477 (1980)); and neutralization of activity (Bowen-Pope et al., *Proc. Natl. Acad. Sci. USA*, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., *Mol. Ther.*, 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler et al., *Nature*, 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

2. Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene*, 25:263-269 (1983); Sambrook et al., supra; Ausubel et al., supra), as are PCR methods (see, U.S. Pat. Nos. 4,683,195 and 4,683,202; PCR Protocols: A Guide to Methods and Applications (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 μmol scale protocol. Alternatively, syntheses at the 0.2 μmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

3. Modifying siRNA Sequences

In certain aspects, siRNA molecules comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA molecule strikes a balance between reduction or abrogation of the immunostimulatory properties of the siRNA and retention of RNAi activity. As a non-limiting example, an siRNA molecule that targets a gene of interest can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence target gene expression.

Examples of modified nucleotides suitable for use in the invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in siRNA molecules. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.*, 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.*, 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl)nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxy ribonucleotides, modified (e.g., 2'OMe) and/or unmodified uridine ribonucleotides, and/or any other combination of modified (e.g., 2'OMe) and unmodified nucleotides.

Additional examples of modified nucleotides and types of chemical modifications that can be introduced into siRNA molecules are described, e.g., in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

4. Target Genes

The siRNA molecules of the invention can be used to downregulate or silence the translation (i.e., expression) of one or more genes associated with tumorigenesis or cell transformation (e.g., cancer), such as genes involved in p53 ubiquitination (e.g., COP1, CSN5), c-Jun ubiquitination (e.g., RBX1), histone deacetylation (e.g., HDAC2), cell cycle regulation (e.g., CDK4, WEE1, FOXM1), transcriptional regulation (e.g., R1 (RAM2)), or combinations thereof. In particular embodiments, the present invention provides a cocktail of two, three, four, five, six, seven, eight, nine, ten, or more siRNA molecules that silences the expression of multiple genes expressed in cancer. In some embodiments, the cocktail of siRNA molecules is fully encapsulated in a lipid particle such as a nucleic acid-lipid particle (e.g., SNALP). The siRNA molecules may be co-encapsulated in the same lipid particle, or each siRNA species present in the cocktail may be formulated in separate particles.

Examples of gene sequences associated with tumorigenesis or cell transformation (e.g., cancer or other neoplasia) include, but are not limited to, serine/threonine kinases such as polo-like kinase 1 (PLK-1) (Genbank Accession No. NM_005030; Barr et al., *Nat. Rev. Mol. Cell Biol.*, 5:429-440 (2004)) and cyclin-dependent kinase 4 (CDK4) (Genbank Accession No. NM_000075); ubiquitin ligases such as COP1 (RFWD2; Genbank Accession Nos. NM_022457 and NM_001001740) and ring-box 1 (RBX1) (ROC1; Genbank Accession No. NM_014248); tyrosine kinases such as WEE1 (Genbank Accession Nos. NM_003390 and NM_001143976); mitotic kinesins such as Eg5 (KSP, KIF11; Genbank Accession No. NM_004523); transcription factors such as forkhead box M1 (FOXM1) (Genbank Accession Nos. NM_202002, NM_021953, and NM_202003) and RAM2 (R1 or CDCA7L; Genbank Accession Nos. NM_018719, NM_001127370, and NM_001127371); inhibitors of apoptosis such as XIAP (Genbank Accession No. NM_001167); COP9 signalosome subunits such as CSN1, CSN2, CSN3, CSN4, CSN5 (JAB1; Genbank Accession No. NM_006837); CSN6, CSN7A, CSN7B, and CSN8; and histone deacetylases such as HDAC1, HDAC2 (Genbank Accession No. NM_001527), HDAC3, HDAC4, HDAC5, HDAC6, HDAC7, HDAC8, HDAC9, etc.

Non-limiting examples of siRNA molecules targeting the PLK-1 gene include those described herein and in U.S. Patent Publication Nos. 20050107316 and 20070265438; and PCT Publication No. WO 09/082,817, the disclosures of which are herein incorporated by reference in their entirety for all purposes. Non-limiting examples of siRNA molecules targeting the Eg5 and XIAP genes include those described in U.S. Patent Publication No. 20090149403, the disclosure of which is herein incorporated by reference in its entirety for all purposes. Non-limiting examples of siRNA molecules targeting the CSN5 gene include those described in PCT Publication No. WO 09/129,319, the disclosure of which is herein incorporated by reference in its entirety for all purposes.

Additional examples of gene sequences associated with tumorigenesis or cell transformation include translocation sequences such as MLL fusion genes, BCR-ABL (Wilda et al., *Oncogene,* 21:5716 (2002); Scherr et al., *Blood,* 101:1566 (2003)), TEL-AML1, EWS-FLI1, TLS-FUS, PAX3-FKHR, BCL-2, AML1-ETO, and AML1-MTG8 (Heidenreich et al., *Blood,* 101:3157 (2003)); overexpressed sequences such as multidrug resistance genes (Nieth et al., *FEBS Lett.,* 545:144 (2003); Wu et al, *Cancer Res.* 63:1515 (2003)), cyclins (Li et al., *Cancer Res.,* 63:3593 (2003); Zou et al., *Genes Dev.,* 16:2923 (2002)), beta-catenin (Verma et al., *Clin Cancer Res.,* 9:1291 (2003)), telomerase genes (Kosciolek et al., *Mol Cancer Ther.,* 2:209 (2003)), c-MYC, N-MYC, BCL-2, growth factor receptors (e.g., EGFR/ErbB1 (Genbank Accession Nos. NM_005228, NM_201282, NM_201283, and NM_201284; see also, Nagy et al. *Exp. Cell Res.,* 285:39-49 (2003)), ErbB2/HER-2 (Genbank Accession Nos. NM_004448 and NM_001005862), ErbB3 (Genbank Accession Nos. NM_001982 and NM_001005915), and ErbB4 (Genbank Accession Nos. NM_005235 and NM_001042599)), angiogenic genes (e.g., VEGF (Reich et al., *Mol. Vis.,* 9:210 (2003)), PGF, VEGFR-1 (Flt-1), VEGFR-2 (KDR/Flk-1), etc.), and cell receptor ligand genes (e.g., cytokines, growth factors, etc.); and mutated sequences such as RAS (Tuschl and Borkhardt, *Mol. Interventions,* 2:158 (2002)). Non-limiting examples of siRNA molecules targeting the EGFR gene include those described in U.S. Patent Publication No. 20090149403, the disclosure of which is herein incorporated by reference in its entirety for all purposes. siRNA molecules that target VEGFR genes are set forth in, e.g., GB 2396864; U.S. Patent Publication No. 20040142895; and CA 2456444, the disclosures of which are herein incorporated by reference in their entirety for all purposes.

Silencing of sequences that encode DNA repair enzymes find use in combination with the administration of chemotherapeutic agents (Collis et al., *Cancer Res.,* 63:1550 (2003)). Genes encoding proteins associated with tumor migration are also target sequences of interest, for example, integrins, selectins, and metalloproteinases. The foregoing examples are not exclusive. Those of skill in the art will understand that any whole or partial gene sequence that facilitates or promotes tumorigenesis or cell transformation, tumor growth, or tumor migration can be included as a template sequence.

Angiogenic genes are able to promote the formation of new vessels. Angiogenic genes of particular interest include, but are not limited to, vascular endothelial growth factor (VEGF) (Reich et al., *Mol. Vis.,* 9:210 (2003)), placental growth factor (PGF), VEGFR-1 (Flt-1), VEGFR-2 (KDR/Flk-1), and the like. siRNA molecules that target VEGFR genes are set forth in, e.g., GB 2396864; U.S. Patent Publication No. 20040142895; and CA 2456444, the disclosures of which are herein incorporated by reference in their entirety for all purposes.

Cell receptor ligand genes include ligands that are able to bind to cell surface receptors (e.g., cytokine receptors, growth factor receptors, receptors with tyrosine kinase activity, G-protein coupled receptors, insulin receptor, EPO receptor, etc.) to modulate (e.g., inhibit) the physiological pathway that the receptor is involved in (e.g., cell proliferation, tumorigenesis, cell transformation, mitogenesis, etc.). Non-limiting examples of cell receptor ligand genes include cytokines (e.g., TNF-α, interferons such as IFN-α, IFN-β, and IFN-γ, interleukins such as IL-1α, IL-1β, IL-2, IL-4, IL-5, IL-6, IL-7, IL-8, IL-9, IL-10, IL-12, IL-13, IL-15, IL-17, IL-18, IL-20, IL-23, IL-27, chemokines, etc.), growth factors (e.g., EGF, HB-EGF, VEGF, PEDF, SDGF, bFGF, HGF, TGF-α, TGF-β, BMP1-BMP15, PDGF, IGF, NGF, β-NGF, BDNF, NT3, NT4, GDF-9, CGF, G-CSF, GM-CSF, GDF-8, EPO, TPO, etc.), insulin, glucagon, G-protein coupled receptor ligands, etc.

In addition to its utility in silencing the expression of any of the above-described genes for therapeutic purposes, the siRNA described herein are also useful in research and development applications as well as diagnostic, prophylactic, prognostic, clinical, and other healthcare applications. As a non-limiting example, the siRNA can be used in target validation studies directed at testing whether a gene of interest has the potential to be a therapeutic target. The siRNA can also be used in target identification studies aimed at discovering genes as potential therapeutic targets.

5. Exemplary siRNA Embodiments

In some embodiments, each strand of the siRNA molecule comprises from about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). In one particular embodiment, the siRNA is chemically synthesized. The siRNA molecules of the invention are capable of silencing the expression of a target sequence in vitro and/or in vivo.

In other embodiments, the siRNA comprises at least one modified nucleotide. In certain embodiments, the siRNA comprises one, two, three, four, five, six, seven, eight, nine, ten, or more modified nucleotides in the double-stranded region. In particular embodiments, less than about 50% (e.g., less than about 50%, 45%, 40%, 35%, 30%, 25%, 20%, 15%, 10%, or 5%) of the nucleotides in the double-stranded region of the siRNA comprise modified nucleotides. In preferred embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 30%-40%, 35%-40%, 5%-35%, 10%-35%, 15%-35%, 20%-35%, 25%-35%, 30%-35%, 5%-30%, 10%-30%, 15%-30%, 20%-30%, 25%-30%, 5%-25%, 10%-25%, 15%-25%, 20%-25%, 5%-20%, 10%-20%, 15%-20%, 5%-15%, 10%-15%, or 5%-10%) of the nucleotides in the double-stranded region of the siRNA comprise modified nucleotides.

In further embodiments, the siRNA comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, e.g., 2'OMe-guanosine nucleotides, 2'OMe-uridine nucleotides, 2'OMe-adenosine nucleotides, 2'OMe-cytosine nucleotides, or mixtures thereof. In one particular embodiment, the siRNA comprises at least one 2'OMe-guanosine nucleotide, 2'OMe-uridine nucleotide, or mixtures thereof. In certain instances, the siRNA does not comprise 2'OMe-cytosine nucleotides. In other embodiments, the siRNA comprises a hairpin loop structure.

In certain embodiments, the siRNA comprises modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In other embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In another embodiment, an unmodified or modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to a negative control (e.g., buffer only, an siRNA sequence that targets a different gene, a scrambled siRNA sequence, etc.).

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. In certain embodiments, the 3' overhang on the sense and/or antisense strand independently comprises one, two, three, four, or more modified nucleotides such as 2'OMe nucleotides and/or any other modified nucleotide described herein or known in the art.

In particular embodiments, siRNAs are administered using a carrier system such as a nucleic acid-lipid particle (e.g., SNALP). In a preferred embodiment, the nucleic acid-lipid particle comprises: (a) one or more (e.g., a cocktail of at least 2, 3, 4, 5, 6, 7, or 8) siRNA molecules targeting the COP1, CSN5, RBX1, HDAC2, CDK4, WEE1, FOXM1, and/or R1 genes; (b) a cationic lipid of Formula I-XVI or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA). In another preferred embodiment, a combination of siRNA molecules targeting the COP1, CSN5, RBX1, HDAC2, CDK4, WEE1, FOXM1, and/or R1 genes is administered using the nucleic acid-lipid particles described herein, and the siRNAs present in the cocktail are either co-encapsulated in the same particle or are encapsulated in separate particles such that there is only one type of siRNA species in each particle.

B. Dicer-Substrate dsRNA

As used herein, the term "Dicer-substrate dsRNA" or "precursor RNAi molecule" is intended to include any precursor molecule that is processed in vivo by Dicer to produce an active siRNA which is incorporated into the RISC complex for RNA interference of a target gene.

In one embodiment, the Dicer-substrate dsRNA has a length sufficient such that it is processed by Dicer to produce an siRNA. According to this embodiment, the Dicer-substrate dsRNA comprises (i) a first oligonucleotide sequence (also termed the sense strand) that is between about 25 and about 60 nucleotides in length (e.g., about 25-60, 25-55, 25-50, 25-45, 25-40, 25-35, or 25-30 nucleotides in length), preferably between about 25 and about 30 nucleotides in length (e.g., 25, 26, 27, 28, 29, or 30 nucleotides in length), and (ii) a second oligonucleotide sequence (also termed the antisense strand) that anneals to the first sequence under biological conditions, such as the conditions found in the cytoplasm of a cell. The second oligonucleotide sequence may be between about 25 and about 60 nucleotides in length (e.g., about 25-60, 25-55, 25-50, 25-45, 25-40, 25-35, or 25-30 nucleotides in length), and is preferably between about 25 and about 30 nucleotides in length (e.g., 25, 26, 27, 28, 29, or 30 nucleotides in length). In addition, a region of one of the sequences, particularly of the antisense strand, of the Dicer-substrate dsRNA has a sequence length of at least about 19 nucleotides, for example, from about 19 to about 60 nucleotides (e.g., about 19-60, 19-55, 19-50, 19-45, 19-40, 19-35, 19-30, or 19-25 nucleotides), preferably from about 19 to about 23 nucleotides (e.g., 19, 20, 21, 22, or 23 nucleotides) that are sufficiently complementary to a nucleotide sequence of the RNA produced from the target gene to trigger an RNAi response.

In a second embodiment, the Dicer-substrate dsRNA has several properties which enhance its processing by Dicer. According to this embodiment, the dsRNA has a length sufficient such that it is processed by Dicer to produce an siRNA and has at least one of the following properties: (i) the dsRNA is asymmetric, e.g., has a 3'-overhang on the antisense strand; and/or (ii) the dsRNA has a modified 3'-end on the sense strand to direct orientation of Dicer binding and processing of the dsRNA to an active siRNA. According to this latter embodiment, the sense strand comprises from about 22 to about 28 nucleotides and the antisense strand comprises from about 24 to about 30 nucleotides.

In one embodiment, the Dicer-substrate dsRNA has an overhang on the 3'-end of the antisense strand. In another embodiment, the sense strand is modified for Dicer binding and processing by suitable modifiers located at the 3'-end of the sense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the Dicer-substrate dsRNA has an overhang on the 3'-end of the antisense strand and the sense strand is modified for Dicer processing. In another embodiment, the 5'-end of the sense strand has a phosphate. In another embodiment, the 5'-end of the antisense strand has a phosphate. In another embodiment, the antisense strand or the sense strand or both strands have one or more 2'-β-methyl (2'OMe) modified nucleotides. In another embodiment, the antisense strand contains 2'OMe modified nucleotides. In another embodiment, the antisense stand contains a 3'-overhang that is comprised of 2'OMe modified nucleotides. The antisense strand could also include additional 2'OMe modified nucleotides. The sense and antisense strands anneal under biological conditions, such as the conditions found in the cytoplasm of a cell. In addition, a region of one of the sequences, particularly of the antisense strand, of the Dicer-substrate dsRNA has a sequence length of at least about 19 nucleotides, wherein these nucleotides are in the 21-nucleotide region adjacent to the 3'-end of the antisense strand and are sufficiently complementary to a nucleotide sequence of the RNA produced from the target gene. Further, in accordance with this embodiment, the Dicer-substrate dsRNA may also have one or more of the following additional properties: (a) the antisense strand has a right shift from the typical 21-mer (i.e., the antisense strand includes nucleotides on the right side of the molecule when compared to the typical 21-mer); (b) the strands may not be completely complementary, i.e., the strands may contain simple mismatch pairings; and (c) base modifications such as locked nucleic acid(s) may be included in the 5'-end of the sense strand.

In a third embodiment, the sense strand comprises from about 25 to about 28 nucleotides (e.g., 25, 26, 27, or 28 nucleotides), wherein the 2 nucleotides on the 3'-end of the sense strand are deoxyribonucleotides. The sense strand contains a phosphate at the 5'-end. The antisense strand comprises from about 26 to about 30 nucleotides (e.g., 26, 27, 28, 29, or 30 nucleotides) and contains a 3'-overhang of 1-4 nucleotides. The nucleotides comprising the 3'-overhang are modified with 2'OMe modified ribonucleotides. The antisense strand contains alternating 2'OMe modified nucleotides beginning at the first monomer of the antisense strand adjacent to the 3'-overhang, and extending 15-19 nucleotides from the first monomer adjacent to the 3'-overhang. For example, for a 27-nucleotide antisense strand and counting the first base at the 5'-end of the antisense strand as position number 1, 2'OMe modifications would be placed at bases 9, 11, 13, 15, 17, 19, 21, 23, 25, 26, and 27. In one embodiment, the Dicer-substrate dsRNA has the following structure:

```
5'-pXXXXXXXXXXXXXXXXXXXXXXXDD-3'

3'-YXXXXXXXXXXXXXXXXXXXXXXXXp-5'
``` wherein "X"=RNA, "p"=a phosphate group, "X"=2'OMe RNA, "Y" is an overhang domain comprised of 1, 2, 3, or 4 RNA monomers that are optionally 2'OMe RNA monomers, and "D"=DNA. The top strand is the sense strand, and the bottom strand is the antisense strand.

In a fourth embodiment, the Dicer-substrate dsRNA has several properties which enhance its processing by Dicer. According to this embodiment, the dsRNA has a length sufficient such that it is processed by Dicer to produce an siRNA and at least one of the following properties: (i) the dsRNA is asymmetric, e.g., has a 3'-overhang on the sense strand; and (ii) the dsRNA has a modified 3'-end on the antisense strand to direct orientation of Dicer binding and processing of the dsRNA to an active siRNA. According to this embodiment, the sense strand comprises from about 24 to about 30 nucleotides (e.g., 24, 25, 26, 27, 28, 29, or 30 nucleotides) and the antisense strand comprises from about 22 to about 28 nucleotides (e.g., 22, 23, 24, 25, 26, 27, or 28 nucleotides). In one embodiment, the Dicer-substrate dsRNA has an overhang on the 3'-end of the sense strand. In another embodiment, the antisense strand is modified for Dicer binding and processing by suitable modifiers located at the 3'-end of the antisense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the dsRNA has an overhang on the 3'-end of the sense strand and the antisense strand is modified for Dicer processing. In one embodiment, the antisense strand has a 5'-phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3'-end of antisense strand and are sufficiently complementary to a nucleotide sequence of the RNA produced from the target gene. Further, in accordance with this embodiment, the Dicer-substrate dsRNA may also have one or more of the following additional properties: (a) the antisense strand has a left shift from the typical 21-mer (i.e., the antisense strand includes nucleotides on the left side of the molecule when compared to the typical 21-mer); and (b) the strands may not be completely complementary, i.e., the strands may contain simple mismatch pairings.

In a preferred embodiment, the Dicer-substrate dsRNA has an asymmetric structure, with the sense strand having a 25-base pair length, and the antisense strand having a 27-base pair length with a 2 base 3'-overhang. In certain instances, this dsRNA having an asymmetric structure further contains 2 deoxynucleotides at the 3'-end of the sense strand in place of two of the ribonucleotides. In certain other instances, this dsRNA having an asymmetric structure further contains 2'OMe modifications at positions 9, 11, 13, 15, 17, 19, 21, 23, and 25 of the antisense strand (wherein the first base at the 5'-end of the antisense strand is position 1). In certain additional instances, this dsRNA having an asymmetric structure further contains a 3'-overhang on the antisense strand comprising 1, 2, 3, or 4 2'OMe nucleotides (e.g., a 3'-overhang of 2'OMe nucleotides at positions 26 and 27 on the antisense strand).

In another embodiment, Dicer-substrate dsRNAs may be designed by first selecting an antisense strand siRNA sequence having a length of at least 19 nucleotides. In some instances, the antisense siRNA is modified to include about 5 to about 11 ribonucleotides on the 5'-end to provide a length of about 24 to about 30 nucleotides. When the antisense strand has a length of 21 nucleotides, 3-9, preferably 4-7, or more preferably 6 nucleotides may be added on the 5'-end. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 22 to about 28 nucleotides. The sense strand is substantially complementary with the antisense strand to anneal to the antisense strand under biological conditions. In one embodiment, the sense strand is synthesized to contain a modified 3'-end to direct Dicer processing of the antisense strand. In another embodiment, the antisense strand of the dsRNA has a 3'-overhang. In a further embodiment, the sense strand is synthesized to contain a modified 3'-end for Dicer binding and processing and the antisense strand of the dsRNA has a 3'-overhang.

In a related embodiment, the antisense siRNA may be modified to include about 1 to about 9 ribonucleotides on the 5'-end to provide a length of about 22 to about 28 nucleotides. When the antisense strand has a length of 21 nucleotides, 1-7, preferably 2-5, or more preferably 4 ribonucleotides may be added on the 3'-end. The added ribonucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 24 to about 30 nucleotides. The sense strand is substantially complementary with the antisense strand to anneal to the antisense strand under biological conditions. In one embodiment, the antisense strand is synthesized to contain a modified 3'-end to direct Dicer processing. In another embodiment, the sense strand of the dsRNA has a 3'-overhang. In a further embodiment, the antisense strand is synthesized to contain a modified 3'-end for Dicer binding and processing and the sense strand of the dsRNA has a 3'-overhang.

Suitable Dicer-substrate dsRNA sequences can be identified, synthesized, and modified using any means known in the art for designing, synthesizing, and modifying siRNA sequences. In certain embodiments, Dicer-substrate dsRNAs may silence one or more genes expressed in cancer, and preferably silence the expression of the COP1, CSN5, RBX1, HDAC2, CDK4, WEE1, FOXM1, and/or R1 genes. In particular embodiments, Dicer-substrate dsRNAs are administered using a carrier system such as a nucleic acid-lipid particle (e.g., SNALP). In a preferred embodiment, the nucleic acid-lipid particle comprises: (a) one or more (e.g., a cocktail of at least 2, 3, 4, 5, 6, 7, or 8) Dicer-substrate dsRNA molecules targeting the COP1, CSN5, RBX1, HDAC2, CDK4, WEE1, FOXM1, and/or R1 genes; (b) a cationic lipid of Formula I-XVI or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA). In another preferred embodiment, a combination of Dicer-substrate dsRNA molecules targeting the COP1, CSN5, RBX1, HDAC2, CDK4, WEE1, FOXM1, and/or R1 genes is administered using the nucleic acid-lipid particles described herein, and the Dicer-substrate dsRNAs present in the cocktail are either co-encapsulated in the same particle or are encapsulated in separate particles such that there is only one type of Dicer-substrate dsRNA species in each particle.

Additional embodiments related to the Dicer-substrate dsRNAs of the invention, as well as methods of designing and synthesizing such dsRNAs, are described in U.S. Patent Publication Nos. 20050244858, 20050277610, and 20070265220, and U.S. application Ser. No. 12/794,701, filed Jun. 4, 2010, the disclosures of which are herein incorporated by reference in their entirety for all purposes.

C. shRNA

A "small hairpin RNA" or "short hairpin RNA" or "shRNA" includes a short RNA sequence that makes a tight hairpin turn that can be used to silence gene expression via RNA interference. The shRNAs of the invention may be chemically synthesized or transcribed from a transcriptional cassette in a DNA plasmid. The shRNA hairpin structure is cleaved by the cellular machinery into siRNA, which is then bound to the RNA-induced silencing complex (RISC).

The shRNAs of the invention are typically about 15-60, 15-50, or 15-40 (duplex) nucleotides in length, more typically about 15-30, 15-25, or 19-25 (duplex) nucleotides in length, and are preferably about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, preferably about 20-24, 21-22, or 21-23 nucleotides in length, and the double-stranded shRNA is about 15-60, 15-50, 15-40, 15-30, 15-25, or 19-25 base pairs in length, preferably about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), preferably from about 19 to about 40 nucleotides in length (e.g., about 19-40, 19-35, 19-30, or 19-25 nucleotides in length), more preferably from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In preferred embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional shRNA sequences include, but are not limited to, asymmetric shRNA precursor polynucleotides such as those described in PCT Publication Nos. WO 2006/074108 and WO 2009/076321, the disclosures of which are herein incorporated by reference in their entirety for all purposes. For example, PCT Publication No. WO 2006/074108 discloses self-protected oligonucleotides comprising a region having a sequence complementary to one, two, three, or more same or different target mRNA sequences (e.g., multivalent shRNAs) and one or more self-complementary regions. Similarly, PCT Publication No. WO 2009/076321 discloses self-forming asymmetric precursor polynucleotides comprising a targeting region comprising a polynucleotide sequence complementary to a region of one, two, three, or more same or different target mRNA sequences (e.g., multivalent shRNAs); a first self-complementary region; and a second self-complementary region, wherein the first and second self-complementary regions are located one at each end of the targeting region and both self-complementary regions form stem-loop structures, wherein the first self-complementary region is capable of being cleaved by a RNase III endoribonuclease that is not a class IV DICER endoribonuclease, and wherein both self-complementary regions comprise a nucleotide sequence that is complementary to a region of the target gene sequence, but wherein a portion of the target sequence present in the targeting region does not have a complementary sequence in either of the self-complementary regions.

Suitable shRNA sequences can be identified, synthesized, and modified using any means known in the art for designing, synthesizing, and modifying siRNA sequences. In certain embodiments, shRNAs may silence one or more genes expressed in cancer, and preferably silence the expression of the COP1, CSN5, RBX1, HDAC2, CDK4, WEE1, FOXM1, and/or R1 genes. In particular embodiments, shRNAs are administered using a carrier system such as a nucleic acid-lipid particle (e.g., SNALP). In preferred embodiments, the nucleic acid-lipid particle comprises: (a) one or more (e.g., a cocktail of at least 2, 3, 4, 5, 6, 7, or 8) shRNA molecules targeting the COP1, CSN5, RBX1, HDAC2, CDK4, WEE1, FOXM1, and/or R1 genes; (b) a cationic lipid of Formula I-XVI or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA). In another preferred embodiment, a combination of shRNA molecules targeting the COP1, CSN5, RBX1, HDAC2, CDK4, WEE1, FOXM1, and/or R1 genes is administered using the nucleic acid-lipid particles described herein, and the shRNAs present in the cocktail are either co-encapsulated in the same particle or are encapsulated in separate particles such that there is only one type of shRNA species in each particle.

Additional embodiments related to the shRNAs of the invention, as well as methods of designing and synthesizing such shRNAs, are described in U.S. patent application Ser. No. 12/794,701, filed Jun. 4, 2010, the disclosure of which is herein incorporated by reference in its entirety for all purposes.

D. aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., Nat. Biotech., 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein. In other embodiments, aiRNA molecules may be used to silence one or more genes expressed in cancer, and preferably silence the expression of the COP1, CSN5, RBX1, HDAC2, CDK4, WEE1, FOXM1, and/or R1 genes.

In particular embodiments, aiRNAs are administered using a carrier system such as a nucleic acid-lipid particle (e.g., SNALP). In preferred embodiments, the nucleic acid-lipid particle comprises: (a) one or more (e.g., a cocktail of at least 2, 3, 4, 5, 6, 7, or 8) aiRNA molecules targeting the COP1, CSN5, RBX1, HDAC2, CDK4, WEE1, FOXM1, and/or R1 genes; (b) a cationic lipid of Formula I-XVI or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA). In another preferred embodiment, a combination of aiRNA molecules targeting the COP1, CSN5, RBX1, HDAC2, CDK4, WEE1, FOXM1, and/or R1 genes is administered using the nucleic acid-lipid particles described herein, and the aiRNAs present in the cocktail are either co-encapsulated in the same particle or are encapsulated in separate particles such that there is only one type of aiRNA species in each particle.

Suitable aiRNA sequences can be identified, synthesized, and modified using any means known in the art for designing, synthesizing, and modifying siRNA sequences. Additional embodiments related to the aiRNA molecules of the invention are described in U.S. Patent Publication No. 20090291131 and PCT Publication No. WO 09/127,060, the disclosures of which are herein incorporated by reference in their entirety for all purposes.

E. miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNA molecules is described, e.g., in Lagos-Quintana et al., *Science*, 294:853-858; Lau et al., *Science*, 294:858-862; and Lee et al., *Science*, 294:862-864.

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature*, 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., *Nature*, 409:363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.*, 16:530-535 (2006)). The remaining strand, known as the anti-guide or passenger strand, is degraded as a RISC complex substrate (Gregory et al., *Cell*, 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, miRNA molecules may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In some embodiments, miRNA molecules may be used to silence one or more genes expressed in cancer, and preferably silence the expression of the COP1, CSN5, RBX1, HDAC2, CDK4, WEE1, FOXM1, and/or R1 genes. In particular embodiments, miRNAs are administered using a carrier system such as a nucleic acid-lipid particle (e.g., SNALP). In a preferred embodiment, the nucleic acid-lipid particle comprises: (a) one or more (e.g., a cocktail of at least 2, 3, 4, 5, 6, 7, or 8) aiRNA molecules targeting the COP1, CSN5, RBX1, HDAC2, CDK4, WEE1, FOXM1, and/or R1 genes; (b) a cationic lipid of Formula I-XVI or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA). In another preferred embodiment, a combination of miRNA molecules targeting the COP1, CSN5, RBX1, HDAC2, CDK4, WEE1, FOXM1, and/or R1 genes is administered using the nucleic acid-lipid particles described herein, and the miRNAs present in the cocktail are either co-encapsulated in the same particle or are encapsulated in separate particles such that there is only one type of miRNA species in each particle.

In other embodiments, one or more agents that block the activity of an miRNA targeting COP1, CSN5, RBX1, HDAC2, CDK4, WEE1, FOXM1, and/or R1 mRNA are administered using a lipid particle of the invention (e.g., a nucleic acid-lipid particle such as SNALP). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target RNA.

Additional embodiments related to the miRNA molecules of the invention are described in U.S. Patent Publication No. 20090291131 and PCT Publication No. WO 09/127,060, the disclosures of which are herein incorporated by reference in their entirety for all purposes.

V. Lipid Particles

In certain aspects, the present invention provides lipid particles comprising one or more therapeutic nucleic acids (e.g., interfering RNA such as siRNA) and one or more cationic (amino) lipids or salts thereof. In some embodiments, the lipid particles of the invention further comprise one or more non-cationic lipids. In other embodiments, the lipid particles further comprise one or more conjugated lipids capable of reducing or inhibiting particle aggregation.

Lipid particles include, but are not limited to, lipid vesicles such as liposomes. As used herein, a lipid vesicle includes a structure having lipid-containing membranes enclosing an aqueous interior. In particular embodiments, lipid vesicles comprising one or more of the cationic lipids described herein are used to encapsulate nucleic acids within the lipid vesicles. In other embodiments, lipid vesicles comprising one or more of the cationic lipids described herein are complexed with nucleic acids to form lipoplexes.

The lipid particles of the invention preferably comprise a therapeutic nucleic acid such as an interfering RNA (e.g., siRNA), a cationic lipid, a non-cationic lipid, and a conjugated lipid that inhibits aggregation of particles. In some embodiments, the therapeutic nucleic acid is fully encapsulated within the lipid portion of the lipid particle such that the therapeutic nucleic acid in the lipid particle is resistant in aqueous solution to enzymatic degradation, e.g., by a nuclease. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. The lipid particles of the invention also typically have a lipid:nucleic acid ratio (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1.

In preferred embodiments, the lipid particles of the invention are serum-stable nucleic acid-lipid particles (SNALP) which comprise an interfering RNA (e.g., dsRNA such as siRNA, Dicer-substrate dsRNA, shRNA, aiRNA, and/or miRNA), a cationic lipid (e.g., one or more cationic lipids of Formula I-XVI or salts thereof as set forth herein), a non-cationic lipid (e.g., mixtures of one or more phospholipids and cholesterol), and a conjugated lipid that inhibits aggregation of the particles (e.g., one or more PEG-lipid conjugates). The SNALP may comprise at least 1, 2, 3, 4, 5, 6, 7, 8, 9, 10, or more unmodified and/or modified interfering RNA molecules (e.g., siRNA) that target one or more genes expressed in cancer as described herein. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the nucleic acid may be fully encapsulated within the lipid portion of the particle, thereby protecting the nucleic acid from nuclease degradation. In preferred embodiments, a SNALP comprising a nucleic acid such as an interfering RNA is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., *Gene Ther.*, 6:271-281 (1999)).

In other embodiments, the present invention provides a nucleic acid-lipid particle (e.g., SNALP) composition comprising a plurality of nucleic acid-lipid particles.

In some instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the nucleic acid encapsulated therein.

In other instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input nucleic acid is encapsulated in the particles.

Depending on the intended use of the lipid particles of the invention, the proportions of the components can be varied and the delivery efficiency of a particular formulation can be measured using, e.g., an endosomal release parameter (ERP) assay.

In particular embodiments, the present invention provides a lipid particle (e.g., SNALP) composition comprising a plurality of lipid particles described herein and an antioxidant. In certain instances, the antioxidant in the lipid particle composition reduces, prevents, and/or inhibits the degradation of a cationic lipid present in the lipid particle. In instances wherein the active agent is a therapeutic nucleic acid such as an interfering RNA (e.g., siRNA), the antioxidant in the lipid particle composition reduces, prevents, and/or inhibits the degradation of the nucleic acid payload, e.g., by reducing, preventing, and/or inhibiting the formation of adducts between the nucleic acid and the cationic lipid. Non-limiting examples of antioxidants include hydrophilic antioxidants such as chelating agents (e.g., metal chelators such as ethylenediaminetetraacetic acid (EDTA), citrate, and the like), lipophilic antioxidants (e.g., vitamin E isomers, polyphenols, and the like), salts thereof; and mixtures thereof. If needed, the antioxidant is typically present in an amount sufficient to prevent, inhibit, and/or reduce the degradation of the cationic lipid and/or active agent present in the particle, e.g., at least about 20 mM EDTA or a salt thereof, or at least about 100 mM citrate or a salt thereof. An antioxidant such as EDTA and/or citrate may be included at any step or at multiple steps in the lipid particle formation process described in Section VI (e.g., prior to, during, and/or after lipid particle formation).

Additional embodiments related to methods of preventing the degradation of cationic lipids and/or active agents (e.g., therapeutic nucleic acids) present in lipid particles, compositions comprising lipid particles stabilized by these methods, methods of making these lipid particles, and methods of delivering and/or administering these lipid particles are described in U.S. Provisional Application No. 61/265,671, entitled "SNALP Formulations Containing Antioxidants," filed Dec. 1, 2009, the disclosure of which is herein incorporated by reference in its entirety for all purposes.

A. Cationic Lipids

Any of a variety of cationic lipids or salts thereof may be used in the lipid particles of the present invention (e.g., SNALP), either alone or in combination with one or more other cationic lipid species or non-cationic lipid species. In particular embodiments, one or more of the cationic lipids of Formula I-XVI or salts thereof as set forth herein may be used in the lipid particles of the present invention (e.g., SNALP), either alone or in combination with one or more other cationic lipid species or non-cationic lipid species. The cationic lipids include the (R) and/or (S) enantiomers thereof.

In some embodiments, the cationic lipid comprises a racemic mixture. In other embodiments, the cationic lipid comprises a mixture of one or more diastereomers. In certain embodiments, the cationic lipid is enriched in one enantiomer, such that the cationic lipid comprises at least about 55%, 60%, 65%, 70%, 75%, 80%, 85%, 90%, or 95% enantiomeric excess. In certain other embodiments, the cationic lipid is enriched in one diastereomer, such that the cationic lipid comprises at least about 55%, 60%, 65%, 70%, 75%, 80%, 85%, 90%, or 95% diastereomeric excess. In certain additional embodiments, the cationic lipid is chirally pure (e.g., comprises a single optical isomer). In further embodiments, the cationic lipid is enriched in one optical isomer (e.g., an optically active isomer), such that the cationic lipid comprises at least about 55%, 60%, 65%, 70%, 75%, 80%, 85%, 90%, or 95% isomeric excess. The present invention provides the synthesis of the cationic lipids of Formulas I-XVI as a racemic mixture or in optically pure form.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids.

The term "salts" includes any anionic and cationic complex, such as the complex formed between a cationic lipid disclosed herein and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfate, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" mean that, when substituted, at least one hydrogen atom is replaced with a substituent. In the case of an oxo substituent (=O), two hydrogen atoms are replaced. In this regard, substituents include, but are not limited to, oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O) NR$^x$R$^y$, —SO$_n$R$^x$, and —SO$_n$NR$^x$R$^y$, wherein n is 0, 1, or 2, R$^x$ and R$^y$ are the same or different and are independently hydrogen, alkyl, or heterocycle, and each of the alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O) R$^x$, —C(=O)OR$^x$, —C(=O)NR$^x$R$^y$, —SO$_n$R$^x$, and —SO$_n$-NR$^x$R$^y$. The term "optionally substituted," when used before a list of substituents, means that each of the substituents in the list may be optionally substituted as described herein.

The term "halogen" includes fluoro, chloro, bromo, and iodo.

In one aspect, cationic lipids of Formula I having the following structure (or salts thereof) are useful in the present invention:

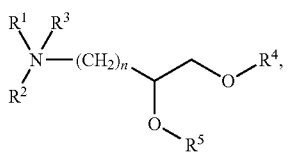

(I)

wherein R$^1$ and R$^2$ are either the same or different and are independently hydrogen (H) or an optionally substituted C$_1$-C$_6$ alkyl, C$_2$-C$_6$ alkenyl, or C$_2$-C$_6$ alkynyl, or R$^1$ and R$^2$ may join to form an optionally substituted heterocyclic ring of 4 to 6 carbon atoms and 1 or 2 heteroatoms selected from the group consisting of nitrogen (N), oxygen (O), and mixtures thereof;

R$^3$ is either absent or is hydrogen (H) or a C$_1$-C$_6$ alkyl to provide a quaternary amine;

R$^4$ and R$^5$ are either the same or different and are independently an optionally substituted C$_{10}$-C$_{24}$ alkyl, C$_{10}$-C$_{24}$ alkenyl, C$_{10}$-C$_{24}$ alkynyl, or C$_{10}$-C$_{24}$ acyl, wherein at least one of R$^4$ and R$^5$ comprises at least two sites of unsaturation; and n is 0, 1, 2, 3, or 4.

In some embodiments, R$^1$ and R$^2$ are independently an optionally substituted C$_1$-C$_4$ alkyl, C$_2$-C$_4$ alkenyl, or C$_2$-C$_4$ alkynyl. In one preferred embodiment, R$^1$ and R$^2$ are both methyl groups. In other preferred embodiments, n is 1 or 2. In other embodiments, R$^3$ is absent when the pH is above the pK$_a$ of the cationic lipid and R$^3$ is hydrogen when the pH is below the pK$_a$ of the cationic lipid such that the amino head group is protonated. In an alternative embodiment, R$^3$ is an optionally substituted C$_1$-C$_4$ alkyl to provide a quaternary amine. In further embodiments, R$^4$ and R$^5$ are independently an optionally substituted C$_{12}$-C$_{24}$, C$_{12}$-C$_{22}$, C$_{12}$-C$_{20}$, C$_{14}$-C$_{24}$, C$_{14}$-C$_{22}$, C$_{14}$-C$_{20}$, C$_{16}$-C$_{24}$, C$_{16}$-C$_{22}$, or C$_{16}$-C$_{20}$ alkyl, alkenyl, alkynyl, or acyl group (i.e., C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, or C$_{24}$ alkyl, alkenyl, alkynyl, or acyl group). In certain embodiments, at least one or both R$^4$ and R$^5$ independently comprises at least 2, 3, 4, 5, or 6 sites of unsaturation (e.g., 2, 3, 4, 5, 6, 2-3, 2-4, 2-5, or 2-6 sites of unsaturation).

In certain instances, R$^4$ and R$^5$ may independently comprise a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, R$^4$ and R$^5$ are both linoleyl moieties. In other instances, the octadecatrienyl moiety is a linolenyl moiety or a γ-linolenyl moiety. In particular embodiments, R$^4$ and R$^5$ are both linolenyl moieties or γ-linolenyl moieties. In certain instances, R$^4$ and R$^5$ are different, e.g., R$^4$ is a tetradectrienyl (C$_{14}$) and R$^5$ is linoleyl (C$_{18}$). In a preferred embodiment, the cationic lipid of Formula I is symmetrical, i.e., R$^4$ and R$^5$ are both the same. In further embodiments, the double bonds present in one or both R$^4$ and R$^5$ may be in the cis and/or trans configuration.

In some groups of embodiments to the cationic lipids of Formula I, R$^4$ and R$^5$ are either the same or different and are independently selected from the group consisting of:

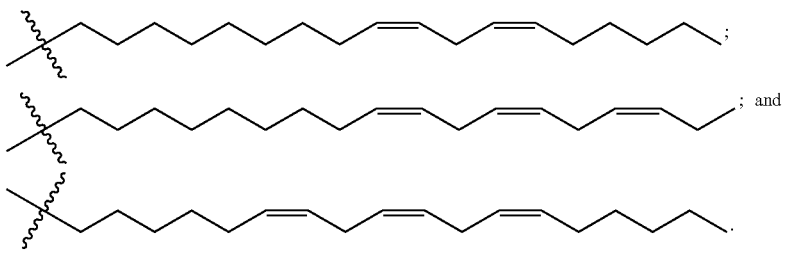

In particular embodiments, the cationic lipid of Formula I comprises 1,2-dilinoleyloxy-N,N-dimethylaminopropane (DLinDMA), 1,2-dilinolenyloxy-N,N-dimethylaminopropane (DLenDMA), or mixtures thereof.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

In another aspect, cationic lipids of Formula II having the following structure (or salts thereof) are useful in the present invention:

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl ($C_{18}$), etc. In certain other instances, $R^3$ and $R^4$ are different, i.e., $R^3$ is tetradectrienyl ($C_{14}$) and $R^4$ is linoleyl ($C_{18}$). In a preferred embodiment, the cationic lipid of Formula II is symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from the group consisting of dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

The synthesis of cationic lipids such as DLinDMA and DLenDMA, as well as additional cationic lipids falling within the scope of Formulas I and II, is described in U.S. Patent Publication No. 20060083780, the disclosure of which is herein incorporated by reference in its entirety for all purposes.

In yet another aspect, cationic lipids of Formula III having the following structure (or salts thereof) are useful in the present invention:

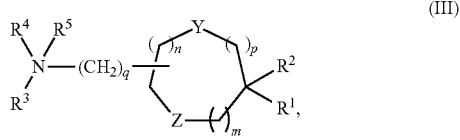

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^3$ and $R^4$ are independently an optionally substituted $C_1$-$C_4$ alkyl, $C_2$-$C_4$ alkenyl, or $C_2$-$C_4$ alkynyl. In a preferred embodiment, $R^3$ and $R^4$ are both methyl groups. In one embodiment, q is 1 or 2. In another embodiment, q is 1-2, 1-3, 1-4, 2-3, or 2-4. In further embodiments, $R^5$ is absent when the pH is above the $pK_a$ of the cationic lipid and $R^5$ is hydrogen when the pH is below the $pK_a$ of the cationic lipid such that the amino head group is protonated. In an alternative embodiment, $R^5$ is an optionally substituted $C_1$-$C_4$ alkyl to provide a quaternary amine. In additional embodiments, Y and Z are both O.

In other embodiments, $R^1$ and $R^2$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In certain embodiments, at least one or both $R^1$ and $R^2$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, $R^1$ and $R^2$ are both linoleyl moieties. In other instances, the octadecatrienyl moiety is a linolenyl moiety or a γ-linolenyl moiety. In particular embodiments, $R^1$ and $R^2$ are both linolenyl moieties or γ-linolenyl moieties.

In embodiments where one or both $R^1$ and $R^2$ independently comprises at least 1, 2, 3, 4, 5, or 6 sites of unsaturation, the double bonds present in one or both $R^1$ and $R^2$ may be in the cis and/or trans configuration. In certain instances, $R^1$ and $R^2$ are both the same, e.g., $R^1$ and $R^2$ are both linoleyl ($C_{18}$) moieties, etc. In certain other instances, $R^1$ and $R^2$ are different, e.g., $R^1$ is a tetradectrienyl ($C_{14}$) moiety and $R^2$ is a linoleyl ($C_{18}$) moiety. In a preferred embodiment, the cationic lipid of Formula III is symmetrical, i.e., $R^1$ and $R^2$ are both the same. In another preferred embodiment, at least one or both $R^1$ and $R^2$ comprises at least two sites of unsaturation (e.g., 2, 3, 4, 5, 6, 2-3, 2-4, 2-5, or 2-6 sites of unsaturation).

In embodiments where one or both $R^1$ and $R^2$ independently comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety. In particular embodiments, $R^1$ and $R^2$ are both phytanyl moieties.

In some groups of embodiments to the cationic lipids of Formula III, $R^1$ and $R^2$ are either the same or different and are independently selected from the group consisting of:

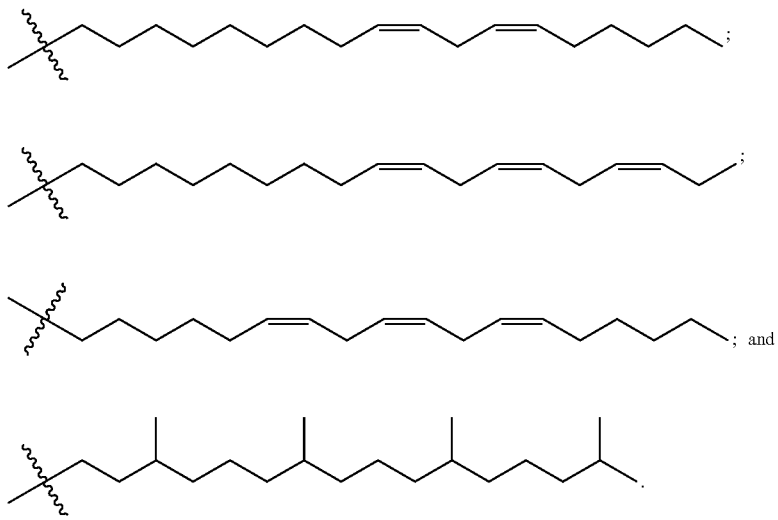

In certain embodiments, cationic lipids falling within the scope of Formula III include, but are not limited to, the following: 2,2-dilinoleyl-4-(2-dimethylaminoethyl)-[1,3]-dioxolane (DLin-K-C2-DMA; "XTC2" or "C2K"), 2,2-dilinoleyl-4-dimethylaminomethyl-[1,3]-dioxolane (DLin-K-DMA), 2,2-dilinoleyl-4-(3-dimethylaminopropyl)-[1,3]-dioxolane (DLin-K-C3-DMA; "C3K"), 2,2-dilinoleyl-4-(4-dimethylaminobutyl)-[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ),2,2-dioleoyl-4-dimethylaminomethyl-[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.Cl), 2,2-dilinoleyl-4,5-bis(dimethylaminomethyl)[1,3]-dioxolane (DLin-$K^2$-DMA), 2,2-dilinoleyl-4-methylpiperzine-[1,3]-dioxolane (D-Lin-K-N-methylpiperzine), DLen-C2K-DMA, γ-DLen-C2K-DMA, DPan-C2K-DMA, DPan-C3K-DMA, or mixtures thereof. In preferred embodiments, the cationic lipid of Formula III comprises DLin-K-C2-DMA and/or DLin-K-DMA.

In some embodiments, the cationic lipids of Formula III form a salt (preferably a crystalline salt) with one or more anions. In one particular embodiment, the cationic lipid of Formula III is the oxalate (e.g., hemioxalate) salt thereof, which is preferably a crystalline salt.

The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.Cl, DLin-$K^2$-DMA, D-Lin-K-N-methylpiperzine, as well as additional cationic lipids, is described in PCT Publication No. WO 2010/042877, the disclosure of which is incorporated herein by reference in its entirety for all purposes.

The synthesis of cationic lipids such as DLin-K-DMA, as well as additional cationic lipids, is described in PCT Publication No. WO 09/086,558, the disclosure of which is herein incorporated by reference in its entirety for all purposes.

In a preferred embodiment, cationic lipids of Formula IV having the following structure (or salts thereof) are useful in the present invention:

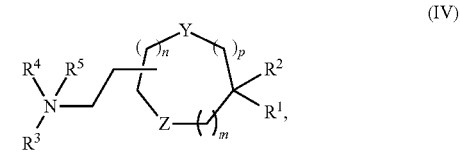

(IV)

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; and Y and Z are either the same or different and are independently O, S, or NH.

In some embodiments, $R^3$ and $R^4$ are independently an optionally substituted $C_1$-$C_4$ alkyl, $C_2$-$C_4$ alkenyl, or $C_2$-$C_4$ alkynyl. In a preferred embodiment, $R^3$ and $R^4$ are both methyl groups. In further embodiments, $R^5$ is absent when the pH is above the $pK_a$ of the cationic lipid and $R^5$ is hydrogen when the pH is below the $pK_a$ of the cationic lipid such that the amino head group is protonated. In an alternative embodiment, $R^5$ is an optionally substituted $C_1$-$C_4$ alkyl to provide a quaternary amine. In additional embodiments, Y and Z are both O.

In other embodiments, $R^1$ and $R^2$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In certain embodiments, at least one or both $R^1$ and $R^2$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, $R^1$ and $R^2$ are both linoleyl moieties. In other instances, the octadecatrienyl moiety is a linolenyl moiety or a γ-linolenyl moiety. In particular embodiments, $R^1$ and $R^2$ are both linolenyl moieties or γ-linolenyl moieties.

In embodiments where one or both $R^1$ and $R^2$ independently comprises at least 1, 2, 3, 4, 5, or 6 sites of unsaturation, the double bonds present in one or both $R^1$ and $R^2$ may be in the cis and/or trans configuration. In certain instances, $R^1$ and $R^2$ are both the same, e.g., $R^1$ and $R^2$ are both linoleyl ($C_{18}$) moieties, etc. In certain other instances, $R^1$ and $R^2$ are different, e.g., $R^1$ is a tetradectrienyl ($C_{14}$) moiety and $R^2$ is a linoleyl ($C_{18}$) moiety. In a preferred embodiment, the cationic lipid of Formula IV is symmetrical, i.e., $R^1$ and $R^2$ are both the same. In another preferred embodiment, at least one or both $R^1$ and $R^2$ comprises at least two sites of unsaturation (e.g., 2, 3, 4, 5, 6, 2-3, 2-4, 2-5, or 2-6 sites of unsaturation).

In embodiments where one or both $R^1$ and $R^2$ independently comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety. In particular embodiments, $R^1$ and $R^2$ are both phytanyl moieties.

In some groups of embodiments to the cationic lipids of Formula IV, $R^1$ and $R^2$ are either the same or different and are independently selected from the group consisting of In certain embodiments, cationic lipids falling within the scope of Formula IV include, but are not limited to, the following: 2,2-dilinoleyl-4-(2-dimethylaminoethyl)-[1,3]-dioxolane (DLin-K-C2-DMA; "XTC2" or "C2K"), DLen-C2K-DMA, γ-DLen-C2K-DMA, DPan-C2K-DMA, or mixtures thereof. In preferred embodiments, the cationic lipid of Formula IV comprises DLin-K-C2-DMA.

In some embodiments, the cationic lipids of Formula IV form a salt (preferably a crystalline salt) with one or more anions. In one particular embodiment, the cationic lipid of Formula IV is the oxalate (e.g., hemioxalate) salt thereof, which is preferably a crystalline salt.

The synthesis of DLin-K-C2-DMA (C2K) is described in PCT Publication No. WO 2010/042877, the disclosure of which is incorporated herein by reference in its entirety for all purposes.

In a further aspect, cationic lipids of Formula V having the following structure are useful in the present invention:

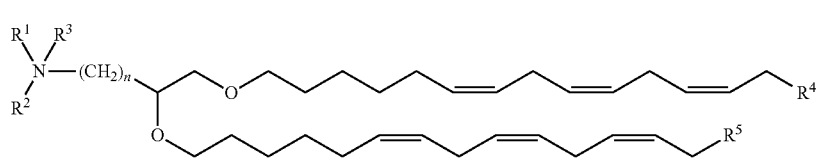

(V)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either absent or present and when present are either the same or different and are independently an optionally substituted $C_1$-$C_{10}$ alkyl or $C_2$-$C_{10}$ alkenyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, $R^4$ and $R^5$ are both butyl groups. In yet another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary

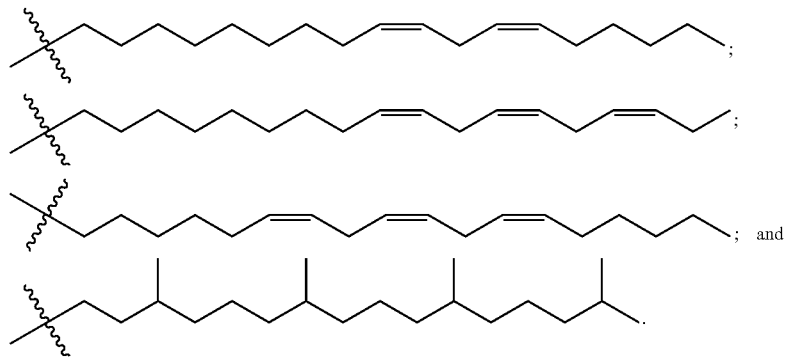

amine. In further embodiments, $R^4$ and $R^5$ are independently an optionally substituted $C_2$-$C_6$ or $C_2$-$C_4$ alkyl or $C_2$-$C_6$ or $C_2$-$C_4$ alkenyl.

In an alternative embodiment, the cationic lipid of Formula V comprises ester linkages between the amino head group and one or both of the alkyl chains. In some embodiments, the cationic lipid of Formula V forms a salt (preferably a crystalline salt) with one or more anions. In one particular embodiment, the cationic lipid of Formula V is the oxalate (e.g., hemioxalate) salt thereof, which is preferably a crystalline salt.

Although each of the alkyl chains in Formula V contains cis double bonds at positions 6, 9, and 12 (i.e., cis,cis,cis-$\Delta^6$,$\Delta^9$, $\Delta^{12}$), in an alternative embodiment, one, two, or three of these double bonds in one or both alkyl chains may be in the trans configuration.

In a particularly preferred embodiment, the cationic lipid of Formula V has the structure:

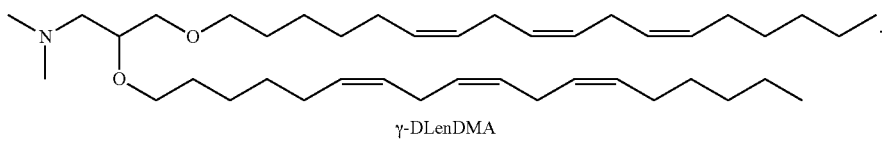 [SMILES: CCCCC/C=C\C/C=C\C/C=C\CCCCCOCC(CN(C)C)OCCCCC/C=C\C/C=C\C/C=C\CCCCC]

γ-DLenDMA

In another aspect, cationic lipids of Formula VI having the following structure are useful in the present invention:

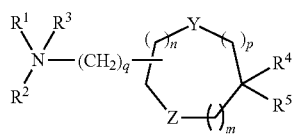

(VI)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least three sites of unsaturation or a substituted $C_{12}$-$C_{24}$ alkyl; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl (3,7,11,15-tetramethyl-hexadecanyl) moiety. In other preferred embodiments, $R^4$ and $R^5$ are both phytanyl moieties.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl (3,7,11,15-tetramethyl-hexadecanoyl) moiety.

In embodiments where at least one of $R^4$ and $R^5$ comprises at least three sites of unsaturation, the double bonds present in one or both alkyl chains may be in the cis and/or trans configuration. In some embodiments, $R^4$ and $R^5$ are independently selected from the group consisting of a dodecatrienyl moiety, a tetradectrienyl moiety, a hexadecatrienyl moiety, an octadecatrienyl moiety, an icosatrienyl moiety, and a phytanyl moiety, as well as acyl derivatives thereof (e.g., linolenoyl, γ-linolenoyl, phytanoyl, etc.). In certain instances, the octadecatrienyl moiety is a linolenyl moiety or a γ-linolenyl moiety. In preferred embodiments, $R^4$ and $R^5$ are both linolenyl moieties or γ-linolenyl moieties. In particular embodiments, $R^4$ and $R^5$ independently comprise a backbone of from about 16 to about 22 carbon atoms, and one or both of $R^4$ and $R^5$ independently comprise at least three, four, five, or six sites of unsaturation.

In some embodiments, the cationic lipid of Formula VI forms a salt (preferably a crystalline salt) with one or more anions. In one particular embodiment, the cationic lipid of Formula VI is the oxalate (e.g., hemioxalate) salt thereof, which is preferably a crystalline salt.

In a particularly preferred embodiment, the cationic lipid of Formula VI has a structure selected from the group consisting of:

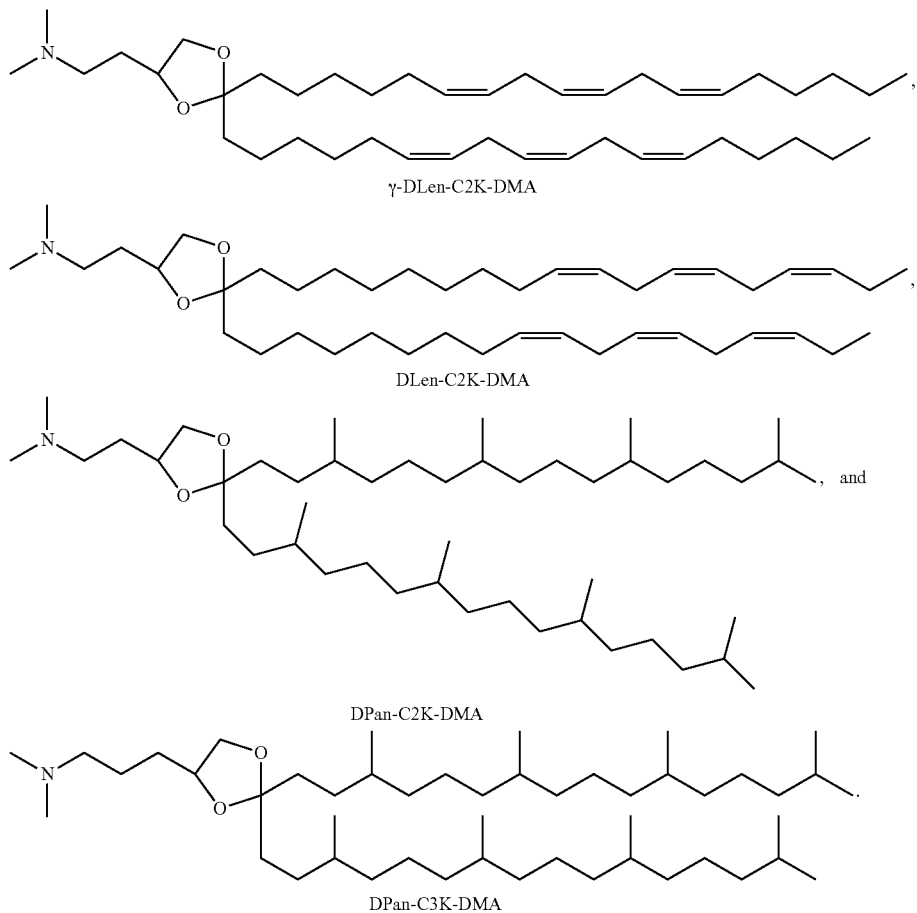

γ-DLen-C2K-DMA

DLen-C2K-DMA

DPan-C2K-DMA, and

DPan-C3K-DMA

In yet another aspect, cationic lipids of Formula VII having the following structure are useful in the present invention:

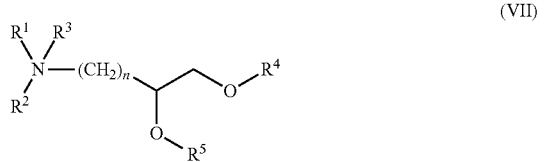

(VII)

or salts thereof, wherein: $R^1$ and $R^2$ are joined to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^1$ and $R^2$ are joined to form a heterocyclic ring of 5 carbon atoms and 1 nitrogen atom. In certain instances, the heterocyclic ring is substituted with a substituent such as a hydroxyl group at the ortho, meta, and/or para positions. In a preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula VII forms a salt (preferably a crystalline salt) with one or more anions. In one particular embodiment, the cationic lipid of Formula VII is the oxalate (e.g., hemioxalate) salt thereof, which is preferably a crystalline salt.

In a particularly preferred embodiment, the cationic lipid of Formula VII has a structure selected from the group consisting of:

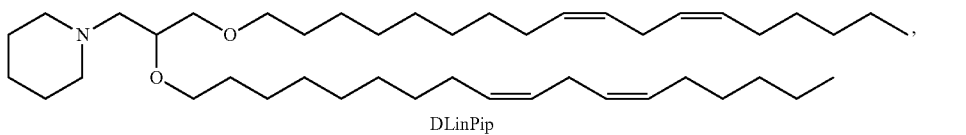
DLinPip

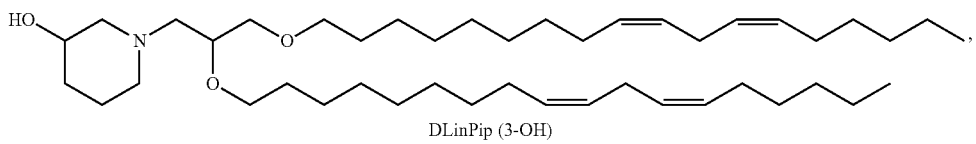
DLinPip (3-OH)

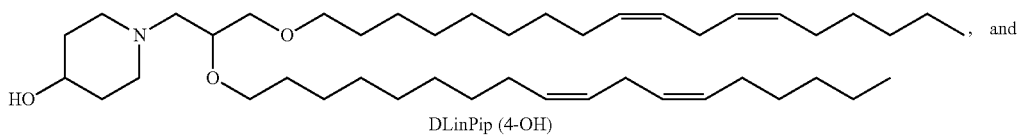
DLinPip (4-OH)

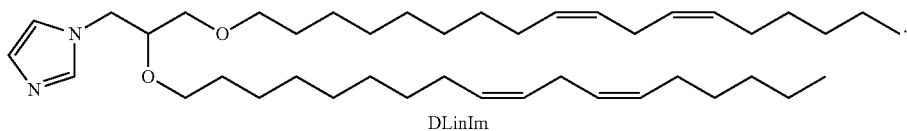
DLinIm

In still yet another aspect, cationic lipids of Formula VIII having the following structure are useful in the present invention:

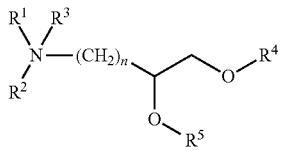

(VIII)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula VIII forms a salt (preferably a crystalline salt) with one or more anions. In one particular embodiment, the cationic lipid of Formula VIII is the oxalate (e.g., hemioxalate) salt thereof, which is preferably a crystalline salt.

In a particularly preferred embodiment, the cationic lipid of Formula VIII has a structure selected from the group consisting of:

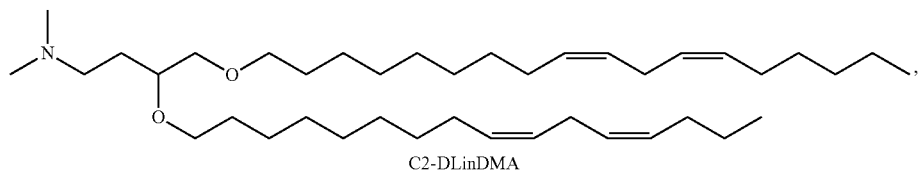
C2-DLinDMA

-continued

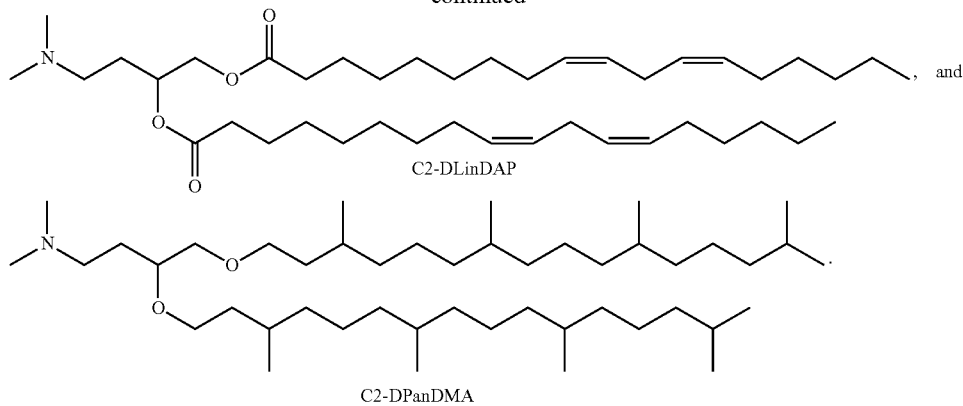

C2-DLinDAP

C2-DPanDMA

In another aspect, cationic lipids of Formula IX having the following structure are useful in the present invention:

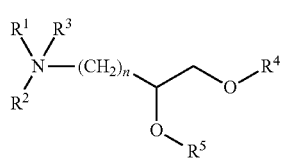

(IX)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl.

In some embodiments, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In certain instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl.

In other embodiments, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In particular embodiments, $R^4$ is a linoleyl moiety, and $R^5$ is a $C_6$ alkyl moiety, a $C_6$ alkenyl moiety, an octadecyl moiety, an oleyl moiety, a linolenyl moiety, a γ-linolenyl moiety, or a phytanyl moiety. In other embodiments, one of $R^4$ or $R^5$ is a phytanyl moiety.

In some embodiments, the cationic lipid of Formula IX forms a salt (preferably a crystalline salt) with one or more anions. In one particular embodiment, the cationic lipid of Formula IX is the oxalate (e.g., hemioxalate) salt thereof, which is preferably a crystalline salt.

In a particularly preferred embodiment, the cationic lipid of Formula IX is an asymmetric lipid having a structure selected from the group consisting of:

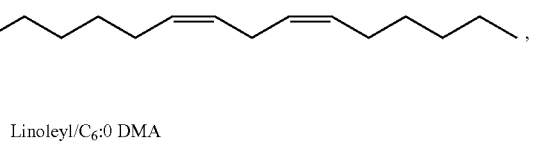

Linoleyl/C$_6$:0 DMA

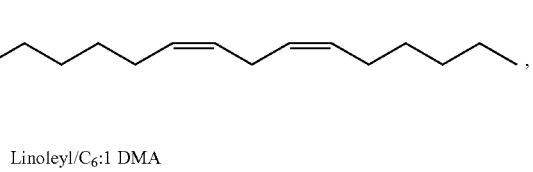

Linoleyl/C$_6$:1 DMA

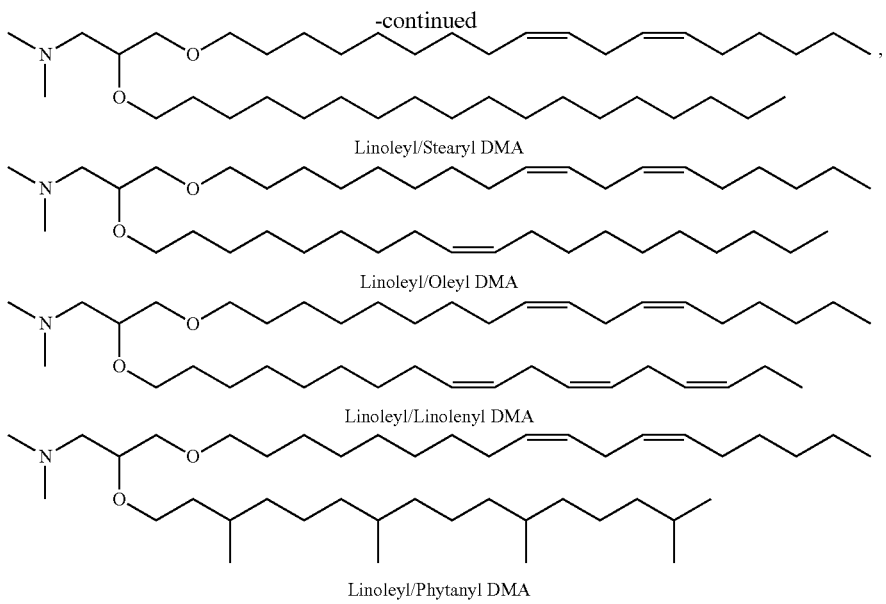

Linoleyl/Stearyl DMA

Linoleyl/Oleyl DMA

Linoleyl/Linolenyl DMA

Linoleyl/Phytanyl DMA

In yet another aspect, cationic lipids of Formula X having the following structure are useful in the present invention:

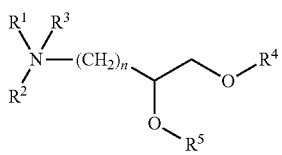

(X)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least four sites of unsaturation or a substituted $C_{12}$-$C_{24}$ alkyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl (3,7,11,15-tetramethyl-hexadecanyl) moiety.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl (3,7,11,15-tetramethyl-hexadecanoyl) moiety.

In embodiments where at least one of $R^4$ and $R^5$ comprises at least four sites of unsaturation, the double bonds present in one or both alkyl chains may be in the cis and/or trans configuration. In a particular embodiment, $R^4$ and $R^5$ independently comprise four, five, or six sites of unsaturation. In some instances, $R^4$ comprises four, five, or six sites of unsaturation and $R^5$ comprises zero, one, two, three, four, five, or six sites of unsaturation. In other instances, $R^4$ comprises zero, one, two, three, four, five, or six sites of unsaturation and $R^5$ comprises four, five, or six sites of unsaturation. In a preferred embodiment, both $R^4$ and $R^5$ comprise four, five, or six sites of unsaturation. In particular embodiments, $R^4$ and $R^5$ independently comprise a backbone of from about 18 to about 24 carbon atoms, and one or both of $R^4$ and $R^5$ independently comprise at least four, five, or six sites of unsaturation.

In some embodiments, the cationic lipid of Formula X forms a salt (preferably a crystalline salt) with one or more anions. In one particular embodiment, the cationic lipid of Formula X is the oxalate (e.g., hemioxalate) salt thereof, which is preferably a crystalline salt.

In a particularly preferred embodiment, the cationic lipid of Formula X has a structure selected from the group consisting of:

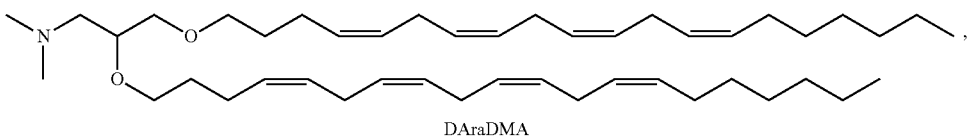

DAraDMA

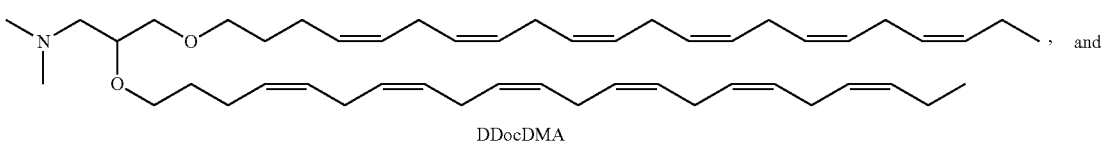, and

DDocDMA

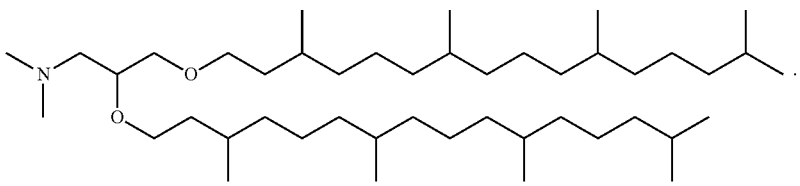.

DPanDMA

In still yet another aspect, cationic lipids of Formula XI having the following structure are useful in the present invention:

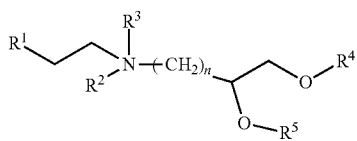

or salts thereof, wherein: $R^1$ is hydrogen (H) or —$(CH_2)_q$—$NR^6R^7R^8$, wherein: $R^6$ and $R^7$ are either the same or different and are independently an optionally substituted $C_1$-$C_6$ alkyl, $C_2$-$C_6$ alkenyl, or $C_2$-$C_6$ alkynyl, or $R^6$ and $R^7$ may join to form an optionally substituted heterocyclic ring of 4 to 6 carbon atoms and 1 or 2 heteroatoms selected from the group consisting of nitrogen (N), oxygen (O), and mixtures thereof; $R^8$ is either absent or is hydrogen (H) or a $C_1$-$C_6$ alkyl to provide a quaternary amine; and q is 0, 1, 2, 3, or 4; $R^2$ is an optionally substituted $C_1$-$C_6$ alkyl, $C_2$-$C_6$ alkenyl, or $C_2$-$C_6$ alkynyl; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^2$ is an optionally substituted $C_1$-$C_4$ alkyl, $C_2$-$C_4$ alkenyl, or $C_2$-$C_4$ alkynyl. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In certain embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In further embodiments, $R^6$ and $R^7$ are independently an optionally substituted $C_1$-$C_4$ alkyl, $C_2$-$C_4$ alkenyl, or $C_2$-$C_4$ alkynyl. In other embodiments, $R^8$ is absent when the pH is above the $pK_a$ of the cationic lipid and $R^8$ is hydrogen when the pH is below the $pK_a$ of the cationic lipid such that the amino head group is protonated. In an alternative embodiment, $R^8$ is an optionally substituted $C_1$-$C_4$ alkyl to provide a quaternary amine.

In a preferred embodiment, $R^1$ is hydrogen and $R^2$ is an ethyl group. In another preferred embodiment, $R^6$ and $R^7$ are both methyl groups. In certain instances, n is 1. In certain other instances, q is 1.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula XI forms a salt (preferably a crystalline salt) with one or more anions. In one particular embodiment, the cationic lipid of Formula XI is the oxalate (e.g., hemioxalate) salt thereof, which is preferably a crystalline salt.

In a particularly preferred embodiment, the cationic lipid of Formula XI has a structure selected from the group consisting of:

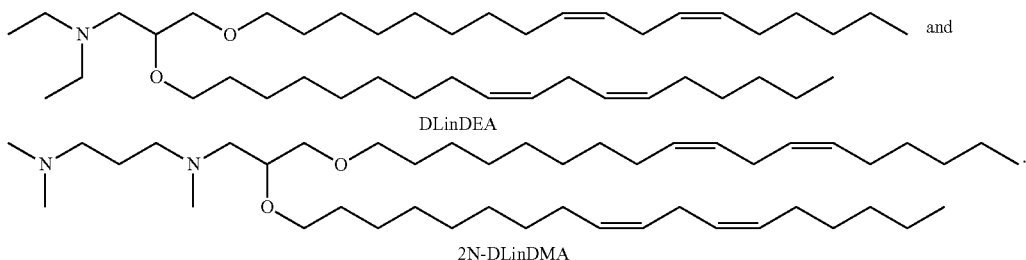

DLinDEA

2N-DLinDMA

In another aspect, cationic lipids of Formula XII having the following structure are useful in the present invention:

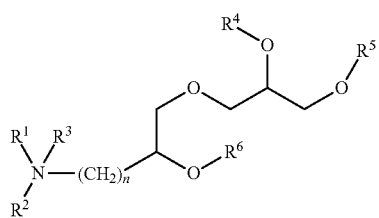

(XII)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$, $R^5$, and $R^6$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$, $R^5$, and $R^6$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$, $R^5$, and $R^6$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$, $R^5$, and $R^6$ are all linoleyl moieties, linolenyl moieties, γ-linolenyl moieties, or phytanyl moieties.

In some embodiments, the cationic lipid of Formula XII forms a salt (preferably a crystalline salt) with one or more anions. In one particular embodiment, the cationic lipid of Formula XII is the oxalate (e.g., hemioxalate) salt thereof, which is preferably a crystalline salt.

In a particularly preferred embodiment, the cationic lipid of Formula XII has a structure selected from the group consisting of:

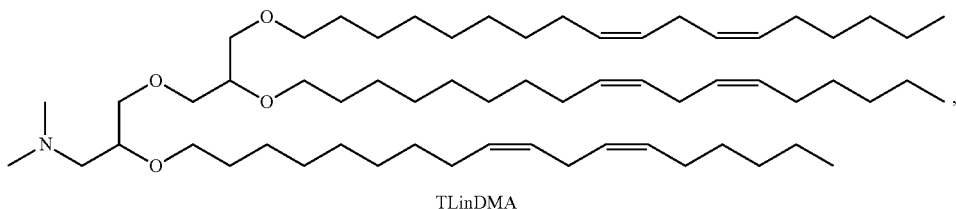

TLinDMA

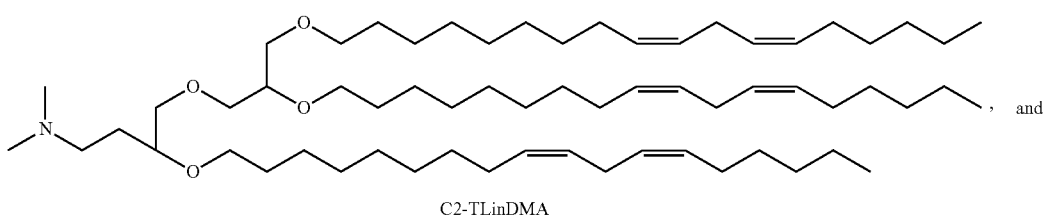

C2-TLinDMA

-continued

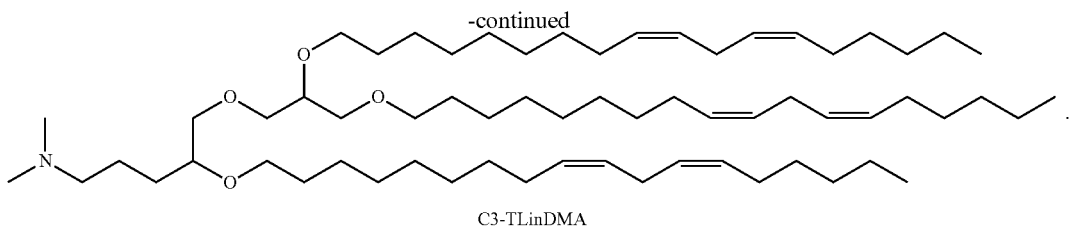

C3-TLinDMA

In yet another aspect, cationic lipids of Formula XIII having the following structure are useful in the present invention:

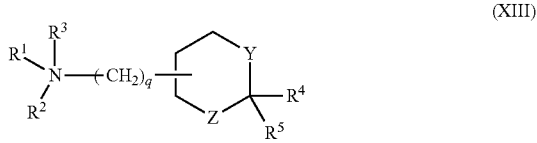

(XIII)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; q is 0, 1, 2, 3, or 4; and Y and Z are either the same or different and are independently O, S, or NH, wherein if q is 1, $R^1$ and $R^2$ are both methyl groups, $R^4$ and $R^5$ are both linoleyl moieties, and Y and Z are both O, then the alkylamino group is attached to one of the two carbons adjacent to Y or Z (i.e., at the '4' or '6' position of the 6-membered ring).

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In a particular embodiments, Y and Z are both oxygen (O). In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In other embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

The alkylamino head group of Formula XIII may be attached to the '4' or '5' position of the 6-membered ring as shown below in an exemplary embodiment wherein $R^1$ and $R^2$ are both methyl groups:

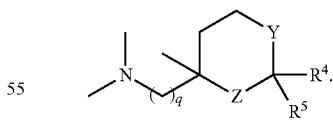

Head Group at '4' Position; or

Head Group at '5' Position.

In further embodiments, the 6-membered ring of Formula XIII may be substituted with 1, 2, 3, 4, or 5 independently selected $C_1$-$C_6$ alkyl, $C_2$-$C_6$ alkenyl, $C_2$-$C_6$ alkynyl, $C_1$-$C_6$ alkoxyl, or hydroxyl substituents. In one particular embodiment, the 6-membered ring is substituted with 1, 2, 3, 4, or 5 independently selected $C_1$-$C_4$ alkyl (e.g., methyl, ethyl, propyl, or butyl) substituents. An exemplary embodiment of a cationic lipid of Formula XIII having a substituted 6-membered ring (methyl group attached to the '4' position) and wherein $R^1$ and $R^2$ are both methyl groups is shown below:

In particular embodiments, the cationic lipids of Formula XIII may be synthesized using 2-hydroxymethyl-1,4-butanediol and 1,3,5-pentanetriol (or 3-methyl-1,3,5-pentanetriol) as starting materials.

In some embodiments, the cationic lipid of Formula XIII forms a salt (preferably a crystalline salt) with one or more anions. In one particular embodiment, the cationic lipid of Formula XIII is the oxalate (e.g., hemioxalate) salt thereof, which is preferably a crystalline salt.

In a particularly preferred embodiment, the cationic lipid of Formula XIII has the structure:

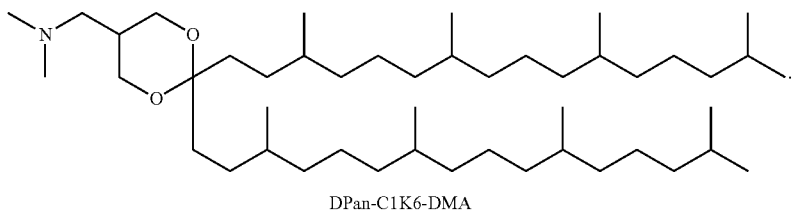 [SMILES: CC(C)CCCC(C)CCCC(C)CCCC(C)CCC1(CCC(C)CCCC(C)CCCC(C)CCCC(C)C)OCC(CN(C)C)CO1]

DPan-C1K6-DMA

In still yet another aspect, the present invention provides a cationic lipid of Formula XIV having the following structure:

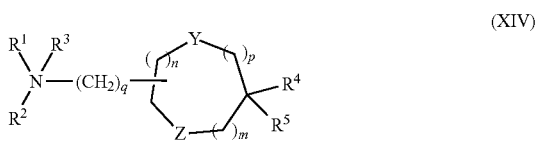

(XIV)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least one site of unsaturation in the trans (E) configuration; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, at least one of $R^4$ and $R^5$ further comprises one, two, three, four, five, six, or more sites of unsaturation in the cis and/or trans configuration. In some instances, $R^4$ and $R^5$ are independently selected from any of the substituted or unsubstituted alkyl or acyl groups described herein, wherein at least one or both of $R^4$ and $R^5$ comprises at least one, two, three, four, five, or six sites of unsaturation in the trans configuration. In one particular embodiment, $R^4$ and $R^5$ independently comprise a backbone of from about 12 to about 22 carbon atoms (e.g., 12, 13, 14, 15, 16, 17, 18, 19, 20, 21, or 22 carbon atoms), and one or both of $R^4$ and $R^5$ independently comprise at least one, two, three, four, five, or six sites of unsaturation in the trans configuration. In some preferred embodiments, at least one of $R^4$ and $R^5$ comprises an (E)-heptadeceyl moiety. In other preferred embodiments, $R^4$ and $R^5$ are both (E)-8-heptadeceyl moieties.

In some embodiments, the cationic lipid of Formula XIV forms a salt (preferably a crystalline salt) with one or more anions. In one particular embodiment, the cationic lipid of Formula XIV is the oxalate (e.g., hemioxalate) salt thereof, which is preferably a crystalline salt.

In a particularly preferred embodiment, the cationic lipid of Formula XIV has the structure:

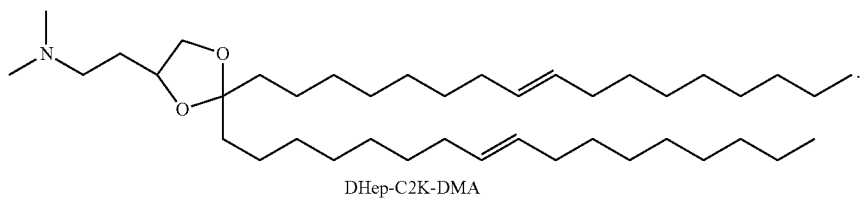 [SMILES: CCCCCCCC/C=C/CCCCCCCC1(CCCCCCC/C=C/CCCCCCCC)OCC(CCN(C)C)O1]

DHep-C2K-DMA

In another aspect, the present invention provides a cationic lipid of Formula XV having the following structure:

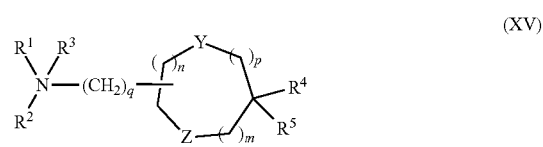

(XV)

or salts thereof, wherein: $R^1$ and $R^2$ are joined to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are joined to form a heterocyclic ring of 5 carbon atoms and 1 nitrogen atom. In certain instances, the heterocyclic ring is substituted with a substituent such as a hydroxyl group at the ortho, meta, and/or para positions. In a preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula XV forms a salt (preferably a crystalline salt) with one or more anions. In one particular embodiment, the cationic lipid of Formula XV is the oxalate (e.g., hemioxalate) salt thereof, which is preferably a crystalline salt.

In a particularly preferred embodiment, the cationic lipid of Formula XV has the structure:

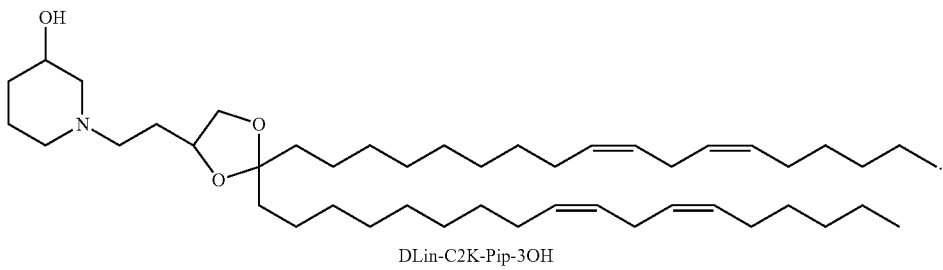 [SMILES: CCCCC/C=C\C/C=C\CCCCCCCCC1(CCCCCCCC/C=C\C/C=C\CCCCC)OCC(CCN2CCCC(O)C2)O1]

DLin-C2K-Pip-3OH optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine;

$R^4$ and $R^5$ are either the same or different and are independently a substituted $C_{12}$-$C_{24}$ alkyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In one particular embodiment, n is 1. In another particular embodiment, n is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl (3,7,11,15-tetramethyl-hexadecanyl) moiety. In particular embodiments, $R^4$ and $R^5$ are both phytanyl moieties.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl (3,7,11,15-tetramethyl-hexadecanoyl) moiety. In particular embodiments, $R^4$ and $R^5$ are both phytanoyl moieties.

In some embodiments, the cationic lipid of Formula XVI forms a salt (preferably a crystalline salt) with one or more anions. In one particular embodiment, the cationic lipid of Formula XVI is the oxalate (e.g., hemioxalate) salt thereof, which is preferably a crystalline salt.

In a particularly preferred embodiment, the cationic lipid of Formula XVI has a structure selected from the group consisting of:

In yet another aspect, the present invention provides a cationic lipid of Formula XVI having the following structure:

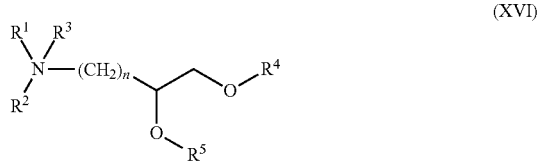

(XVI)

or salts thereof, wherein:

$R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an

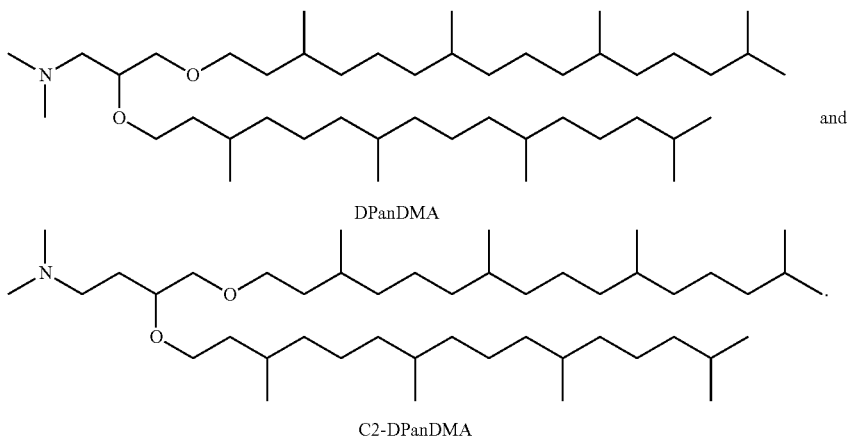

DPanDMA and

C2-DPanDMA

The synthesis of cationic lipids of Formulas V-XVI is described in PCT Application No. PCT/CA2010/001029, filed Jun. 30, 2010, the disclosure of which is herein incorporated by reference in its entirety for all purposes.

Other cationic lipids or salts thereof which may be included in the lipid particles of the present invention include, but are not limited to, 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride (DOTAP.Cl), dilinoleylmethyl-3-dimethylaminopropionate (DLin-M-K-DMA; also known as DLin-M-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl) cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS),3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ),3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), and mixtures thereof.

Additional cationic lipids or salts thereof which may be included in the lipid particles of the present invention include, without limitation, cationic lipids such as (6Z,9Z,28Z,31Z)-heptatriaconta-6,9,28,31-tetraen-19-yl 4-(dimethylamino) butanoate (DLin-M-C3-DMA or "MC3") and certain analogs thereof as described in U.S. Provisional Patent Application No. 61/334,104, entitled "Novel Cationic Lipids and Methods of Use Thereof," filed May 12, 2010, and PCT Publication Nos. WO 2010/054401, WO 2010/054405, WO 2010/054406, and WO 2010/054384, the disclosures of which are herein incorporated by reference in their entirety for all purposes.

The synthesis of cationic lipids such as DO-C-DAP, DMDAP, DOTAP.Cl, DLin-M-K-DMA, as well as additional cationic lipids, is described in PCT Publication No. WO 2010/042877, the disclosure of which is incorporated herein by reference in its entirety for all purposes.

The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086,558, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes.

The synthesis of a number of other cationic lipids and related analogs has been described in U.S. Pat. Nos. 5,208, 036; 5,264,618; 5,279,833; 5,283,185; 5,753,613; and 5,785, 992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from GIBCO/BRL); LIPOFECTAMINE® (including DOSPA and DOPE, available from GIBCO/BRL); and TRANSFECTAM® (including DOGS, available from Promega Corp.).

In some embodiments, the cationic lipid comprises from about 45 mol % to about 90 mol %, from about 45 mol % to about 85 mol %, from about 45 mol % to about 80 mol %, from about 45 mol % to about 75 mol %, from about 45 mol % to about 70 mol %, from about 45 mol % to about 65 mol %, from about 45 mol % to about 60 mol %, from about 45 mol % to about 55 mol %, from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol % or from about 55 mol % to about 70 mol % (or any fraction thereof or range therein) of the total lipid present in the particle.

In certain preferred embodiments, the cationic lipid comprises from about 50 mol % to about 58 mol %, from about 51 mol % to about 59 mol %, from about 51 mol % to about 58 mol %, from about 51 mol % to about 57 mol %, from about 52 mol % to about 58 mol %, from about 52 mol % to about 57 mol %, from about 52 mol % to about 56 mol %, or from about 53 mol % to about 55 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof or range therein) of the total lipid present in the particle. In certain other embodiments, the cationic lipid comprises (at least) about 66, 67, 68, 69, 70, 71, 72, 73, 74, 75, 76, 77, 78, 79, 80, 81, 82, 83, 84, 85, 86, 87, 88, 89, or 90 mol % (or any fraction thereof or range therein) of the total lipid present in the particle.

In additional embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127,060, U.S. application Ser. No. 12/794,701, filed Jun. 4, 2010, and U.S. application Ser. No. 12/828,189, filed Jun. 30, 2010, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in the 1:57 lipid particle (e.g., SNALP) formulation, the target amount of cationic lipid is 57.1 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of cationic lipid is 54.06 mol %, but the actual amount of cationic lipid may be ±5 mol %, ±4 mol %, ±3 mol %, ±2 mol %, ±1 mol %, 0.75 mol %, ±0.5 mol %, 0.25 mol %, or ±0.1 mol % of that target amount, with the balance of the formulation being made up of other lipid components (adding up to 100 mol % of total lipids present in the particle).

B. Non-Cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127,060, the disclosure of which is herein incorporated by reference in its entirety for all purposes.

In some embodiments, the non-cationic lipid present in the lipid particles (e.g., SNALP) comprises or consists of a mixture of one or more phospholipids and cholesterol or a derivative thereof. In other embodiments, the non-cationic lipid present in the lipid particles (e.g., SNALP) comprises or consists of one or more phospholipids, e.g., a cholesterol-free lipid particle formulation. In yet other embodiments, the non-cationic lipid present in the lipid particles (e.g., SNALP) comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a 1:57 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a 7:54 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle. In other embodiments, the cholesterol component in the mixture comprises about 36, 37, 38, 39, 40, 41, 42, 43, 44, or 45 mol % (or any fraction thereof or range therein) of the total lipid present in the particle. Typically, a 1:57 lipid particle formulation comprising a mixture of phospholipid and cholesterol may comprise cholesterol or a cholesterol derivative at about 34 mol % (or any fraction thereof), e.g., in a mixture with a phospholipid such as DPPC or DSPC at about 7 mol % (or any fraction thereof) of the total lipid present in the particle. Typically, a 7:54 lipid particle formulation comprising a mixture of phospholipid and cholesterol may comprise cholesterol or a cholesterol derivative at about 32 mol % (or any fraction thereof), e.g., in a mixture with a phospholipid such as DPPC or DSPC at about 7 mol % (or any fraction thereof) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle. As a non-limiting example, a 1:62 lipid particle formulation may comprise cholesterol at about 37 mol % (or any fraction thereof) of the total lipid present in the particle. As another non-limiting example, a 7:58 lipid particle formulation may comprise cholesterol at about 35 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127,060, U.S. application Ser. No. 12/794,701, filed Jun. 4, 2010, and U.S. application Ser. No. 12/828,189, filed Jun. 30, 2010, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by ±5 mol %. For example, in the 1:57 lipid particle (e.g., SNALP) formulation, the target amount of phospholipid is 7.1 mol % and the target amount of cholesterol is 34.3 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, +0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of phospholipid is 6.75 mol % and the target amount of cholesterol is 32.43 mol %, but the actual amount of phospholipid may be ±2 mol %, ±1.5 mol %, ±1 mol %, ±0.75 mol %, +0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

C. Lipid Conjugates

In addition to cationic and non-cationic lipids, the lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086,558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-dioxaoctanyl]carbamoyl-w-methyl-poly(ethylene glycol) (2KPEG-DMG). The synthesis of 2KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S—NHS, HO-PEG-NH$_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (Me-PEG-CH$_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" includes, without limitation, compounds described in U.S. Pat. Nos. 6,320,017 and 6,586,559, the disclosures of which are herein incorporated by reference in their entirety for all purposes. These compounds include a compound having the formula:

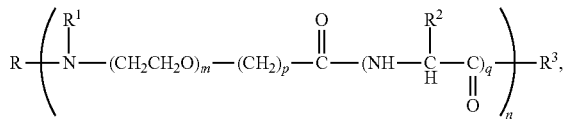

(XVII)

wherein R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

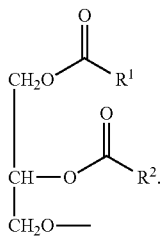

(XVIII)

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

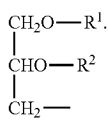

(XIX)

In a preferred embodiment, the PEG-lipid is a PEG-DAA conjugate having the following formula:

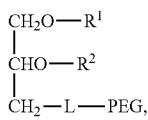

(XX)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula XX above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

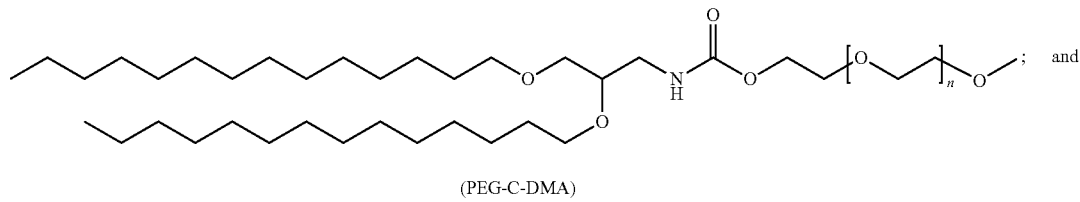

(PEG-C-DMA)

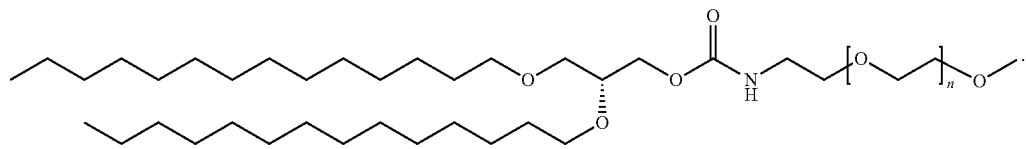

(PEG-C-DOMG)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles (e.g., SNALP) of the present invention can further comprise cationic poly(ethylene glycol) (PEG) lipids or CPLs (see, e.g., Chen et al., *Bioconj. Chem.*, 11:433-437 (2000); U.S. Pat. No. 6,852,334; PCT Publication No. WO 00/62813, the disclosures of which are herein incorporated by reference in their entirety for all purposes).

Suitable CPLs include compounds of Formula XXI:

A-W—Y                                    (XXI), wherein A, W, and Y are as described below.

With reference to Formula XXI, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N—N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatible polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

Additional examples, percentages, and/or ranges of lipid conjugates suitable for use in the lipid particles of the invention are described in PCT Publication No. WO 09/127,060, U.S. application Ser. No. 12/794,701, filed Jun. 4, 2010, U.S. application Ser. No. 12/828,189, filed Jun. 30, 2010, U.S. Provisional Application No. 61/294,828, filed Jan. 13, 2010, U.S. Provisional Application No. 61/295, 140, filed Jan. 14, 2010, and PCT Publication No. WO 2010/006282, the disclosures of which are herein incorporated by reference in their entirety for all purposes.

It should be understood that the percentage of lipid conjugate (e.g., PEG-lipid) present in the lipid particles of the invention is a target amount, and that the actual amount of lipid conjugate present in the formulation may vary, for example, by ±2 mol %. For example, in the 1:57 lipid particle (e.g., SNALP) formulation, the target amount of lipid conjugate is 1.4 mol %, but the actual amount of lipid conjugate may be ±0.5 mol %, ±0.4 mol %, ±0.3 mol %, ±0.2 mol %, ±0.1 mol %, or ±0.05 mol % of that target amount, with the balance of the formulation being made up of other lipid components (adding up to 100 mol % of total lipids present in the particle). Similarly, in the 7:54 lipid particle (e.g., SNALP) formulation, the target amount of lipid conjugate is 6.76 mol %, but the actual amount of lipid conjugate may be ±2 mol %, ±1.5 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle (e.g., SNALP) size.

VI. Preparation of Lipid Particles

The lipid particles of the present invention, e.g., SNALP, in which a nucleic acid such as an interfering RNA (e.g., siRNA) is entrapped within the lipid portion of the particle and is protected from degradation, can be formed by any method known in the art including, but not limited to, a continuous mixing method, a direct dilution process, and an in-line dilution process.

In particular embodiments, the cationic lipids may comprise one or more lipids of Formulas I-XVI or salts thereof, alone or in combination with other cationic lipid species. In other embodiments, the non-cationic lipids may comprise one or more lipids including egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the present invention provides nucleic acid-lipid particles (e.g., SNALP) produced via a continuous mixing method, e.g., a process that includes providing an aqueous solution comprising a nucleic acid (e.g., interfering RNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles (e.g., SNALP) produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles (e.g., SNALP) produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles are precondensed as described in, e.g., U.S. patent application Ser. No. 09/744,103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle (e.g., SNALP) will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 µg nucleic acid per 10 mg total lipid or a nucleic acid to lipid mass ratio of about 0.01 to about 0.08 and, more preferably, about 0.04, which corresponds to 1.25 mg of total lipid per 50 µg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle (e.g., SNALP) will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making SNALP-CPLs (CPL-containing SNALP) are discussed herein. Two general techniques include the "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

VII. Kits

The present invention also provides lipid particles (e.g., SNALP) in kit form. In some embodiments, the kit comprises a container which is compartmentalized for holding the various elements of the lipid particles (e.g., the active agents or therapeutic agents such as nucleic acids and the individual lipid components of the particles). Preferably, the kit comprises a container (e.g., a vial or ampoule) which holds the lipid particles of the invention (e.g., SNALP), wherein the particles are produced by one of the processes set forth herein. In certain embodiments, the kit may further comprise an endosomal membrane destabilizer (e.g., calcium ions). The kit typically contains the particle compositions of the invention, either as a suspension in a pharmaceutically acceptable carrier or in dehydrated form, with instructions for their rehydration (if lyophilized) and administration.

As explained herein, the lipid particles of the present invention can be tailored to preferentially target particular tissues, organs, or tumors of interest. In certain instances, preferential targeting of lipid particles such as SNALP may be carried out by controlling the composition of the particle itself. For example, it has been found that the 1:57 PEG-C-DSA SNALP formulation can be used to preferentially target solid tumors outside of the liver, whereas the 1:57 PEG-C-DMA SNALP formulation can be used to preferentially target solid liver tumors (including hepatocellular carcinoma (HCC) and liver metastatic disease). It has also been discovered that the 7:54 lipid particle (e.g., 7:54 DLinDMA SNALP) formulation can be used to preferentially target solid tumors such as liver tumors and tumors outside of the liver. The tumor targeting abilities of these lipid particles is described in PCT Publication No. WO 2009/127060, and in U.S. application Ser. No. 12/828,189, filed Jun. 30, 2010, the disclosures of which are herein incorporated by reference in their entirety for all purposes. In preferred embodiments, the kits of the invention comprise these lipid particles, wherein the particles are present in a container as a suspension or in dehydrated form. Such kits are particularly advantageous for use in providing effective inhibition of cancer cell proliferation and/or induction of cancer cell apoptosis.

In certain instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

VIII. Administration of Lipid Particles

Once formed, the lipid particles of the invention (e.g., SNALP) are particularly useful for introducing interfering RNA (e.g., siRNA) targeting one or more genes associated with tumorigenesis or cell transformation (such as COP1, CSN5, RBX1, HDAC2, CDK4, WEE1, FOXM1, R1, or combinations thereof) into cells. Accordingly, the present invention also provides methods for introducing one or more interfering RNA (e.g., siRNA) into a cell. Preferably, the cell is a tumor cell such as, e.g., a cell present in a solid tumor. In certain embodiments, the cell may be a non-tumor cell that produces one or more angiogenic and/or growth factors associated with tumorigenesis or cell transformation. The methods are carried out in vitro or in vivo by first forming the particles as described above and then contacting the particles with the cells (e.g., cells of a solid tumor) for a period of time sufficient for delivery of the interfering RNA to the cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid (e.g., interfering RNA) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle (e.g., SNALP) is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention (e.g., SNALP) are particularly useful in methods for the therapeutic delivery of one or more nucleic acids comprising an interfering RNA sequence (e.g., siRNA). In particular, it is an object of the present invention to provide in vitro and in vivo methods for treatment of cancer in a mammal (e.g., a rodent such as a mouse or a primate such as a human, chimpanzee, or monkey) by downregulating or silencing the transcription and/or translation of one or more target nucleic acid sequences or genes of interest (such as COP1, CSN5, RBX1, HDAC2, CDK4, WEE1, FOXM1, R1, or combinations thereof). As a non-limiting example, the methods of the invention are useful for the in vivo delivery of interfering RNA (e.g., siRNA) to a tumor or other neoplasia of a mammalian subject for the treatment of cancer. In certain embodiments, the cancerous condition is associated with expression and/or overexpression of a gene or combination of genes (such as COP1, CSN5, RBX1, HDAC2, CDK4, WEE1, FOXM1, and/or R1), and expression or overexpression of the gene or combination of genes is reduced by the interfering RNA (e.g., siRNA). In certain other embodiments, a therapeutically effective amount of the lipid particle formulation may be administered to the mammal. In some instances, one, two, three, four, five, six, seven, eight, nine, ten, or more interfering RNA molecules (e.g., siRNA) are formulated into a SNALP (i.e., co-encapsulated in the same particle), and the particles are administered to patients requiring such treatment. In other instances, one, two, three, four, five, six, seven, eight, nine, ten, or more interfering RNA molecules (e.g., siRNA) are each formulated into a different SNALP (i.e., encapsulated in separate particles such that there is only one type of siRNA species per particle), and a mixture (i.e., combination, cocktail, pool, etc.) of the different particles is administered to patients requiring such treatment. In certain instances, cells are removed from a patient, the interfering RNA is delivered in vitro (e.g., using a SNALP described herein), and the cells are reinjected into the patient.

A. In vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are non-immunogenic, are small in size, and are suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.*, 101:512 (1983); Mannino et al., *Biotechniques*, 6:682 (1988); Nicolau et al., *Crit. Rev. Ther. Drug Carrier Syst.*, 6:239 (1989); and Behr, *Acc. Chem. Res.*, 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

In embodiments where the lipid particles of the present invention (e.g., SNALP) are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In some embodiments, the presence of a therapeutic nucleic acid such as an interfering RNA (e.g., siRNA) is detectable in cells of a tumor such as a solid tumor at about 8, 12, 24, 36, 48, 60, 72 or 96 hours after administration. In certain other embodiments, downregulation of expression of a target sequence by an interfering RNA (e.g., siRNA) is detectable at about 8, 12, 24, 36, 48, 60, 72 or 96 hours after administration. In yet other embodiments, downregulation of expression of a target sequence by an interfering RNA (e.g., siRNA) occurs preferentially in tumor cells. In further embodiments, the presence or effect of an interfering RNA (e.g., siRNA) in cells at a site proximal or distal to the site of administration or in cells of a tumor is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., Am. J. Sci., 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic nucleic acid (e.g., interfering RNA) suspended in diluents such as water, saline, or PEG 400; (b) capsules, sachets, or tablets, each containing a predetermined amount of a therapeutic nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic nucleic acid (e.g., interfering RNA) in a flavor, e.g., sucrose, as well as pastilles comprising the therapeutic nucleic acid in an inert base, such as gelatin and glycerin or sucrose and acacia emulsions, gels, and the like containing, in addition to the therapeutic nucleic acid, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic nucleic acid (e.g., interfering RNA) to lipid, the particular therapeutic nucleic acid used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In vitro Administration

For in vitro applications, the delivery of therapeutic nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells (e.g., tumor cells).

Contact between the cells and the lipid particles, when carried out in vitro, takes place in a biologically compatible medium. The concentration of particles varies widely depending on the particular application, but is generally between about 1 μmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2\times10^4$ cells/ml. The concentration of the suspension added to the cells is preferably of from about 0.01 to 0.2 μg/ml, more preferably about 0.1 μg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP or other lipid particle based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure down-regulation of transcription or translation of a target sequence in the presence or absence of an interfering RNA (e.g., siRNA). By comparing the ERPs for each of the various SNALP or other lipid particles, one can readily determine the optimized system, e.g., the SNALP or other lipid particle that has the greatest uptake in the cell.

C. Cells for Delivery of Lipid Particles

The compositions and methods of the present invention are particularly well suited for treating cancer or other neoplasia by targeting, e.g., genes associated with tumorigenesis or cell transformation in vivo. In preferred embodiments, a therapeutic nucleic acid such as an interfering RNA (e.g., siRNA) is preferentially delivered to cancer cells (e.g., cells of a solid tumor) including, but not limited to, liver cancer cells, lung cancer cells, colon cancer cells, rectal cancer cells, anal cancer cells, bile duct cancer cells, small intestine cancer cells, stomach (gastric) cancer cells, esophageal cancer cells, gallbladder cancer cells, pancreatic cancer cells, appendix cancer cells, breast cancer cells, ovarian cancer cells, cervical cancer cells, prostate cancer cells, renal cancer cells, cancer cells of the central nervous system, glioblastoma tumor cells, skin cancer cells, lymphoma cells, choriocarcinoma tumor cells, head and neck cancer cells, osteogenic sarcoma tumor cells, and blood cancer cells.

In other embodiments, a therapeutic nucleic acid such as an interfering RNA (e.g., siRNA) is delivered to hepatocytes, hematopoietic precursor (stem) cells, fibroblasts, keratinocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like.

In vivo delivery of lipid particles such as SNALP encapsulating a nucleic acid (e.g., an interfering RNA) is suited for targeting tumor cells of any cell type. The methods and compositions can be employed with tumor cells of a wide variety of vertebrates, including mammals, such as, e.g, canines, felines, equines, bovines, ovines, caprines, rodents (e.g., mice, rats, and guinea pigs), lagomorphs, swine, and primates (e.g. monkeys, chimpanzees, and humans).

D. Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a therapeutic nucleic acid such as an interfering RNA (e.g., siRNA) sequence, detection of the target sequence of interest (i.e., by detecting expression or reduced expression of the sequence of interest), or a combination thereof.

1. Detection of Particles

Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C&EN* 36; The *Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomeli et al., *J. Clin. Chem.*, 35:1826 (1989); Landegren et al., *Science*, 241:1077 (1988); Van Brunt, *Biotechnology*, 8:291 (1990); Wu and Wallace, *Gene*, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of polynucleotides, where necessary, is typically performed by either native acrylamide gel electrophoresis or by anion exchange HPLC as described in Pearson et al., *J. Chrom.*, 255:137 149 (1983). The sequence of the synthetic polynucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

IX. EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Materials and Methods siRNA: All siRNA molecules used in these studies were chemically synthesized and annealed using standard procedures. The target siRNA sequences used in these studies are shown in Tables 11-30. In particular embodiments, the interfering RNA (e.g., siRNA) of the present invention comprises: a sense strand comprising nucleotides 1-19 of any one of the sense strand sequences set forth in Tables 11-30; and an antisense strand comprising nucleotides 1-19 of any one of the antisense strand sequences set forth in Tables 11-30. In other particular embodiments, the interfering RNA (e.g., siRNA) of the present invention comprises: a sense strand selected from any one of the sense strand sequences set forth in Tables 11-30; and an antisense strand selected from any one of the antisense strand sequences set forth in Tables 11-30. The βgal478 siRNA sequences are as follows:

Sense strand: 5'-mGAAGmGCCAGACmGCmGAA-UUAdTdT-3' (SEQ ID NO: 236);

Antisense strand: 5'-UAAUmUCGCGmUCUGGCC-mUUCdTdT-3' (SEQ ID NO: 237).

mU=2'OMe-uridine; mG=2'OMe-guanosine; dT=deoxythymidine.

Lipid encapsulation of siRNA: In some embodiments, siRNA molecules of the invention were encapsulated into serum-stable nucleic acid-lipid particles (SNALP) composed of the following lipids: (1) the lipid conjugate PEG2000-C-DMA (3-N—[(-methoxypoly(ethylene glycol)2000)carbamoyl]-1,2-dimyristyloxypropylamine); (2) the cationic lipid DLinDMA (1,2-dilinoleyloxy-3-(N,N-dimethyl)aminopropane); (3) the phospholipid DPPC (1,2-dipalmitoyl-sn-glycero-3-phosphocholine) (Avanti Polar Lipids; Alabaster, Ala.);

and (4) synthetic cholesterol (Sigma-Aldrich Corp.; St. Louis, Mo.) in the molar ratio 1.4:57.1:7.1:34.3, respectively. In other words, siRNA molecules were encapsulated into SNALP of the following "1:57" formulation: 1.4% PEG2000-C-DMA; 57.1% DLinDMA; 7.1% DPPC; and 34.3% cholesterol.

It should be understood that the 1:57 formulation is a target formulation, and that the amount of lipid (both cationic and non-cationic) present and the amount of lipid conjugate present in the formulation may vary. Typically, in the 1:57 formulation, the amount of cationic lipid will be 57.1 mol % 5 mol %, and the amount of lipid conjugate will be 1.4 mol % 0.5 mol %, with the balance of the 1:57 formulation being made up of non-cationic lipid (e.g., phospholipid, cholesterol, or a mixture of the two).

For vehicle controls, empty particles with identical lipid composition may be formed in the absence of siRNA.

Cell culture and transfection of siRNA in vitro: The human liver cancer cell lines, Huh7 and HepG2, were purchased from American Type Culture Collection. The cells were maintained in DMEM/F-12 media (Mediatech) supplemented with 10% fetal bovine serum (Atlanta Biologicals) at 37° C. in the presence of 5% $CO_2$. To examine the phenotypic changes in the HCC cells, before the day of transfection, 25% confluency of the cells were seeded on 96-well plates in 100 µl of culture media without antibiotics. SNALP-formulated siRNA or siRNA-LF2000 complexes (i.e., lipoplexes) were added to Huh7 and HepG2 cells. The cultures were exchanged with fresh media 24 h after transfection and incubated for 2-3 days further. To compare the effects of target siRNA molecules, identical quantities of NC #1 siRNA+ lipids were also added to the same number of cells and assayed simultaneously. For other assays, which are needed to transfect cells in different tissue culture formats, the amounts of lipids, siRNA, cells, and medium was proportioned to the relative surface area according to the manufacturer's protocol.

Measurement of cell proliferation and apoptotic cell death: Control and target siRNA molecules were studied for their growth inhibitory effects using the Vybrant MTT Cell Proliferation Assay (Invitrogen) as recommended by the manufacturer. The cells were measured for absorbance at 540 nm with an ELISA reader, SpectraMAX 190 (Molecular Devices). The percentage of growth inhibition of cells in each well treated with naked siRNA or SNALP-formulated siRNA was calculated by comparing the optical density with those of untreated control, using the following formula: 1–(absorbance of an experimental well/absorbance of a sham control well)×100. After transfection of siRNA, the induction of apoptosis was measured in cells cultured in vitro by using the ApoStrand ELISA Apoptosis Detection Kit (Biomol International) that detects the denatured DNA to single-stranded DNA formed in apoptotic cells, but not in the necrotic cells or in cells with DNA breaks in the absence of apoptosis.

Detection of target gene transcripts and polypeptides: After the transfection of siRNA, the change of target gene expression in mRNA level was detected with real-time quantitative RT-PCR. Total RNA preparation was carried out with Tri reagent (Molecular Research Center) according to the protocol recommended by the manufacturer. Total RNA (1 µg) was reverse transcribed by using random primers supplied in the High-Capacity cDNA Archieve Kit (Applied Biosystems). To quantify gene expression, cDNA of the target gene was amplified by using a pair of primers, Power SYBR Green PCR Master Mix, and an ABI 7700HT PCR Machine (both from Applied Biosystems) according to the manufacturer's instructions. To normalize the amount of total RNA present in each reaction, the GAPDH gene was amplified simultaneously. All reactions were performed in triplicate.

Quantification of proteins after siRNA treatment was performed with the Western blotting method. The amount of total proteins was determined with the BCA Protein Assay Kit (Pierce). 100 µg of total protein was run on 4-20% SDS-polyacrylamide gels and transferred onto PVDF membrane (Invitrogen). The membrane was blocked by incubating with 5% milk/Tris-buffered saline plus Tween 20 (TBST) and then incubated with primary antibodies to the target protein, p53 (FL-393), and p21 (C-19) (Santa Cruz Biotechnology). Depending on the source of antibody production, the secondary antibody of horseradish peroxidase (HRP)-conjugated anti-rabbit IgG (Pierce), anti-goat IgG (Santa Cruz), or anti-mouse IgG (Amersham) was added, and immunoreactive bands were visualized with the ECL Plus Western Blotting Detection System (GE Healthcare). The loading of equal amounts was assessed by probing the same membrane with ACTIN antibody (NeoMarker).

Mouse strains and animal care: The immunodeficient mice used in the studies were male SCID-beige, 5-6 weeks old (Charles River Laboratories). Animal housing and care were in accordance with the guidelines from the Animal Care and Use Committee at the U.S. National Cancer Institute. These studies were approved by the Institutional Review Board of the U.S. National Cancer Institute.

Generation of HCC cell lines permanently expressing luciferase: Using Lipofectamine 2000, Huh7 cells were transfected with the pGL4.17 vector (Promega) expressing firefly luciferase and the zeocin resistance gene. To enhance the expression of the luciferase gene, the β-actin promoter from the pCAGEN plasmid (Addgene) was subcloned into the multiple cloning site of pGL4.17. Cells were selected for antibiotic resistance with Geneticin (Gibco), and surviving colonies were amplified and screened for bioluminescence in complete media supplemented with 150 µg/ml D-luciferin (Biosynth) by in vitro imaging with the IVIS Imaging System (Xenogen). A suitable Huh7-1H6 clone was selected in terms of stable luminescence in vitro and used for further studies.

Systemic administration of SNALP-formulated siRNA and bioluminescence imaging (BLI) in vivo: A total number of $5 \times 10^5$ Huh7-luc$^+$ cells in 50 µl of PBS buffer (with $Ca^{2+}$ and $Mg^{2+}$ ions) was transplanted into the spleen of 5-6 week-old male SCID-beige mice, and 30 seconds after cell injection spleen was removed to evade tumor formations in other organs except in liver, which is induced by cell migrations through the circulatory system. Tumors were detectable from day 7 by BLI, and kept growing exponentially up to day 28. Beginning at 8 days after transplantation, mice were randomized and administered SNALP-formulated siRNA formulations as an i.v. injection into the lateral tail vein at a dosage of 2 mg/kg. Injections were performed three to four times over a period of 3-5 sec with a 3-day interval. Tumor growth in the liver was monitored by BLI for 4-weeks with 3-4 day intervals, using an IVIS Imaging System (Xenogen). Images and measurements of luciferase signals were obtained and analyzed using the Living Image Software (Xenogen). Ten minutes prior to in vivo imaging, mice were anesthetized using 1-3% isoflurane (Abbott Laboratories) and received the substrate luciferin (Biosynth) at 150 mg/kg in DPBS by an i.p. injection. Regions of interest (ROI) from displayed images were drawn around the tumor sites and quantified as photons/second using the Living Image Software.

Histopathology: To confirm the presence of neoplastic cells, liver tissues were preserved with 10% formalin solution and histological examination (paraffin embedding, sectioning, and H&E staining) was performed by Histoserv.

Cytokine induction assays: Flt3-ligand derived murine dendritic cells (Flt3L DC) were generated as described by Gilliet et al. (*J. Exp. Med.*, 195:953-958) using 100 ng/ml murine Flt3-ligand (PeproTech Inc.; Rocky Hill, N.J.) supplemented media. Femurs and tibiae of female Balb/C mice were isolated and rinsed in sterile PBS. The ends of bones were cut and marrow harvested in complete media (RPMI 1640, 10% heat inactivated FBS, 1% penicillin/streptomycin, 2 mM L-glutamine, 1 mM sodium pyruvate, 25 mM HEPES, 50 µM 2-mercaptoethanol). Bone marrow cells were passed through a 70 µm strainer, centrifuged at 1000 rpm for 7 minutes, and resuspended in complete media supplemented with 100 ng/ml murine Flt3L to $2 \times 10^6$ cells/ml. 2 mls of cells were seeded in 6-well plates and 1 ml fresh complete media added every two or three days. On day 9 of culture, non-adherent cells were washed in complete media and plated into 96-well plates at concentrations ranging from 0.5 to $2.5 \times 10^5$ cells/well. SNALP were diluted in PBS and added to Flt3L DC cultures at 5 µg/ml siRNA. Cells were incubated for 24 hours at 37° C. before supernatants were assayed for cytokines by ELISA.

Cytokine ELISA: IL-6 or IFN-α levels in culture supernatants of mouse Flt3L dendricytes were quantified using a sandwich ELISA kit according to manufacturer's instructions (BD Biosciences; San Jose, Calif.).

Example 2

Therapeutic Targeting of COP1 or WEE1 with siRNA for the Treatment of Cancer

This example illustrates that (1) siRNA-mediated knockdown of COP1 or WEE1 expression inhibited the proliferation of cells from a variety of human HCC cell lines; (2) treatment with siRNA targeting COP1 or WEE1 increased apoptosis of human HCC cells by restoring the protein levels of the p53 tumor suppressor; (3) WEE1 silencing decreased the size of side population-containing cancer stem cells (CSC), indicating that targeting the WEE1 gene is effective in anti-CSC therapy; and (4) systemic delivery of SNALP containing chemically modified COP1 or WEE1 siRNA effectively suppressed neoplastic growth in a mouse model of metastatic human liver cancer.

COP1 and WEE1 siRNA sequences used in this study

Table 11 provides a list of exemplary siRNA sequences targeting human COP1 gene expression.

TABLE 11 siRNA sequences that target human COP1 gene expression.

| siRNA | Target or Sense Strand Sequence (5' → 3') | Antisense Strand Sequence (5' → 3') |
|---|---|---|
| COP1-1 | GGACACCGUAAAGCAGUCU*tt* (SEQ ID NO: 51) | AGACUGCUUUACGGUGUCC*tt* (SEQ ID NO: 52) |
| COP1-2 | GGAAUGCUUGUCCAAGUUU*tt* (SEQ ID NO: 238) | AAACUUGGACAAGCAUUCC*tg* SEQ ID NO: 239) |
| COP1-3 | GCAACGACUUCGUAUGCCC*tt* (SEQ ID NO: 240) | GGGCAUACGAAGUCGUUGC*tt* (SEQ ID NO: 241) |

3'-overhangs are indicated in bold and italicized. The 3'-overhangs on one or both strands of the siRNA molecule may alternatively comprise 1-4 deoxythymidine (t) nucleotides, 1-4 modified and/or unmodified uridine (U) ribonucleotides, or 1-4 unmodified and/or modified ribonucleotides or deoxyribonucleotides having complementarity to the target sequence or the complementary strand thereof. In certain instances, the sense and/or antisense strand of the siRNA molecule lacks 3'-overhangs (i.e., does not contain the sequence indicated in bold and italicized). Lower case letters = 2'-deoxy nucleotides.

Table 12 provides a list of exemplary siRNA sequences targeting human WEE1 gene expression.

TABLE 12 siRNA sequences that target human WEE1 gene expression.

| siRNA | Target or Sense Strand Sequence (5' → 3') | Antisense Strand Sequence (5' → 3') |
|---|---|---|
| WEE1-1 | GGUAUAUUCAUUCAAUGUC*tt* (SEQ ID NO: 242) | GACAUUGAAUGAAUAUACC*tc* (SEQ ID NO: 243) |
| WEE1-2 | GGCUGGAUGGAUGCAUUUA*tt* (SEQ ID NO: 116) | UAAAUGCAUCCAUCCAGCC*tc* (SEQ ID NO: 117) |
| WEE1-3 | GGACAGUGUCGUCGUAGAA*tt* (SEQ ID NO: 244) | UUCUACGACGACACUGUCC*tg* (SEQ ID NO: 245) |

3'-overhangs are indicated in bold and italicized. The 3'-overhangs on one or both strands of the siRNA molecule may alternatively comprise 1-4 deoxythymidine (t) nucleotides, 1-4 modified and/or unmodified uridine (U) ribonucleotides, or 1-4 unmodified and/or modified ribonucleotides or deoxyribonucleotides having complementarity to the target sequence or the complementary strand thereof. In certain instances, the sense and/or antisense strand of the siRNA molecule lacks 3'-overhangs (i.e., does not contain the sequence indicated in bold and italicized). Lower case letters = 2'-deoxy nucleotides.

TABLE 13

Table 13 provides a list of chemically modified COP1-1 siRNA molecules containing 2'OMe nucleotides at selective positions within the double-stranded region.
2'OMe-modified siRNA sequences that target human COP1 gene expression.

| siRNA | Target or Sense Strand Sequence (5' → 3') | Antisense Strand Sequence (5' → 3') |
|---|---|---|
| COP1-1/5 | GGACACCGUAAAGCAGUCU*tt* (SEQ ID NO: 51) | AGACUGCUUUACGGUGUCC*tt* (SEQ ID NO: 246) |
| COP1-1/6 | GGACACCGUAAAGCAGUCU*tt* (SEQ ID NO: 51) | AGACUGCUUUACGGUGUCC*tt* (SEQ ID NO: 247) |
| COP1-1/7 | GGACACCGUAAAGCAGUCU*tt* (SEQ ID NO: 51) | AGACUGCUUUACGGUGUCC*tt* (SEQ ID NO: 59) |
| COP1-3/2 | GGACACCGUAAAGCAGUCU*tt* (SEQ ID NO: 248) | AGACUGCUUUACGGUGUCC*tt* (SEQ ID NO: 52) |

TABLE 13-continued

Table 13 provides a list of chemically modified COP1-1 siRNA molecules containing 2'OMe nucleotides at selective positions within the double-stranded region.
2'OMe-modified siRNA sequences that target human COP1 gene expression.

| Target or Sense Strand Sequence siRNA(5' → 3') | Antisense Strand Sequence (5' → 3') |
|---|---|
| COP1-GGACACCGUAAAGCAGUCU*tt* 3/5 (SEQ ID NO: 248) | AGACUGCUUUACGGUGUCC*tt* (SEQ ID NO: 246) |
| COP1-GGACACCGUAAAGCAGUCU*tt* 3/6 (SEQ ID NO: 248) | AGACUGCUUUACGGUGUCC*tt* (SEQ ID NO: 247) |
| COP1-GGACACCGUAAAGCAGUCU*tt* 3/7 (SEQ ID NO: 248) | AGACUGCUUUACGGUGUCC*tt* (SEQ ID NO: 59) |
| COP1-GGACACCGUAAAGCAGUCU*tt* 4/2 (SEQ ID NO: 58) | AGACUGCUUUACGGUGUCC*tt* (SEQ ID NO: 52) |
| COP1-GGACACCGUAAAGCAGUCU*tt* 4/5 (SEQ ID NO: 58) | AGACUGCUUUACGGUGUCC*tt* (SEQ ID NO: 246) |
| COP1-GGACACCGUAAAGCAGUCU*tt* 4/6 (SEQ ID NO: 58) | AGACUGCUUUACGGUGUCC*tt* (SEQ ID NO: 247) |
| COP1-GGACACCGUAAAGCAGUCU*tt* 4/7 (SEQ ID NO: 58) | AGACUGCUUUACGGUGUCC*tt* (SEQ ID NO: 59) |

2'OMe nucleotides are indicated in bold and underlined. 3'-overhangs are indicated in bold and italicized. The 3'-overhangs on one or both strands of the siRNA molecule may alternatively comprise 1-4 deoxythymidine (t) nucleotides, 1-4 modified and/or unmodified uridine (U) ribonucleotides, or 1-4 unmodified and/or modified ribonucleotides or deoxyribonucleotides having complementarity to the target sequence or the complementary strand thereof. In certain instances, the sense and/or antisense strand of the siRNA molecule lacks 3'-overhangs (i.e., does not contain the sequence indicated in bold and italicized). Lower case letters = 2'-deoxy nucleotides.

Table 14 provides a list of chemically modified WEE1-2 siRNA molecules containing 2'OMe nucleotides at selective positions within the double-stranded region.

TABLE 14

2'OMe-modified siRNA sequences that target human WEE1 gene expression.

| Target or Sense Strand Sequence siRNA(5' → 3') | Antisense Strand Sequence (5' → 3') |
|---|---|
| WEE1-GGCUGGAUGGAUGCAUUUAUU 1/6 (SEQ ID NO: 249) | UAAAUGCAUCCAUCCAGCC*UC* (SEQ ID NO: 126) |
| WEE1-GGCUGGAUGGAUGCAUUUAUU 1/7 (SEQ ID NO: 249) | UAAAUGCAUCCAUCCAGCC*UC* (SEQ ID NO: 252) |
| WEE1-GGCUGGAUGGAUGCAUUUAUU 1/8 (SEQ ID NO: 249) | UAAAUGCAUCCAUCCAGCC*UC* (SEQ ID NO: 253) |
| WEE1-GGCUGGAUGGAUGCAUUUAUU 1/9 (SEQ ID NO: 249) | UAAAUGCAUCCAUCCAGCC*UC* (SEQ ID NO: 254) |
| WEE1-GGCUGGAUGGAUGCAUUUAUU 3/2 (SEQ ID NO: 250) | UAAAUGCAUCCAUCCAGCC*UC* (SEQ ID NO: 255) |
| WEE1-GGCUGGAUGGAUGCAUUUAUU 3/6 (SEQ ID NO: 250) | UAAAUGCAUCCAUCCAGCC*UC* (SEQ ID NO: 126) |
| WEE1-GGCUGGAUGGAUGCAUUUAUU 3/7 (SEQ ID NO: 250) | UAAAUGCAUCCAUCCAGCC*UC* (SEQ ID NO: 252) |
| WEE1-GGCUGGAUGGAUGCAUUUAUU 3/8 (SEQ ID NO: 250) | UAAAUGCAUCCAUCCAGCC*UC* (SEQ ID NO: 253) |
| WEE1-GGCUGGAUGGAUGCAUUUAUU 3/9 (SEQ ID NO: 250) | UAAAUGCAUCCAUCCAGCC*UC* (SEQ ID NO: 254) |
| WEE1-GGCUGGAUGGAUGCAUUUAUU 4/2 (SEQ ID NO: 251) | UAAAUGCAUCCAUCCAGCC*UC* (SEQ ID NO: 255) |
| WEE1-GGCUGGAUGGAUGCAUUUAUU 4/6 (SEQ ID NO: 251) | UAAAUGCAUCCAUCCAGCC*UC* (SEQ ID NO: 126) |
| WEE1-GGCUGGAUGGAUGCAUUUAUU 4/7 (SEQ ID NO: 251) | UAAAUGCAUCCAUCCAGCC*UC* (SEQ ID NO: 252) |
| WEE1-GGCUGGAUGGAUGCAUUUAUU 4/8 (SEQ ID NO: 251) | UAAAUGCAUCCAUCCAGCC*UC* (SEQ ID NO: 253) |
| WEE1-GGCUGGAUGGAUGCAUUUAUU 4/9 (SEQ ID NO: 251) | UAAAUGCAUCCAUCCAGCC*UC* (SEQ ID NO: 254) |
| WEE1-GGCUGGAUGGAUGCAUUUAUU 5/2 (SEQ ID NO: 125) | UAAAUGCAUCCAUCCAGCC*UC* (SEQ ID NO: 255) |
| WEE1-GGCUGGAUGGAUGCAUUUAUU 5/6 (SEQ ID NO: 125) | UAAAUGCAUCCAUCCAGCC*UC* (SEQ ID NO: 126) |
| WEE1-GGCUGGAUGGAUGCAUUUAUU 5/7 (SEQ ID NO: 125) | UAAAUGCAUCCAUCCAGCC*UC* (SEQ ID NO: 252) |
| WEE1-GGCUGGAUGGAUGCAUUUAUU 5/8 (SEQ ID NO: 125) | UAAAUGCAUCCAUCCAGCC*UC* (SEQ ID NO: 253) |
| WEE1-GGCUGGAUGGAUGCAUUUAUU 5/9 (SEQ ID NO: 125) | UAAAUGCAUCCAUCCAGCC*UC* (SEQ ID NO: 254) |

2'OMe nucleotides are indicated in bold and underlined. 3'-overhangs are indicated in bold and italicized. The 3'-overhangs on one or both strands of the siRNA molecule may alternatively comprise 1-4 deoxythymidine (t) nucleotides, 1-4 modified and/or unmodified uridine (U) ribonucleotides, or 1-4 unmodified and/or modified ribonucleotides or deoxyribonucleotides having complementarity to the target sequence or the complementary strand thereof. In certain instances, the sense and/or antisense strand of the siRNA molecule lacks 3'-overhangs (i.e., does not contain the sequence indicated in bold and italicized).

Silencing of COP1 or WEE1 inhibits the proliferation and cell cycle progression of Human HCC cells The effects of COP1 or WEE1 gene knockdown using human HCC cell lines were examined. To inactivate COP1 gene expression, Huh7 and HepG2 cells were treated with three different siRNA (COP1-1, COP1-2, and COP1-3). Similarly, WEE1 gene expression was inactivated by treating Huh7 and HepG2 cells with three different siRNA (WEE1-1, WEE1-2, and WEE1-3). The silencing of target gene expression was confirmed by quantitative real-time RT-PCR and Western blotting. Cell growth was then analyzed by MTT and FACS analysis, and apoptosis was estimated by ELISA for detection of ssDNA. In addition, flow cytometry was used to determine the size of side population (SP) defined by efflux of Hoechst 33342 dye and shown to be enriched in cancer stem cells as an approach to study the response of cancer stem cells to gene therapy.

Figure 2:
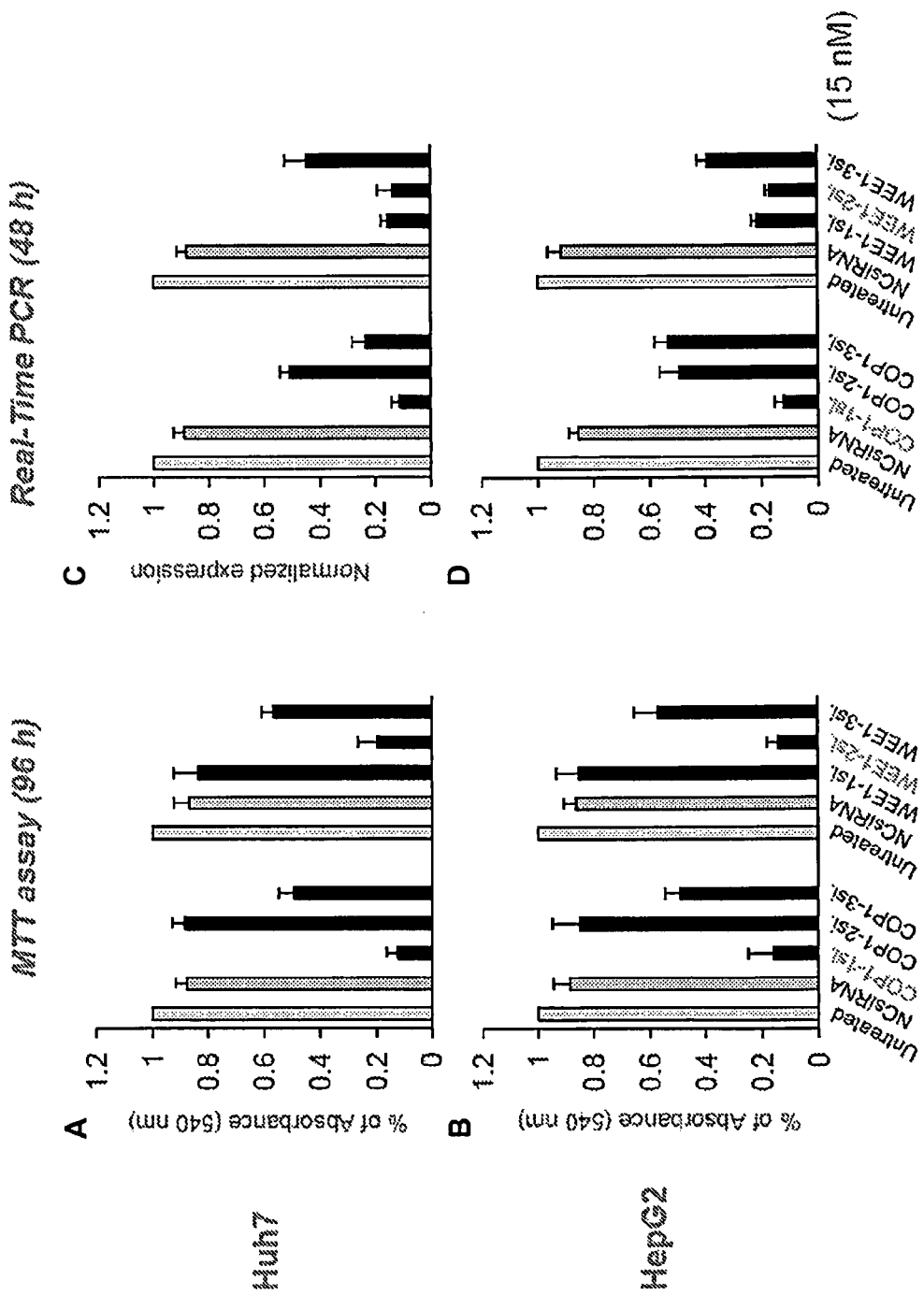
FIG. 2 illustrates that COP1 or WEE1 gene silencing decreased HCC cell survival in a cell viability assay and reduced target mRNA levels in a quantitative real-time RT-PCR assay. (A, B) Growth inhibition of Huh7 (A) or HepG2 (B) cells after transfection with 15 nM of three COP1-specific siRNA or three WEE1-specific siRNA was examined by an MTT assay 4 days after treatment. The cells that were untreated (sham) and treated with NC siRNA were assayed simultaneously. Results are presented as mean percentage of absorbance at 540 nm±s.d. (C, D) Real-time RT-PCR analysis of COP1 or WEE1 gene expression in Huh7 (C) or HepG2 (D) cells treated with the COP1-specific siRNA or the WEE1-specific siRNA. Total RNA was extracted at 48 hours after treatment with 15 nM of the siRNA. In all PCR experiments, expression was calculated relative to GAPDH and is normalized to untreated control. Each bar value represents the mean±s.d. of triplicate experiments. NCsiRNA=negative control siRNA.

FIG. 2 shows that COP1 or WEE1 gene silencing decreased HCC cell survival in a cell viability assay and reduced target mRNA levels in a quantitative real-time RT-PCR assay. Among the siRNA tested, the COP1-1 and WEE1-2 siRNA molecules were the most effective in inhibiting HCC cell growth. In contrast, negative control (NC) siRNA revealed only marginal inhibition of Huh7 and HepG2 cell growth at the same concentrations when compared to no treatment. Similar results were observed in Huh1 and PLC/PRF/5 cells upon 48 hour treatment with 15 nM COP1-1 or WEE1-2 siRNA, demonstrating the inhibition of cell growth in a variety of HCC cell lines. Quantitative analysis of target mRNA was performed to test the effect of siRNA on COP1 or WEE1 gene expression in both Huh7 and HepG2 cells. A 48 hour treatment with 15 nM COP1-1 or WEE1-2 siRNA resulted in the greatest reduction of target mRNA in Huh7 and HepG2 cells among the siRNA tested.

FIG. 3 shows that COP1 gene silencing with COP1-1 siRNA decreased HCC cell survival as detected by light microscopy. Similar results with regard to WEE1 gene silencing were obtained with WEE1-2 siRNA. As such, the observed phenotypic changes in cell morphology confirmed the results of the cell proliferation assay.

Figure 4:
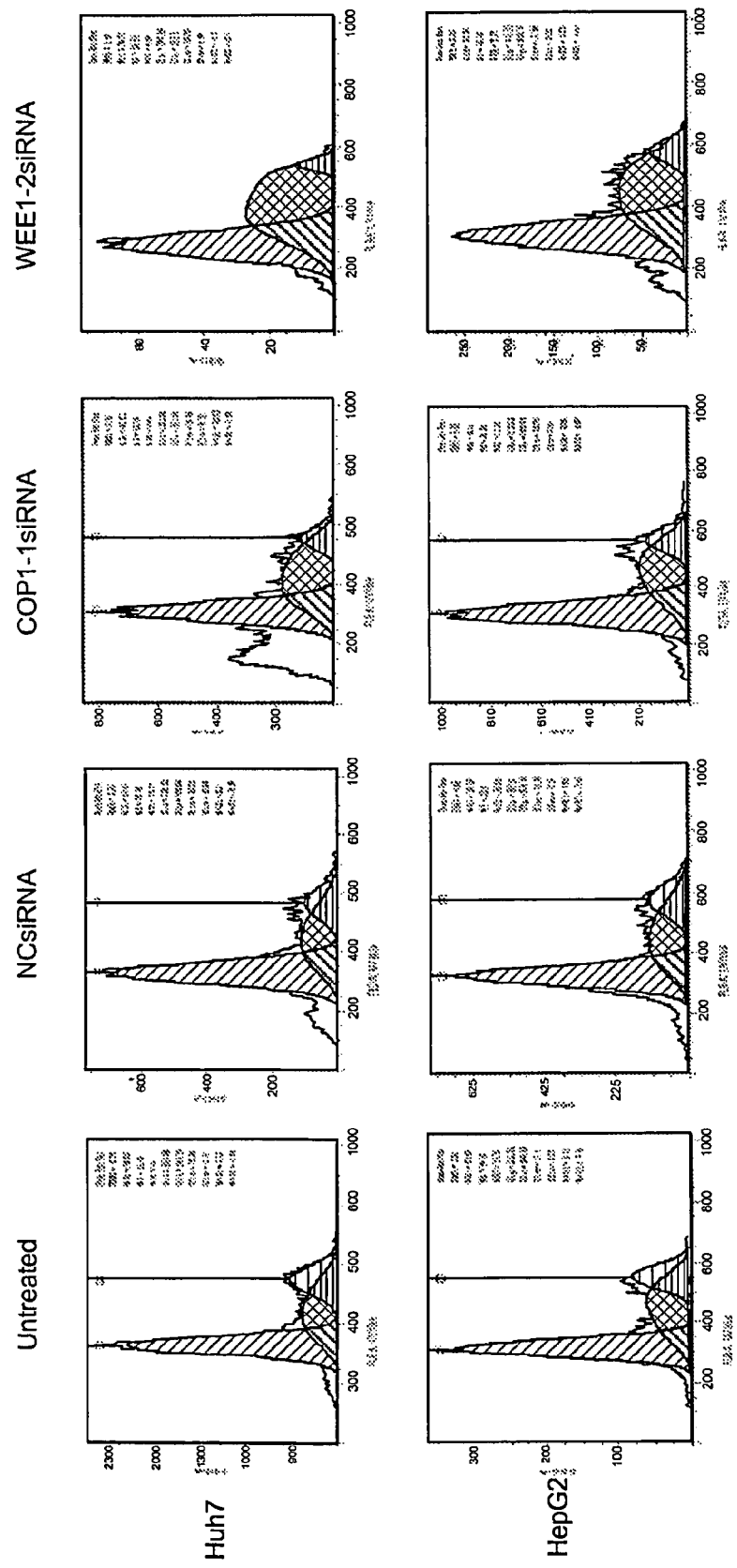
FIG. 4 illustrates that COP1 or WEE1 gene silencing is associated with cell cycle arrest in the G1 phase. The effect of COP1-1 or WEE1-2 siRNA on cell cycle progression of HCC cells was determined by cell cycle analysis after transfection of Huh7 or HepG2 cells with 15 nM of COP1-1 or WEE1-2 siRNA for 48 hours. The analysis was performed on an equal number of cells ($10^4$ events) by flow cytometry after staining of DNA with propium iodide. The cells that were untreated or treated with NCsiRNA were assayed simultaneously.

FIG. 4 shows that COP1 or WEE1 gene silencing is associated with cell cycle arrest in the G1 phase. In terms of the effect on cell cycle progression, compared to control treatments, target gene silencing by COP1 or WEE1 siRNA generally increased the G0/G1 population with a compensatory decrease in G2/M phase of both Huh7 and HepG2 cells, ultimately inducing a cell cycle arrest in the G1 phase.

Figure 5:
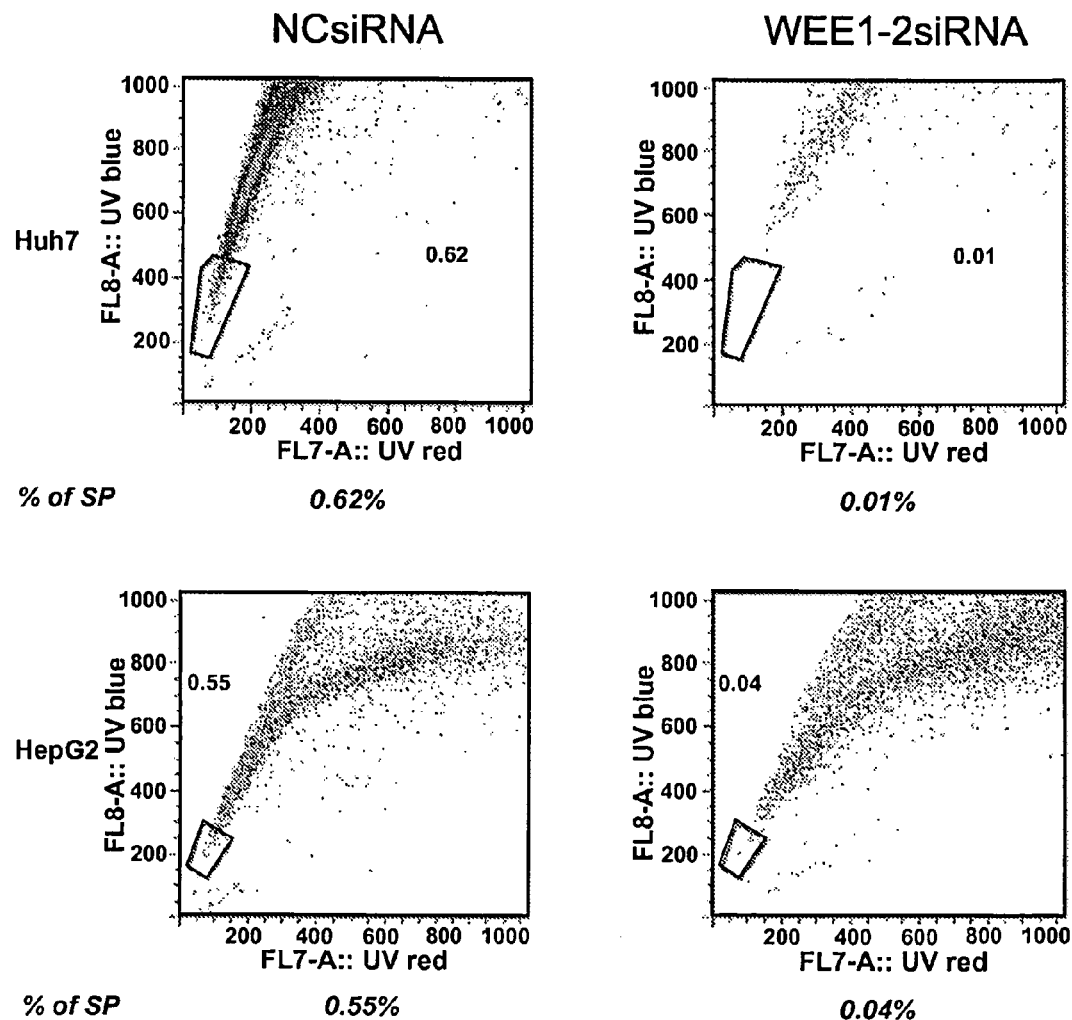
FIG. 5 illustrates that silencing of WEE1 expression was capable of reducing the proportion of side population (SP) cells. Changes in SP fraction after transfection of Huh7 or HepG2 cells with 15 nM of WEE1-2 siRNA for 48 hours were analyzed. Flow cytometry was used to determine the size of SP defined by efflux of Hoechst 33342 dye and shown to be enriched in cancer stem cells. The cells that were treated with NCsiRNA were assayed simultaneously.

FIG. 5 shows that silencing of WEE1 gene expression was capable of reducing the proportion of side population (SP) cells. This indicates that targeting of the WEE1 gene is effective in anticancer stem cell therapy. In particular, flow cytometry was used to determine the size of SP cells defined by the efflux of Hoechst 33342 dye and shown to be enriched in cancer stem cells as an approach to study the response of cancer stem cells to siRNA therapy.

These results demonstrate that siRNA-mediated knockdown of COP1 or WEE1 blocks the proliferation and cell cycle progression of human HCC cells.

Figure 6:
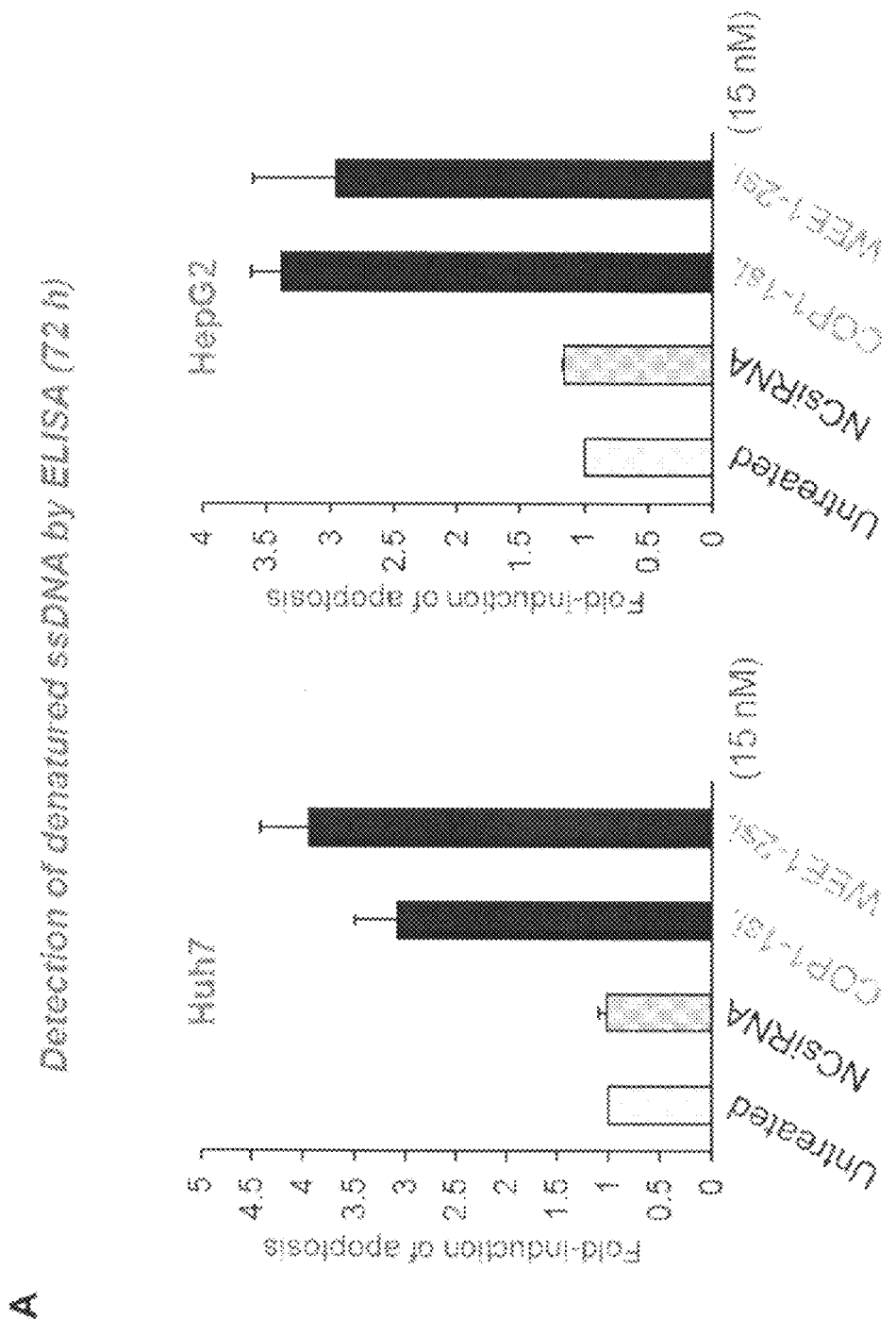
FIG. 6 illustrates that COP1 or WEE1 gene silencing increased apoptosis by restoring p53 and p21 levels. (A) Detection of apoptotic progression in Huh7 or HepG2 cells 3 d after transfection with 15 nM of COP1-1 or WEE1-2 siRNA. The cells that were untreated (sham) and treated with NCsiRNA were assayed simultaneously. Results are shown as the mean fold-induction of apoptosis±s.d. of three independent experiments. (B) Western blot analysis of COP1, WEE1, p53, and p21 protein expression in Huh7 or HepG2 cells that were untreated (Sham) or treated with 15 nM of NCsiRNA or COP1-1 or WEE1-2 siRNA for 48 h.
Figure 6:
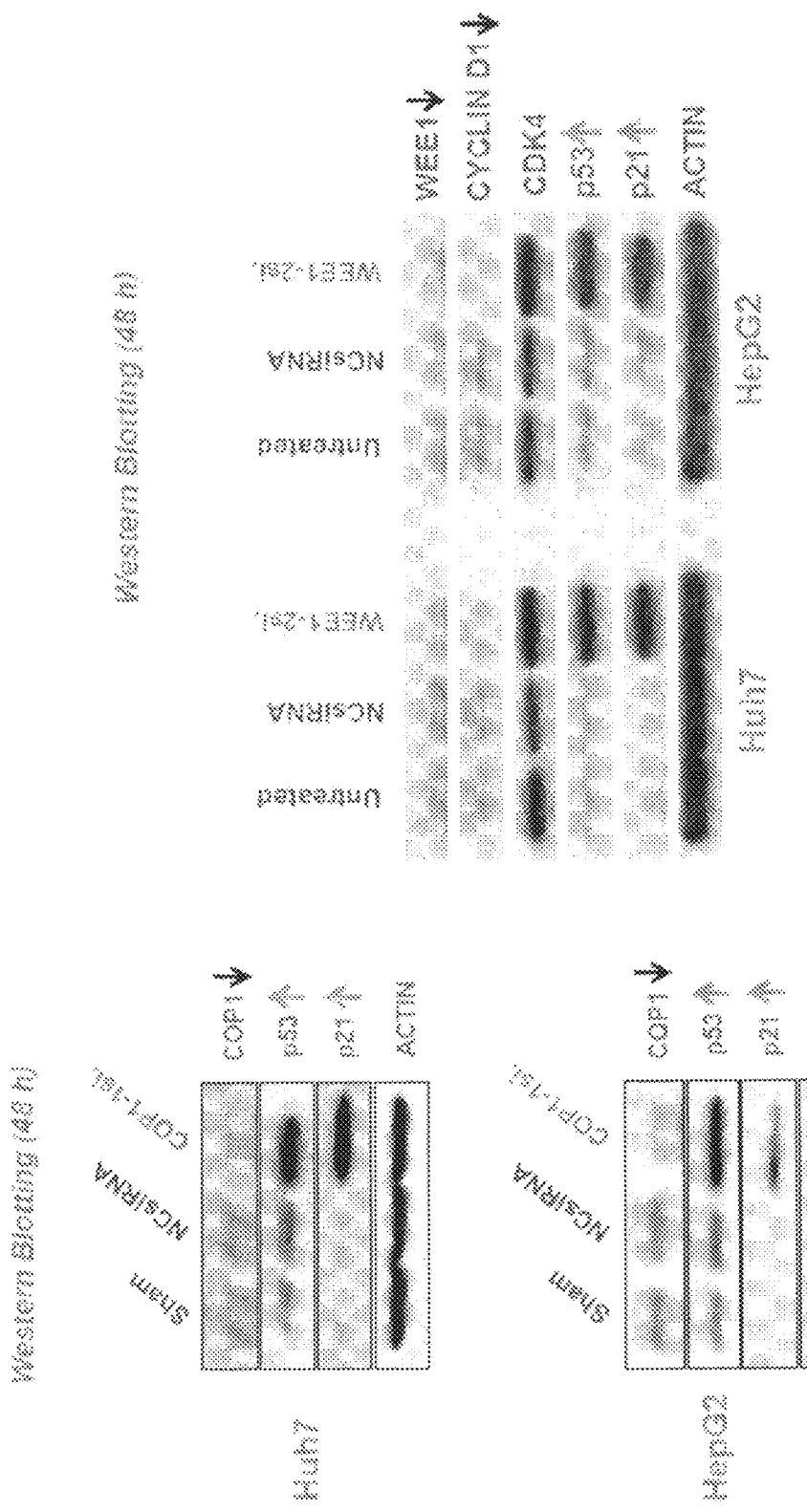

COP1 or WEE1 siRNA treatment induces apoptosis by functional restoration of p53 tumor suppressor To analyze whether the cancer cell death caused by COP1 or WEE1 siRNA treatment reflected the induction of apoptosis, Huh7 and HepG2 cells treated with 15 nM of COP1-1 or WEE1-2 siRNA for 3 days were subjected to an assay that detects denatured DNA within cells, which is an indicator of the changes in chromatin associated with apoptotic progression. FIG. 6A shows that COP1-deficient Huh7 and HepG2 cells exhibited ~3-3.5 fold increase in apoptosis as compared with negative control (NC) siRNA-treated cells, a property which was directly correlated with the extent of downregulation of COP1 mRNA levels. Similarly, WEE1-deficient Huh7 and HepG2 cells exhibited ~3-4 fold increase in apoptosis as compared with NCsiRNA-treated cells, a property which was directly correlated with the extent of downregulation of WEE1 mRNA levels.

Furthermore, the levels of p53 and its responder p21 were restored when HCC cells were undergoing apoptotic progression through downregulation of COP1 or WEE1 protein by siRNA treatment. In particular, FIG. 6B shows that when HCC cells were undergoing apoptotic progression through the downregulation of COP1 or WEE1 protein, the level of intracellular total p53 protein was increased as compared to treatment with an equal amount of NCsiRNA. Similar to the elevation of p53 levels, cellular p21 levels increased in Huh7 and HepG2 cells. These results indicate that the growth inhibition of HCC cells by COP1 or WEE1 siRNA is mediated by apoptotic induction that is triggered by functional restoration of the p53 tumor suppressor.

Construction of in vivo evaluation model with systemic silencing of the COP1 or WEE1 gene For systemic validation of therapeutic targets using siRNA, it is essential to establish an HCC mouse model, a stable system for siRNA delivery to target tissue, and persistent monitoring of tumor response after treatment. Recently, a new in vivo molecular imaging method to detect tumors in animals has emerged based on visible light emission from luciferase-expressing cells or tissues (Contag et al., NeoRev., 1:e225-232 (2000)). Therefore, bioluminescent human HCC cells which constitutively express luciferase were established for both the development of HCC orthotopic xenograft models and detection of their response by target siRNA administration. The β-actin promoter was subcloned upstream of the luciferase gene in the pGL4.17 reporter vector to enhance its expression within cells, and then transfected into Huh7 cells.

Figure 7:
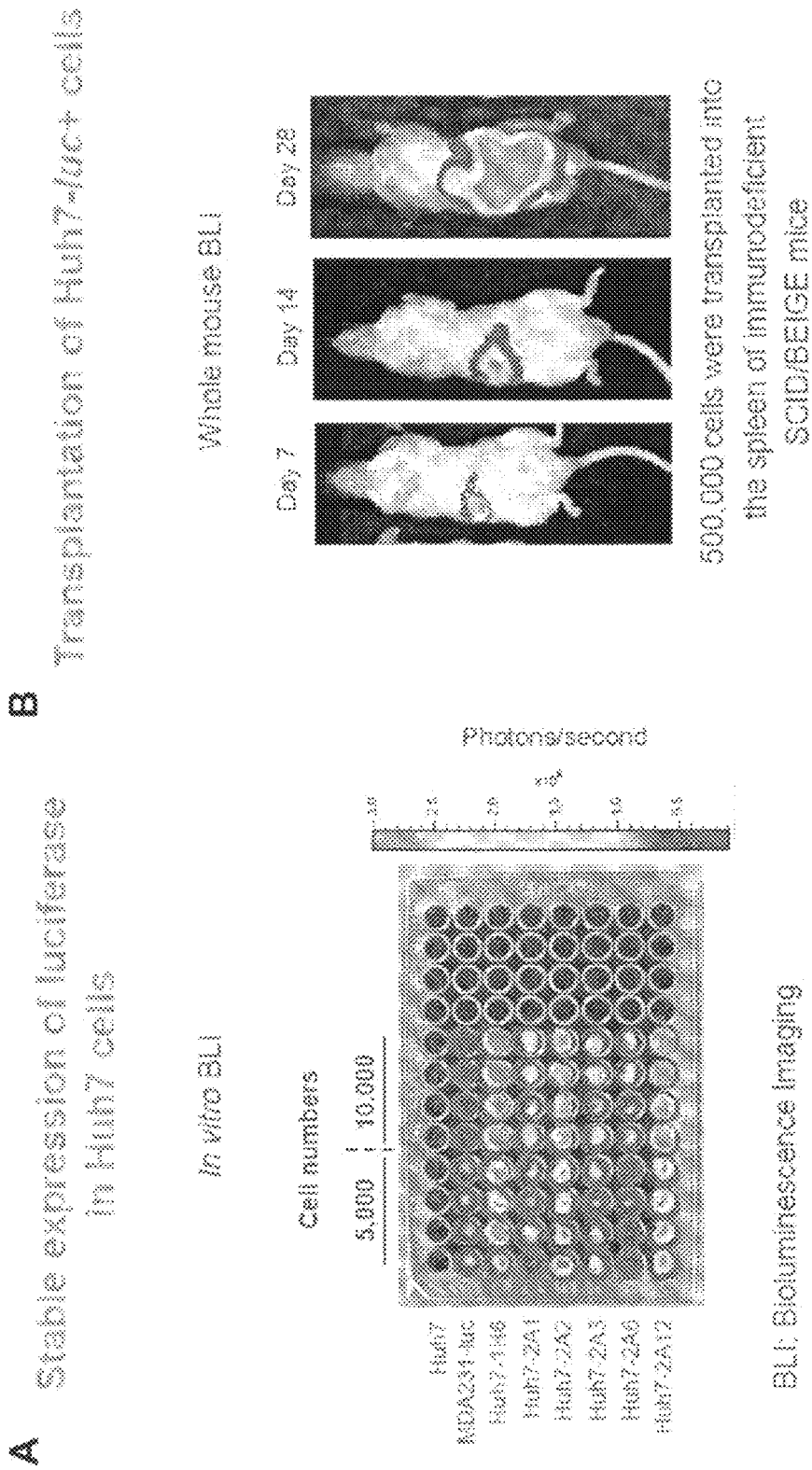
FIG. 7 illustrates the establishment of an Huh7-luc$^+$ orthotopic liver transplantation (OLT) model. This figure shows the stable expression of luciferase in Huh7 cells and transplantation of Huh7-luc$^+$ cells into the spleen of immunodeficient mice. (A) Screening of clones that are stably expressing luciferase by in vitro BLI. Cells were diluted to 5,000 or 10,000, plated in four wells, and imaged for 10 sec after the addition of luciferin (150 µg/ml final) to media. (B) In vivo analysis of tumor cell liver colonization. $5 \times 10^5$ Huh7-luc$^+$ cells were transplanted into the spleen of SCID-beige mice, and tumor growth in the liver was assessed by whole mouse BLI with a regular interval.

FIG. 7A shows that among the numerous foci grown under the condition of antibiotic selection, the Huh7-1H6 clone that had a highest level of luciferase expression was selected and named Huh7-luc$^+$ cells. About half a million bioluminescent Huh7 cells permanently expressing luciferase were transplanted into the spleen of immunodeficient SCID-beige mice to establish an Huh7-luc$^+$ HCC orthotopic xenograft model for the in vivo evaluation of COP1 and WEE1 as therapeutic targets. Right after the cell injection, spleens were removed. FIG. 7B shows that tumors were detectable from day 7 by bioluminescence imaging (BLI), and kept growing exponentially up to day 28.

This technique can also be used to generate HepG2-luc$^+$, Huh1-luc$^+$, and PLC-luc$^+$ cells and transplanted into mice to establish an orthotopic xenograft model for the in vivo evaluation of COP1 and WEE1 as therapeutic targets.

Selection of modified COP1 and WEE1 siRNA for in vivo applications

Figure 8:
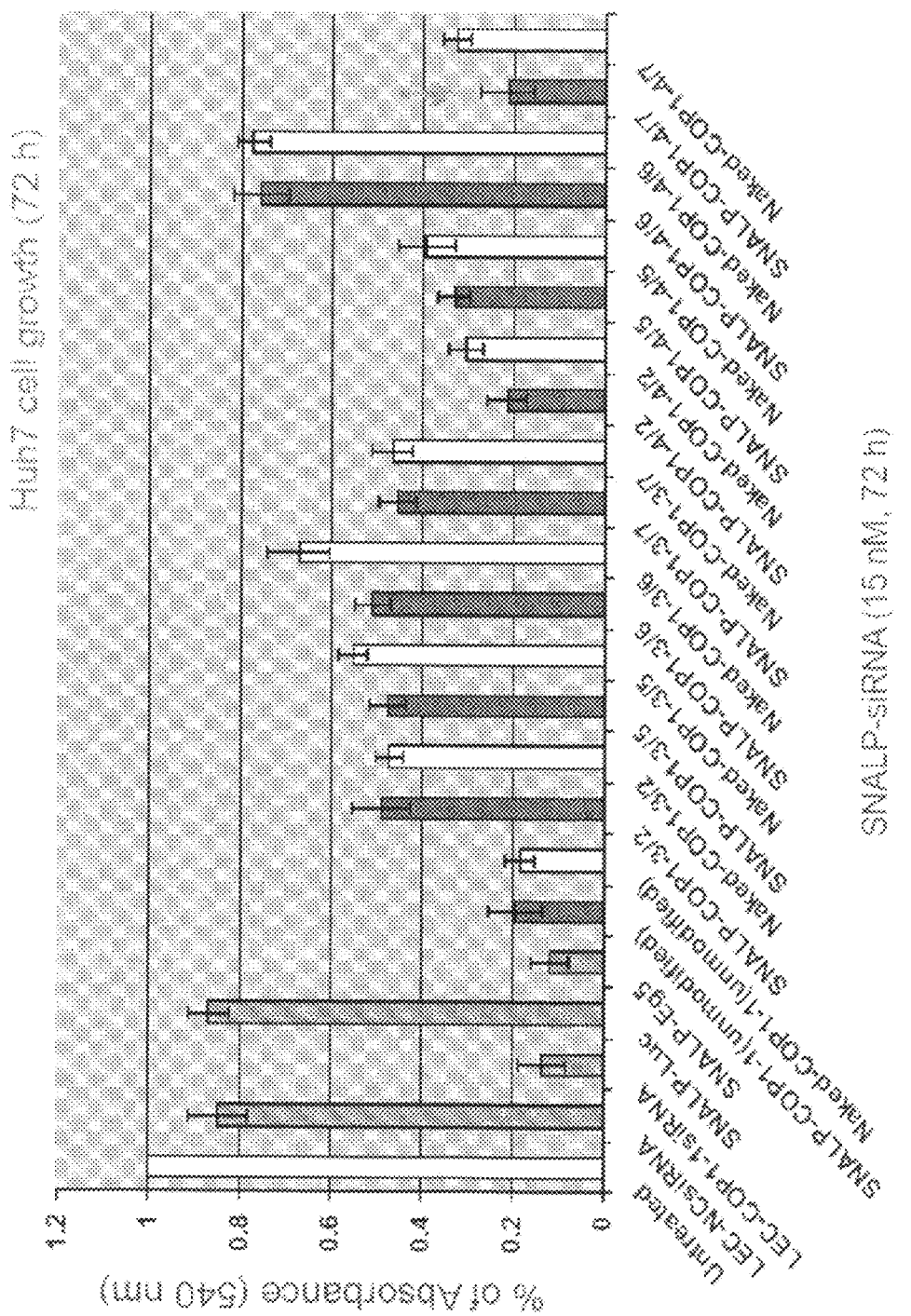
FIG. 8 illustrates the inhibition of Huh7-luc$^+$ cell growth after transfection with 15 nM of SNALP-formulated or naked unmodified or modified COP1-1 siRNA. The cells were examined by an MTT assay 3 days after the treatment. SNALP containing Luciferase (Luc) siRNA was used as a negative control, and SNALP containing Eg5 siRNA was used as a positive control. Results are shown as the mean percentage of absorbance at 540 nm±s.d.

Various COP1 siRNA molecules set forth in Tables 11 and 12 were encapsulated into SNALP and evaluated for their inhibitory effects on cell growth in vitro. The human HCC cell line Huh7 was treated with COP1 SNALP formulations and their effect on cell viability was evaluated. Viability of cell cultures is expressed as % viability relative to PBS treated controls. FIG. 8 shows that unmodified as well as 2'OMe-modified COP1-1 siRNA were effective at inhibiting the growth of Huh7 cells. In particular, COP1-1 (unmodified) siRNA, COP1-4/2 siRNA, and COP1-4/7 siRNA were highly potent at killing Huh7 cells. SNALP-formulated COP1 siRNA were generally more potent at inhibiting Huh7 cell growth as compared to naked COP1 siRNA. SNALP containing Luciferase (Luc) siRNA was used as a negative control, and SNALP containing Eg5 siRNA was used as a positive control.

Figure 9:
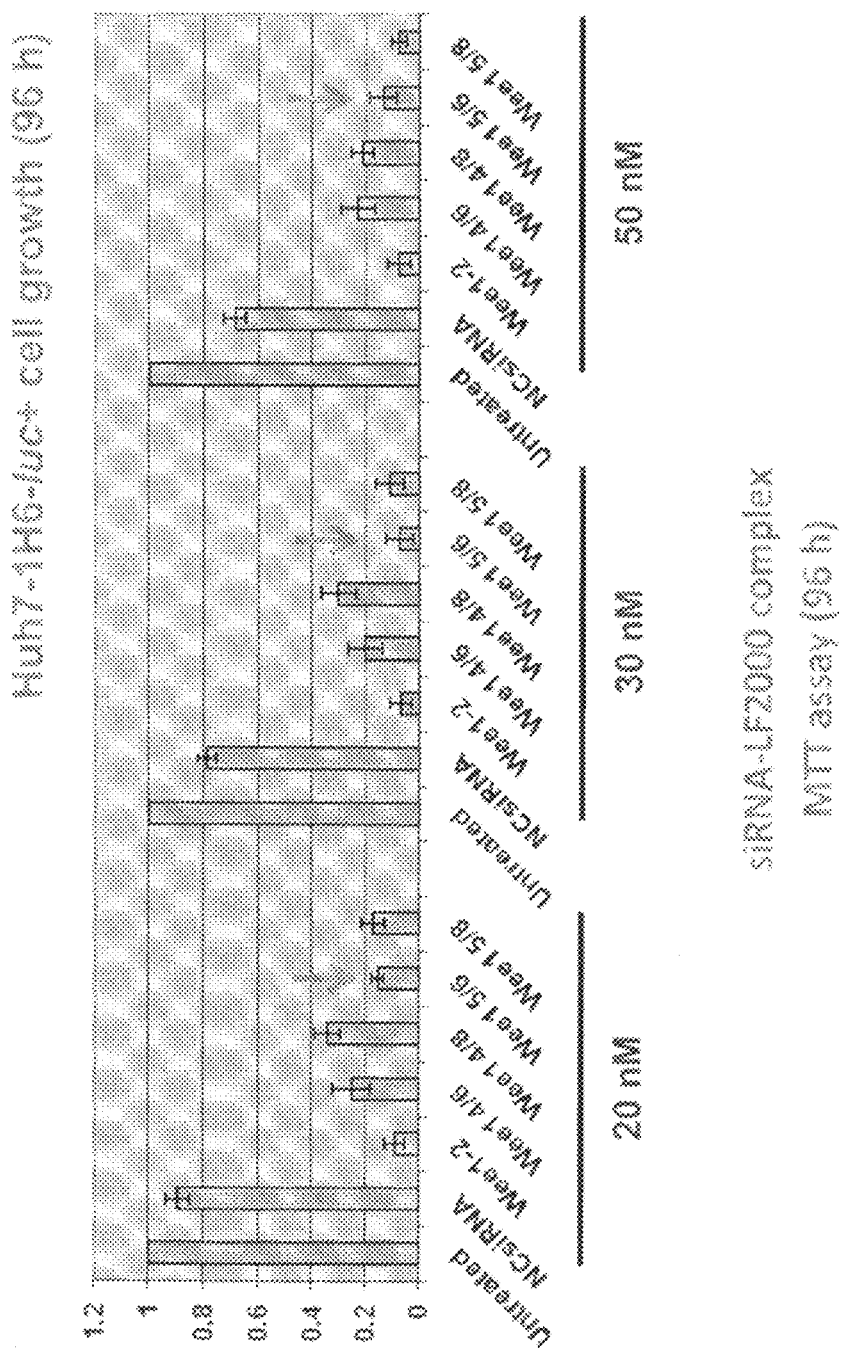
FIG. 9 illustrates the inhibition of Huh7-luc$^+$ cell growth after transfection with 20, 30, or 50 nM of unmodified or modified WEE1-2 siRNA complexed with Lipofectamine 2000 (LF2000). The cells were examined by an MTT assay 4 days after the treatment. Results are shown as the mean percentage of absorbance at 540 nm±s.d.

Various WEE1 siRNA molecules set forth in Tables 13 and 14 were evaluated for their inhibitory effects on cell growth in vitro. Huh7-luc$^+$ cells were treated with WEE1 siRNA and their effect on cell viability was evaluated. Viability of cell cultures is expressed as % viability relative to PBS treated controls. FIG. 9 shows that unmodified as well as 2'OMe-modified WEE1 siRNA were effective at inhibiting the growth of Huh7-luc$^+$ cells. In particular, WEE1-2 (unmodified) siRNA, WEE1-5/6 siRNA, and WEE1-5/8 siRNA were highly potent at killing Huh7-luc$^+$ cells at all doses tested. Similar results were obtained with HepG2 cells transfected with SNALP-formulated WEE1 siRNA as shown in FIG. 10.

SNALP-formulated COP1 siRNA were evaluated for their immunostimulatory activity in vitro. Flt3L DC cultures from mouse bone marrow were treated with unmodified or 2'OMe-modified COP1 SNALP at 5 µg/ml for 24 hours. IFN-α and IL-6 levels in the culture supernatants were assayed as an indicator of immune stimulation by a particular COP1 siRNA. FIG. 11 shows that SNALP containing unmodified (native) COP1-1 siRNA induced high levels of IFN-α and IL-6 in murine Flt3L DC cultures, which was indicative of robust immune stimulation. However, 2'OMe-modified variants of COP1-1 such as COP1-4/7 siRNA induced minimal IFN-α and IL-6 responses in this cell culture system.

FIG. 12 shows that the COP1-4/7 siRNA was selected for in vivo studies in the HCC mouse model because it was comparable in potency to the unmodified COP1-1 siRNA at inhibiting Huh7-luc⁺ cell growth and at reducing COP1 gene expression, but it induced a minimal cytokine response in murine Flt3L DC cultures. Similarly, WEE1-5/6 siRNA was selected for in vivo studies in the HCC mouse model because it was comparable in potency to the unmodified WEE1-2 siRNA at inhibiting Huh7-luc⁺ cell growth.

Systemic inhibition of orthotopic liver tumor growth with COP1 or WEE1 siRNA

Eight days after transplantation of Huh7-luc⁺ cells, SNALP containing COP1-4/7 or WEE1-5/6 siRNA were systemically delivered to the liver through a tail vein injection four times (days 8, 11, 14, and 18) at a dosage of 2 mg/kg. Tumor relapses were monitored by BLI up to 28 days after cell transplantation.

FIG. 13 shows that systemic delivery of COP1-4/7 or WEE1-5/6 siRNA effectively prevented orthotopic tumor growth in the liver in a mouse model of metastatic human liver cancer compared to a control administration of SNALP containing siRNA targeting β-galactosidase (FIGS. 13A-B). Correlating with the level of bioluminescent signals on day 28, gross inspection revealed that the livers in mice treated with COP1-4/7 or WEE1-5/6 siRNA had a significantly lower number of tumors or a complete absence of tumors (FIG. 13C). Histological analysis also revealed that livers treated with control siRNA produced tumors, indicating a significant degree of cellular proliferation, whereas COP1-4/7 or WEE1-5/6 siRNA treatment inhibited tumor spreading, even at the modest dose (FIG. 13C). Liver to body weight ratios were also lower in COP1-4/7 or WEE1-5/6 siRNA-treated versus control siRNA-treated mice, further confirming tumor growth suppression (FIG. 13D). The imaging, liver morphology, and liver histology results shown in FIG. 13 are representative of the animals belonging to that treatment group. There was also no induction of IFN-β in both control siRNA-treated and COP1-4/7 siRNA-treated mice as measured in serum 48 hours after SNALP administration.

FIG. 14 shows the effect of SNALP-formulated COP1-4/7 siRNA treatment on the relative survival of mice bearing Huh7-luc⁺ orthotopic xenografts. SNALP containing COP1-4/7 siRNA or β-gal siRNA were systemically delivered to the liver through a tail vein injection three times (days 18, 21, and 24) at a dosage of 2 or 4 mg/kg. Mice treated with COP1 SNALP exhibited a statistically significant increase in survival time as compared to control mice.

FIG. 15 shows the systemic inhibition of HepG2-luc⁺ orthotopic liver tumors with COP1-4/7 siRNA. Eleven days after transplantation of HepG2-luc⁺ cells, SNALP containing COP1-4/7 siRNA were systemically delivered to the liver through a tail vein injection four times (days 11, 14, 17, and 21) at a dosage of 2 mg/kg. Tumor relapses were monitored by BLI up to 28 days after cell transplantation. As observed with the Huh7-luc⁺ orthotopic xenograft model, systemic delivery of COP1-4/7 siRNA to mice bearing HepG2-luc⁺ orthotopic xenografts effectively prevented tumor growth in the liver compared to a control administration of SNALP containing siRNA targeting β-gal (FIGS. 15A-B). Gross inspection revealed that the livers in mice treated with COP1-4/7 siRNA had a significantly lower number of tumors or a complete absence of tumors (FIG. 15C). Histological analysis also revealed that livers treated with control siRNA produced tumors, indicating a significant degree of cellular proliferation, whereas COP1-4/7 siRNA treatment inhibited tumor spreading, even at the modest dose (FIG. 15C). The imaging, liver morphology, and liver histology results shown in FIG. 15 are representative of the animals belonging to that treatment group.

FIG. 16 shows the inhibition of liver tumor growth in a variety of different mouse models upon systemic delivery of either SNALP-formulated COP1 or WEE1 siRNA. In particular, systemic delivery of COP1-4/7 or WEE1-5/6 siRNA to mice bearing Huh7-luc⁺, HepG2-luc⁺, or Huh1-luc⁺ orthotopic xenografts effectively prevented tumor growth in the liver compared to a control administration of SNALP containing β-gal siRNA.

These results demonstrate that siRNA-mediated knockdown of the COP1 or WEE1 gene inhibits proliferation of a variety of HCC cell lines. Treatment with COP1 or WEE1 siRNA also increases apoptosis of HCC cells by restoring the protein level of the p53 tumor suppressor and/or by disrupting normal cell cycle regulation. These results further demonstrate that WEE1 silencing decreases the size of side population-containing cancer stem cells (CSC), indicating that targeting the WEE1 gene is effective in anti-CSC therapy. Moreover, these results demonstrate that systemic delivery of SNALP-formulated COP1 or WEE1 siRNA effectively suppresses neoplastic growth in a mouse model of metastatic human liver cancer. This study illustrates that COP1 and WEE1 are important regulators of HCC cell growth and survival, and that p53 ubiquitination and cell cycle regulation represent target pathways for human HCC treatment.

Conclusion

This example demonstrates that the potency of systemic delivery of siRNA targeting COP1 or WEE1 without overt toxicity is a clinically viable therapeutic modality for the treatment of cancers such as liver cancer (e.g., HCC) and other solid tumors. In particular, this example illustrates that COP1 and WEE1 are important regulators of HCC cell growth and survival, and are attractive targets for HCC therapy. Importantly, this example shows that SNALP containing siRNA targeting COP1 or WEE1 gene expression are efficacious for the in vivo delivery and treatment of cancers such as liver cancer.

Example 3

Therapeutic Targeting of HDAC2 with siRNA for the Treatment of Cancer

This example illustrates that (1) siRNA-mediated knockdown of HDAC2 expression inhibited the proliferation of cells from human HCC cell lines; (2) treatment with siRNA targeting HDAC2 increased apoptosis of human HCC cells by restoring the protein levels of the p53 tumor suppressor; and (3) systemic delivery of SNALP containing chemically modified HDAC2 siRNA effectively suppressed neoplastic growth in a mouse model of metastatic human liver cancer.

HDAC2 siRNA Sequences Used in this Study

Table 15 provides a list of exemplary siRNA sequences targeting human HDAC2 gene expression.

TABLE 15 siRNA sequences that target human HDAC2 gene expression.

| siRNA |
| --- |
| HDAC2-1 |
| HDAC2-2 |
| HDAC2-3 |

Table 16 provides a list of chemically modified HDAC2-1 siRNA molecules containing 2'OMe nucleotides at selective positions within the double-stranded region.

TABLE 16

2'OMe-modified siRNA sequences that target human HDAC2 gene expression.
siRNA

HDAC2-1/6
HDAC2-1/7
HDAC2-1/8
HDAC2-3/2
HDAC2-3/6
HDAC2-3/7
HDAC2-3/8
HDAC2-4/2
HDAC2-4/6
HDAC2-4/7
HDAC2-4/8
HDAC2-5/2
HDAC2-5/6
HDAC2-5/7
HDAC2-5/8

Silencing of HDAC2 inhibits the proliferation and cell cycle progression of human HCC cells The effects of HDAC2 gene knockdown using human HCC cell lines were examined. To inactivate HDAC2 gene expression, Huh7 and HepG2 cells were treated with three different siRNA (HDAC2-1, HDAC2-2, and HDAC2-3). The silencing of target gene expression was confirmed by Western blotting. Cell growth was analyzed by MTT and FACS analysis, and apoptosis was estimated by ELISA for detection of ssDNA.

FIG. 17 shows that HDAC2 gene silencing decreased HCC cell survival in a cell viability assay. Among the siRNA tested, the HDAC2-1 siRNA was the most effective in inhibiting HCC cell growth at all concentrations (5, 10, 15, and 20 nM).

FIG. 18 shows that HDAC2 gene silencing is associated with cell cycle arrest in the G1 phase. In terms of the effect on cell cycle progression, compared to control treatments, target gene silencing by HDAC2 siRNA generally increased the G0/G1 population with a compensatory decrease in G2/M phase of both Huh7 and HepG2 cells, ultimately inducing a cell cycle arrest in the G1 phase.

These results demonstrate that siRNA-mediated knockdown of HDAC2 blocks the proliferation and cell cycle progression of human HCC cells.

HDAC2 siRNA treatment induces apoptosis by functional restoration of p53 tumor suppressor To analyze whether the cancer cell death caused by HDAC2 siRNA treatment reflected the induction of apoptosis, Huh7 and HepG2 cells treated with 15 nM of HDAC2-1 siRNA for 3 days were subjected to an assay that detects denatured DNA within cells, which is an indicator of the changes in chromatin associated with apoptotic progression. FIG. 19A shows that HDAC2-deficient Huh7 and HepG2 cells exhibited ~2 fold increase in apoptosis as compared with negative control (NC) siRNA-treated cells.

Furthermore, the levels of p53 and its responder p21 were restored when HCC cells were undergoing apoptotic progression through downregulation of HDAC2 protein by siRNA treatment. In particular, FIG. 19B shows that when HCC cells were undergoing apoptotic progression through the downregulation of HDAC2 protein, the level of intracellular total p53 protein was increased as compared to treatment with an equal amount of NCsiRNA. Similar to the elevation of p53 levels, cellular p21 levels increased in Huh7 and HepG2 cells. These results indicate that the growth inhibition of HCC cells by HDAC2 siRNA is mediated by apoptotic induction that is triggered by functional restoration of the p53 tumor suppressor.

Selection of modified HDAC2 siRNA for in vivo applications

Various HDAC2 siRNA molecules set forth in Tables 15 and 16 were encapsulated into SNALP and evaluated for their inhibitory effects on cell growth in vitro. The human HCC cell line Huh7 was treated with HDAC2 SNALP formulations and their effect on cell viability was evaluated. Viability of cell cultures is expressed as % viability relative to PBS treated controls. FIG. 20 shows that unmodified as well as 2'OMe-modified HDAC2-1 siRNA were effective at inhibiting the growth of Huh7 cells. In particular, HDAC2-1 (unmodified) siRNA, HDAC2-3/6 siRNA, and HDAC2-3/7 siRNA were highly potent at killing Huh7 cells. SNALP containing Luciferase (Luc) siRNA was used as a negative control, and SNALP containing Eg5 or COP1-4/7 siRNA was used as positive controls.

SNALP-formulated HDAC2 siRNA were evaluated for their immunostimulatory activity in vitro. Flt3L DC cultures from mouse bone marrow were treated with unmodified or 2'OMe-modified HDAC2 SNALP at 5 µg/ml for 24 hours. IL-6 and p56 IFIT1 mRNA levels in the culture supernatants were assayed as an indicator of immune stimulation by a particular HDAC2 siRNA. FIG. 21 shows that SNALP containing 2'OMe-modified variants of HDAC2-1 induced a minimal IL-6 response in this cell culture system. FIG. 22 shows that SNALP containing unmodified HDAC2-1 siRNA induced high levels of p56 IFIT1 mRNA in murine Flt3L DC cultures, which was indicative of robust immune stimulation. However, 2'OMe-modified variants of HDAC2-1 such as HDAC2-3/7 siRNA did not significantly elevate p56 IFIT1 mRNA levels.

HDAC2-3/7 siRNA was selected for in vivo studies in the Huh7-luc$^+$ HCC orthotopic xenograft mouse model because it was comparable in potency to the unmodified HDAC2-1 siRNA at inhibiting Huh7 cell growth, but induced a minimal immune response.

Systemic inhibition of orthotopic liver tumor growth with HDAC2 siRNA

Eight days after transplantation of Huh7-luc$^+$ cells, SNALP containing HDAC2-3/7 siRNA were systemically delivered to the liver through a tail vein injection four times (days 8, 11, 15, and 18) at a dosage of 2 mg/kg. Tumor relapses were monitored by BLI up to 28 days after cell transplantation.

FIG. 23 shows that systemic delivery of HDAC2-3/7 siRNA effectively prevented orthotopic tumor growth in the liver in a mouse model of metastatic human liver cancer compared to a control administration of SNALP containing siRNA targeting β-gal (FIG. 23A-B). Correlating with the level of bioluminescent signals on day 28, gross inspection revealed that the livers in mice treated with HDAC2-3/7 siRNA had a significantly lower number of tumors or a complete absence of tumors (FIG. 23C). Histological analysis also revealed that livers treated with control siRNA produced tumors, indicating a significant degree of cellular proliferation, whereas HDAC2-3/7 siRNA treatment inhibited tumor spreading, even at the modest dose (FIG. 23D).

These results demonstrate that siRNA-mediated knockdown of the HDAC2 gene inhibits proliferation and increases apoptosis in Huh7 and HepG2 cell lines. These results further demonstrate that systemic delivery of SNALP-formulated HDAC2 siRNA effectively suppresses neoplastic growth in a mouse model of metastatic human liver cancer. This study illustrates that HDAC2 is an important regulator of HCC cell growth and survival, and that histone deacetylation represents a target pathway for human HCC treatment.

Conclusion

This example demonstrates that the potency of systemic delivery of siRNA targeting HDAC2 without overt toxicity is a clinically viable therapeutic modality for the treatment of cancers such as liver cancer (e.g., HCC) and other solid tumors. In particular, this example illustrates that HDAC2 is an important regulator of HCC cell growth and survival, and is an attractive target for HCC therapy. Importantly, this example shows that SNALP containing siRNA targeting HDAC2 gene expression are efficacious for the in vivo delivery and treatment of cancers such as liver cancer.

Example 4

Therapeutic Targeting of RBX1 with siRNA for the Treatment of Cancer

This example illustrates that (1) siRNA-mediated knockdown of RBX1 expression inhibited the proliferation of cells from human HCC cell lines; and (2) systemic delivery of SNALP containing chemically modified RBX1 siRNA effectively suppressed neoplastic growth in a mouse model of metastatic human liver cancer.

RBX1 siRNA sequences used in this study

Table 17 provides a list of exemplary siRNA sequences targeting human RBX1 gene expression.

TABLE 17

| siRNA sequences that target human RBX1 gene expression. |
| --- |
| siRNA |
| RBX1-1 |
| RBX1-2 |
| RBX1-3 |

Table 18 provides a list of chemically modified RBX1-2 siRNA molecules containing 2'OMe nucleotides at selective positions within the double-stranded region.

TABLE 18

| 2'OMe-modified siRNA sequences that target human RBX1 gene expression. |
| --- |
| siRNA |
| RBX1-1/5 |
| RBX1-1/6 |
| RBX1-1/7 |
| RBX1-3/2 |
| RBX1-3/5 |
| RBX1-3/6 |
| RBX1-3/7 |
| RBX1-4/2 |
| RBX1-4/5 |
| RBX1-4/6 |
| RBX1-4/7 |

Selection of modified RBX1 siRNA for in vivo applications

Various RBX1 siRNA molecules set forth in Tables 17 and 18 were encapsulated into SNALP and evaluated for their inhibitory effects on cell growth in vitro. The human HCC cell line Huh7 was treated with RBX1 SNALP formulations and their effect on cell viability was evaluated. Viability of cell cultures is expressed as % viability relative to PBS treated controls. FIG. 24 shows that unmodified as well as 2'OMe-modified RBX1-2 siRNA were effective at inhibiting the growth of Huh7 cells. In particular, RBX1-2 (unmodified) siRNA and RBX1-3/6 siRNA (as well as several others) were highly potent at killing Huh7 cells. SNALP containing Luciferase (Luc) siRNA was used as a negative control, and SNALP containing Eg5 or COP1-4/7 siRNA was used as positive controls.

SNALP-formulated RBX1 siRNA were evaluated for their immunostimulatory activity in vitro. Flt3L DC cultures from mouse bone marrow were treated with unmodified or 2'OMe-modified RBX1 SNALP at 5 µg/ml for 24 hours. IFN-α and IL-6 levels in the culture supernatants were assayed as an indicator of immune stimulation by a particular RBX1 siRNA. FIG. 25 shows that SNALP containing unmodified (native) RBX1-2 siRNA induced high levels of IFN-α and IL-6 in murine Flt3L DC cultures, which was indicative of robust immune stimulation. However, 2'OMe-modified variants of RBX1-2 such as RBX1-3/6 siRNA induced minimal IFN-α and IL-6 responses in this cell culture system.

RBX1-3/6 siRNA was selected for in vivo studies in the Huh7-luc+ HCC orthotopic xenograft mouse model because it was comparable in potency to the unmodified RBX1-2 siRNA at inhibiting Huh7 cell growth, but induced a minimal immune response.

Systemic inhibition of orthotopic liver tumor growth with RBX1 siRNA

Eight days after transplantation of Huh7-luc+ cells, SNALP containing RBX1-3/6 siRNA were systemically delivered to the liver through a tail vein injection four times (days 8, 11, 15, and 18) at a dosage of 2 mg/kg. Tumor relapses were monitored by BLI up to 28 days after cell transplantation.

FIG. 26 shows that systemic delivery of RBX1-3/6 siRNA effectively prevented orthotopic tumor growth in the liver in a mouse model of metastatic human liver cancer compared to a control administration of SNALP containing siRNA targeting β-gal (FIGS. 26A-B). Correlating with the level of bioluminescent signals on day 28, gross inspection revealed that the livers in mice treated with RBX1-3/6 siRNA had a significantly lower number of tumors or a complete absence of tumors (FIG. 26C). Histological analysis also revealed that livers treated with control siRNA produced tumors, indicating a significant degree of cellular proliferation, whereas RBX1-3/6 siRNA treatment inhibited tumor spreading, even at the modest dose (FIG. 26C). The liver morphology and histology images shown in FIG. 26 are representative of the animals belonging to that treatment group.

These results demonstrate that siRNA-mediated knockdown of the RBX1 gene inhibits Huh7 cell growth. These results further demonstrate that systemic delivery of SNALP-formulated RBX1 siRNA effectively suppresses neoplastic growth in a mouse model of metastatic human liver cancer. This study illustrates that RBX1 is an important regulator of HCC cell growth and survival, and that c-Jun ubiquitination represents a target pathway for human HCC treatment.

Conclusion

This example demonstrates that the potency of systemic delivery of siRNA targeting RBX1 without overt toxicity is a clinically viable therapeutic modality for the treatment of cancers such as liver cancer (e.g., HCC) and other solid tumors. In particular, this example illustrates that RBX1 is an important regulator of HCC cell growth and survival, and is an attractive target for HCC therapy. Importantly, this example shows that SNALP containing siRNA targeting RBX1 gene expression are efficacious for the in vivo delivery and treatment of cancers such as liver cancer.

Example 5

Therapeutic Targeting of CDK4 with siRNA for the Treatment of Cancer

This example illustrates that (1) siRNA-mediated knockdown of CDK4 expression inhibited the proliferation of cells from human HCC cell lines; and (2) systemic delivery of SNALP containing chemically modified CDK4 siRNA effectively suppressed neoplastic growth in a mouse model of metastatic human liver cancer.
CDK4 siRNA sequences used in this study
Table 19 provides a list of exemplary siRNA sequences targeting human CDK4 gene expression.

TABLE 19

| siRNA sequences that target human CDK4 gene expression. |
| --- |
| siRNA |
| CDK4-1 |
| CDK4-2 |
| CDK4-3 |

Table 20 provides a list of chemically modified CDK4-1 siRNA molecules containing 2'OMe nucleotides at selective positions within the double-stranded region.

TABLE 20

| 2'OMe-modified siRNA sequences that target human CDK4 gene expression. |
| --- |
| siRNA |
| CDK4-1/6 |
| CDK4-1/7 |
| CDK4-1/8 |
| CDK4-1/9 |
| CDK4-3/2 |
| CDK4-3/6 |
| CDK4-3/7 |
| CDK4-3/8 |
| CDK4-3/9 |
| CDK4-4/2 |
| CDK4-4/6 |
| CDK4-4/7 |
| CDK4-4/8 |
| CDK4-4/9 |
| CDK4-5/2 |
| CDK4-5/6 |
| CDK4-5/7 |
| CDK4-5/8 |
| CDK4-5/9 |

Selection of modified CDK4 siRNA for in vivo applications

Various CDK4 siRNA molecules set forth in Tables 19 and 20 were evaluated for their inhibitory effects on cell growth in vitro. Huh7-luc$^+$ and HepG2-luc$^+$ cells were treated with CDK4 siRNA and their effect on cell viability was evaluated. Viability of cell cultures is expressed as % viability relative to PBS treated controls. FIG. 27 shows that unmodified as well as 2'OMe-modified CDK4-1 siRNA were effective at inhibiting the growth of Huh7-luc$^+$ (A) and HepG2-luc$^+$ (B) cells. In particular, CDK4-1 (unmodified) siRNA and CDK4-3/7 siRNA (as well as several others) were highly potent at killing Huh7-luc$^+$ and HepG2-luc$^+$ cells.

CDK4-3/7 siRNA was selected for in vivo studies in the Huh7-luc$^+$ HCC orthotopic xenograft mouse model.
Systemic inhibition of orthotopic liver tumor growth with CDK4 siRNA Eight days after transplantation of Huh7-luc$^+$ cells, SNALP containing CDK4-3/7 siRNA were systemically delivered to the liver through a tail vein injection four times (days 8, 11, 15, and 18) at a dosage of 2 mg/kg. Tumor relapses were monitored by BLI up to 28 days after cell transplantation.

FIG. 28 shows that systemic delivery of CDK4-3/7 siRNA effectively prevented orthotopic tumor growth in the liver in a mouse model of metastatic human liver cancer compared to a control administration of SNALP containing siRNA targeting β-gal (FIGS. 28A-B). Correlating with the level of bioluminescent signals on day 28, gross inspection revealed that the livers in mice treated with CDK4-3/7 siRNA had a significantly lower number of tumors or a complete absence of tumors (FIG. 28C). Histological analysis also revealed that livers treated with control siRNA produced tumors, indicating a significant degree of cellular proliferation, whereas CDK4-3/7 siRNA treatment inhibited tumor spreading, even at the modest dose (FIG. 28C). The liver morphology and histology images shown in FIG. 28 are representative of the animals belonging to that treatment group.

These results demonstrate that siRNA-mediated knockdown of the CDK4 gene inhibits Huh7 and HepG2 cell growth. These results further demonstrate that systemic delivery of SNALP-formulated CDK4 siRNA effectively suppresses neoplastic growth in a mouse model of metastatic human liver cancer. This study illustrates that CDK4 is an important regulator of HCC cell growth and survival, and that cell cycle regulation represents a target pathway for human HCC treatment.

Conclusion

This example demonstrates that the potency of systemic delivery of siRNA targeting CDK4 without overt toxicity is a clinically viable therapeutic modality for the treatment of cancers such as liver cancer (e.g., HCC) and other solid tumors. In particular, this example illustrates that CDK4 is an important regulator of HCC cell growth and survival, and is an attractive target for HCC therapy. Importantly, this example shows that SNALP containing siRNA targeting CDK4 gene expression are efficacious for the in vivo delivery and treatment of cancers such as liver cancer.

Example 6

Therapeutic Targeting of CSN5 with siRNA for the Treatment of Cancer

This example illustrates that (1) siRNA-mediated knockdown of CSN5 expression inhibited the proliferation of cells from human HCC cell lines; and (2) systemic delivery of SNALP containing chemically modified CSN5 siRNA effectively suppressed neoplastic growth in a mouse model of metastatic human liver cancer. Additional siRNA sequence and experimental data information directed to targeting of the CSN5 gene is described in PCT Application No. PCT/US2009/40685, filed Apr. 15, 2009, the disclosure of which is herein incorporated by reference in its entirety for all purposes.
CSN5 siRNA sequences used in this study
Table 21 provides a list of exemplary siRNA sequences targeting human CSN5 gene expression.

TABLE 21

| siRNA sequences that target human CSN5 gene expression. |
| --- |
| siRNA |
| CSN5-1 |
| CSN5-2 |
| CSN5-3 |

Table 22 provides a list of chemically modified CSN5-2 siRNA molecules containing 2'OMe nucleotides at selective positions within the double-stranded region.

TABLE 22

2'OMe-modified siRNA sequences that target human CSN5 gene expression.
siRNA

CSN5-1/6
CSN5-1/7
CSN5-1/8
CSN5-1/9
CSN5-3/2
CSN5-3/6
CSN5-3/7
CSN5-3/8
CSN5-3/9
CSN5-4/2
CSN5-4/6
CSN5-4/7
CSN5-4/8
CSN5-4/9
CSN5-5/2
CSN5-5/6
CSN5-5/7
CSN5-5/8
CSN5-5/9

Silencing of CSN5 inhibits the proliferation of human HCC cells

Given the significance of p53 and p27 in hepatocarcinogenesis, the effects of CSN5 gene knockdown using human HCC cell lines were examined. To inactivate CSN5 gene expression, Huh7 and HepG2 cells were treated with three different siRNA (CSN5-1, CSN5-2, and CSN5-3). FIG. 29 shows that CSN5 gene silencing decreased HCC cell survival in a cell viability assay and reduced CSN5 mRNA levels in a quantitative real-time RT-PCR assay. Among the siRNA tested, the CSN5-2 siRNA was the most effective in inhibiting HCC cell growth. Huh7 and HepG2 cells transfected with CSN5-2 siRNA for 4 days showed ~68% and ~77% growth inhibition, respectively (FIGS. 29A-B). In contrast, negative control (NC) siRNA revealed only marginal inhibition of Huh7 and HepG2 cell growth (i.e., less than 14% and 13% inhibition) at the same concentrations when compared to no treatment. Quantitative analysis of target mRNA was performed to test the effect of siRNA on CSN5 gene expression in both Huh7 and HepG2 cells. A 48 hour treatment with 15 nM CSN5-2 siRNA resulted in ~87% and ~90% reduction of target mRNA in Huh7 and HepG2 cells, respectively (FIGS. 29C-D).

Selection of modified CSN5 siRNA for in vivo applications

Various CSN5 siRNA molecules set forth in Tables 21 and 22 were encapsulated into SNALP and evaluated for their inhibitory effects on cell growth in vitro. Huh7-luc$^+$ cells were treated with CSN5 SNALP formulations and their effect on cell viability was evaluated. Viability of cell cultures is expressed as % viability relative to PBS treated controls. FIG. 30A shows that unmodified as well as 2'OMe-modified CSN5-2 siRNA were effective at inhibiting the growth of Huh7 cells. In particular, CSN5-2 (unmodified) siRNA and CSN5-3/8 siRNA were highly potent at killing Huh7-luc$^+$ cells. SNALP containing Luciferase (Luc) siRNA was used as a negative control, and SNALP containing Eg5 siRNA was used as a positive control.

SNALP-formulated CSN5 siRNA were evaluated for their immunostimulatory activity in vitro. Flt3L DC cultures from mouse bone marrow were treated with unmodified or 2'OMe-modified CSN5 SNALP at 5 μg/ml for 24 hours. IL-6 levels in the culture supernatants were assayed as an indicator of immune stimulation by a particular CSN5 siRNA. FIG. 30B shows that SNALP containing unmodified (native) CSN5-2 siRNA induced high levels of IL-6 in murine Flt3L DC cultures, which was indicative of robust immune stimulation. However, 2'OMe-modified variants of CSN5-2 such as CSN5-3/8 siRNA induced a minimal IL-6 response in this cell culture system.

CSN5-3/8 siRNA was selected for in vivo studies in the Huh7-luc$^+$ HCC orthotopic xenograft mouse model because it was comparable in potency to the unmodified CSN5-2 siRNA at inhibiting cancer cell growth, but induced a minimal immune response.

Systemic inhibition of orthotopic liver tumor growth with CSN5 siRNA

Eight days after transplantation of Huh7-luc$^+$ cells, SNALP containing CSN5-3/8 siRNA were systemically delivered to the liver through a tail vein injection four times (days 8, 11, 14, and 18) at a dosage of 2 mg/kg. Tumor relapses were monitored by BLI up to 28 days after cell transplantation.

Compared to a control administration of SNALP containing siRNA targeting β-galactosidase, systemic delivery of CSN5-3/8 siRNA effectively prevented orthotopic tumor growth in the liver in a mouse model of metastatic human liver cancer (FIGS. 31A-B). Correlating with the level of bioluminescent signals on day 28, gross inspection revealed that the livers in mice treated with CSN5-3/8 siRNA had a significantly lower number of tumors or a complete absence of tumors (FIGS. 31C-D). Histological analysis also revealed that livers treated with control siRNA produced tumors, indicating a significant degree of cellular proliferation. In contrast, CSN5-3/8 siRNA treatment inhibited tumor spreading, even at the modest dose. The imaging, liver morphology, and liver histology results shown in FIG. 31 are representative of the animals belonging to that treatment group.

These results demonstrate that siRNA-mediated knockdown of the CSN5 gene inhibits proliferation of Huh7 and HepG2 cells. These results further demonstrate that systemic delivery of SNALP-formulated CSN5 siRNA effectively suppresses neoplastic growth in a mouse model of metastatic human liver cancer. This study illustrates that CSN5 is an important regulator of HCC cell growth and survival, and that p53 ubiquitination represents a target pathway for human HCC treatment.

Conclusion

This example demonstrates that the potency of systemic delivery of siRNA targeting CSN5 without overt toxicity is a clinically viable therapeutic modality for the treatment of cancers such as liver cancer (e.g., HCC) and other solid tumors. In particular, this example illustrates that CSN5 is an important regulator of HCC cell growth and survival, and is an attractive target for HCC therapy. Importantly, this example shows that SNALP containing siRNA targeting CSN5 gene expression are efficacious for the in vivo delivery and treatment of cancers such as liver cancer.

Example 7

Therapeutic Targeting of FOXM1 with siRNA for the Treatment of Cancer

This example illustrates that (1) siRNA-mediated knockdown of FOXM1 gene expression inhibited the proliferation of human HCC cells; and (2) chemically modified FOXM1 siRNA were non-immunostimulatory.

FOXM1 siRNA Sequences Used in this Study

Table 23 provides a list of exemplary siRNA sequences targeting human FOXM1 gene expression.

TABLE 23 siRNA sequences that target human FOXM1 gene expression.
siRNA

FOXM1-1
FOXM1-2
FOXM1-3

Table 24 provides a list of chemically modified FOXM1-1 siRNA molecules containing 2'OMe nucleotides at selective positions within the double-stranded region.

TABLE 24

2'OMe-modified siRNA sequences that target human FOXM1 gene expression.
siRNA

FOXM1-1/6
FOXM1-1/7
FOXM1-1/8
FOXM1-1/9
FOXM1-3/2
FOXM1-3/6
FOXM1-3/7
FOXM1-3/8
FOXM1-3/9
FOXM1-4/2
FOXM1-4/6
FOXM1-4/7
FOXM1-4/8
FOXM1-4/9
FOXM1-5/2
FOXM1-5/6
FOXM1-5/7
FOXM1-5/8
FOXM1-5/9

Selection of Modified FOXM1 siRNA for In Vivo Applications

Various FOXM1 siRNA molecules set forth in Tables 23 and 24 were evaluated for their inhibitory effects on cell growth in vitro. Huh7-luc⁺ cells were treated with FOXM1 siRNA and their effect on cell viability was evaluated. Viability of cell cultures is expressed as % viability relative to PBS treated controls. FIG. 32A shows that unmodified as well as 2'OMe-modified FOXM1-1 siRNA were effective at inhibiting the growth of Huh7-luc⁺ cells. In particular, FOXM1-1 (unmodified) siRNA, FOXM1-5/6 siRNA, and FOXM1-5/7 siRNA were highly potent at killing Huh7-luc⁺ cells.

SNALP-formulated FOXM1 siRNA were evaluated for their immunostimulatory activity in vitro. Flt3L DC cultures from mouse bone marrow were treated with unmodified or 2'OMe-modified FOXM1 SNALP at 5 μg/ml for 24 hours. IL-6 levels in the culture supernatants were assayed as an indicator of immune stimulation by a particular FOXM1 siRNA. FIG. 32B shows that SNALP containing unmodified (native) FOXM1-1 siRNA induced high levels of IL-6 in murine Flt3L DC cultures, which was indicative of robust immune stimulation. However, 2'OMe-modified variants of FOXM1-1 such as FOXM1-5/6 siRNA induced a minimal IL-6 response in this cell culture system.

FOXM1-5/6 siRNA was selected for in vivo studies in the Huh7-luc⁺ HCC orthotopic xenograft mouse model because it was comparable in potency to the unmodified FOXM1-1 siRNA at inhibiting cancer cell growth, but induced a minimal immune response.

Example 8

Therapeutic Targeting of R1 (RAM2) with siRNA for the Treatment of Cancer

This example illustrates that (1) siRNA-mediated knockdown of R1 gene expression inhibited the proliferation of human HCC cells; and (2) chemically modified R1 siRNA were non-immunostimulatory.

R1 siRNA Sequences Used in this Study

Table 25 provides a list of exemplary siRNA sequences targeting human R1 gene expression.

TABLE 25 siRNA sequences that target human R1 gene expression.
siRNA

R1-1
R1-2
R1-3

Table 26 provides a list of chemically modified R1-2 siRNA molecules containing 2'OMe nucleotides at selective positions within the double-stranded region.

TABLE 26

2'OMe-modified siRNA sequences that target human R1 gene expression.
siRNA

R1-1/6
R1-1/7
R1-1/8
R1-1/9
R1-3/2
R1-3/6
R1-3/7
R1-3/8
R1-3/9
R1-4/2
R1-4/6
R1-4/7
R1-4/8
R1-4/9
R1-5/2
R1-5/6
R1-5/7
R1-5/8
R1-5/9

Selection of Modified R1 siRNA for In Vivo Applications

Various R1 siRNA molecules set forth in Tables 25 and 26 were evaluated for their inhibitory effects on cell growth in vitro. Huh7-luc⁺ cells were treated with R1 siRNA and their effect on cell viability was evaluated. Viability of cell cultures is expressed as % viability relative to PBS treated controls. FIG. 33A shows that unmodified as well as 2'OMe-modified R1-2 siRNA were effective at inhibiting the growth of Huh7-luc⁺ cells. In particular, R1-2 (unmodified) siRNA, R1-4/7 siRNA, R1-5/8 siRNA, and R1-5/9 siRNA were highly potent at killing Huh7-luc⁺ cells.

SNALP-formulated R1 siRNA were evaluated for their immunostimulatory activity in vitro. Flt3L DC cultures from mouse bone marrow were treated with unmodified or 2'OMe-modified R1SNALP at 5 μg/ml for 24 hours. IL-6 levels in the culture supernatants were assayed as an indicator of immune stimulation by a particular R1 siRNA. FIG. 33B shows that SNALP containing unmodified (native) R1-2 siRNA induced high levels of IL-6 in murine Flt3L DC cultures, which was indicative of robust immune stimulation. However, 2'OMe-modified variants of R1-2 such as R1-5/8 siRNA induced a minimal IL-6 response in this cell culture system.

R1-5/8 siRNA was selected for in vivo studies in the Huh7-luc+ HCC orthotopic xenograft mouse model because it was comparable in potency to the unmodified R1-2 siRNA at inhibiting cancer cell growth, but induced a minimal immune response.

Example 9

Combinatorial Silencing of Genes Expressed in Cancer

This example illustrates that a cocktail of siRNA sequences targeting multiple genes expressed in cancer substantially increased apoptosis of human HCC cells as compared to the individual siRNA sequences.

HepG2 cells were treated with either a single siRNA or a combination of 2 siRNAs and the effect on the induction of apoptosis was evaluated. FIG. 34 shows that numerous combinations of siRNA sequences were effective at inducing the apoptosis of cancer cells. In particular, the following cocktails of siRNAs exhibited a significant increase in apoptosis compared with negative control (NC) siRNA-treated cells: (1) COP1-1 siRNA+WEE1-2 siRNA; (2) COP1-1 siRNA+CSN5-2 siRNA; (3) COP1-1 siRNA+RBX1-2 siRNA; (4) COP1-1 siRNA+CDK4-1 siRNA; (5) CSN5-2 siRNA+WEE1-2 siRNA; (6) RBX1-2 siRNA+WEE1-2 siRNA; (7) RBX1-2 siRNA+CDK4-1 siRNA; and (8) WEE1-2 siRNA+CDK4-1 siRNA. These siRNA combinations were selected for in vivo studies in the Huh7-luc+ HCC orthotopic xenograft mouse model.

Example 10

Additional Exemplary Unmodified and Chemically Modified siRNA Targeting WEE1

This example illustrates the design and testing of additional unmodified and 2'OMe-modified WEE1 siRNA sequences that find utility in the treatment of cancers such as liver cancer (e.g., HCC) and other solid tumors.

Table 27 provides additional exemplary siRNA sequences targeting human WEE1 gene expression.

TABLE 27

Additional siRNA sequences that target human WEE1 gene expression.

| Target or Sense Strand Sequence siRNA(5' → 3') | Antisense Strand Sequence (5' → 3') |
|---|---|
| WEE1-GCUGGCGAACAAAUGUAAACA 60 (SEQ ID NO: 256) | UUUACAUUUGUUCGCCAGCAC (SEQ ID NO: 257) |
| WEE1-CUCCUCAAGUGAAUAUUAAUC 1828 (SEQ ID NO: 258) | UUAAUAUUCACUUGAGGAGUC (SEQ ID NO: 259) |
| WEE1-CAUGGAAGCCAGUGAUUAUGA 1937 (SEQ ID NO: 260) | AUAAUCACUGGCUUCCAUGUC (SEQ ID NO: 261) |
| WEE1-CCCGGUAUACAACAGAAUUUC 2017 (SEQ ID NO: 262) | AAUUCUGUUGUAUACCGGGAC (SEQ ID NO: 263) |
| WEE1-CCGGUAUACAACAGAAUUUCA 2018 (SEQ ID NO: 264) | AAAUUCUGUUGUAUACCGGGA (SEQ ID NO: 265) |
| WEE1-AGGCUGGAUGGAUGCAUUUAU 2094 (SEQ ID NO: 266) | AAAUGCAUCCAUCCAGCCUCU (SEQ ID NO: 267) |

TABLE 27-continued

Additional siRNA sequences that target human WEE1 gene expression.

| Target or Sense Strand Sequence siRNA(5' → 3') | Antisense Strand Sequence (5' → 3') |
|---|---|
| WEE1-GAUGCAUUUAUGCCAUUAAGC 2104 (SEQ ID NO: 268) | UUAAUGGCAUAAAUGCAUCCA (SEQ ID NO: 269) |
| WEE1-AUGCAUUUAUGCCAUUAAGCG 2105 (SEQ ID NO: 270) | CUUAAUGGCAUAAAUGCAUCC (SEQ ID NO: 271) |
| WEE1-UCUCAUGUAGUUCGAUAUUUC 2208 (SEQ ID NO: 272) | AAUAUCGAACUACAUGAGAAU (SEQ ID NO: 273) |
| WEE1-CCGAGGCUUGAGGUAUAUUCA 2372 (SEQ ID NO: 274) | AAUAUACCUCAAGCCUCGGCC (SEQ ID NO: 275) |
| WEE1-UUUGGUUCACAUGGAUAUAAA 2402 (SEQ ID NO: 276) | UAUAUCCAUGUGAACCAAAGA (SEQ ID NO: 277) |
| WEE1-GUGCUUUCCCAAGAAUUUACA 2748 (SEQ ID NO: 278) | UAAAUUCUUGGGAAAGCACUU (SEQ ID NO: 279) |
| WEE1-UCCACCACCCAGAGUAAUAGA 3003 (SEQ ID NO: 280) | UAUUACUCUGGGUGGUGGACC (SEQ ID NO: 281) |
| WEE1-UCUGUCAGCCUUACUAUAUAC 3057 (SEQ ID NO: 282) | AUAUAGUAAGGCUGACAGAGC (SEQ ID NO: 283) |
| WEE1-CUGUCAGCCUUACUAUAUACU 3058 (SEQ ID NO: 127) | UAUAUAGUAAGGCUGACAGAG (SEQ ID NO: 128) |
| WEE1-GAGGAAGCUAGGUUGAAAUCA 3119 (SEQ ID NO: 284) | AUUUCAACCUAGCUUCCUCUU (SEQ ID NO: 285) |
| WEE1-UGGUGGUGUGCUGCUUUAUAGU 3337 (SEQ ID NO: 286) | UAUAAGCAGCACACCACCACA (SEQ ID NO: 287) |
| WEE1-GUGUGUCCAUCUUAUAUUUCU 3497 (SEQ ID NO: 288) | AAAUAUAAGAUGGACACACAG (SEQ ID NO: 289) |
| WEE1-AGGUAUUGCCUUGUGAAUUUG 3607 (SEQ ID NO: 290) | AAUUCACAAGGCAAUACCUCC (SEQ ID NO: 291) |
| WEE1-GGUAUUGCCUUGUGAAUUUGC 3608 (SEQ ID NO: 292) | AAAUUCACAAGGCAAUACCUC (SEQ ID NO: 293) |

3'-overhangs are indicated in bold and italicized. The 3'-overhangs on one or both strands of the siRNA molecule may alternatively comprise 1-4 deoxythymidine (t) nucleotides, 1-4 modified and/or unmodified uridine (U) ribonucleotides, or 1-4 unmodified and/or modified ribonucleotides or deoxyribonucleotides having complementarity to the target sequence or the complementary strand thereof. In certain instances, the sense and/or antisense strand of the siRNA molecule lacks 3'-overhangs (i.e., does not contain the sequence indicated in bold and italicized).

Table 28 provides a list of chemically modified WEE1-3058 siRNA molecules containing 2'OMe nucleotides at selective positions within the double-stranded region.

TABLE 28

Exemplary 2'OMe-modified WEE1-3058 siRNA sequences.

| siRNA | Target or Sense Strand Sequence (5' → 3') | Antisense Strand Sequence (5' → 3') |
|---|---|---|
| WEE1-3058-S/4 | CUGUCAGCCUUACUAUAUA*CU* (SEQ ID NO: 127) | UAUAUAGUAAGGCUGACAG*AG* (SEQ ID NO: 296) |
| WEE1-3058-S/5 | CUGUCAGCCUUACUAUAUA*CU* (SEQ ID NO: 127) | UAUAUAGUAAGGCUGACAG*AG* (SEQ ID NO: 137) |
| WEE1-3058-S/6 | CUGUCAGCCUUACUAUAUA*CU* (SEQ ID NO: 127) | UAUAUAGUAAGGCUGACAG*AG* (SEQ ID NO: 297) |
| WEE1-3058-S/7 | CUGUCAGCCUUACUAUAUA*CU* (SEQ ID NO: 127) | UAUAUAGUAAGGCUGACAG*AG* (SEQ ID NO: 298) |
| WEE1-3058-1/AS | CUGUCAGCCUUACUAUAUA*CU* (SEQ ID NO: 136) | UAUAUAGUAAGGCUGACAG*AG* (SEQ ID NO: 128) |
| WEE1-3058-1/4 | CUGUCAGCCUUACUAUAUA*CU* (SEQ ID NO: 136) | UAUAUAGUAAGGCUGACAG*AG* (SEQ ID NO: 296) |
| WEE1-3058-1/5 | CUGUCAGCCUUACUAUAUA*CU* (SEQ ID NO: 136) | UAUAUAGUAAGGCUGACAG*AG* (SEQ ID NO: 137) |
| WEE1-3058-1/6 | CUGUCAGCCUUACUAUAUA*CU* (SEQ ID NO: 136) | UAUAUAGUAAGGCUGACAG*AG* (SEQ ID NO: 297) |
| WEE1-3058-1/7 | CUGUCAGCCUUACUAUAUA*CU* (SEQ ID NO: 136) | UAUAUAGUAAGGCUGACAG*AG* (SEQ ID NO: 298) |
| WEE1-3058-2/AS | CUGUCAGCCUUACUAUAUA*CU* (SEQ ID NO: 294) | UAUAUAGUAAGGCUGACAG*AG* (SEQ ID NO: 128) |
| WEE1-3058-2/4 | CUGUCAGCCUUACUAUAUA*CU* (SEQ ID NO: 294) | UAUAUAGUAAGGCUGACAG*AG* (SEQ ID NO: 296) |
| WEE1-3058-2/5 | CUGUCAGCCUUACUAUAUA*CU* (SEQ ID NO: 294) | UAUAUAGUAAGGCUGACAG*AG* (SEQ ID NO: 137) |
| WEE1-3058-2/6 | CUGUCAGCCUUACUAUAUA*CU* (SEQ ID NO: 294) | UAUAUAGUAAGGCUGACAG*AG* (SEQ ID NO: 297) |
| WEE1-3058-2/7 | CUGUCAGCCUUACUAUAUA*CU* (SEQ ID NO: 294) | UAUAUAGUAAGGCUGACAG*AG* (SEQ ID NO: 298) |
| WEE1-3058-3/AS | CUGUCAGCCUUACUAUAUA*CU* (SEQ ID NO: 295) | UAUAUAGUAAGGCUGACAG*AG* (SEQ ID NO: 128) |
| WEE1-3058-3/4 | CUGUCAGCCUUACUAUAUA*CU* (SEQ ID NO: 295) | UAUAUAGUAAGGCUGACAG*AG* (SEQ ID NO: 296) |
| WEE1-3058-3/5 | CUGUCAGCCUUACUAUAUA*CU* (SEQ ID NO: 295) | UAUAUAGUAAGGCUGACAG*AG* (SEQ ID NO: 137) |
| WEE1-3058-3/6 | CUGUCAGCCUUACUAUAUA*CU* (SEQ ID NO: 295) | UAUAUAGUAAGGCUGACAG*AG* (SEQ ID NO: 297) |
| WEE1-3058-3/7 | CUGUCAGCCUUACUAUAUA*CU* (SEQ ID NO: 295) | UAUAUAGUAAGGCUGACAG*AG* (SEQ ID NO: 298) |

2'OMe nucleotides are indicated in bold and underlined. 3'-overhangs are indicated in bold and italicized. The 3'-overhangs on one or both strands of the siRNA molecule may alternatively comprise 1-4 deoxythymidine (t) nucleotides, 1-4 modified and/or unmodified uridine (U) ribonucleotides, or 1-4 unmodified and/or modified ribonucleotides or deoxyribonucleotides having complementarity to the target sequence or the complementary strand thereof. In certain instances, the sense and/or antisense strand of the siRNA molecule lacks 3'-overhangs (i.e., does not contain the sequence indicated in bold and italicized).

The effects of WEE1 gene knockdown using HepG2 cells were examined with the additional WEE1 siRNA sequences set forth in Table 27. Viability of cell cultures is expressed as % viability relative to PBS treated controls. FIG. 35 shows that numerous WEE1 siRNAs were as effective as WEE1-2 siRNA or more efficacious than WEE1-2 siRNA at inhibiting the growth of cancer cells. In particular, WEE1-1828 siRNA, WEE1-1937 siRNA, WEE1-2018 siRNA, WEE1-2104 siRNA, and WEE1-3058 siRNA were highly potent at killing HepG2 cells.

FIG. 36 shows a dose-response curve analysis for each of these WEE1 siRNA sequences. SNALP-formulated WEE1 siRNAs displayed dose-dependent inhibition of HepG2 cell growth. The half maximal inhibitory concentration ($IC_{50}$) was the lowest for WEE1-3058 siRNA. The WEE1-3058 siRNA also exhibited mouse cross-reactivity as it was capable of potently inhibiting the growth of mouse Neuro2a cells.

Various 2'OMe-modified WEE1-3058 siRNA molecules set forth in Table 28 were evaluated for their inhibitory effects on cell growth in vitro. HepG2 cells were treated with unmodified and 2'OMe-modified WEE1-3058 siRNA and their effect on cell viability was evaluated. FIG. 37 shows that unmodified as well as 2'OMe-modified WEE1-3058 siRNA were effective at inhibiting the growth of HepG2 cells. In particular, the unmodified WEE1-3058 siRNA and WEE1-3058-1/5 siRNA (as well as several others) were highly potent at killing HepG2 cells. The WEE1-3058-1/5 siRNA was selected for in vivo studies in the Huh7-luc⁺ HCC orthotopic xenograft mouse model.

Example 11

Additional Exemplary Unmodified and Chemically Modified siRNA Targeting COP1

This example illustrates the design and testing of additional unmodified and 2'OMe-modified COP1 siRNA sequences that find utility in the treatment of cancers such as liver cancer (e.g., HCC) and other solid tumors.

Table 29 provides additional exemplary siRNA sequences targeting human COP1 gene expression.

TABLE 29

Additional siRNA sequences that target human COP1 gene expression.

| Target or Sense Strand Sequence siRNA(5' → 3') | Antisense Strand Sequence (5' → 3') |
|---|---|
| COP1-AGAGUUUGGAGGACAAUAA*UA* 739 (SEQ ID NO: 299) | UUAUUGUCCUCCAAACUCU*GA* SEQ ID NO: 300) |
| COP1-GAGUUUGGAGGACAAUAAU*AG* 740 (SEQ ID NO: 301) | AUUAUUGUCCUCCAAACUC*UG* (SEQ ID NO: 302) |
| COP1-GACCAUCUGUAUCCUAAUU*UC* 795 (SEQ ID NO: 303) | AAUUAGGAUACAGAUGGUC*AA* (SEQ ID NO: 304) |
| COP1-AGGUUGCAAGAAGAAAUAA*GA* 1060 (SEQ ID NO: 305) | UUAUUUCUUCUUGCAACCU*UG* (SEQ ID NO: 306) |
| COP1-UAGCACAGUGCCUCAAUUU*GA* 1181 (SEQ ID NO: 60) | AAAUUGAGGCACUGUGCUA*UC* (SEQ ID NO: 61) |
| COP1-CAUCACACAGUAGUAUUAU*UG* 1213 (SEQ ID NO: 307) | AUAAUACUACUGUGUGAUG*GA* (SEQ ID NO: 308) |
| COP1-GAAACAGCCUUGGUAUAAU*AG* 1286 (SEQ ID NO: 309) | AUUAUACCAAGGCUGUUUC*UU* (SEQ ID NO: 310) |
| COP1-AAGCCAGUUGGAUGAAUUU*CA* 1412 (SEQ ID NO: 311) | AAAUUCAUCCAACUGGCUU*GC* (SEQ ID NO: 312) |

TABLE 29-continued

Additional siRNA sequences that target human COP1 gene expression.

| Target or Sense Strand Sequence siRNA(5' → 3') | Antisense Strand Sequence (5' → 3') |
|---|---|
| COP1-GUUGGAGUGUUGACUUUAA*UU* 1801 (SEQ ID NO: 313) | UUAAAGUCAACACUCCAAC*AC* (SEQ ID NO: 314) |
| COP1-UUGGAGUGUUGACUUUAAU*UU* 1802 (SEQ ID NO: 315) | AUUAAAGUCAACACUCCAA*CA* (SEQ ID NO: 316) |
| COP1-UGGAGUGUUGACUUUAAUU*UG* 1803 (SEQ ID NO: 317) | AAUUAAAGUCAACACUCCA*AC* (SEQ ID NO: 318) |
| COP1-GGAGUGUUGACUUUAAUUU*GA* 1804 (SEQ ID NO: 319) | AAAUUAAAGUCAACACUCC*AA* (SEQ ID NO: 320) |
| COP1-AAUGUGUGCUGUGUUUAAAU*UC* 1923 (SEQ ID NO: 321) | AUUUAACACAGCACACAUU*AG* (SEQ ID NO: 322) |
| COP1-AUGUGUGCUGUGUUUAAAUU*CA* 1924 (SEQ ID NO: 323) | AAUUUAACACAGCACACAU*UA* (SEQ ID NO: 324) |
| COP1-UGUGAGUGGUGAGGAAAUU*GU* 2075 (SEQ ID NO: 325) | AAUUUCCUCACCACUCACA*AA* (SEQ ID NO: 326) |
| COP1-GGCUUCCAAUGGAGAUUAU*AU* 2198 (SEQ ID NO: 327) | AUAAUCUCCAUUGGAAGCC*AG* (SEQ ID NO: 328) |
| COP1-AACAGUCAGGGUACAAUUA*AG* 2412 (SEQ ID NO: 329) | UAAUUGUACCCUGACUGUU*AG* (SEQ ID NO: 330) |
| COP1-ACAGUCAGGGUACAAUUAA*GG* 2413 (SEQ ID NO: 331) | UUAAUUGUACCCUGACUGU*UA* (SEQ ID NO: 332) |
| COP1-GGGUUAACUCAAGUCAAAU*UG* 2452 (SEQ ID NO: 333) | AUUUGACUUGAGUUAACCC*UU* (SEQ ID NO: 334) |
| COP1-GGUUAACUCAAGUCAAAUU*GU* 2453 (SEQ ID NO: 335) | AAUUUGACUUGAGUUAACC*CU* (SEQ ID NO: 336) |
| COP1-ACUUGAUCCUGCUGAAAUA*CA* 2474 (SEQ ID NO: 337) | UAUUUCAGCAGGAUCAAGU*AC* (SEQ ID NO: 338) |
| COP1-UGUGAUAGGGAAACAAAUU*CU* 2705 (SEQ ID NO: 339) | AAAUUGUUUCCCUAUCACA*AA* (SEQ ID NO: 340) |

3'-overhangs are indicated in bold and italicized. The 3'-overhangs on one or both strands of the siRNA molecule may alternatively comprise 1-4 deoxythymidine (t) nucleotides, 1-4 modified and/or unmodified uridine (U) ribonucleotides, or 1-4 unmodified and/or modified ribonucleotides or deoxyribonucleotides having complementarity to the target sequence or the complementary strand thereof. In certain instances, the sense and/or antisense strand of the siRNA molecule lacks 3'-overhangs (i.e., does not contain the sequence indicated in bold and italicized).

Table 30 provides a list of chemically modified COP1-1181 siRNA molecules containing 2'OMe nucleotides at selective positions within the double-stranded region.

TABLE 30

Exemplary 2'OMe-modified COP1-1181 siRNA sequences.

| siRNA | Target or Sense Strand Sequence (5' → 3') | Antisense Strand Sequence (5' → 3') |
|---|---|---|
| COP1-1181-S/4 | UAGCACAGUGCCUCAAUUU*GA* (SEQ ID NO: 60) | AAAUUGAGGCACUGUGCUAU*UC* (SEQ ID NO: 344) |
| COP1-1181-S/5 | UAGCACAGUGCCUCAAUUU*GA* (SEQ ID NO: 60) | AAAUUGAGGCACUGUGCUAU*UC* (SEQ ID NO: 345) |

TABLE 30-continued

Exemplary 2'OMe-modified COP1-1181 siRNA sequences.

| siRNA | Target or Sense Strand Sequence (5' → 3') | Antisense Strand Sequence (5' → 3') |
|---|---|---|
| COP1-1181-S/6 | UAGCACAGUGCCUCAAUUUGA (SEQ ID NO: 60) | AAAUUGAGGCACUGUGCUAUC (SEQ ID NO: 346) |
| COP1-1181-S/7 | UAGCACAGUGCCUCAAUUUGA (SEQ ID NO: 60) | AAAUUGAGGCACUGUGCUAUC (SEQ ID NO: 347) |
| COP1-1181-1/AS | UAGCACAGUGCCUCAAUUUGA (SEQ ID NO: 341) | AAAUUGAGGCACUGUGCUAUC (SEQ ID NO: 61) |
| COP1-1181-1/4 | UAGCACAGUGCCUCAAUUUGA (SEQ ID NO: 341) | AAAUUGAGGCACUGUGCUAUC (SEQ ID NO: 344) |
| COP1-1181-1/5 | UAGCACAGUGCCUCAAUUUGA (SEQ ID NO: 341) | AAAUUGAGGCACUGUGCUAUC (SEQ ID NO: 345) |
| COP1-1181-1/6 | UAGCACAGUGCCUCAAUUUGA (SEQ ID NO: 341) | AAAUUGAGGCACUGUGCUAUC (SEQ ID NO: 346) |
| COP1-1181-1/7 | UAGCACAGUGCCUCAAUUUGA (SEQ ID NO: 341) | AAAUUGAGGCACUGUGCUAUC (SEQ ID NO: 347) |
| COP1-1181-2/AS | UAGCACAGUGCCUCAAUUUGA (SEQ ID NO: 342) | AAAUUGAGGCACUGUGCUAUC (SEQ ID NO: 61) |
| COP1-1181-2/4 | UAGCACAGUGCCUCAAUUUGA (SEQ ID NO: 342) | AAAUGAGGCACUGUGCUAUC (SEQ ID NO: 344) |
| COP1-1181-2/5 | UAGCACAGUGCCUCAAUUUGA (SEQ ID NO: 342) | AAAUUGAGGCACUGUGCUAUC (SEQ ID NO: 345) |
| COP1-1181-2/6 | UAGCACAGUGCCUCAAUUUGA (SEQ ID NO: 342) | AAAUUGAGGCACUGUGCUAUC (SEQ ID NO: 346) |
| COP1-1181-2/7 | UAGCACAGUGCCUCAAUUUGA (SEQ ID NO: 342) | AAAUUGAGGCACUGUGCUAUC (SEQ ID NO: 347) |
| COP1-1181-3/AS | UAGCACAGUGCCUCAAUUUGA (SEQ ID NO: 343) | AAAUUGAGGCACUGUGCUAUC (SEQ ID NO: 61) |
| COP1-1181-3/4 | UAGCACAGUGCCUCAAUUUGA (SEQ ID NO: 343) | AAAUGAGGCACUGUGCUAUC (SEQ ID NO: 344) |
| COP1-1181-3/5 | UAGCACAGUGCCUCAAUUUGA (SEQ ID NO: 343) | AAAUUGAGGCACUGCUAUC (SEQ ID NO: 345) |
| COP1-1181-3/6 | UAGCACAGUGCCUCAAUUUGA (SEQ ID NO: 343) | AAAUUGAGGCACUGUGCUAUC (SEQ ID NO: 346) |
| COP1-1181-3/7 | UAGCACAGUGCCUCAAUUUGA (SEQ ID NO: 343) | AAAUUGAGGCACUGUGCUAUC (SEQ ID NO: 347) |

2'OMe nucleotides are indicated in bold and underlined. 3'-overhangs are indicated in bold and italicized. The 3'-overhangs on one or both strands of the siRNA molecule may alternatively comprise 1-4 deoxythymidine (t) nucleotides, 1-4 modified and/or unmodified uridine (U) ribonucleotides, or 1-4 unmodified and/or modified ribonucleotides or deoxyribonucleotides having complementarity to the target sequence or the complementary strand thereof. In certain instances, the sense and/or antisense strand of the siRNA molecule lacks 3'-overhangs (i.e., does not contain the sequence indicated in bold and italicized).

The effects of COP1 gene knockdown using HepG2 cells were examined with the additional COP1 siRNA sequences set forth in Table 29. Viability of cell cultures is expressed as % viability relative to PBS treated controls. FIG. 38 shows that numerous COP1 siRNAs were as effective as COP1-1 siRNA or more efficacious than COP1-1 siRNA at inhibiting the growth of cancer cells. In particular, COP1-739 siRNA, COP1-795 siRNA, COP1-1181 siRNA, COP1-2412 siRNA, and COP1-2453 siRNA were highly potent at killing HepG2 cells.

FIG. 39 shows a dose-response curve analysis for each of these COP1 siRNA sequences. SNALP-formulated COP1 siRNAs displayed dose-dependent inhibition of HepG2 cell growth.

Example 12

Additional Exemplary siRNA Molecules Targeting Genes Expressed in Cancer

Omitted.

FIGS. 42-47 from U.S. Provisional Application No. 61/377,439, which figures are herein incorporated by reference in their entirety for all purposes, provide additional non-limiting examples of siRNA molecules that are suitable for modulating (e.g., silencing) expression of the HDAC2, RBX1, CDK4, CSN5, FOXM1, and R1 genes, respectively. In some embodiments, the sense strand comprises or consists of one of the target sequences set forth in FIGS. 42-47 from U.S. Provisional Application No. 61/377,439 (wherein the "T" nucleotide may be replaced with "U"). In other embodiments, the antisense strand comprises or consists of a sequence that is complementary to (e.g., specifically hybridizes to) one of the target sequences set forth in FIGS. 42-47 from U.S. Provisional Application No. 61/377,439.

The number next to each target or sense strand sequence (5'→3') refers to the nucleotide position of the 5' base of that sequence relative to the COP1 mRNA sequence NM_022457, WEE1 mRNA sequence NM_003390, HDAC2 mRNA sequence NM_001527, RBX1 mRNA sequence NM_014248, CDK4 mRNA sequence NM_000075, CSN5 mRNA sequence NM_006837, FOXM1 mRNA sequence NM_021953, or R1 mRNA sequence NM_018719.

In certain embodiments, the sense and/or antisense strand of the siRNA comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In some instances, the sense and/or antisense strand of the siRNA contains 3' overhangs. The 3' overhangs on one or both strands of the siRNA may comprise 1-4 deoxythymidine (t) nucleotides, 1-4 modified and/or unmodified uridine (U) ribonucleotides, or 1-4 unmodified and/or modified ribonucleotides or deoxyribonucleotides having complementarity to the target sequence or the complementary strand thereof. In particular embodiments, the sense and/or antisense strand of the siRNA comprises or consists of "tt" (i.e., "dTdT") or "UU" 3' overhangs. In other instances, the sense and/or antisense strand of the siRNA lacks 3' overhangs.

Example 13

Systemic Treatment of Human Hepatocellular Carcinoma by RNA Interference Targeting p53 Ubiquitination Hepatocellular carcinoma (HCC) is the fifth most common cancer worldwide and the third most lethal neoplasm, causing an estimated 600,000 deaths annually (1). In the United States, the incidence of HCC has doubled over the past two decades, and despite recent improvements in treatment and diagnostics, only 30-40% of patients with HCC are eligible for curative treatments (1,2). Recent genomics analyses identified COP1 and CSN5 in a screen for survival genes in human HCC (3,4). Both genes regulate p53 activity via proteasome-dependent degradation. This example addresses whether targeting of COP1 or CSN5 can provide a novel therapeutic modality against human HCC. Silencing of each gene by small interfering RNA (siRNA) inhibited proliferation of HCC cells and increased apoptotic cell death through the restoration of p53 function. Systemic delivery of the modified target siRNAs by stable nucleic acid-lipid particles (SNALP) remarkably suppressed neoplastic growth and increased survival without eliciting immune response in an orthotopic xenograft mouse model. Analysis of COP1 knockdown signature revealed that antitumor effect in vivo was driven by a p53-dependent apoptosis. The study illustrates that the p53 ubiquitination pathway is an attractive target for treating HCC and provides an important new step towards the potential clinical application of siRNA utilizing SNALP technology.

HCCs are phenotypically and genetically heterogeneous tumors driven by diverse molecular mechanisms (5). However, HCC exhibits certain common traits selected through genomic and epigenetic alterations (6) which cause unrestricted proliferation and/or resistance to cell death (7,8). Identification of the common genomic alterations may provide a paradigm for prevention and treatment of HCC through targeted therapy (9). Using Cox proportional hazards survival analysis, we have recently identified a limited number of genes that could accurately predict patient survival and have provided new molecular insights into HCC pathogenesis (3). HCC from the low survival subclass displayed up-regulation of genes involved in ubiquitination, histone modification, etc., suggesting an etiological involvement of these processes in accelerating HCC progression. Among the survival genes was constitutively photomorphogenic 1 (COP1), an E3-ubiquitin ligase acting as a negative regulator of p53 tumor suppressor via ubiquitin-proteasome system (UPS) (10) and implicated in tumorigenesis (11). Our microarray analysis also revealed a consistent up-regulation of the fifth subunit of COP9 signalosome (CSN5, JAB1) gene in the early HCC relative to dysplastic stage implying that CSN5 is one of the early markers of malignant conversion (4). The CSN5 complex also targets p53 for degradation through the UPS in coordination with Mdm2 as well as the CDK inhibitor p27 (12-14).

p53 plays a pivotal role as a "safe-guardian" of genome preventing cellular transformation (15). Functional loss of p53 by ubiquitination and subsequent deregulation of p53-responsive pathways is one of the most consistent molecular alterations in tumorigenesis (9,16,17). Given the significance of UPS in downregulating p53 activities, the goal of this study was to examine the antitumor effects of silencing COP1 and CSN5 expression by systemic administration of siRNA encapsulated in stable nucleic acid-lipid particles (SNALP). RNA interference (RNAi) is an intrinsic cellular mechanism for gene silencing which triggers a sequence-specific degradation of target mRNA (18,19), and is increasingly used as a promising therapeutic strategy (20). We have previously described the development of SNALP as an effective systemic delivery vehicle for targeting siRNA to murine and primate liver as well as solid tumors and have demonstrated robust therapeutic silencing of endogenous hepatocyte, tumor or viral gene transcripts in the absence of any measurable immune response (21-23).

Here we report validation of the therapeutic potential of COP1 and CSN5. For each gene, three specific siRNAs were designed and tested for growth inhibition in the human HCC derived cell lines, Huh7 and HepG2, as determined by MTT assay, FACS analysis and microscopy (FIGS. 40a,c,d,f,g). This screen identified COP1-1 and CSN5-2 as the most potent siRNAs. Treatment with 15 nM each caused a strong reduction in growth rate of HCC cells which ranged between 68-88% and was paralleled by a similar degree of target mRNA silencing (FIGS. 40b,e). The same concentration of negative control (NC) siRNA caused only a marginal effect on HCC growth. The efficacy of the target siRNAs against tumor cell growth was re-affirmed in the additional HCC cell lines, Huh1 and PLC/PRF/5 (FIG. 40h).

The major functions of COP1 and CSN5 are to antagonize p53 and/or p27 activities via the ubiquitin-proteasome system (10,13,14). Significantly, induction of apoptosis caused by the siRNA targeting of either gene was associated with restoration of p53 function as judged by a marked increase in the levels of p53 and its direct target p21, indicating that siRNA-induced cell death was p53-dependent (FIG. 41). Silencing of CSN5 also amplified p27 levels, albeit to a lesser degree.

Next, we used a subcutaneous model of transplantation of Huh7 cells to examine whether in vitro results of COP1 silencing are relevant for in vivo cancer therapy. FIG. 42 shows that intratumoral administration of COP1-1 siRNA caused a significant dose-dependent growth inhibition as compared to tumors injected with the same concentrations of NC siRNA. The suppression of tumor growth persisted during the following 3 weeks, particularly in the group of mice which received a higher COP1-1 siRNA dose, and was highly significant at the endpoint of experiment.

The therapeutic efficacy of COP1 and CSN5 siRNAs was further evaluated in orthotopic xenograft models using luciferase-expressing HCC reporter cell lines and a SNALP formulation optimized for delivery of siRNA into liver (22). To prevent immune activation by the formulated siRNA, the native COP1-1, CSN5-2 and non-targeting control βgal478 sequences were modified by selective incorporation of 2'-O-methyl (2'OMe) uridine and/or guanosine nucleosides into the siRNA duplex (23,24). COP1-4/7 was selected as the most effective 2'OMe-modified siRNA for growth inhibition (>70%) and target mRNA silencing (>90%) (FIGS. 43a,b). SNALP-COP1 4/7 caused minimal activation of interferon or proinflammatory cytokine responses as compared to administration of SNALP-COP1-1 (FIG. 43c). With the same procedures, the 2'OMe variant CSN5-3/8 was chosen for in vivo targeting of CSN5.

Four intravenous injections of SNALP-COP1 4/7 and CSN5 3/8 caused a significant reduction or a complete absence of Huh7-luc$^+$-derived tumors in liver as compared to a control group receiving SNALP-βgal478 based on bioluminescence imaging (BLI) and microscopic examination (FIGS. 44a-d). In both cases, a dose of 2 mg/kg showed a potent and long-lasting effect resulting in more than a 12- and 7-fold decrease in tumor growth, respectively, 10 days after the last treatment. SNALP-COP1 4/7 was also very effective against intrahepatic tumors established from HepG2-luc$^+$ cells (FIG. 45).

As the ultimate goal of any targeted therapy is to prolong survival, we next allowed Huh7-luc$^+$ cells to engraft longer and form larger tumors before commencing siRNA therapy, thus mimicking an advanced stage of HCC at the time of diagnosis. Although three injections of the tested dose (4 mg/kg) failed to reverse tumor growth, the treatment yielded a statistically significant increase in survival of HCC-bearing mice, without induction of IFN-β (FIG. 44e, FIG. 43d).

Finally, to obtain insight into the molecular basis of the anti-tumor effect caused by COP1 silencing, we performed microarray based gene expression analysis. The comparison of gene expression profiles in tumors treated with a single injection of either SNALP-βgal478 or SNALP-COP1 4/7 identified 540 differentially expressed genes (P<0.05) (FIG. 48a). Notably, PAK2, HSPA1B, BAG3, GAS1 and DIDO1 genes, which are functionally involved in apoptosis, were up-regulated, while the genes associated with an inflammatory response, such as FGG, CCL5, CXCR4, SERPINA3, NUPR1 and ANXA2, were down-regulated (FIG. 47). The Ingenuity Pathway Analysis revealed 5 dominant networks (score>35) including the canonical pathways of p53, Wnt/β-catenin and death receptor signaling (FIGS. 48-49). Using the PathwayStudio tool, we identified common regulators functionally interconnected with p53 and/or NF-κB functions, including up- (MYC, DUSP1, HSPA1A and APP) and down-regulated (BCL2, TNF, CDC25C and MDM2) genes (FIG. 46b).

Inactivation of p53 is a common molecular event in HBV-, HCV- and aflatoxin-B1-induced HCC (5). In this study, we demonstrate the potential of targeting p53 ubiquitination pathway for cancer treatment by RNAi silencing of COP1 or CSN5 that negatively regulate p53 activity. Currently, significant efforts are being devoted to the development of therapeutic approaches which can reactivate a protective function of p53 (25). Functional loss of p53 during carcinogenesis can be mediated by degradation or mutation. p53 degradation mediated by UPS is a universal event promoting tumor development (16,26). 43% of HBV- and HCV-related HCC as well as 35% of aflatoxin-B1 related HCC are due to mutations in the p53 gene, whereas in the remaining HCC p53 is suppressed by reversible degradation (5). In this regard, targeting COP1 and/or CSN5 can be applied to most cancers if at least one of these proteins is up-regulated during carcinogenesis. Interestingly, siRNA-induced depletion of COP1 promoted apoptosis in vitro both in p53-wild type (HepG2, Huh1) and p53-mutant (Huh7, PLC/PRF/5) HCC cells exhibiting Y220C and R249S mutations, respectively (FIG. 50). On the contrary, COP1 silencing did not induce apoptosis in p53-null (Hep3B) HCC cells. Further studies are clearly warranted to investigate the mechanisms of apoptotic progression in HCC cells with different p53 mutational status via inactivation of COP1 protein.

The primary obstacle for therapeutic application of RNAi is the lack of efficient delivery to target cells in vivo. Systemic delivery of a modified siRNA by SNALP has unique technical advantages (27,28). First, the formulated siRNA can evade both glomerular filtration and serum nucleases, thus increasing the half-life of the circulating siRNA and consequently permitting a reduced dosing regimen. Second, 2'OMe-modification abrogates the siRNA's capacity to activate immune responses and therefore minimizes the potential toxicity and off-target effects caused by unmodified siRNA (23,24,29). Finally, the lipid particles can be engineered to selectively distribute the siRNA to target tissues such as the liver or solid tumors where they facilitate cellular uptake of the siRNA and avoid significant drug accumulation in other non-target tissues outside of the reticulo-endothelial system (22,23).

Interference with COP1 and CSN5 in vivo showed strong antitumor activity and decreased the growth rate of HCC xenografts. The differences in tumor growth between control and target siRNA-treated groups reached more than 7-fold, exceeding the criteria for promising therapeutic compounds established by the NCI. Moreover, systemic COP1 silencing increased the survival of mice carrying human HCC xenografts. At a molecular level, COP1 knockdown in tumors caused alterations of p53 target genes including MDM2. Additionally, it triggered upregulation of MYC consistent with a recent observation that activation of the ARF/p53 intrinsic tumor surveillance pathway requires MYC overexpression (30). In conclusion, this study is the first in vivo proof-of-principle that the targeting of COP1 or CSN5 by systemic siRNA treatment could be used for a cancer therapy to reactivate the p53 pathway.

Methods siRNA.

All native siRNA duplexes used for in vitro tests were chemically synthesized by Ambion. The 2'OMe-modified siRNA COP1-4/7, CSN5-3/8 and βgal478 (29) were synthesized and annealed by Integrated DNA Technologies at 100 mg scale. Negative control siRNA molecules that do not target any endogenous transcript were used for control experiments. Silencer Negative Control #1 siRNA (Ambion) and SNALP-formulated βgal478siRNA (29) were used for in vitro and in vivo studies, respectively. A detailed list of all siRNA used in this study is provided in FIG. 51. siRNA were formulated into SNALP suitable for in vivo delivery to the liver as described previously (22,23).

Cell culture and transfection of siRNA in vitro. The human liver cancer cell lines, Huh7 and HepG2, were maintained in DMEM/F-12 media (Mediatech) supplemented with 10% fetal bovine serum (Atlanta Biologicals) at 37° C. in the presence of 5% $CO_2$. Cells were seeded at 25% confluence in 96-well plates one day before transfection in 100 μl of culture media without antibiotics. 0.2 and 0.3 μl of Lipofectamine 2000 were mixed with siRNA molecules in a volume of 50 μl Opti-MEM I (both from Invitrogen) and added to Huh7 and HepG2 cells, respectively. The medium was replaced 24 h after transfection. The negative control siRNA (NCsiRNA) was used in the same quantity and transfected to the cells simultaneously.

Measurement of cell proliferation and apoptotic cell death. The growth inhibitory effects of control and target siRNAs were studied using the Vybrant MTT Cell Proliferation Assay (Invitrogen) as recommended by the manufacturer. Absorbance was measured at 540 nm using an ELISA reader SpectraMAX 190 (Molecular Devices). The percentage of cell viability was calculated by comparing the optical density using the following formula: 1−(absorbance of an experimental well/absorbance of an untreated control well)×100. The induction of apoptosis was measured using ApoStrand ELISA Apoptosis Detection Kit (Biomol International) that detects the denatured single-stranded DNA formed in apoptotic cells, but not in the necrotic cells or cells with DNA breaks.

Quantitative RT-PCR. The changes in target gene expression on mRNA level were detected using real-time quantitative RT-PCR. Total RNA was isolated using Tri reagent (Molecular Research Center) according to the protocol recommended by the manufacturer. One μg of RNA was reverse transcribed using random primers supplied in the High-Capacity cDNA Archieve Kit (Applied Biosystems). To quantify gene expression, cDNA of COP1 and CSN5 genes were amplified using corresponding pair of primers (COP1: forward, 5'-GCACGTTAGCATCAAGACGA-3' (SEQ ID NO: 348); reverse, 5'-ACAATCCCGGTCAAATTCAA-3' (SEQ ID NO: 349), CSN5: forward 5'-TCTGCTGAAGATG-GTGATGC-3' (SEQ ID NO: 350); reverse, 5'-GCCAACCT-GTTTTGCATTTT-3' (SEQ ID NO: 351)) synthesized by Operon, Power SYBR Green PCR Master Mix and ABI 7700HT PCR Machine (both from Applied Biosystems). The mRNA levels of GAPDH were used for normalization. All reactions were performed in triplicate.

Western blotting. The amount of total proteins was determined with the BCA Protein Assay Kit (Pierce). 100 μg of total protein was run in 4-20% SDS-polyacrylamide gel and transferred onto PVDF membrane (Invitrogen). The membrane was blocked by incubating with 5% milk/Trisbuffered saline plus Tween20 (TBST), and incubated with primary antibodies against human COP1 (K-16), CSN5 (FL-334), p53 (FL-393), p21 (C-19) and p27 (F-8) (all from Santa Cruz Biotechnology). The secondary antibodies used were horseradish peroxidase (HRP)-conjugated anti-rabbit IgG (Pierce), anti-goat IgG (Santa Cruz) or anti-mouse IgG (Amersham). Immunoreactive bands were visualized using ECL Plus Western Blotting Detection System (GE Healthcare). The loading of equal amount was assessed by probing the same membrane with ACTIN antibody (NeoMarker). Multiple proteins were detected on the same membrane by incubating membranes in stripping buffer (100 mM β-mercaptoethanol, 2% SDS, and 62.5 mM Tris at pH 6.8) for 20 min at 55° C. and then restaining them.

Cytokine ELISA. The production of IFN-α, IFN-β (PBL Biomedical Laboratories) and IL-6 (BD Biosciences) cytokines was determined in culture supernatant of mouse Flt3L-derived dendritic cells (23) or in mouse serum by sandwich ELISA kits according to the manufacturer's protocol.

Tumor therapy with native siRNA. $5\times10^5$ Huh7 cells were subcutaneously inoculated in 50 μl PBS buffer into lower flank of athynic male Balb/c nude mice (7-8 weeks old). After 15 days when the tumors had reached an average volume of ~50-60 $mm^3$, the tumor bearing mice were treated with Silencer In Vivo Ready COP1-1 siRNA duplex (Ambion) complexed with Lipofectamine 2000. siRNA was diluted with nuclease-free water. The final concentrations of siRNA were 12.5 and 25 μM in total volume 30 μl. As a negative control, we used the same doses of Silencer In Vivo Ready NC #1 siRNA (Ambion) mixed with the cationic lipids. Each therapeutic reagent was injected intra-tumor three times with a 3-day interval. Tumor diameters were measured at 3-day intervals with digital calipers, and the tumor volume in $mm^3$ was calculated by the formula: volume=(width)$^2$×length/2.

Generation of HCC reporter cell lines permanently expressing luciferase. Using Lipofectamine 2000, Huh7 and HepG2 cells were transfected with pGL4.17 vector (Promega) expressing firefly luciferase and zeocin resistance gene. To enhance the expression of luciferase gene, β-actin promoter from pCAGEN plasmid (Addgene) was subcloned into multicloning site of pGL4.17. Cells were selected for antibiotic resistance with Geneticin (Gibco), and surviving colonies were amplified and screened for bioluminescence in complete media supplemented with 150 μg/ml D-luciferin (Biosynth) by in vitro imaging (IVIS Imaging System, Xenogen). One clone was selected per each cell line (Huh7-1H6 and HepG2-1A1) and used throughout the study.

Systemic administration of SNALP-formulated siRNA and BLI in vivo. 6-week-old male SCID/Beige mice (Charles River) were anesthetized by inhalation of 5% isoflorane in oxygen. $5\times10^5$ cells in 50 μL phosphate-buffered saline were injected into the splenic pulp using a 27-gauge needle. Spleens were removed 30 sec after injection. Wounds were closed in two layers using 3-0 silk suture and surgical clips. Body and liver weights were recorded at death. Animals were housed in an AAALAC facility and cared for in accordance with the guidelines from the Animal Care and Use Committee at the US National Cancer Institute, NIH. Mice with liver tumors derived from Huh7-luc$^+$ or HepG2-luc$^+$ cells were randomly assigned to treatment or control groups based on bioluminescence imaging before initiation of siRNA-therapy. SNALP-formulated siRNAs (2 mg/kg) were injected into the lateral tail vein four times with a 3-day interval. Tumor growth was monitored by BLI for 4-weeks with 3-4 day intervals using an IVIS Imaging System. Images and measurements of luciferase signals were analyzed using Living Image Software (Xenogen). Ten minutes prior to in vivo imaging, mice were anesthesized using 1-3% isoflurane (Abbott Laboratories) and received the substrate luciferin (Biosynth) at 150 mg/kg in DPBS by an i.p. injection. Regions of interest (ROI) from displayed images were drawn around the tumor sites and quantified as photons/second using the software. For survival analysis, $5 \times 10^5$ Huh7-luc$^+$ cells were transplanted into spleen as described above. Two and half weeks after transplantation, mice were randomized and intravenously administered with 4 mg/kg SNALP-COP1 4/7 siRNA. Injections were performed three times with a 3-day interval. The experiment was terminated on day 56 after tumor implantation because of the high tumor burden in the control group of mice.

Microarray analysis. Biotin-labeled cRNA was linearly amplified according to manufacturer's specification (AMIL1791; Ambion, Austin, Tex.). As input, 200 ng total RNA from tumor was used for the in vitro transcription (IVT) reactions which were incubated for 16 h at 37° C. The efficiency of this single round amplification was measured by NanoDrop (ND1000, Thermo Scientific). Hybridization, washing, detection (Cy3-streptavidin, Amersham Biosciences, GE Healthcare) and scanning were performed on an Illumina iScan system (Illumina) using reagents and following protocols supplied by the manufacturer. Briefly, the biotinylated cRNA (750 ng/sample) was hybridized on Sentrix whole genome beadchips human Ref-8v3 for 18 h at 58° C. while rocking (5 rpm). The beadchip covers ~24,000 RefSeq transcripts. Image analysis and data extraction were performed automatically using Illumina GenomeScan Software.

Pathway analysis. To explore the functional relationships among the genes with altered expression in the tumors treated with SNALP-COP1 4/7 siRNA, a pathway analysis was carried out with the Ingenuity Pathway Analysis tool (Ariadne Genomics). Using the approach, we examined functional associations among genes and generated the gene networks with high significance on the basis that they had more of the interconnected genes present than would be expected by chance. The significance of each network was estimated by scoring system provided by Ingenuity. The scores are determined by the number of differentially expressed genes within each of the networks and the strength of the associations among network members. Once overrepresented genes that are functionally relevant in gene networks are identified, we validated their functional association by using the independent pathway analysis tool PathwayStudio (Ariadne Genomics).

Statistical analyses. We determined statistical differences by Bootstrap Test with 10,000 repetitions for small sample sizes (n≤4), and one sided Student's t-test, or Mann-Whitney U-test for larger sample size using the R statistical software (v. 2.6.1). The values of P≤0.05 and P≤0.01 were considered statistically significant (*) and highly significant (**), respectively.

REFERENCES

1. Llovet, J. M., Burroughs A. & Bruix J. Hepatocellular carcinoma. Lancet 362, 1907-1917 (2003).
2. Llovet, J. M. & Bruix J. Molecular targeted therapies in hepatocellular carcinoma. Hepatology 48, 1312-1327 (2008).
3. Lee, J. S. et al. Classification and prediction of survival in hepatocellular carcinoma by gene expression profiling. Hepatology 40, 667-676 (2004).
4. Kaposi-Novak, P. et al. Central role of c-Myc during malignant conversion in human hepatocarcinogenesis. Cancer Res. 69, 2775-2782 (2009).
5. Franzi, P. A. & DePinho R. A. Hepatocellular carcinoma pathogenesis: from genes to environment. Nat. Rev. Cancer 6, 674-687 (2006).
6. Thorgeirsson, S. S. & Grisham, J. W. Molecular pathogenesis of human hepatocellular carcinoma. Nat. Genet. 31, 339-346 (2002).
7. Feitelson, M. A. et al. Genetic mechanisms of hepatocarcinogenesis. Oncogene 21, 2593-2604 (2002).
8. Arsura, M. & Cavin, L. G. Nuclear factor-kappaB and liver carcinogenesis. Cancer Lett. 229, 157-169 (2005).
9. Roberts, L. R. & Gores, G. J. Hepatocellular carcinoma: molecular pathways and new therapeutic targets. Semin. Liver Dis. 25, 212-225 (2005).
10. Dornan, D. et al. The ubiquitin ligase COP1 is a critical negative regulator of p53. Nature 429, 86-92 (2004).
11. Dornan, D. et al. COP1, the negative regulator of p53, is overexpressed in breast and ovarian adenocarcinomas. Cancer Res. 64, 7226-7230 (2004).
12. Wei, N., Serino G. & Deng, X. W. The COP9 signalosome: more than a protease. Trends Biochem. Sci. 33, 592-600 (2008).
13. Oh, W. et al. Jab1 induces the cytoplasmic localization and degradation of p53 in coordination with Hdm2. J. Biol. Chem. 281, 17457-17465 (2006).
14. Tomoda, K., Kubota, Y. & Kato, J. Degradation of the cyclin-dependent-kinase inhibitor p27Kip1 is instigated by Jab1. Nature 398, 160-165 (1999).
15. Vogelstein B., Lane, D. & Levine A. J. Surfing the p53 network. Nature 408, 307-310 (2000).
16. Burger, A. M. & Seth, A. K. The ubiquitin-mediated protein degradation pathway in cancer: therapeutic implications. Eur. J. Cancer 40, 2217-2229 (2004).
17. Harris, S. L. & Levine, A. J. The p53 pathway: positive and negative feedback loops. Oncogene 24, 2899-2908 (2005).
18. Fire, A. et al. Potent and specific genetic interference by double stranded RNA in *Caenorhabditis elegans*. Nature 391, 806-811 (1998).
19. Elbashir, S. M. et al. Duplexes of 21-nucleotide RNAs mediate RNA interference in cultured mammalian cells. Nature 411, 494-498 (2001).
20. Hannon, G. J. & Rossi, J. J. Unlocking the potential of the human genome with RNA interference. Nature 431, 371-378 (2004).
21. Morrissey, D. V. et al. Potent and persistent in vivo anti-HBV activity of chemically modified siRNAs. Nat. Biotechnol. 23, 1002-1007 (2005).
22. Zimmermann, T. S. et al. RNAi-mediated gene silencing in non-human primates. Nature 441, 111-114 (2006).
23. Judge, A. D. et al. Confirming the RNAi-mediated mechanism of action of siRNA-based cancer therapeutics in mice. J. Clin. Invest. 119, 661-673 (2009).

24. Judge, A. D., Bola, G., Lee, A. C. H. & MacLachlan, I. Design of noninflammatory synthetic siRNA mediating potent gene silencing in vivo. Mol. Ther. 13, 494-504 (2005).
25. Vazquez, A., Bond, E. A., Levine, A. J. & Bond, G. L. The genetics of the p53 pathway, apoptosis and cancer therapy. Nat. Rev. Drug Discovery 7, 979-987 (2008).
26. Nalepa, G., Rolfe, M. & Harper, J. W. Drug discovery in the ubiquitin-proteasome system. Nat. Rev. Drug Discovery 5, 596-613 (2006).
27. Rossi, J. J. SNALPing siRNAs in vivo. Gene Ther. 13, 583-584 (2006).
28. Whitehead, K. A., Langer, R. & Andersen, D. G. Knocking down barriers: advances in siRNA delivery. Nat. Rev. Drug Discovery 8, 129-138 (2009).
29. Judge, A. D. et al. Sequence-dependent stimulation of the mammalian innate immune response. Nat. Biotechnol. 23, 457-462 (2005).
30. Murphy, D. J. et al. Distinct thresholds govern Myc's biological output in vivo. Cancer Cell 14, 447-457 (2008).

Example 14

Definition of Ubiquitination Modulator COP1 as a Novel Therapeutic Target in Human Hepatocellular Carcinoma Abstract Development of targeted therapeutics for hepatocellular carcinoma (HCC) remains a major challenge. The ubiquitination modulator COP1 regulates p53 activity by ubiquitination and it is frequently overexpressed in human HCC. In this study we tested the hypothesis that COP1 blockade by siRNA-mediated inhibition could affect the course of HCC progression. The COP1 isoform COP1-1 was selected as the most effective target for siRNAs in terms of growth inhibition and apoptotic induction in several HCC cell lines. Growth inhibition occurred in HCC cells that retained wild-type p53 or expressed mutant p53 (Y220C or R249S), whereas p53 null Hep3B cells were resistant. Microarray expression analysis revealed that the anti-proliferative effects of COP1-1 blockade were driven by a common subset of molecular alterations including a p53-associated functional network. In an orthotopic mouse xenograft model of HCC, systemic delivery of a modified COP1 siRNA by stable nucleic-acid-lipid particles (SNALP) suppressed neoplastic growth in liver without unwanted immune responses. Our findings provide the first demonstration that COP1 is a promising target for systemic therapy of HCC.

Précis

A tractable new approach for treating liver cancer by targeting a specific p53 ubiquitination pathway is demonstrated herein using an application of SNALP nanoparticle technology.

Introduction

HCC is the third most lethal neoplasm causing an estimated 600,000 deaths annually (1). In the United States the incidence of HCC has doubled over the past two decades, with only 30-40% of patients being eligible for curative treatments due to the late diagnosis, underlying liver disease and lack of effective treatment options (2-4). HCCs are phenotypically and genetically heterogeneous tumors driven by diverse molecular mechanisms (5). However, HCCs exhibit certain common traits selected through genomic and epigenetic alterations (6,7). Identification of both common and subclass specific genomic alterations may provide an opportunity for treatment of HCC through targeted therapy (8).

We have previously observed that COP1, an E3-ubiquitin ligase also known as RFWD2, is generally overexpressed in human HCC and could accurately predict patient survival (9). Even though the overall biological role of the mammalian COP1 is yet to be defined, several functions have been elucidated (10). In particular, COP1 has been shown to act as a negative regulator of p53 via ubiquitination (11). Given the significance of p53 and the altered expression of UPI in human cancer, we have tested whether the targeting of COP1 could affect the course of HCC progression. Here we report that siRNA-mediated knockdown of COP1 inhibited proliferation and induced apoptosis in HCC cells through common molecular alterations. We also show that systemic silencing of COP1 effectively suppressed human HCC cell growth in an orthotopic xenograft mouse model, indicating that COP1 is a promising target for systemic HCC therapy.

Materials and Methods

Cell lines and siRNA treatment. PLC, Hep3B, and HepG2 obtained from the American Type Culture Collection (ATCC), Huh7 from Riken Cell Bank (deposited by Dr. Nam-Ho Huh) and Huh1 from Health Science Research Resource Bank were passaged for fewer than 6 months. ATCC performed cell line authentication using DNA fingerprinting by short tandem repeat analysis. Riken and Health Science Research Resource cell banks did not provide information on method of authentication. All cell lines were karyotyped upon receipt for future reference. All native siRNA duplexes used for in vitro studies were chemically synthesized by Ambion. Cells were transiently transfected with 15 nM control siRNA (Negative Control #1) or COP1-specific siRNA complexed with Lipofectamine 2000 (Invitrogen). 2'OMe-modified siRNA COP1-4/7 and βgal478 were synthesized and annealed by Integrated DNA Technologies, and formulated into SNALP suitable for in vivo delivery to liver as described (12-14). A list of siRNAs is provided in FIG. 52. Vybrant MTT Cell Proliferation Assay (Invitrogen) and ApoStrand ELISA Apoptosis Detection Kit (Biomol International) were used to evaluate the biological effects of siRNA treatment. qRT-PCR and immunoblotting were performed using standard methods as described herein.

Cytokine ELISA. The production of cytokines in culture supernatant of mouse FIt3L dendrocytes or in mouse serum was measured by sandwich ELISA kits for IFN-α, IFN-β (PBL Biomedical Laboratories) and IL-6 (BD Biosciences).

Systemic administration of SNALP-formulated siRNA in vivo. Animals were housed in an AAALAC facility and cared for in accordance with the guidelines from the Animal Care and Use Committee at the National Cancer Institute, NIH. Huh7-luc+ ($5 \times 10^5$) or HepG2-luc+ ($7 \times 10^5$) cells were injected into the splenic pulp of 6-week-old male SCID/Beige mice (Charles River). SNALP-formulated siRNAs (2 mg/kg) were injected into the lateral tail vein four times with a 3-day interval. Tumor growth was monitored by bioluminescence imaging for 4-weeks with 3-4 day intervals using an IVIS Imaging System.

Microarray experiments. Microarray was performed on human Ref-8v3 microarrays (illumina) as recommended by the manufacturer. RNAs were isolated 48 h after the transfection of NCsiRNA or COP1-1siRNA to Huh7, HepG2 and Hep3B cells. Detailed procedures and pathway analysis are described below. The complete microarray data have been submitted to Gene Expression Omnibus database with accession number GSE21955 (http://www.ncbi.nlm.nih.gov/geo).

Quantitative RT-PCR and Western blotting. The changes in target gene expression on mRNA level were detected using quantitative RT-PCR. Total RNA was isolated using Tri reagent (Molecular Research Center) according to the protocol recommended by the manufacturer. One μg of RNA was reverse transcribed using random primers supplied in the High-Capacity cDNA Archieve Kit (Applied Biosystems). To quantify gene expression, cDNA of COP1 was amplified using corresponding pair of primers (forward, 5'-GCACGT-TAGCATCAAGACGA-3' (SEQ ID NO: 348); reverse, 5'-ACAATCCCGGTCAAATTCAA-3' (SEQ ID NO: 349)) synthesized by Operon, Power SYBR Green PCR Master Mix and ABI 7700HT PCR Machine (both from Applied Biosystems). The mRNA levels of GAPDH were used for normalization. All reactions were performed in triplicate. The amount of total proteins was determined with the BCA Protein Assay Kit (Pierce). 100 μg of total protein were run in 4-20% SDS-polyacrylamide gel and transferred onto PVDF membrane (Invitrogen). The membrane was blocked by incubating with 5% milk/Tris-buffered saline plus Tween20 (TBST), and incubated with primary antibodies against human COP1 (K-16), p53 (FL-393) and p21 (C-19) (all from Santa Cruz Biotechnology). The secondary antibodies were horseradish peroxidase (HRP)-conjugated anti-rabbit IgG (Pierce) or anti-goat IgG (Santa Cruz). Immunoreactive bands were visualized using ECL Plus Western Blotting Detection System (GE Healthcare). The loading of equal amount was assessed by probing the same membrane with ACTIN antibody (NeoMarker). Multiple proteins were detected on the same membrane by incubating membranes in stripping buffer (100 mM β-mercaptoethanol, 2% SDS, and 62.5 mM Tris at pH 6.8) for 20 min at 55° C. and then restaining them.

Microarray and pathway analysis. Biotin-labeled cRNA was linearly amplified according to manufacturer's specification (AMIL1791; Ambion, Austin, Tex.). As input, 200 ng total RNA from tumor was used for the in vitro transcription (IVT) reactions which were incubated for 16 h at 37° C. The efficiency of this single round amplification was measured by NanoDrop (ND1000, Thermo Scientific). Hybridization, washing, detection (Cy3-streptavidin, Amersham Biosciences, GE Healthcare) and scanning were performed on an Illumina iScan system (Illumina) using reagents and following protocols supplied by the manufacturer. Briefly, the biotinylated cRNA (750 ng/sample) was hybridized on Sentrix whole genome beadchips human Ref-8v3 for 18 h at 58° C. while rocking (5 rpm). The beadchip covers ~24,000 RefSeq transcripts. Image analysis and data extraction were performed automatically using Illumina GenomeScan Software. To explore the functional relationships among the genes with altered expression in the HCC cells treated with COP1-1siRNA, a pathway analysis was carried out with the Ingenuity Pathway Analysis tool (Ingenuity Systems). Using the approach, we examined functional associations among genes and generated the gene networks with high significance on the basis that they had more of the interconnected genes present than would be expected by chance. The significance of each network was estimated by scoring system provided by Ingenuity. The scores are determined by the number of differentially expressed genes within each of the networks and the strength of the associations among network members. Once over-represented genes that are functionally relevant in gene networks are identified, we validated their functional association by using the independent pathway analysis tool Pathway-Studio (Ariadne Genomics).

Generation of HCC cell lines permanently expressing luciferase. Using Lipofectamine 2000, Huh7 or HepG2 cells were transfected with pGL4.17 vector (Promega) expressing firefly luciferase and neomycin resistance gene. To enhance the expression of the luciferase gene, β-actin promoter from pCAGEN plasmid (Addgene) was subcloned into the multi-cloning site of pGL4.17. Cells were selected for antibiotic resistance with Geneticin (Gibco), and surviving colonies were amplified and then screened for bioluminescence in complete media supplemented with 150 μg/ml D-luciferin (Biosynth) by in vitro imaging using an IVIS Imaging System (Xenogen). One clone per each cell line was selected based on the stable luminescence in vitro and used for further studies.

Bioluminescence imaging. Tumor growth was monitored by bioluminescence imaging for 4-weeks with 3-4 day intervals using an IVIS Imaging System. Briefly, ten minutes prior to in vivo imaging, mice were anesthetized using 1-3% isoflurane (Abbott Laboratories) and received the substrate luciferin (Biosynth) at 150 mg/kg in DPBS by an i.p. injection. Images and measurements of luciferase signals were analyzed using Living Image Software (Xenogen). Regions of interest (ROI) from displayed images were drawn around the tumor sites and quantified as photons/second using the software.

Results and Discussion

Silencing of COP1 inhibits proliferation and induces apoptosis of human HCC cells. To examine the biological effects of COP1 knockdown, two HCC cell lines with wild type (wt) p53 (HepG2) and mutant (mt) p53 (Huh7: Y220C) were treated with three COP1-specific (COP1-1, COP1-2 and COP1-3) siRNA for 4 days and analyzed for growth inhibition. This screen identified COP1-1 as the most potent siRNA. COP1 knockdown caused a strong reduction in growth rate in both cell lines which ranged between 84-88% and was paralleled by a similar degree of target mRNA silencing (FIGS. 53A and 54A). The Western blot experiments confirmed that the protein levels of COP1 were also reduced in COP1siRNA-treated HCC cell lines (FIGS. 54B and C).

Analysis of cell cycle progression by FACS showed that COP1-1siRNA increased the G0/G1 population while decreasing the fraction of cells in G2/M phase in both Huh7 and HepG2 cells, consistent with a cell cycle arrest in G1-phase (FIG. 53B). Furthermore, COP1 treatment caused a strong induction of apoptotic cell death (FIG. 53C). Significantly, COP1 depletion was similarly effective in suppressing the growth of two additional HCC cell lines, Huh1 and PLC/PRF/5, expressing wt and mt p53 (R249S), respectively, whereas p53-null Hep3B cells were significantly more resistant (FIG. 53D).

Microarray Analysis of Global Gene Expression Changes in COP1 siRNA-Treated HCC Cell Lines. To understand the mechanism of action of COP1 in HCC cells, we performed expression profile analysis. For this purpose, three HCC cell lines with different genetic status of p53 were treated with either NCsiRNA or COP1-1siRNA for 48 hours and subjected to illumina microarray analysis. The number of differentially expressed genes which displayed more than a 2-fold change was 522 (179 up- and 343 down-regulated genes) and 462 (167 up- and 295 down-regulated genes) in COP1siRNA-treated HepG2 and Huh7 cells, respectively. Consistent with COP1 function as a negative regulator of p53 protein (11), several genes affected by COP1 inactivation were known/putative targets of p53. As expected, p53 was among the predominant pathways affected by differentially regulated genes by COP1 knockdown in HepG2 and Huh7 cells (FIGS. 55A and B). In HepG2 cells, COP1 silencing increased expression of apoptosis-related (NOS2A and BIK) and antiproliferative (BTG2, GLIPR1 and FHL2) genes which was paralleled by down-regulation of key molecules involved in a wide range of cellular responses to hypoxia (HIF1α), growth (IGF1R, ABL1, POLK) and differentiation (HDAC5). Consistent with phenotypic changes, COP1-depleted Huh7 cells also displayed changes in p53-associated group of genes functionally involved in regulation of apoptosis, growth and differentiation including CASP6, GLIPR1, FHL2, GADD45A, ABL1, BCL6, and GDF15 genes. However, COP1 inactivation increased the p53 protein levels only in HepG2 cells with wt p53 and did not affect the p53 abundance in Huh7 cells which carry Y220C mutation increasing p53 protein stability (FIGS. 54B and C) (15). At present, the knowledge on the molecular basis for mutant p53 gain of function is limited (16), and we cannot exclude that COP1 inactivation does not activate classical p53 pathway in Huh7 cells or has an indirect effect on p53 pathway through intermediate molecules.

To further explore the molecular mechanisms of COP1 response, we have generated a common COP1 knockdown signature consisting of 78 deregulated genes (FIG. 56) Using the Ingenuity Pathway Analysis software, we then identified common statistically significant pathway networks (score>19) which were strongly associated with NF-κB, HNF4α, p53 and TNF, indicating that molecular alterations in diverse oncogenic pathways may cooperatively result in the growth inhibition of HCC cells in response to COP1 inactivation (FIGS. 57 and 58). Given the statistical and biological relevance to the study, we focused on the p53 network (#3). Our results showed that despite a limited gene to gene overlap, the expressions of seven genes, known to be associated with p53 pathway, such as FOXO3, NEDD8, TAP1, RFWD2 (COP1), FHL2, ABL1 and GLIPR1, was commonly deregulated (FIG. 55C). Knockdown of COP1 in p53-null Hep3B cells did not affect any of these genes, except for the RFWD2 (COP1) target gene (FIG. 55C). The p53-null cells were also significantly more resistant to growth inhibition caused by COP1 silencing, indicating that the COP1 knockdown phenotype is associated with p53 function. In particular, our microarray analysis identified a common upregulation of glioma pathogenesis-related protein 1 (GLIPR1) (FIGS. 55C and D). GLIPR1 is a novel p53 target gene shown to exert tumor suppressor activities through upregulation of ROS-JNK pathway in p53+/+ and p53+/− genetic background (17). Indeed, increase in GLIPR1 protein and JNK phosphorylation were found only in Hun7 and HepG2 but not in p53-null Hep3B cells, indicating that activation of GLIPR1/JNK pathway might be a common mechanism of growth inhibition and apoptotic induction engaged by COP1 inactivation.

Systemic Delivery of COP1siRNA by SNALP Suppresses Liver Tumor Growth in Vivo. Ultimately, we confirmed the therapeutic potential of COP1 in vivo, using two human xenograft models. First, statistically significant inhibition of tumor growth was observed in a subcutaneous model of transplantation in nude/athymic mice (FIG. 59). Direct injections of native COP1-1siRNA into the tumors established from Huh7 cells caused a dose-dependent reduction in tumor mass. As a final validation of antitumor efficacy of COP1 in vivo, we established an orthotopic xenograft model in SCID/Beige mice using luciferase-expressing HCC reporter cell lines and a SNALP formulation optimized for delivery of siRNA into liver. Recently, we have described the development of SNALP as an effective systemic delivery vehicle for targeting siRNA to murine and primate liver as well as solid tumors and have demonstrated robust therapeutic silencing of endogenous hepatocyte, tumor and viral gene transcripts in the absence of any measurable immune response (12-14). To prevent immune activation by the formulated siRNA, the native COP1-1 and non-targeting control βgal478 sequences were modified by selective incorporation of 2'-O-methyl (2'OMe) uridine and guanosine nucleosides into the siRNA duplex (18). COP1-4/7 was selected as the most effective 2'OMe-modified siRNA for growth inhibition (>70%) and target mRNA silencing (>90%) (FIGS. 60A and B). The modified COP1 4/7 caused minimal activation of cytokines, such as IFN-α and IL-6 (FIG. 60C). Additionally, systemic injection of SNALP-COP1 4/7 did not increase the production of IFN-β in serum collected 48 h after delivery (FIG. 60D). Four intravenous injections of SNALP-COP1 4/7 significantly suppressed the growth of Huh7-luc+- or HepG2-luc+-derived tumors in liver as compared to a control group receiving SNALP-βgal478 based on bioluminescence imaging and microscopic examination (FIG. 61). In both cases, a dose of 2 mg/kg showed a potent and long lasting effect resulting in a more than 12- and 9-fold decrease in tumor growth, respectively, 10 days after the last treatment and thereby exceeding the NCI criteria for promising therapeutic compounds. In conclusion, this is the first demonstration that COP1 is an important regulator of HCC growth and survival. Accordingly, COP1 represents a promising molecular target for systemic therapy of a wide spectrum of human HCC.

References

1. Parkin D M, Bray F, Ferlay J, Pisani P. Global cancer statistics. CA Cancer J Clin 2005; 55:74-108.
2. Llovet J M, Bruix J. Molecular targeted therapies in hepatocellular carcinoma. Hepatology 2008; 48:1312-27.
3. Bruix J, Sherman M. Management of hepatocellular carcinoma. Hepatology 2005; 42:1208-36.
4. Llovet J M, Ricci S, Mazzaferro V, et al. Sorafenib in advanced hepatocellular carcinoma. N Engl J Med 2008; 359:378-90.
5. Farazi P A, DePinho R A. Hepatocellular carcinoma pathogenesis: from genes to environment. Nat Rev Cancer 2006; 6:674-87.
6. Thorgeirsson S S, Grisham J W. Molecular pathogenesis of human hepatocellular carcinoma. Nat Genet 2002; 31:339-46.
7. Feitelson M A, Sun B, Satiroglu Tufan N L, et al. Genetic mechanisms of hepatocarcinogenesis. Oncogene 2002; 21:2593-604.
8. Roberts L R, Gores G J. Hepatocellular carcinoma: molecular pathways and new therapeutic targets. Semin Liver Dis 2005; 25:212-25.
9. Lee J S, Chu I S, Heo J, et al. Classification and prediction of survival in hepatocellular carcinoma by gene expression profiling. Hepatology 2004; 40:667-76.
10. Kato J Y, Yoneda-Kato N. Mammalian COP9 signalosome. Genes Cells 2009; 14:1209-25.
11. Dornan D, Wertz I, Shimizu H, et al. The ubiquitin ligase COP1 is a critical negative regulator of p53. Nature 2004; 429:86-92.
12. Morrissey D V, Lockridge J A, Shaw L, et al. Potent and persistent in vivo anti-HBV activity of chemically modified siRNAs. Nat Biotechnol 2005; 23:1002-7.
13. Zimmermann T S, Lee A C, Akinc A, et al. RNAi-mediated gene silencing in non-human primates. Nature 2006; 441:111-4.
14. Judge A D, Robbins M, Tavakoli I, et al. Confirming the RNAi-mediated mechanism of action of siRNA-based cancer therapeutics in mice. J Clin Invest 2009; 119:661-73.
15. Hsu I C, Tokiwa W, Bennett R A, et al. p53 gene mutation and integrated hepatitis B viral DNA sequences in human liver cancer cell lines. Carcinogenesis 1993; 14:987-992.
16. Weisz L, Oren M, Rotter V. Transcription regulation by mutant p53. Oncogene 2007; 26:2202-2211.
17. Li L, Fattah E A, Cao G, et al. Glioma pathogenesis-related protein 1 exerts tumor suppressor activities through proapoptotic reactive oxygen species-cJun-NH2 kinase signaling. Cancer Res 2008; 68:434-43.

18. Judge A D, Bola G, Lee A C, MacLachlan I. Design of noninflammatory synthetic siRNA mediating potent gene silencing in vivo. Mol Ther 2005; 13:494-504.

Example 15

Characterization of Inflammatory Response to SNALP Formulations in Human Whole Blood Inflammatory response to SNALPs containing one or more interfering RNAs (e.g., siRNAs) targeting one or more genes expressed in cancer (e.g., COP1, WEE1, HDAC2, RBX1, CDK4, CSN5, FOXM1, and/or R1) can be evaluated by measuring cytokine induction ex vivo in whole blood samples taken from human subjects. In certain instances, the SNALPs can contain either no siRNA payload ("empty") or an siRNA payload comprising one or a pool of siRNAs. The siRNAs tested can include, e.g., any of the COP1, WEE1, HDAC2, RBX1, CDK4, CSN5, FOXM1, and/or R1 siRNA molecules described herein, whether alone or in combination (e.g., COP1 siRNA+WEE1 siRNA). Briefly, fresh blood is isolated, immediately diluted 1:1 with 0.9% saline solution, and plated 0.45 mL/well into 48 well tissue culture treated plates. SNALPs are diluted in formulation PBS and added to the plated blood samples at a concentration of either 300 nM or 1200 nM. After 24 hours, the plates are centrifuged at 1200 rpm for 20 minutes and the supernatant (plasma) is collected. Cytokine induction (e.g., TNFα, IL-8, etc.) can be measured by ELISA and/or Cytometric Bead Array.

In particular embodiments, increasing the number of selective 2'OMe modifications to an siRNA sequence (e.g., 2'OMe modifications at G's and/or U's in the double-stranded and/or 3' overhang regions of the siRNA sequence) can decrease the immunostimulatory response to the siRNA.

Example 16

In Vitro and In Vivo Activity Screen of Modified siRNAs Targeting Cancer Genes in SNALP Formulations COP1, WEE1, HDAC2, RBX1, CDK4, CSN5, FOXM1, or R1 siRNAs of the same nucleotide sequence can be modified to incorporate an increasing number and/or alternate patterns of 2'OMe nucleotides. Numerous different sense strands and antisense strands can be designed. Double-stranded siRNAs can be generated by mix and match annealing of all possible combinations of sense strands and antisense strands. The number of modifications for double-stranded siRNAs can range, e.g., from 5 to 11 2'OMe nucleotides in the double-stranded region. Additionally, some of the patterns of modification include 2'OMe-modified nucleotides in the 3' overhang of one or both strands of the siRNA, such that the number of modifications is further increased in the entire siRNA molecule.

SNALP formulations containing encapsulated COP1, WEE1, HDAC2, RBX1, CDK4, CSN5, FOXM1, and/or R1 siRNAs can be prepared as described herein. For in vitro siRNA activity assays, cell lines such as Hep3B, HepG2, HT29, LS174T, and Neuro2a cells can be cultured in 96 well plates in the presence of SNALP-formulated siRNA. Cell viability can be assessed after 72 h using the resazurin dye CellTiter Blue (Promega Corp), and mRNA silencing activity can be assessed in replicate plates at 24 h by the bDNA assay (Panomics Inc.). The level of Caspase 3 and 7 enzyme activity in siRNA-treated cells can be assessed using the fluorescent Caspase 3/7 substrate (Z-DEVD)2-Rhodamine 110 reagent Apo-ONE (Promega Corp.).

For in vivo siRNA activity assays, an intrahepatic tumor model can be utilized. Liver tumors are established in mice by direct intrahepatic injection of Hep3B or Neuro2a tumor cells. Female scid/beige mice (Charles River Laboratories) and/or male A/J mice (Jackson Laboratories) are used as hosts for the Hep3B or Neuro2a tumors. Animals can receive Anafen by SC injection immediately prior to surgery. Individual mice can be anaesthetized by isoflourane gas inhalation and eye lube applied to prevent excessive eye drying. While maintained under gas anaesthesia, a single 1.5 cm incision across the midline can be made below the sternum and the left lateral hepatic lobe exteriorized. $1 \times 10^6$ Hep3B cells or $1 \times 10^5$ Neuro2a cells suspended in 25 µL PBS can be injected slowly into the lobe at a shallow angle using a Hamilton syringe and 30 G needle. A swab is then applied to the puncture wound to stop any bleeding prior to suturing. Mice are allowed to recover from anaesthesia in a sterile cage and monitored closely for 2-4 h before being returned to conventional housing. Eight to 11 days after tumor implantation, mice can be randomized into treatment groups. SNALP formulations containing fully encapsulated COP1, WEE1, HDAC2, RBX1, CDK4, CSN5, FOXM1, and/or R1 duplexes or PBS vehicle control are administered by standard intravenous injection via the lateral tail vein, calculated on a mg siRNA/kg basis according to individual animal weights (10 mL/kg injection volume). Body weights are then monitored throughout the duration of the study as an indicator of developing tumor burden and treatment tolerability. For efficacy studies, defined humane endpoints are determined as a surrogate for survival. Assessments are made by qualified veterinary technicians based on a combination of clinical signs, weight loss, and abdominal distension to define the day of euthanization due to tumor burden.

A subcutaneous tumor model can also be utilized for in vivo siRNA activity assays. Hep3B tumors can be established in female scid/beige mice by subcutaneous injection of $3 \times 10^6$ cells in 50 µL PBS into the left hind flank. Mice are randomized into treatment groups 10-17 days after seeding as tumors became palpable. SNALP formulations containing fully encapsulated COP1, WEE1, HDAC2, RBX1, CDK4, CSN5, FOXM1, and/or R1 duplexes are administered as described above. Tumors can be measured in 2 dimensions (Width× Length) to assess tumor growth using digital calipers. Tumor volume can be calculated using the equation a×b×b/2 where a and b=largest and smallest diameters, respectively, and expressed as group mean+/−SD.

For the in vivo siRNA activity assays, human target and GAPDH mRNA can be measured in tumor lystes by the QuantiGene bDNA assay (Panomics) per the manufacturer's instructions (Quantigene 1.0 Manual). Human-specific target and GAPDH(NM_002046) probe sets can be designed to have minimal cross-reactivity to the mouse counterpart mRNA. Data can be expressed as the mean target:GAPDH ratio+/−SD of individual animals.

In particular embodiments, increasing the number of selective 2'OMe modifications to the siRNA sequence (e.g., 2'OMe modifications at G's and/or U's in the double-stranded and/or 3' overhang regions of the siRNA sequence) does not decrease activity, and in some cases increases silencing activity.

It is to be understood that the above description is intended to be illustrative and not restrictive. Many embodiments will be apparent to those of skill in the art upon reading the above description. The scope of the invention should, therefore, be determined not with reference to the above description, but

What is claimed is:

1. A composition comprising an siRNA that silences WEE1 gene expression, wherein the siRNA comprises a sense strand consisting of SEQ ID NO:136 and a complementary antisense strand consisting of SEQ ID NO:137.

2. The composition of claim 1, further comprising one or more interfering RNA that silence the expression of one or more genes selected from the group consisting of ring finger and WD repeat domain 2, E3 ubiquitin protein ligase (RFWD2 or COP 1), histone deacetylase 2 (HDAC2), ring-box 1, E3 ubiquitin protein ligase (RBX 1), cyclin-dependent kinase 4 (CDK4), COP9 signalosome subunit 5 (CSN5), forkhead box M1 (FOXM1), cell division cycle associated 7-like (CDCA7L or R1 or RAM2), and combinations thereof.

3. The composition of claim 1, further comprising an interfering RNA that silences COP1 gene expression, wherein the antisense strand of the COP1 interfering RNA comprises one of the antisense strand sequences selected from the group consisting of SEQ ID NOS:2, 4, 6, 8, 10, 12, 14, 16, 18, 20, 22, 24, 26, 28, 30, 32, 34, 36, 38, 40, 42, 44, 46, 48, 50, 52, 59, 61, 246, 247, 344, 345, 346, and 347, and/or wherein the sense strand of the COP1 interfering RNA comprises one of the sense strand sequences selected from the group consisting of SEQ ID NOS:1, 3, 5, 7, 9, 11, 13, 15, 17, 19, 21, 23, 25, 27, 29, 31, 33, 35, 37, 39, 41, 43, 45, 47, 49, 51, 58, 60, 248, 341, 342, and 343.

4. The composition of claim 1, further comprising a pharmaceutically acceptable carrier.

5. A nucleic acid-lipid particle comprising:
   (a) a composition of claim 1;
   (b) a cationic lipid; and
   (c) a non-cationic lipid.

6. A method for introducing an siRNA that silences WEE1 gene expression into a cell, the method comprising:
   contacting the cell with a composition of claim 1.

7. A method for the in vivo delivery of an siRNA that silences WEE1 gene expression, the method comprising:
   administering to a mammal a composition of claim 1.

8. A method for treating a cell proliferative disorder in a mammal in need thereof, the method comprising:
   administering to the mammal a therapeutically effective amount of a composition of claim 1.

* * * * *

SEQUENCE LISTING

```
<160> NUMBER OF SEQ ID NOS: 355

<210> SEQ ID NO 1
<211> LENGTH: 19
<212> TYPE: RNA
<213> ORGANISM: Artificial Sequence
<220> FEATURE:
<223> OTHER INFORMATION: COP1-1 sense

<400> SEQUENCE: 1
ggacaccgua aagcagucu                                           19

<210> SEQ ID NO 2
<211> LENGTH: 19
<212> TYPE: RNA
<213> ORGANISM: Artificial Sequence
<220> FEATURE:
<223> OTHER INFORMATION: COP1-1 antisense

<400> SEQUENCE: 2
agacugcuuu acgugucc                                            19

<210> SEQ ID NO 3
<211> LENGTH: 19
<212> TYPE: RNA
<213> ORGANISM: Artificial Sequence
<220> FEATURE:
<223> OTHER INFORMATION: COP1-2 sense

<400> SEQUENCE: 3
ggaaugcuug uccaaguuu                                           19

<210> SEQ ID NO 4
<211> LENGTH: 19
<212> TYPE: RNA
<213> ORGANISM: Artificial Sequence
<220> FEATURE:
<223> OTHER INFORMATION: COP1-2 antisense

<400> SEQUENCE: 4
aaacuuggac aagcauucc                                           19

<210> SEQ ID NO 5
<211> LENGTH: 19
<212> TYPE: RNA
<213> ORGANISM: Artificial Sequence
<220> FEATURE:
<223> OTHER INFORMATION: COP1-3 sense

<400> SEQUENCE: 5
gcaacgacuu cguaugccc                                           19

<210> SEQ ID NO 6
<211> LENGTH: 19
<212> TYPE: RNA
<213> ORGANISM: Artificial Sequence
<220> FEATURE:
<223> OTHER INFORMATION: COP1-3 antisense

<400> SEQUENCE: 6
gggcauacga agucguugc                                           19
```

```
<210> SEQ ID NO 7
<211> LENGTH: 19
<212> TYPE: RNA
<213> ORGANISM: Artificial Sequence
<220> FEATURE:
<223> OTHER INFORMATION: COP1-739 sense

<400> SEQUENCE: 7
agaguuugga ggacaauaa                                                19

<210> SEQ ID NO 8
<211> LENGTH: 19
<212> TYPE: RNA
<213> ORGANISM: Artificial Sequence
<220> FEATURE:
<223> OTHER INFORMATION: COP1-739 antisense

<400> SEQUENCE: 8
uuauuguccu ccaaacucu                                                19

<210> SEQ ID NO 9
<211> LENGTH: 19
<212> TYPE: RNA
<213> ORGANISM: Artificial Sequence
<220> FEATURE:
<223> OTHER INFORMATION: COP1-740 sense

<400> SEQUENCE: 9
gaguuuggag gacaauaau                                                19

<210> SEQ ID NO 10
<211> LENGTH: 19
<212> TYPE: RNA
<213> ORGANISM: Artificial Sequence
<220> FEATURE:
<223> OTHER INFORMATION: COP1-740 antisense

<400> SEQUENCE: 10
auuauugucc uccaaacuc                                                19

<210> SEQ ID NO 11
<211> LENGTH: 19
<212> TYPE: RNA
<213> ORGANISM: Artificial Sequence
<220> FEATURE:
<223> OTHER INFORMATION: COP1-795 sense

<400> SEQUENCE: 11
gaccaucugu auccuaauu                                                19

<210> SEQ ID NO 12
<211> LENGTH: 19
<212> TYPE: RNA
<213> ORGANISM: Artificial Sequence
<220> FEATURE:
<223> OTHER INFORMATION: COP1-795 antisense

<400> SEQUENCE: 12
aauuaggaua cagaugguc                                                19

<210> SEQ ID NO 13
<211> LENGTH: 19
<212> TYPE: RNA
<213> ORGANISM: Artificial Sequence
<220> FEATURE:
<223> OTHER INFORMATION: COP1-1060 sense
```

```
<400> SEQUENCE: 13
agguugcaag aagaaauaa                                                      19

<210> SEQ ID NO 14
<211> LENGTH: 19
<212> TYPE: RNA
<213> ORGANISM: Artificial Sequence
<220> FEATURE:
<223> OTHER INFORMATION: COP1-1060 antisense

<400> SEQUENCE: 14
uuauuucuuc uugcaaccu                                                      19

<210> SEQ ID NO 15
<211> LENGTH: 19
<212> TYPE: RNA
<213> ORGANISM: Artificial Sequence
<220> FEATURE:
<223> OTHER INFORMATION: COP1-1181 sense

<400> SEQUENCE: 15
uagcacagug ccucaauuu                                                      19

<210> SEQ ID NO 16
<211> LENGTH: 19
<212> TYPE: RNA
<213> ORGANISM: Artificial Sequence
<220> FEATURE:
<223> OTHER INFORMATION: COP1-1181 antisense

<400> SEQUENCE: 16
aaauugaggc acugugcua                                                      19

<210> SEQ ID NO 17
<211> LENGTH: 19
<212> TYPE: RNA
<213> ORGANISM: Artificial Sequence
<220> FEATURE:
<223> OTHER INFORMATION: COP1-1213 sense

<400> SEQUENCE: 17
caucacacag uaguauuau                                                      19

<210> SEQ ID NO 18
<211> LENGTH: 19
<212> TYPE: RNA
<213> ORGANISM: Artificial Sequence
<220> FEATURE:
<223> OTHER INFORMATION: COP1-1213 antisense

<400> SEQUENCE: 18
auaauacuac ugugugaug                                                      19

<210> SEQ ID NO 19
<211> LENGTH: 19
<212> TYPE: RNA
<213> ORGANISM: Artificial Sequence
<220> FEATURE:
<223> OTHER INFORMATION: COP1-1286 sense

<400> SEQUENCE: 19
gaaacagccu ugguauaau                                                      19

<210> SEQ ID NO 20
```

-continued

```
<211> LENGTH: 19
<212> TYPE: RNA
<213> ORGANISM: Artificial Sequence
<220> FEATURE:
<223> OTHER INFORMATION: COP1-1286  antisense

<400> SEQUENCE: 20
auuauaccaa ggcuguuuc                                                19

<210> SEQ ID NO 21
<211> LENGTH: 19
<212> TYPE: RNA
<213> ORGANISM: Artificial Sequence
<220> FEATURE:
<223> OTHER INFORMATION: COP1-1412 sense

<400> SEQUENCE: 21
aagccaguug gaugaauuu                                                19

<210> SEQ ID NO 22
<211> LENGTH: 19
<212> TYPE: RNA
<213> ORGANISM: Artificial Sequence
<220> FEATURE:
<223> OTHER INFORMATION: COP1-1412 antisense

<400> SEQUENCE: 22
aaauucaucc aacuggcuu                                                19

<210> SEQ ID NO 23
<211> LENGTH: 19
<212> TYPE: RNA
<213> ORGANISM: Artificial Sequence
<220> FEATURE:
<223> OTHER INFORMATION: COP1-1801 sense

<400> SEQUENCE: 23
guuggagugu ugacuuuaa                                                19

<210> SEQ ID NO 24
<211> LENGTH: 19
<212> TYPE: RNA
<213> ORGANISM: Artificial Sequence
<220> FEATURE:
<223> OTHER INFORMATION: COP1-1801 antisense

<400> SEQUENCE: 24
uuaaagucaa cacuccaac                                                19

<210> SEQ ID NO 25
<211> LENGTH: 19
<212> TYPE: RNA
<213> ORGANISM: Artificial Sequence
<220> FEATURE:
<223> OTHER INFORMATION: COP1-1802 sense

<400> SEQUENCE: 25
uuggaguguu gacuuuaau                                                19

<210> SEQ ID NO 26
<211> LENGTH: 19
<212> TYPE: RNA
<213> ORGANISM: Artificial Sequence
<220> FEATURE:
<223> OTHER INFORMATION: COP1-1802 antisense

<400> SEQUENCE: 26
```
auuaaaguca acacuccaa                                                  19

<210> SEQ ID NO 27
<211> LENGTH: 19
<212> TYPE: RNA
<213> ORGANISM: Artificial Sequence
<220> FEATURE:
<223> OTHER INFORMATION: COP1-1803 sense

<400> SEQUENCE: 27
uggaguguug acuuuaauu                                                  19

<210> SEQ ID NO 28
<211> LENGTH: 19
<212> TYPE: RNA
<213> ORGANISM: Artificial Sequence
<220> FEATURE:
<223> OTHER INFORMATION: COP1-1803 antisense

<400> SEQUENCE: 28
aauuaaaguc aacacucca                                                  19

<210> SEQ ID NO 29
<211> LENGTH: 19
<212> TYPE: RNA
<213> ORGANISM: Artificial Sequence
<220> FEATURE:
<223> OTHER INFORMATION: COP1-1804 sense

<400> SEQUENCE: 29
ggaguguuga cuuuaauuu                                                  19

<210> SEQ ID NO 30
<211> LENGTH: 19
<212> TYPE: RNA
<213> ORGANISM: Artificial Sequence
<220> FEATURE:
<223> OTHER INFORMATION: COP1-1804 antisense

<400> SEQUENCE: 30
aaauuaaagu caacacucc                                                  19

<210> SEQ ID NO 31
<211> LENGTH: 19
<212> TYPE: RNA
<213> ORGANISM: Artificial Sequence
<220> FEATURE:
<223> OTHER INFORMATION: COP1-1923 sense

<400> SEQUENCE: 31
aaugugugcu guguuaaau                                                  19

<210> SEQ ID NO 32
<211> LENGTH: 19
<212> TYPE: RNA
<213> ORGANISM: Artificial Sequence
<220> FEATURE:
<223> OTHER INFORMATION: COP1-1923 antisense

<400> SEQUENCE: 32
auuuaacaca gcacacauu                                                  19

<210> SEQ ID NO 33
<211> LENGTH: 19
<212> TYPE: RNA

```
<213> ORGANISM: Artificial Sequence
<220> FEATURE:
<223> OTHER INFORMATION: COP1-1924 sense

<400> SEQUENCE: 33
augugugcug uguuaaauu                                                19

<210> SEQ ID NO 34
<211> LENGTH: 19
<212> TYPE: RNA
<213> ORGANISM: Artificial Sequence
<220> FEATURE:
<223> OTHER INFORMATION: COP1-1924 antisense

<400> SEQUENCE: 34
aauuuaacac agcacacau                                                19

<210> SEQ ID NO 35
<211> LENGTH: 19
<212> TYPE: RNA
<213> ORGANISM: Artificial Sequence
<220> FEATURE:
<223> OTHER INFORMATION: COP1-2075 sense

<400> SEQUENCE: 35
ugugaguggu gaggaaauu                                                19

<210> SEQ ID NO 36
<211> LENGTH: 19
<212> TYPE: RNA
<213> ORGANISM: Artificial Sequence
<220> FEATURE:
<223> OTHER INFORMATION: COP1-2075 antisense

<400> SEQUENCE: 36
aauuuccuca ccacucaca                                                19

<210> SEQ ID NO 37
<211> LENGTH: 19
<212> TYPE: RNA
<213> ORGANISM: Artificial Sequence
<220> FEATURE:
<223> OTHER INFORMATION: COP1-2198 sense

<400> SEQUENCE: 37
ggcuuccaau ggagauuau                                                19

<210> SEQ ID NO 38
<211> LENGTH: 19
<212> TYPE: RNA
<213> ORGANISM: Artificial Sequence
<220> FEATURE:
<223> OTHER INFORMATION: COP1-2198 antisense

<400> SEQUENCE: 38
auaaucucca uuggaagcc                                                19

<210> SEQ ID NO 39
<211> LENGTH: 19
<212> TYPE: RNA
<213> ORGANISM: Artificial Sequence
<220> FEATURE:
<223> OTHER INFORMATION: COP1-2412 sense

<400> SEQUENCE: 39
aacagucagg guacaauua                                                19
```

```
<210> SEQ ID NO 40
<211> LENGTH: 19
<212> TYPE: RNA
<213> ORGANISM: Artificial Sequence
<220> FEATURE:
<223> OTHER INFORMATION: COP1-2412 antisense

<400> SEQUENCE: 40
uaauuguacc cugacuguu                                              19

<210> SEQ ID NO 41
<211> LENGTH: 19
<212> TYPE: RNA
<213> ORGANISM: Artificial Sequence
<220> FEATURE:
<223> OTHER INFORMATION: COP1-2413 sense

<400> SEQUENCE: 41
acagucaggg uacaauuaa                                              19

<210> SEQ ID NO 42
<211> LENGTH: 19
<212> TYPE: RNA
<213> ORGANISM: Artificial Sequence
<220> FEATURE:
<223> OTHER INFORMATION: COP1-2413 antisense

<400> SEQUENCE: 42
uuaauuguac ccugacugu                                              19

<210> SEQ ID NO 43
<211> LENGTH: 19
<212> TYPE: RNA
<213> ORGANISM: Artificial Sequence
<220> FEATURE:
<223> OTHER INFORMATION: COP1-2452 sense

<400> SEQUENCE: 43
ggguuaacuc aagucaaau                                              19

<210> SEQ ID NO 44
<211> LENGTH: 19
<212> TYPE: RNA
<213> ORGANISM: Artificial Sequence
<220> FEATURE:
<223> OTHER INFORMATION: COP1-2452 antisense

<400> SEQUENCE: 44
auuugacuug aguuaaccc                                              19

<210> SEQ ID NO 45
<211> LENGTH: 19
<212> TYPE: RNA
<213> ORGANISM: Artificial Sequence
<220> FEATURE:
<223> OTHER INFORMATION: COP1-2453 sense

<400> SEQUENCE: 45
gguuaacuca agucaaauu                                              19

<210> SEQ ID NO 46
<211> LENGTH: 19
<212> TYPE: RNA
<213> ORGANISM: Artificial Sequence
<220> FEATURE:
```

```
<223> OTHER INFORMATION: COP1-2453 antisense

<400> SEQUENCE: 46
aauuugacuu gaguuaacc                                                   19

<210> SEQ ID NO 47
<211> LENGTH: 19
<212> TYPE: RNA
<213> ORGANISM: Artificial Sequence
<220> FEATURE:
<223> OTHER INFORMATION: COP1-2472 sense

<400> SEQUENCE: 47
acuugauccu gcugaaaua                                                   19

<210> SEQ ID NO 48
<211> LENGTH: 19
<212> TYPE: RNA
<213> ORGANISM: Artificial Sequence
<220> FEATURE:
<223> OTHER INFORMATION: COP1-2474 antisense

<400> SEQUENCE: 48
uauuucagca ggaucaagu                                                   19

<210> SEQ ID NO 49
<211> LENGTH: 19
<212> TYPE: RNA
<213> ORGANISM: Artificial Sequence
<220> FEATURE:
<223> OTHER INFORMATION: COP1-2705 sense

<400> SEQUENCE: 49
ugugauaggg aaacaaauu                                                   19

<210> SEQ ID NO 50
<211> LENGTH: 19
<212> TYPE: RNA
<213> ORGANISM: Artificial Sequence
<220> FEATURE:
<223> OTHER INFORMATION: COP1-2705 antisense

<400> SEQUENCE: 50
aauuuguuuc ccuaucaca                                                   19

<210> SEQ ID NO 51
<211> LENGTH: 21
<212> TYPE: RNA
<213> ORGANISM: Artificial Sequence
<220> FEATURE:
<223> OTHER INFORMATION: COP1-1 sense with overhang
<220> FEATURE:
<221> NAME/KEY: modified_base
<222> LOCATION: (20)..(21)
<223> OTHER INFORMATION: n = deoxythymidine

<400> SEQUENCE: 51
ggacaccgua aagcagucun n                                                21

<210> SEQ ID NO 52
<211> LENGTH: 21
<212> TYPE: RNA
<213> ORGANISM: Artificial Sequence
<220> FEATURE:
<223> OTHER INFORMATION: COP1-1 antisense with overhang
<220> FEATURE:
<221> NAME/KEY: modified_base
```

```
<222> LOCATION: (20)..(21)
<223> OTHER INFORMATION: n = deoxythymidine

<400> SEQUENCE: 52
agacugcuuu acgguguccn n                                              21

<210> SEQ ID NO 53
<211> LENGTH: 19
<212> TYPE: RNA
<213> ORGANISM: Artificial Sequence
<220> FEATURE:
<223> OTHER INFORMATION: COP1-1 antisense modified
<220> FEATURE:
<221> NAME/KEY: modified_base
<222> LOCATION: (8)...(17)
<223> OTHER INFORMATION: n = um

<400> SEQUENCE: 53
agacugcnuu acggngncc                                                 19

<210> SEQ ID NO 54
<211> LENGTH: 19
<212> TYPE: RNA
<213> ORGANISM: Artificial Sequence
<220> FEATURE:
<223> OTHER INFORMATION: COP1-1 antisense modified
<220> FEATURE:
<221> NAME/KEY: modified_base
<222> LOCATION: (9)...(15)
<223> OTHER INFORMATION: n = um

<400> SEQUENCE: 54
agacugcunu acggngucc                                                 19

<210> SEQ ID NO 55
<211> LENGTH: 19
<212> TYPE: RNA
<213> ORGANISM: Artificial Sequence
<220> FEATURE:
<223> OTHER INFORMATION: COP1-1 antisense modified
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (14)...(14)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 55
agacuncuun acgnugncc                                                 19

<210> SEQ ID NO 56
<211> LENGTH: 19
<212> TYPE: RNA
<213> ORGANISM: Artificial Sequence
<220> FEATURE:
<223> OTHER INFORMATION: COP1-1 sense modified
<220> FEATURE:
<221> NAME/KEY: modified_base
<222> LOCATION: (8)...(17)
<223> OTHER INFORMATION: n = gm
```

```
<400> SEQUENCE: 56
gnacaccnua aancanucu                                                  19

<210> SEQ ID NO 57
<211> LENGTH: 19
<212> TYPE: RNA
<213> ORGANISM: Artificial Sequence
<220> FEATURE:
<223> OTHER INFORMATION: COP1-1 sense modified
<220> FEATURE:
<221> NAME/KEY: modified_base
<222> LOCATION: (2)...(2)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (13)...(13)
<223> OTHER INFORMATION: n = gm

<400> SEQUENCE: 57
gnacaccgna aancagucu                                                  19

<210> SEQ ID NO 58
<211> LENGTH: 21
<212> TYPE: RNA
<213> ORGANISM: Artificial Sequence
<220> FEATURE:
<223> OTHER INFORMATION: COP1-4/7 sense
<220> FEATURE:
<221> NAME/KEY: modified_base
<222> LOCATION: (2)...(16)
<223> OTHER INFORMATION: n = gm
<220> FEATURE:
<221> NAME/KEY: modified_base
<222> LOCATION: (20)...(21)
<223> OTHER INFORMATION: n = deoxythymidine

<400> SEQUENCE: 58
gnacaccnua aancanucun n                                               21

<210> SEQ ID NO 59
<211> LENGTH: 21
<212> TYPE: RNA
<213> ORGANISM: Artificial Sequence
<220> FEATURE:
<223> OTHER INFORMATION: COP1-4/7 antisense
<220> FEATURE:
<221> NAME/KEY: modified_base
<222> LOCATION: (8)...(17)
<223> OTHER INFORMATION: n = um
<220> FEATURE:
<221> NAME/KEY: modified_base
<222> LOCATION: (20)...(21)
<223> OTHER INFORMATION: n = deoxythymidine

<400> SEQUENCE: 59
agacugcnuu acggngnccn n                                               21

<210> SEQ ID NO 60
<211> LENGTH: 21
<212> TYPE: RNA
<213> ORGANISM: Artificial Sequence
<220> FEATURE:
<223> OTHER INFORMATION: COP1-1181 sense

<400> SEQUENCE: 60
uagcacagug ccucaauuug a                                               21
```

```
<210> SEQ ID NO 61
<211> LENGTH: 21
<212> TYPE: RNA
<213> ORGANISM: Artificial Sequence
<220> FEATURE:
<223> OTHER INFORMATION: COP1-1181 antisense

<400> SEQUENCE: 61
aaauugaggc acugugcuau c                                              21

<210> SEQ ID NO 62
<211> LENGTH: 19
<212> TYPE: RNA
<213> ORGANISM: Artificial Sequence
<220> FEATURE:
<223> OTHER INFORMATION: COP1-1181 antisense modified
<220> FEATURE:
<221> NAME/KEY: modified_base
<222> LOCATION: (5)...(13)
<223> OTHER INFORMATION: n = um
<220> FEATURE:
<221> NAME/KEY: modified_base
<222> LOCATION: (14)...(14)
<223> OTHER INFORMATION: n = gm

<400> SEQUENCE: 62
aaaungaggc acnnugcua                                                 19

<210> SEQ ID NO 63
<211> LENGTH: 19
<212> TYPE: RNA
<213> ORGANISM: Artificial Sequence
<220> FEATURE:
<223> OTHER INFORMATION: COP1-1181 antisense modified
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 63
aaauugagnc acugngcna                                                 19

<210> SEQ ID NO 64
<211> LENGTH: 19
<212> TYPE: RNA
<213> ORGANISM: Artificial Sequence
<220> FEATURE:
<223> OTHER INFORMATION: COP1-1181 antisense modified
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (13)...(13)
<223> OTHER INFORMATION: n = u

<400> SEQUENCE: 64
aaauugagnc acngugcua                                                 19

<210> SEQ ID NO 65
<211> LENGTH: 19
<212> TYPE: RNA
<213> ORGANISM: Artificial Sequence
<220> FEATURE:
```

```
<223> OTHER INFORMATION: COP1-1181 antisense modified
<220> FEATURE:
<221> NAME/KEY: modified_base
<222> LOCATION: (4)...(5)
<223> OTHER INFORMATION: n = um
<220> FEATURE:
<221> NAME/KEY: modified_base
<222> LOCATION: (6)...(16)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 65
aaannnaggc acuguncna                                                    19

<210> SEQ ID NO 66
<211> LENGTH: 19
<212> TYPE: RNA
<213> ORGANISM: Artificial Sequence
<220> FEATURE:
<223> OTHER INFORMATION: COP1-1181 sense modified
<220> FEATURE:
<221> NAME/KEY: modified_base
<222> LOCATION: (3)...(8)
<223> OTHER INFORMATION: n = gm
<220> FEATURE:
<221> NAME/KEY: modified_base
<222> LOCATION: (13)...(13)
<223> OTHER INFORMATION: n = um

<400> SEQUENCE: 66
uancacanug ccncaauuu                                                    19

<210> SEQ ID NO 67
<211> LENGTH: 19
<212> TYPE: RNA
<213> ORGANISM: Artificial Sequence
<220> FEATURE:
<223> OTHER INFORMATION: COP1-1181 sense modified
<220> FEATURE:
<221> NAME/KEY: modified_base
<222> LOCATION: (1)...(19)
<223> OTHER INFORMATION: n = um

<400> SEQUENCE: 67
nagcacagug ccncaannn                                                    19

<210> SEQ ID NO 68
<211> LENGTH: 19
<212> TYPE: RNA
<213> ORGANISM: Artificial Sequence
<220> FEATURE:
<223> OTHER INFORMATION: COP1-1181 sense modified
<220> FEATURE:
<221> NAME/KEY: modified_base
<222> LOCATION: (1)...(1)
<223> OTHER INFORMATION: n = um
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 68
nancacagug ccucaanuu                                                    19
```

```
<210> SEQ ID NO 69
<211> LENGTH: 19
<212> TYPE: RNA
<213> ORGANISM: Artificial Sequence
<220> FEATURE:
<223> OTHER INFORMATION: WEE1-2 antisense

<400> SEQUENCE: 69
uaaaugcauc cauccagcc                                              19

<210> SEQ ID NO 70
<211> LENGTH: 19
<212> TYPE: RNA
<213> ORGANISM: Artificial Sequence
<220> FEATURE:
<223> OTHER INFORMATION: WEE1-3058 antisense

<400> SEQUENCE: 70
uauauaguaa ggcugacag                                              19

<210> SEQ ID NO 71
<211> LENGTH: 19
<212> TYPE: RNA
<213> ORGANISM: Artificial Sequence
<220> FEATURE:
<223> OTHER INFORMATION: CSN5-2 antisense

<400> SEQUENCE: 71
cuuaaaguaa uggugaucc                                              19

<210> SEQ ID NO 72
<211> LENGTH: 19
<212> TYPE: RNA
<213> ORGANISM: Artificial Sequence
<220> FEATURE:
<223> OTHER INFORMATION: WEE1-1 sense

<400> SEQUENCE: 72
gguauauuca uucaauguc                                              19

<210> SEQ ID NO 73
<211> LENGTH: 19
<212> TYPE: RNA
<213> ORGANISM: Artificial Sequence
<220> FEATURE:
<223> OTHER INFORMATION: WEE1-1 antisense

<400> SEQUENCE: 73
gacauugaau gaauauacc                                              19

<210> SEQ ID NO 74
<211> LENGTH: 19
<212> TYPE: RNA
<213> ORGANISM: Artificial Sequence
<220> FEATURE:
<223> OTHER INFORMATION: WEE1-2 sense

<400> SEQUENCE: 74
ggcuggaugg augcauuua                                              19

<210> SEQ ID NO 75
<211> LENGTH: 19
<212> TYPE: RNA
<213> ORGANISM: Artificial Sequence
<220> FEATURE:
<223> OTHER INFORMATION: WEE1-3 sense
```

```
<400> SEQUENCE: 75
ggacaguguc gucguagaa                                                    19

<210> SEQ ID NO 76
<211> LENGTH: 19
<212> TYPE: RNA
<213> ORGANISM: Artificial Sequence
<220> FEATURE:
<223> OTHER INFORMATION: WEE1-3 antisense

<400> SEQUENCE: 76
uucuacgacg acacugucc                                                    19

<210> SEQ ID NO 77
<211> LENGTH: 19
<212> TYPE: RNA
<213> ORGANISM: Artificial Sequence
<220> FEATURE:
<223> OTHER INFORMATION: WEE1-60 sense

<400> SEQUENCE: 77
gcuggcgaac aaauguaaa                                                    19

<210> SEQ ID NO 78
<211> LENGTH: 19
<212> TYPE: RNA
<213> ORGANISM: Artificial Sequence
<220> FEATURE:
<223> OTHER INFORMATION: WEE1-60 antisense

<400> SEQUENCE: 78
uuuacauuug uucgccagc                                                    19

<210> SEQ ID NO 79
<211> LENGTH: 19
<212> TYPE: RNA
<213> ORGANISM: Artificial Sequence
<220> FEATURE:
<223> OTHER INFORMATION: WEE1-1828 sense

<400> SEQUENCE: 79
cuccucaagu gaauauuaa                                                    19

<210> SEQ ID NO 80
<211> LENGTH: 19
<212> TYPE: RNA
<213> ORGANISM: Artificial Sequence
<220> FEATURE:
<223> OTHER INFORMATION: WEE1-1828 antisense

<400> SEQUENCE: 80
uuaauauuca cuugaggag                                                    19

<210> SEQ ID NO 81
<211> LENGTH: 19
<212> TYPE: RNA
<213> ORGANISM: Artificial Sequence
<220> FEATURE:
<223> OTHER INFORMATION: WEE1-1937 sense

<400> SEQUENCE: 81
cauggaagcc agugauuau                                                    19

<210> SEQ ID NO 82
<211> LENGTH: 19
```

```
<212> TYPE: RNA
<213> ORGANISM: Artificial Sequence
<220> FEATURE:
<223> OTHER INFORMATION: WEE1-1937 antisense

<400> SEQUENCE: 82
auaaucacug gcuuccaug                                                    19

<210> SEQ ID NO 83
<211> LENGTH: 19
<212> TYPE: RNA
<213> ORGANISM: Artificial Sequence
<220> FEATURE:
<223> OTHER INFORMATION: WEE1-2017

<400> SEQUENCE: 83
cccgguauac aacagaauu                                                    19

<210> SEQ ID NO 84
<211> LENGTH: 19
<212> TYPE: RNA
<213> ORGANISM: Artificial Sequence
<220> FEATURE:
<223> OTHER INFORMATION: WEE1-2017 antisense

<400> SEQUENCE: 84
aauucuguug uauaccggg                                                    19

<210> SEQ ID NO 85
<211> LENGTH: 19
<212> TYPE: RNA
<213> ORGANISM: Artificial Sequence
<220> FEATURE:
<223> OTHER INFORMATION: WEE1-2018 sense

<400> SEQUENCE: 85
ccgguauaca acagaauuu                                                    19

<210> SEQ ID NO 86
<211> LENGTH: 19
<212> TYPE: RNA
<213> ORGANISM: Artificial Sequence
<220> FEATURE:
<223> OTHER INFORMATION: WEE1-2018 antisense

<400> SEQUENCE: 86
aaauucuguu guauaccgg                                                    19

<210> SEQ ID NO 87
<211> LENGTH: 19
<212> TYPE: RNA
<213> ORGANISM: Artificial Sequence
<220> FEATURE:
<223> OTHER INFORMATION: WEE1-2094 sense

<400> SEQUENCE: 87
aggcuggaug gaugcauuu                                                    19

<210> SEQ ID NO 88
<211> LENGTH: 19
<212> TYPE: RNA
<213> ORGANISM: Artificial Sequence
<220> FEATURE:
<223> OTHER INFORMATION: WEE1-2094 antisense

<400> SEQUENCE: 88
```
aaaugcaucc auccagccu                                                    19

<210> SEQ ID NO 89
<211> LENGTH: 19
<212> TYPE: RNA
<213> ORGANISM: Artificial Sequence
<220> FEATURE:
<223> OTHER INFORMATION: WEE1-2104 sense

<400> SEQUENCE: 89
gaugcauuua ugccauuaa                                                    19

<210> SEQ ID NO 90
<211> LENGTH: 19
<212> TYPE: RNA
<213> ORGANISM: Artificial Sequence
<220> FEATURE:
<223> OTHER INFORMATION: WEE1-2104 antisense

<400> SEQUENCE: 90
uuaauggcau aaaugcauc                                                    19

<210> SEQ ID NO 91
<211> LENGTH: 19
<212> TYPE: RNA
<213> ORGANISM: Artificial Sequence
<220> FEATURE:
<223> OTHER INFORMATION: WEE1-2105 sense

<400> SEQUENCE: 91
augcauuuau gccauuaag                                                    19

<210> SEQ ID NO 92
<211> LENGTH: 19
<212> TYPE: RNA
<213> ORGANISM: Artificial Sequence
<220> FEATURE:
<223> OTHER INFORMATION: WEE1-2105 antisense

<400> SEQUENCE: 92
cuuaauggca uaaaugcau                                                    19

<210> SEQ ID NO 93
<211> LENGTH: 19
<212> TYPE: RNA
<213> ORGANISM: Artificial Sequence
<220> FEATURE:
<223> OTHER INFORMATION: WEE1-2208 sense

<400> SEQUENCE: 93
ucucauguag uucgauauu                                                    19

<210> SEQ ID NO 94
<211> LENGTH: 19
<212> TYPE: RNA
<213> ORGANISM: Artificial Sequence
<220> FEATURE:
<223> OTHER INFORMATION: WEE1-2208 antisense

<400> SEQUENCE: 94
aauaucgaac uacaugaga                                                    19

<210> SEQ ID NO 95
<211> LENGTH: 19
<212> TYPE: RNA
<213> ORGANISM: Artificial Sequence

```
<220> FEATURE:
<223> OTHER INFORMATION: WEE1-2372 sense

<400> SEQUENCE: 95
ccgaggcuug agguauauu                                                19

<210> SEQ ID NO 96
<211> LENGTH: 19
<212> TYPE: RNA
<213> ORGANISM: Artificial Sequence
<220> FEATURE:
<223> OTHER INFORMATION: WEE1-2372 antisense

<400> SEQUENCE: 96
aauauaccuc aagccucgg                                                19

<210> SEQ ID NO 97
<211> LENGTH: 19
<212> TYPE: RNA
<213> ORGANISM: Artificial Sequence
<220> FEATURE:
<223> OTHER INFORMATION: WEE1-2402 sense

<400> SEQUENCE: 97
uuugguucac auggauaua                                                19

<210> SEQ ID NO 98
<211> LENGTH: 19
<212> TYPE: RNA
<213> ORGANISM: Artificial Sequence
<220> FEATURE:
<223> OTHER INFORMATION: WEE1-2402 antisense

<400> SEQUENCE: 98
uauauccaug ugaaccaaa                                                19

<210> SEQ ID NO 99
<211> LENGTH: 19
<212> TYPE: RNA
<213> ORGANISM: Artificial Sequence
<220> FEATURE:
<223> OTHER INFORMATION: WEE1-2748 sense

<400> SEQUENCE: 99
gugcuuuccc aagaauuua                                                19

<210> SEQ ID NO 100
<211> LENGTH: 19
<212> TYPE: RNA
<213> ORGANISM: Artificial Sequence
<220> FEATURE:
<223> OTHER INFORMATION: WEE1-2748 antisense

<400> SEQUENCE: 100
uaaauucuug ggaaagcac                                                19

<210> SEQ ID NO 101
<211> LENGTH: 19
<212> TYPE: RNA
<213> ORGANISM: Artificial Sequence
<220> FEATURE:
<223> OTHER INFORMATION: WEE1-3003 sense

<400> SEQUENCE: 101
uccaccaccc agaguaaua                                                19
```

```
<210> SEQ ID NO 102
<211> LENGTH: 19
<212> TYPE: RNA
<213> ORGANISM: Artificial Sequence
<220> FEATURE:
<223> OTHER INFORMATION: WEE1-3003 antisense

<400> SEQUENCE: 102
uauuacucug gguggugga                                                  19

<210> SEQ ID NO 103
<211> LENGTH: 19
<212> TYPE: RNA
<213> ORGANISM: Artificial Sequence
<220> FEATURE:
<223> OTHER INFORMATION: WEE1-3057 sense

<400> SEQUENCE: 103
ucugucagcc uuacuauau                                                  19

<210> SEQ ID NO 104
<211> LENGTH: 19
<212> TYPE: RNA
<213> ORGANISM: Artificial Sequence
<220> FEATURE:
<223> OTHER INFORMATION: WEE1-3057 antisense

<400> SEQUENCE: 104
auauaguaag gcugacaga                                                  19

<210> SEQ ID NO 105
<211> LENGTH: 19
<212> TYPE: RNA
<213> ORGANISM: Artificial Sequence
<220> FEATURE:
<223> OTHER INFORMATION: WEE1-3058 sense

<400> SEQUENCE: 105
cugucagccu uacuauaua                                                  19

<210> SEQ ID NO 106
<211> LENGTH: 19
<212> TYPE: RNA
<213> ORGANISM: Artificial Sequence
<220> FEATURE:
<223> OTHER INFORMATION: WEE1-3119 sense

<400> SEQUENCE: 106
gaggaagcua gguugaaau                                                  19

<210> SEQ ID NO 107
<211> LENGTH: 19
<212> TYPE: RNA
<213> ORGANISM: Artificial Sequence
<220> FEATURE:
<223> OTHER INFORMATION: WEE1-3119 antisense

<400> SEQUENCE: 107
auuucaaccu agcuuccuc                                                  19

<210> SEQ ID NO 108
<211> LENGTH: 19
<212> TYPE: RNA
<213> ORGANISM: Artificial Sequence
<220> FEATURE:
<223> OTHER INFORMATION: WEE1-3337 sense
```

```
<400> SEQUENCE: 108 uggugguguq cugcuuaua                                            19

<210> SEQ ID NO 109
<211> LENGTH: 19
<212> TYPE: RNA
<213> ORGANISM: Artificial Sequence
<220> FEATURE:
<223> OTHER INFORMATION: WEE1-3337 antisense

<400> SEQUENCE: 109
uauaagcagc acaccacca                                            19

<210> SEQ ID NO 110
<211> LENGTH: 19
<212> TYPE: RNA
<213> ORGANISM: Artificial Sequence
<220> FEATURE:
<223> OTHER INFORMATION: WEE1-3497 sense

<400> SEQUENCE: 110
guguguccau cuuauauuu                                            19

<210> SEQ ID NO 111
<211> LENGTH: 19
<212> TYPE: RNA
<213> ORGANISM: Artificial Sequence
<220> FEATURE:
<223> OTHER INFORMATION: WEE1-3497 antisense

<400> SEQUENCE: 111
aaauauaaga uggacacac                                            19

<210> SEQ ID NO 112
<211> LENGTH: 19
<212> TYPE: RNA
<213> ORGANISM: Artificial Sequence
<220> FEATURE:
<223> OTHER INFORMATION: WEE1-3607 sense

<400> SEQUENCE: 112
agguauugcc uugugaauu                                            19

<210> SEQ ID NO 113
<211> LENGTH: 19
<212> TYPE: RNA
<213> ORGANISM: Artificial Sequence
<220> FEATURE:
<223> OTHER INFORMATION: WEE1-3607 antisense

<400> SEQUENCE: 113
aauucacaag gcaauaccu                                            19

<210> SEQ ID NO 114
<211> LENGTH: 19
<212> TYPE: RNA
<213> ORGANISM: Artificial Sequence
<220> FEATURE:
<223> OTHER INFORMATION: WEE1-3608 sense

<400> SEQUENCE: 114
gguauugccu ugugaauuu                                            19

<210> SEQ ID NO 115
```

```
<211> LENGTH: 19
<212> TYPE: RNA
<213> ORGANISM: Artificial Sequence
<220> FEATURE:
<223> OTHER INFORMATION: WEE1-3608 antisense

<400> SEQUENCE: 115
aaauucacaa ggcaauacc                                                    19

<210> SEQ ID NO 116
<211> LENGTH: 21
<212> TYPE: RNA
<213> ORGANISM: Artificial Sequence
<220> FEATURE:
<223> OTHER INFORMATION: WEE1-2 sense
<220> FEATURE:
<221> NAME/KEY: modified_base
<222> LOCATION: (20)...(21)
<223> OTHER INFORMATION: n = deoxythymidine

<400> SEQUENCE: 116
ggcuggaugg augcauuuan n                                                 21

<210> SEQ ID NO 117
<211> LENGTH: 21
<212> TYPE: RNA
<213> ORGANISM: Artificial Sequence
<220> FEATURE:
<223> OTHER INFORMATION: WEE1-2 antisense
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxycytidine

<400> SEQUENCE: 117
uaaaugcauc cauccagccn n                                                 21

<210> SEQ ID NO 118
<211> LENGTH: 19
<212> TYPE: RNA
<213> ORGANISM: Artificial Sequence
<220> FEATURE:
<223> OTHER INFORMATION: WEE1-2 antisense modified
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (9)...(13)
<223> OTHER INFORMATION: n = um

<400> SEQUENCE: 118
uaaauncanc canccagcc                                                    19

<210> SEQ ID NO 119
<211> LENGTH: 19
<212> TYPE: RNA
<213> ORGANISM: Artificial Sequence
<220> FEATURE:
<223> OTHER INFORMATION: WEE1-2 antisense modified
<220> FEATURE:
<221> NAME/KEY: modified_base
<222> LOCATION: (5)...(5)
<223> OTHER INFORMATION: n = um
<220> FEATURE:
<221> NAME/KEY: modified_base
```

```
<222> LOCATION: (17)...(17)
<223> OTHER INFORMATION: n = gm

<400> SEQUENCE: 119
uaaangcauc cauccancc                                                    19

<210> SEQ ID NO 120
<211> LENGTH: 19
<212> TYPE: RNA
<213> ORGANISM: Artificial Sequence
<220> FEATURE:
<223> OTHER INFORMATION: WEE1-2 antisense modified
<220> FEATURE:
<221> NAME/KEY: modified_base
<222> LOCATION: (9)...(13)
<223> OTHER INFORMATION: n = um
<220> FEATURE:
<221> NAME/KEY: modified_base
<222> LOCATION: (17)...(17)
<223> OTHER INFORMATION: n = gm

<400> SEQUENCE: 120
uaaaugcanc canccancc                                                    19

<210> SEQ ID NO 121
<211> LENGTH: 19
<212> TYPE: RNA
<213> ORGANISM: Artificial Sequence
<220> FEATURE:
<223> OTHER INFORMATION: WEE1-2 antisense modified
<220> FEATURE:
<221> NAME/KEY: modified_base
<222> LOCATION: (6)...(17)
<223> OTHER INFORMATION: n = gm

<400> SEQUENCE: 121
uaaauncauc cauccancc                                                    19

<210> SEQ ID NO 122
<211> LENGTH: 19
<212> TYPE: RNA
<213> ORGANISM: Artificial Sequence
<220> FEATURE:
<223> OTHER INFORMATION: WEE1-2 sense modified
<220> FEATURE:
<221> NAME/KEY: modified_base
<222> LOCATION: (4)...(4)
<223> OTHER INFORMATION: n = um
<220> FEATURE:
<221> NAME/KEY: modified_base
<222> LOCATION: (6)...(13)
<223> OTHER INFORMATION: n = gm

<400> SEQUENCE: 122
ggcngnaugg auncauuua                                                    19

<210> SEQ ID NO 123
<211> LENGTH: 19
<212> TYPE: RNA
<213> ORGANISM: Artificial Sequence
<220> FEATURE:
<223> OTHER INFORMATION: WEE1-2 sense modified
<220> FEATURE:
<221> NAME/KEY: modified_base
<222> LOCATION: (4)...(16)
<223> OTHER INFORMATION: n = gm

<400> SEQUENCE: 123
ggcnggangg angcanuua                                                    19
```

```
<210> SEQ ID NO 124
<211> LENGTH: 19
<212> TYPE: RNA
<213> ORGANISM: Artificial Sequence
<220> FEATURE:
<223> OTHER INFORMATION: WEE1-2 sense modified
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (4)...(17)
<223> OTHER INFORMATION: n = um

<400> SEQUENCE: 124
ngcnggaugg augcaunua                                                  19

<210> SEQ ID NO 125
<211> LENGTH: 21
<212> TYPE: RNA
<213> ORGANISM: Artificial Sequence
<220> FEATURE:
<223> OTHER INFORMATION: WEE1-5/6 sense
<220> FEATURE:
<221> NAME/KEY: modified_base
<222> LOCATION: (4)...(4)
<223> OTHER INFORMATION: n = um
<220> FEATURE:
<221> NAME/KEY: modified_base
<222> LOCATION: (6)...(13)
<223> OTHER INFORMATION: n = gm

<400> SEQUENCE: 125
ggcngnaugg auncauuuau u                                               21

<210> SEQ ID NO 126
<211> LENGTH: 21
<212> TYPE: RNA
<213> ORGANISM: Artificial Sequence
<220> FEATURE:
<223> OTHER INFORMATION: WEE1-5/6 antisense
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (9)...(13)
<223> OTHER INFORMATION: n = um

<400> SEQUENCE: 126
uaaauncanc canccagccu c                                               21

<210> SEQ ID NO 127
<211> LENGTH: 21
<212> TYPE: RNA
<213> ORGANISM: Artificial Sequence
<220> FEATURE:
<223> OTHER INFORMATION: WEE1-3058 sense

<400> SEQUENCE: 127
cugucagccu uacuauauac u                                               21

<210> SEQ ID NO 128
<211> LENGTH: 21
<212> TYPE: RNA
<213> ORGANISM: Artificial Sequence
<220> FEATURE:
<223> OTHER INFORMATION: WEE1-3058 antisense
```

-continued

```
<400> SEQUENCE: 128
uauauaguaa ggcugacaga g                                              21

<210> SEQ ID NO 129
<211> LENGTH: 19
<212> TYPE: RNA
<213> ORGANISM: Artificial Sequence
<220> FEATURE:
<223> OTHER INFORMATION: WEE1-3058 antisense modified
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (15)...(15)
<223> OTHER INFORMATION: n = gm

<400> SEQUENCE: 129
uauanaguaa ggcunacag                                                 19

<210> SEQ ID NO 130
<211> LENGTH: 19
<212> TYPE: RNA
<213> ORGANISM: Artificial Sequence
<220> FEATURE:
<223> OTHER INFORMATION: WEE1-3058 antisense modified
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (14...(14)
<223> OTHER INFORMATION: n = um

<400> SEQUENCE: 130
uauauagnaa gncngacag                                                 19

<210> SEQ ID NO 131
<211> LENGTH: 19
<212> TYPE: RNA
<213> ORGANISM: Artificial Sequence
<220> FEATURE:
<223> OTHER INFORMATION: WEE1-3058 antisense modified
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (14)...(14)
<223> OTHER INFORMATION: n = um
<220> FEATURE:
<221> NAME/KEY: modified_base
<222> LOCATION: (15)...(15)
<223> OTHER INFORMATION: n = gm

<400> SEQUENCE: 131
uauananuaa ggcnnacag                                                 19

<210> SEQ ID NO 132
```

```
<211> LENGTH: 19
<212> TYPE: RNA
<213> ORGANISM: Artificial Sequence
<220> FEATURE:
<223> OTHER INFORMATION: WEE1-3058 antisense modified
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (14)...(14)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 132
uauananuaa ggcngacan                                              19

<210> SEQ ID NO 133
<211> LENGTH: 19
<212> TYPE: RNA
<213> ORGANISM: Artificial Sequence
<220> FEATURE:
<223> OTHER INFORMATION: WEE1-3058 sense modified
<220> FEATURE:
<221> NAME/KEY: modified_base
<222> LOCATION: (2)...(18)
<223> OTHER INFORMATION: n = um

<400> SEQUENCE: 133
cngncagccu nacnanana                                              19

<210> SEQ ID NO 134
<211> LENGTH: 19
<212> TYPE: RNA
<213> ORGANISM: Artificial Sequence
<220> FEATURE:
<223> OTHER INFORMATION: WEE1-3058 sense modified
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (11)...(16)
<223> OTHER INFORMATION: n = um

<400> SEQUENCE: 134
cnnucagccu nacuanaua                                              19

<210> SEQ ID NO 135
<211> LENGTH: 19
<212> TYPE: RNA
<213> ORGANISM: Artificial Sequence
<220> FEATURE:
<223> OTHER INFORMATION: WEE1-3058 sense modified
<220> FEATURE:
<221> NAME/KEY: modified_base
<222> LOCATION: (4)...(4)
<223> OTHER INFORMATION: n = um
<220> FEATURE:
<221> NAME/KEY: modified_base
```

```
<222> LOCATION: (7)...(7)
<223> OTHER INFORMATION: n = gm
<220> FEATURE:
<221> NAME/KEY: modified_base
<222> LOCATION: (14)...(14)
<223> OTHER INFORMATION: n = um

<400> SEQUENCE: 135
cugncanccu uacnauaua                                               19

<210> SEQ ID NO 136
<211> LENGTH: 21
<212> TYPE: RNA
<213> ORGANISM: Artificial Sequence
<220> FEATURE:
<223> OTHER INFORMATION: WEE1-3058-1/5 sense
<220> FEATURE:
<221> NAME/KEY: modified_base
<222> LOCATION: (2)...(18)
<223> OTHER INFORMATION: n = um

<400> SEQUENCE: 136
cngncagccu nacnananac u                                            21

<210> SEQ ID NO 137
<211> LENGTH: 21
<212> TYPE: RNA
<213> ORGANISM: Artificial Sequence
<220> FEATURE:
<223> OTHER INFORMATION: WEE1-3058-1/5 antisense
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (15)...(15)
<223> OTHER INFORMATION: n = gm

<400> SEQUENCE: 137
uauanaguaa ggcunacaga g                                            21

<210> SEQ ID NO 138
<211> LENGTH: 19
<212> TYPE: RNA
<213> ORGANISM: Artificial Sequence
<220> FEATURE:
<223> OTHER INFORMATION: HDAC2-1 sense

<400> SEQUENCE: 138
gccacugccg aagaaauga                                               19

<210> SEQ ID NO 139
<211> LENGTH: 19
<212> TYPE: RNA
<213> ORGANISM: Artificial Sequence
<220> FEATURE:
<223> OTHER INFORMATION: HDAC2-1 antisense

<400> SEQUENCE: 139
ucauuucuuc ggcaguggc                                               19

<210> SEQ ID NO 140
<211> LENGTH: 19
<212> TYPE: RNA
<213> ORGANISM: Artificial Sequence
<220> FEATURE:
<223> OTHER INFORMATION: HDAC2-2 sense
```

-continued

<400> SEQUENCE: 140
gcugugaagu uaaaccgac                                                19

<210> SEQ ID NO 141
<211> LENGTH: 19
<212> TYPE: RNA
<213> ORGANISM: Artificial Sequence
<220> FEATURE:
<223> OTHER INFORMATION: HDAC2-2 antisense

<400> SEQUENCE: 141
gucgguuuaa cuucacagc                                                19

<210> SEQ ID NO 142
<211> LENGTH: 19
<212> TYPE: RNA
<213> ORGANISM: Artificial Sequence
<220> FEATURE:
<223> OTHER INFORMATION: HDAC2-3 sense

<400> SEQUENCE: 142
gccuauuauc ucaaaggug                                                19

<210> SEQ ID NO 143
<211> LENGTH: 19
<212> TYPE: RNA
<213> ORGANISM: Artificial Sequence
<220> FEATURE:
<223> OTHER INFORMATION: HDAC2-3 antisense

<400> SEQUENCE: 143
caccuuugag auaauaggc                                                19

<210> SEQ ID NO 144
<211> LENGTH: 21
<212> TYPE: RNA
<213> ORGANISM: Artificial Sequence
<220> FEATURE:
<223> OTHER INFORMATION: HDAC2-1 sense
<220> FEATURE:
<221> NAME/KEY: modified_base
<222> LOCATION: (20)...(21)
<223> OTHER INFORMATION: n = deoxythymidine

<400> SEQUENCE: 144
gccacugccg aagaaaugan n                                             21

<210> SEQ ID NO 145
<211> LENGTH: 21
<212> TYPE: RNA
<213> ORGANISM: Artificial Sequence
<220> FEATURE:
<223> OTHER INFORMATION: HDAC2-1 antisense
<220> FEATURE:
<221> NAME/KEY: modified_base
<222> LOCATION: (20)...(21)
<223> OTHER INFORMATION: n = deoxythymidine

<400> SEQUENCE: 145
ucauuucuuc ggcaguggcn n                                             21

<210> SEQ ID NO 146
<211> LENGTH: 19
<212> TYPE: RNA
<213> ORGANISM: Artificial Sequence
<220> FEATURE:
<223> OTHER INFORMATION: HDAC2-1 antisense modified

```
<220> FEATURE:
<221> NAME/KEY: modified_base
<222> LOCATION: (5)...(16)
<223> OTHER INFORMATION: n = um

<400> SEQUENCE: 146 ucauucnuc ggcagnggc                                                     19

<210> SEQ ID NO 147
<211> LENGTH: 19
<212> TYPE: RNA
<213> ORGANISM: Artificial Sequence
<220> FEATURE:
<223> OTHER INFORMATION: HDAC2-1 antisense modified
<220> FEATURE:
<221> NAME/KEY: modified_base
<222> LOCATION: (6)...(16)
<223> OTHER INFORMATION: n = um

<400> SEQUENCE: 147
ucauuncuuc ggcagnggc                                                    19

<210> SEQ ID NO 148
<211> LENGTH: 19
<212> TYPE: RNA
<213> ORGANISM: Artificial Sequence
<220> FEATURE:
<223> OTHER INFORMATION: HDAC2-1 antisense modified
<220> FEATURE:
<221> NAME/KEY: modified_base
<222> LOCATION: (4)...(9)
<223> OTHER INFORMATION: n = um
<220> FEATURE:
<221> NAME/KEY: modified_base
<222> LOCATION: (15)...(18)
<223> OTHER INFORMATION: n = gm

<400> SEQUENCE: 148
ucanuucunc ggcanugnc                                                    19

<210> SEQ ID NO 149
<211> LENGTH: 19
<212> TYPE: RNA
<213> ORGANISM: Artificial Sequence
<220> FEATURE:
<223> OTHER INFORMATION: HDAC2-1 sense modified
<220> FEATURE:
<221> NAME/KEY: modified_base
<222> LOCATION: (6)...(17)
<223> OTHER INFORMATION: n = um

<400> SEQUENCE: 149
gccacngccg aagaaanga                                                    19

<210> SEQ ID NO 150
<211> LENGTH: 19
<212> TYPE: RNA
<213> ORGANISM: Artificial Sequence
<220> FEATURE:
<223> OTHER INFORMATION: HDAC2-1 sense modified
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (6)...(6)
<223> OTHER INFORMATION: n = um
<220> FEATURE:
<221> NAME/KEY: modified_base
<222> LOCATION: (13)...(13)
```

```
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 150
nccacngccg aanaaanga                                            19

<210> SEQ ID NO 151
<211> LENGTH: 19
<212> TYPE: RNA
<213> ORGANISM: Artificial Sequence
<220> FEATURE:
<223> OTHER INFORMATION: HDAC2-1 sense modified
<220> FEATURE:
<221> NAME/KEY: modified_base
<222> LOCATION: (7)...(18)
<223> OTHER INFORMATION: n = gm

<400> SEQUENCE: 151
gccacunccg aanaaauna                                            19

<210> SEQ ID NO 152
<211> LENGTH: 21
<212> TYPE: RNA
<213> ORGANISM: Artificial Sequence
<220> FEATURE:
<223> OTHER INFORMATION: HDAC2-3/7 sense
<220> FEATURE:
<221> NAME/KEY: modified_base
<222> LOCATION: (6)...(17)
<223> OTHER INFORMATION: n = um
<220> FEATURE:
<221> NAME/KEY: modified_base
<222> LOCATION: (20)...(21)
<223> OTHER INFORMATION: n = deoxythymidine

<400> SEQUENCE: 152
gccacngccg aagaaangan n                                         21

<210> SEQ ID NO 153
<211> LENGTH: 21
<212> TYPE: RNA
<213> ORGANISM: Artificial Sequence
<220> FEATURE:
<223> OTHER INFORMATION: HDAC2-3/7 antisense
<220> FEATURE:
<221> NAME/KEY: modified_base
<222> LOCATION: (5)...(16)
<223> OTHER INFORMATION: n = um
<220> FEATURE:
<221> NAME/KEY: modified_base
<222> LOCATION: (20)...(21)
<223> OTHER INFORMATION: n = deoxythymidine

<400> SEQUENCE: 153
ucaunucnuc ggcagnggcn n                                         21

<210> SEQ ID NO 154
<211> LENGTH: 19
<212> TYPE: RNA
<213> ORGANISM: Artificial Sequence
<220> FEATURE:
<223> OTHER INFORMATION: RBX1-1 sense

<400> SEQUENCE: 154
gguguguccg uuggacaac                                            19
```

```
<210> SEQ ID NO 155
<211> LENGTH: 19
<212> TYPE: RNA
<213> ORGANISM: Artificial Sequence
<220> FEATURE:
<223> OTHER INFORMATION: RBX1-1 antisense

<400> SEQUENCE: 155
guuguccaau ggacacacc                                              19

<210> SEQ ID NO 156
<211> LENGTH: 19
<212> TYPE: RNA
<213> ORGANISM: Artificial Sequence
<220> FEATURE:
<223> OTHER INFORMATION: RBX1-2 sense

<400> SEQUENCE: 156
ggaaccacau uauggaucu                                              19

<210> SEQ ID NO 157
<211> LENGTH: 19
<212> TYPE: RNA
<213> ORGANISM: Artificial Sequence
<220> FEATURE:
<223> OTHER INFORMATION: RBX1-2 antisense

<400> SEQUENCE: 157
agauccauaa ugugguucc                                              19

<210> SEQ ID NO 158
<211> LENGTH: 19
<212> TYPE: RNA
<213> ORGANISM: Artificial Sequence
<220> FEATURE:
<223> OTHER INFORMATION: RBX1-3 sense

<400> SEQUENCE: 158
gugaaaaagu ggaaugcag                                              19

<210> SEQ ID NO 159
<211> LENGTH: 19
<212> TYPE: RNA
<213> ORGANISM: Artificial Sequence
<220> FEATURE:
<223> OTHER INFORMATION: RBX1-3 antisense

<400> SEQUENCE: 159
cugcauucca cuuuucac                                               19

<210> SEQ ID NO 160
<211> LENGTH: 21
<212> TYPE: RNA
<213> ORGANISM: Artificial Sequence
<220> FEATURE:
<223> OTHER INFORMATION: RBX1-2 sense
<220> FEATURE:
<221> NAME/KEY: modified_base
<222> LOCATION: (20)...(21)
<223> OTHER INFORMATION: n = deoxythymidine

<400> SEQUENCE: 160
ggaaccacau uauggaucun n                                           21

<210> SEQ ID NO 161
<211> LENGTH: 21
<212> TYPE: RNA
```

```
<213> ORGANISM: Artificial Sequence
<220> FEATURE:
<223> OTHER INFORMATION: RBX1-2 antisense
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxyguanosine

<400> SEQUENCE: 161
agauccauaa ugugguuccn n                                              21

<210> SEQ ID NO 162
<211> LENGTH: 19
<212> TYPE: RNA
<213> ORGANISM: Artificial Sequence
<220> FEATURE:
<223> OTHER INFORMATION: HDAC1-2 antisense modified
<220> FEATURE:
<221> NAME/KEY: modified_base
<222> LOCATION: (4)...(17)
<223> OTHER INFORMATION: n = um

<400> SEQUENCE: 162
aganccanaa ugngguncc                                                 19

<210> SEQ ID NO 163
<211> LENGTH: 19
<212> TYPE: RNA
<213> ORGANISM: Artificial Sequence
<220> FEATURE:
<223> OTHER INFORMATION: RBX1-2 antisense modified
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (14)...(14)
<223> OTHER INFORMATION: n = gm

<400> SEQUENCE: 163
agauccanaa ugunguucc                                                 19

<210> SEQ ID NO 164
<211> LENGTH: 19
<212> TYPE: RNA
<213> ORGANISM: Artificial Sequence
<220> FEATURE:
<223> OTHER INFORMATION: RBX1-2 antisense modified
<220> FEATURE:
<221> NAME/KEY: modified_base
<222> LOCATION: (11)...(16)
<223> OTHER INFORMATION: n = um

<400> SEQUENCE: 164
agauccauaa ngnggnucc                                                 19

<210> SEQ ID NO 165
<211> LENGTH: 19
<212> TYPE: RNA
<213> ORGANISM: Artificial Sequence
<220> FEATURE:
<223> OTHER INFORMATION: RBX1-2 sense modified
<220> FEATURE:
<221> NAME/KEY: modified_base
<222> LOCATION: (11)...(11)
<223> OTHER INFORMATION: n = um
```

```
<220> FEATURE:
<221> NAME/KEY: modified_base
<222> LOCATION: (15)...(15)
<223> OTHER INFORMATION: n = gm

<400> SEQUENCE: 165
ggaaccacau naugnaucu                                                    19

<210> SEQ ID NO 166
<211> LENGTH: 19
<212> TYPE: RNA
<213> ORGANISM: Artificial Sequence
<220> FEATURE:
<223> OTHER INFORMATION: RBX1-2 sense modified
<220> FEATURE:
<221> NAME/KEY: modified_base
<222> LOCATION: (2)...(2)
<223> OTHER INFORMATION: n = gm
<220> FEATURE:
<221> NAME/KEY: modified_base
<222> LOCATION: (10)...(14)
<223> OTHER INFORMATION: n = um

<400> SEQUENCE: 166
gnaaccacan uaungaucu                                                    19

<210> SEQ ID NO 167
<211> LENGTH: 21
<212> TYPE: RNA
<213> ORGANISM: Artificial Sequence
<220> FEATURE:
<223> OTHER INFORMATION: RBX1-3/6 sense
<220> FEATURE:
<221> NAME/KEY: modified_base
<222> LOCATION: (11)...(11)
<223> OTHER INFORMATION: n = um
<220> FEATURE:
<221> NAME/KEY: modified_base
<222> LOCATION: (15)...(15)
<223> OTHER INFORMATION: n = gm
<220> FEATURE:
<221> NAME/KEY: modified_base
<222> LOCATION: (20)...(21)
<223> OTHER INFORMATION: n = deoxythymidine

<400> SEQUENCE: 167
ggaaccacau naugnaucun n                                                 21

<210> SEQ ID NO 168
<211> LENGTH: 21
<212> TYPE: RNA
<213> ORGANISM: Artificial Sequence
<220> FEATURE:
<223> OTHER INFORMATION: RBX1-3/6 antisense
<220> FEATURE:
<221> NAME/KEY: modified_base
<222> LOCATION: (4)...(17)
<223> OTHER INFORMATION: n = um
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxyguanosine

<400> SEQUENCE: 168
aganccanaa ugnggunccn n                                                 21

<210> SEQ ID NO 169
```

```
<211> LENGTH: 19
<212> TYPE: RNA
<213> ORGANISM: Artificial Sequence
<220> FEATURE:
<223> OTHER INFORMATION: CDK4-1 sense

<400> SEQUENCE: 169
ggcuuuugag caucccaau                                                19

<210> SEQ ID NO 170
<211> LENGTH: 19
<212> TYPE: RNA
<213> ORGANISM: Artificial Sequence
<220> FEATURE:
<223> OTHER INFORMATION: CDK4-1 antisense

<400> SEQUENCE: 170
auugggaugc ucaaaagcc                                                19

<210> SEQ ID NO 171
<211> LENGTH: 19
<212> TYPE: RNA
<213> ORGANISM: Artificial Sequence
<220> FEATURE:
<223> OTHER INFORMATION: CDK4-2 sense

<400> SEQUENCE: 171
gccgaaacga ucaaggauc                                                19

<210> SEQ ID NO 172
<211> LENGTH: 19
<212> TYPE: RNA
<213> ORGANISM: Artificial Sequence
<220> FEATURE:
<223> OTHER INFORMATION: CDK4-2 antisense

<400> SEQUENCE: 172
gauccuugau cguuucggc                                                19

<210> SEQ ID NO 173
<211> LENGTH: 19
<212> TYPE: RNA
<213> ORGANISM: Artificial Sequence
<220> FEATURE:
<223> OTHER INFORMATION: CDK4-3 sense

<400> SEQUENCE: 173
gcacucuuau cuacauaag                                                19

<210> SEQ ID NO 174
<211> LENGTH: 19
<212> TYPE: RNA
<213> ORGANISM: Artificial Sequence
<220> FEATURE:
<223> OTHER INFORMATION: CDK4-3 antisense

<400> SEQUENCE: 174
cuuauguaga uaagagugc                                                19

<210> SEQ ID NO 175
<211> LENGTH: 21
<212> TYPE: RNA
<213> ORGANISM: Artificial Sequence
<220> FEATURE:
<223> OTHER INFORMATION: CDK4-1 sense
<220> FEATURE:
<221> NAME/KEY: modified_base
```

```
<222> LOCATION: (20)...(21)
<223> OTHER INFORMATION: n = deoxythymidine

<400> SEQUENCE: 175
ggcuuuugag caucccaaun n                                              21

<210> SEQ ID NO 176
<211> LENGTH: 21
<212> TYPE: RNA
<213> ORGANISM: Artificial Sequence
<220> FEATURE:
<223> OTHER INFORMATION: CDK4-1 antisense
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxycytidine

<400> SEQUENCE: 176
auugggaugc ucaaaagccn n                                              21

<210> SEQ ID NO 177
<211> LENGTH: 19
<212> TYPE: RNA
<213> ORGANISM: Artificial Sequence
<220> FEATURE:
<223> OTHER INFORMATION: CDK4-1 antisense modified
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (17)...(17)
<223> OTHER INFORMATION: n = gm

<400> SEQUENCE: 177
auuggnangc ucaaaancc                                                 19

<210> SEQ ID NO 178
<211> LENGTH: 19
<212> TYPE: RNA
<213> ORGANISM: Artificial Sequence
<220> FEATURE:
<223> OTHER INFORMATION: CDK4-1 antisense modified
<220> FEATURE:
<221> NAME/KEY: modified_base
<222> LOCATION: (9)...(9)
<223> OTHER INFORMATION: n = gm

<400> SEQUENCE: 178
auugggaunc ucaaaagcc                                                 19

<210> SEQ ID NO 179
<211> LENGTH: 19
<212> TYPE: RNA
<213> ORGANISM: Artificial Sequence
<220> FEATURE:
<223> OTHER INFORMATION: CDK4-1 antisense modified
<220> FEATURE:
<221> NAME/KEY: modified_base
<222> LOCATION: (5)...(5)
<223> OTHER INFORMATION: n = gm
<220> FEATURE:
```

```
<221> NAME/KEY: modified_base
<222> LOCATION: (11)...(11)
<223> OTHER INFORMATION: n = um
<220> FEATURE:
<221> NAME/KEY: modified_base
<222> LOCATION: (17)...(17)
<223> OTHER INFORMATION: n = gm

<400> SEQUENCE: 179
auugngaugc ncaaaancc                                               19

<210> SEQ ID NO 180
<211> LENGTH: 19
<212> TYPE: RNA
<213> ORGANISM: Artificial Sequence
<220> FEATURE:
<223> OTHER INFORMATION: CDK4-1 antisense modified
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (8)...(8)
<223> OTHER INFORMATION: n = um

<400> SEQUENCE: 180
auunggangc ucaaaagcc                                               19

<210> SEQ ID NO 181
<211> LENGTH: 19
<212> TYPE: RNA
<213> ORGANISM: Artificial Sequence
<220> FEATURE:
<223> OTHER INFORMATION: CDK4-1 sense modified
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (4)...(13)
<223> OTHER INFORMATION: n = um

<400> SEQUENCE: 181
ngcnnungag cancccaau                                               19

<210> SEQ ID NO 182
<211> LENGTH: 19
<212> TYPE: RNA
<213> ORGANISM: Artificial Sequence
<220> FEATURE:
<223> OTHER INFORMATION: CDK4-1 sense modified
<220> FEATURE:
<221> NAME/KEY: modified_base
<222> LOCATION: (1)...(2)
<223> OTHER INFORMATION: n = gm
<220> FEATURE:
<221> NAME/KEY: modified_base
<222> LOCATION: (4)...(6)
<223> OTHER INFORMATION: n = um

<400> SEQUENCE: 182
nncnunugag caucccaau                                               19

<210> SEQ ID NO 183
<211> LENGTH: 19
<212> TYPE: RNA
<213> ORGANISM: Artificial Sequence
<220> FEATURE:
<223> OTHER INFORMATION: CDK4-1 sense modified
```

```
<220> FEATURE:
<221> NAME/KEY: modified_base
<222> LOCATION: (2)...(2)
<223> OTHER INFORMATION: n = gm
<220> FEATURE:
<221> NAME/KEY: modified_base
<222> LOCATION: (5)...(13)
<223> OTHER INFORMATION: n = um

<400> SEQUENCE: 183
gncunuugag cancccaau                                                        19

<210> SEQ ID NO 184
<211> LENGTH: 21
<212> TYPE: RNA
<213> ORGANISM: Artificial Sequence
<220> FEATURE:
<223> OTHER INFORMATION: CDK4-3/7 sense
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (4)...(13)
<223> OTHER INFORMATION: n = um

<400> SEQUENCE: 184
ngcnnungag cancccaauu u                                                     21

<210> SEQ ID NO 185
<211> LENGTH: 21
<212> TYPE: RNA
<213> ORGANISM: Artificial Sequence
<220> FEATURE:
<223> OTHER INFORMATION: CDK4-3/7 antisense
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (17)...(17)
<223> OTHER INFORMATION: n = gm

<400> SEQUENCE: 185
auuggnangc ucaaaanccu c                                                     21

<210> SEQ ID NO 186
<211> LENGTH: 19
<212> TYPE: RNA
<213> ORGANISM: Artificial Sequence
<220> FEATURE:
<223> OTHER INFORMATION: CSN5-1 sense

<400> SEQUENCE: 186
ccauuacuuu aaguacugc                                                        19

<210> SEQ ID NO 187
<211> LENGTH: 19
<212> TYPE: RNA
<213> ORGANISM: Artificial Sequence
<220> FEATURE:
<223> OTHER INFORMATION: CSN5-1 antisense

<400> SEQUENCE: 187
```
gcaguacuua aaguaaugg                                            19

<210> SEQ ID NO 188
<211> LENGTH: 19
<212> TYPE: RNA
<213> ORGANISM: Artificial Sequence
<220> FEATURE:
<223> OTHER INFORMATION: CSN5-2 sense

<400> SEQUENCE: 188
ggaucaccau uacuuuaag                                            19

<210> SEQ ID NO 189
<211> LENGTH: 19
<212> TYPE: RNA
<213> ORGANISM: Artificial Sequence
<220> FEATURE:
<223> OTHER INFORMATION: CSN5-3 sense

<400> SEQUENCE: 189
ccgaaaauca gaagacaaa                                            19

<210> SEQ ID NO 190
<211> LENGTH: 19
<212> TYPE: RNA
<213> ORGANISM: Artificial Sequence
<220> FEATURE:
<223> OTHER INFORMATION: CSN5-3 antisense

<400> SEQUENCE: 190
uuugucuucu gauuuucgg                                            19

<210> SEQ ID NO 191
<211> LENGTH: 21
<212> TYPE: RNA
<213> ORGANISM: Artificial Sequence
<220> FEATURE:
<223> OTHER INFORMATION: CSN5-2 sense
<220> FEATURE:
<221> NAME/KEY: modified_base
<222> LOCATION: (20)...(21)
<223> OTHER INFORMATION: n = deoxythymidine

<400> SEQUENCE: 191
ggaucaccau uacuuuaagn n                                         21

<210> SEQ ID NO 192
<211> LENGTH: 21
<212> TYPE: RNA
<213> ORGANISM: Artificial Sequence
<220> FEATURE:
<223> OTHER INFORMATION: CSK5-2 antisense
<220> FEATURE:
<221> NAME/KEY: modified_base
<222> LOCATION: (20)...(21)
<223> OTHER INFORMATION: n = deoxythymidine

<400> SEQUENCE: 192
cuuaaaguaa uggugauccn n                                         21

<210> SEQ ID NO 193
<211> LENGTH: 19
<212> TYPE: RNA
<213> ORGANISM: Artificial Sequence
<220> FEATURE:
<223> OTHER INFORMATION: CSN5-2 antisense modified
<220> FEATURE:
<221> NAME/KEY: modified_base
<222> LOCATION: (7)...(15)
<223> OTHER INFORMATION: n = gm

<400> SEQUENCE: 193
cuuaaanuaa ugnunaucc                                                    19

<210> SEQ ID NO 194
<211> LENGTH: 19
<212> TYPE: RNA
<213> ORGANISM: Artificial Sequence
<220> FEATURE:
<223> OTHER INFORMATION: CSN5-2 antisense modified
<220> FEATURE:
<221> NAME/KEY: modified_base
<222> LOCATION: (2)...(17)
<223> OTHER INFORMATION: n = um

<400> SEQUENCE: 194
cnuaaaguaa uggugancc                                                    19

<210> SEQ ID NO 195
<211> LENGTH: 19
<212> TYPE: RNA
<213> ORGANISM: Artificial Sequence
<220> FEATURE:
<223> OTHER INFORMATION: CSN5-2 antisense modified
<220> FEATURE:
<221> NAME/KEY: modified_base
<222> LOCATION: (2)...(3)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 195
cnnaaaguaa ungugancc                                                    19

<210> SEQ ID NO 196
<211> LENGTH: 19
<212> TYPE: RNA
<213> ORGANISM: Artificial Sequence
<220> FEATURE:
<223> OTHER INFORMATION: CSN5-2 antisense modified
<220> FEATURE:
<221> NAME/KEY: modified_base
<222> LOCATION: (3)...(14)
<223> OTHER INFORMATION: n = um

<400> SEQUENCE: 196
cunaaaguaa uggngaucc                                                    19

<210> SEQ ID NO 197
<211> LENGTH: 19
<212> TYPE: RNA
<213> ORGANISM: Artificial Sequence
<220> FEATURE:
<223> OTHER INFORMATION: CSN5-2 sense modified
<220> FEATURE:
<221> NAME/KEY: modified_base
<222> LOCATION: (4)...(16)
<223> OTHER INFORMATION: n = um

<400> SEQUENCE: 197
ggancaccau nacnunaag                                                    19

```
<210> SEQ ID NO 198
<211> LENGTH: 19
<212> TYPE: RNA
<213> ORGANISM: Artificial Sequence
<220> FEATURE:
<223> OTHER INFORMATION: CSN5-2 sense modified
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 198
ngaucaccau uacunuaan                                                   19

<210> SEQ ID NO 199
<211> LENGTH: 19
<212> TYPE: RNA
<213> ORGANISM: Artificial Sequence
<220> FEATURE:
<223> OTHER INFORMATION: CSN5-2 sense modified
<220> FEATURE:
<221> NAME/KEY: modified_base
<222> LOCATION: (2)...(2)
<223> OTHER INFORMATION: n = gm
<220> FEATURE:
<221> NAME/KEY: modified_base
<222> LOCATION: (4)...(16)
<223> OTHER INFORMATION: n = um

<400> SEQUENCE: 199
gnancaccau uacunnaag                                                   19

<210> SEQ ID NO 200
<211> LENGTH: 21
<212> TYPE: RNA
<213> ORGANISM: Artificial Sequence
<220> FEATURE:
<223> OTHER INFORMATION: CSN5-3/8 sense
<220> FEATURE:
<221> NAME/KEY: modified_base
<222> LOCATION: (4)...(16)
<223> OTHER INFORMATION: n = um

<400> SEQUENCE: 200
ggancaccau nacnunaagu u                                                21

<210> SEQ ID NO 201
<211> LENGTH: 21
<212> TYPE: RNA
<213> ORGANISM: Artificial Sequence
<220> FEATURE:
<223> OTHER INFORMATION: CSN5-3/8
<220> FEATURE:
<221> NAME/KEY: modified_base
<222> LOCATION: (7)...(15)
<223> OTHER INFORMATION: n = gm

<400> SEQUENCE: 201
cuuaaanuaa ugnunauccu u                                                21

<210> SEQ ID NO 202
<211> LENGTH: 19
```

```
<212> TYPE: RNA
<213> ORGANISM: Artificial Sequence
<220> FEATURE:
<223> OTHER INFORMATION: FOXM1-1 sense

<400> SEQUENCE: 202
ggaccuuuua agacaccca                                                19

<210> SEQ ID NO 203
<211> LENGTH: 19
<212> TYPE: RNA
<213> ORGANISM: Artificial Sequence
<220> FEATURE:
<223> OTHER INFORMATION: FOXM1-1 antisense

<400> SEQUENCE: 203 uggguguucuu aaaaggucc                                               19

<210> SEQ ID NO 204
<211> LENGTH: 19
<212> TYPE: RNA
<213> ORGANISM: Artificial Sequence
<220> FEATURE:
<223> OTHER INFORMATION: FOXM1-2 sense

<400> SEQUENCE: 204
ggaaaugcca cacuuagcg                                                19

<210> SEQ ID NO 205
<211> LENGTH: 19
<212> TYPE: RNA
<213> ORGANISM: Artificial Sequence
<220> FEATURE:
<223> OTHER INFORMATION: FOXM1-2 antisense

<400> SEQUENCE: 205
cgcuaagugu ggcauuucc                                                19

<210> SEQ ID NO 206
<211> LENGTH: 19
<212> TYPE: RNA
<213> ORGANISM: Artificial Sequence
<220> FEATURE:
<223> OTHER INFORMATION: FOXM1-3 sense

<400> SEQUENCE: 206
ggcugcacua ucaacaaua                                                19

<210> SEQ ID NO 207
<211> LENGTH: 19
<212> TYPE: RNA
<213> ORGANISM: Artificial Sequence
<220> FEATURE:
<223> OTHER INFORMATION: FOXM1-3 antisense

<400> SEQUENCE: 207
uauuguugau agugcagcc                                                19

<210> SEQ ID NO 208
<211> LENGTH: 21
<212> TYPE: RNA
<213> ORGANISM: Artificial Sequence
<220> FEATURE:
<223> OTHER INFORMATION: FOXM1-1 sense
<220> FEATURE:
<221> NAME/KEY: modified_base
<222> LOCATION: (20)...(21)
```

```
<223> OTHER INFORMATION: n = deoxythymidine

<400> SEQUENCE: 208
ggaccuuuua agacacccan n                                              21

<210> SEQ ID NO 209
<211> LENGTH: 21
<212> TYPE: RNA
<213> ORGANISM: Artificial Sequence
<220> FEATURE:
<223> OTHER INFORMATION: FOXM1-1 antisense
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxycytidine

<400> SEQUENCE: 209
ugggugucuu aaaagguccn n                                              21

<210> SEQ ID NO 210
<211> LENGTH: 19
<212> TYPE: RNA
<213> ORGANISM: Artificial Sequence
<220> FEATURE:
<223> OTHER INFORMATION: FOXM1-1 antisense modified
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (16...(16)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 210
ugggunucnu aaaagnncc                                                 19

<210> SEQ ID NO 211
<211> LENGTH: 19
<212> TYPE: RNA
<213> ORGANISM: Artificial Sequence
<220> FEATURE:
<223> OTHER INFORMATION: FOXM1-1 antisense modified
<220> FEATURE:
<221> NAME/KEY: modified_base
<222> LOCATION: (7)...(7)
<223> OTHER INFORMATION: n = um
<220> FEATURE:
<221> NAME/KEY: modified_base
<222> LOCATION: (15)...(15)
<223> OTHER INFORMATION: n = gm
<220> FEATURE:
<221> NAME/KEY: modified_base
<222> LOCATION: (17...(17)
<223> OTHER INFORMATION: n = um

<400> SEQUENCE: 211
ugggugncuu aaaangncc                                                 19
```

```
<210> SEQ ID NO 212
<211> LENGTH: 19
<212> TYPE: RNA
<213> ORGANISM: Artificial Sequence
<220> FEATURE:
<223> OTHER INFORMATION: FOXM1-1 antisense modified
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 212
ugggunucuu aaaaggncc                                              19

<210> SEQ ID NO 213
<211> LENGTH: 19
<212> TYPE: RNA
<213> ORGANISM: Artificial Sequence
<220> FEATURE:
<223> OTHER INFORMATION: FOXM1-1 antisense modified
<220> FEATURE:
<221> NAME/KEY: modified_base
<222> LOCATION: (5)...(17)
<223> OTHER INFORMATION: n = um

<400> SEQUENCE: 213
ugggngncuu aaaaggncc                                              19

<210> SEQ ID NO 214
<211> LENGTH: 19
<212> TYPE: RNA
<213> ORGANISM: Artificial Sequence
<220> FEATURE:
<223> OTHER INFORMATION: FOXM1-1 sense modified
<220> FEATURE:
<221> NAME/KEY: modified_base
<222> LOCATION: (1)...(6)
<223> OTHER INFORMATION: n = gm
<220> FEATURE:
<221> NAME/KEY: modified_base
<222> LOCATION: (6)...(8)
<223> OTHER INFORMATION: n = um

<400> SEQUENCE: 214
ngaccnunua agacaccca                                              19

<210> SEQ ID NO 215
<211> LENGTH: 19
<212> TYPE: RNA
<213> ORGANISM: Artificial Sequence
<220> FEATURE:
<223> OTHER INFORMATION: FOXM1-1 sense modified
<220> FEATURE:
<221> NAME/KEY: modified_base
<222> LOCATION: (1)...(2)
<223> OTHER INFORMATION: n = gm
<220> FEATURE:
<221> NAME/KEY: modified_base
<222> LOCATION: (6)...(6)
<223> OTHER INFORMATION: n = um
<220> FEATURE:
<221> NAME/KEY: modified_base
<222> LOCATION: (12)...(12)
<223> OTHER INFORMATION: n = gm

<400> SEQUENCE: 215
nnaccnuuua anacaccca                                              19
```

```
<210> SEQ ID NO 216
<211> LENGTH: 19
<212> TYPE: RNA
<213> ORGANISM: Artificial Sequence
<220> FEATURE:
<223> OTHER INFORMATION: FOXM1-1 sense modified
<220> FEATURE:
<221> NAME/KEY: modified_base
<222> LOCATION: (2)...(2)
<223> OTHER INFORMATION: n = gm
<220> FEATURE:
<221> NAME/KEY: modified_base
<222> LOCATION: (7)...(7)
<223> OTHER INFORMATION: n = um

<400> SEQUENCE: 216
gnaccunuua agacaccca                                               19

<210> SEQ ID NO 217
<211> LENGTH: 21
<212> TYPE: RNA
<213> ORGANISM: Artificial Sequence
<220> FEATURE:
<223> OTHER INFORMATION: FOXM1-5/6 sense
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (6)...(8)
<223> OTHER INFORMATION: n = um

<400> SEQUENCE: 217
ngaccnunua agacacccau u                                            21

<210> SEQ ID NO 218
<211> LENGTH: 21
<212> TYPE: RNA
<213> ORGANISM: Artificial Sequence
<220> FEATURE:
<223> OTHER INFORMATION: FOXM1-5/6 antisense
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 218
ugggunucnu aaaagnnccu c                                            21

<210> SEQ ID NO 219
<211> LENGTH: 19
<212> TYPE: RNA
<213> ORGANISM: Artificial Sequence
<220> FEATURE:
<223> OTHER INFORMATION: R1-1 sense

<400> SEQUENCE: 219
gcaguuguuu ucuagcgca                                               19
```

<210> SEQ ID NO 220
<211> LENGTH: 19
<212> TYPE: RNA
<213> ORGANISM: Artificial Sequence
<220> FEATURE:
<223> OTHER INFORMATION: R1-1 antisense

<400> SEQUENCE: 220
ugcgcuagaa aacaacugc                                                   19

<210> SEQ ID NO 221
<211> LENGTH: 19
<212> TYPE: RNA
<213> ORGANISM: Artificial Sequence
<220> FEATURE:
<223> OTHER INFORMATION: R1-2 sense

<400> SEQUENCE: 221
ggaugucaga ucggcauug                                                   19

<210> SEQ ID NO 222
<211> LENGTH: 19
<212> TYPE: RNA
<213> ORGANISM: Artificial Sequence
<220> FEATURE:
<223> OTHER INFORMATION: R1-2 antisense

<400> SEQUENCE: 222
caaugccgau cugacaucc                                                   19

<210> SEQ ID NO 223
<211> LENGTH: 19
<212> TYPE: RNA
<213> ORGANISM: Artificial Sequence
<220> FEATURE:
<223> OTHER INFORMATION: R1-3 sense

<400> SEQUENCE: 223
ggauuuacgc agagugauc                                                   19

<210> SEQ ID NO 224
<211> LENGTH: 19
<212> TYPE: RNA
<213> ORGANISM: Artificial Sequence
<220> FEATURE:
<223> OTHER INFORMATION: R1-3 antisense

<400> SEQUENCE: 224
gaucacucug cguaaaucc                                                   19

<210> SEQ ID NO 225
<211> LENGTH: 21
<212> TYPE: RNA
<213> ORGANISM: Artificial Sequence
<220> FEATURE:
<223> OTHER INFORMATION: R1-2 sense
<220> FEATURE:
<221> NAME/KEY: modified_base
<222> LOCATION: (20)...(21)
<223> OTHER INFORMATION: n = deoxythymidine

<400> SEQUENCE: 225
ggaugucaga ucggcauugn n                                                21

<210> SEQ ID NO 226

```
<211> LENGTH: 21
<212> TYPE: RNA
<213> ORGANISM: Artificial Sequence
<220> FEATURE:
<223> OTHER INFORMATION: R1-2 antisense
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxycytidine

<400> SEQUENCE: 226
caaugccgau cugacauccn n                                              21

<210> SEQ ID NO 227
<211> LENGTH: 19
<212> TYPE: RNA
<213> ORGANISM: Artificial Sequence
<220> FEATURE:
<223> OTHER INFORMATION: R1-2 antisense modified
<220> FEATURE:
<221> NAME/KEY: modified_base
<222> LOCATION: (4)...(4)
<223> OTHER INFORMATION: n = um
<220> FEATURE:
<221> NAME/KEY: modified_base
<222> LOCATION: (8)...(13)
<223> OTHER INFORMATION: n = gm

<400> SEQUENCE: 227
caangccnau cunacaucc                                                 19

<210> SEQ ID NO 228
<211> LENGTH: 19
<212> TYPE: RNA
<213> ORGANISM: Artificial Sequence
<220> FEATURE:
<223> OTHER INFORMATION: R1-2 antisense modified
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 228
caaugccnau cugacancc                                                 19

<210> SEQ ID NO 229
<211> LENGTH: 19
<212> TYPE: RNA
<213> ORGANISM: Artificial Sequence
<220> FEATURE:
<223> OTHER INFORMATION: R1-2 antisense modified
<220> FEATURE:
<221> NAME/KEY: modified_base
<222> LOCATION: (5)...(5)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 229
caaunccgau cngacancc                                                 19
```

```
<210> SEQ ID NO 230
<211> LENGTH: 19
<212> TYPE: RNA
<213> ORGANISM: Artificial Sequence
<220> FEATURE:
<223> OTHER INFORMATION: R1-2 antisense modified
<220> FEATURE:
<221> NAME/KEY: modified_base
<222> LOCATION: (10)...(17)
<223> OTHER INFORMATION: n = um

<400> SEQUENCE: 230
caaugccgan cugacancc                                              19

<210> SEQ ID NO 231
<211> LENGTH: 19
<212> TYPE: RNA
<213> ORGANISM: Artificial Sequence
<220> FEATURE:
<223> OTHER INFORMATION: R1-2 sense modified
<220> FEATURE:
<221> NAME/KEY: modified_base
<222> LOCATION: (2)...(19)
<223> OTHER INFORMATION: n = gm

<400> SEQUENCE: 231
gnaunucaga ucngcauun                                              19

<210> SEQ ID NO 232
<211> LENGTH: 19
<212> TYPE: RNA
<213> ORGANISM: Artificial Sequence
<220> FEATURE:
<223> OTHER INFORMATION: R1-2 sense modified
<220> FEATURE:
<221> NAME/KEY: modified_base
<222> LOCATION: (4)...(17)
<223> OTHER INFORMATION: n = um

<400> SEQUENCE: 232
ggangncaga ncggcanug                                              19

<210> SEQ ID NO 233
<211> LENGTH: 19
<212> TYPE: RNA
<213> ORGANISM: Artificial Sequence
<220> FEATURE:
<223> OTHER INFORMATION: R1-2 sense modified
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (4)...(4)
<223> OTHER INFORMATION: n = um
<220> FEATURE:
<221> NAME/KEY: modified_base
<222> LOCATION: (14)...(14)
<223> OTHER INFORMATION: n = gm

<400> SEQUENCE: 233
ngangucaga ucgncauug                                              19

<210> SEQ ID NO 234
<211> LENGTH: 21
<212> TYPE: RNA
<213> ORGANISM: Artificial Sequence
<220> FEATURE:
<223> OTHER INFORMATION: R1-5/8 sense
<220> FEATURE:
```

```
<221> NAME/KEY: modified_base
<222> LOCATION: (2)...(19)
<223> OTHER INFORMATION: n = gm

<400> SEQUENCE: 234
gnaunucaga ucngcauunu u                                              21

<210> SEQ ID NO 235
<211> LENGTH: 21
<212> TYPE: RNA
<213> ORGANISM: Artificial Sequence
<220> FEATURE:
<223> OTHER INFORMATION: R1-5/8 antisense
<220> FEATURE:
<221> NAME/KEY: modified_base
<222> LOCATION: (4)...(4)
<223> OTHER INFORMATION: n = um
<220> FEATURE:
<221> NAME/KEY: modified_base
<222> LOCATION: (8)...(13)
<223> OTHER INFORMATION: n = gm

<400> SEQUENCE: 235
caangccnau cunacauccu c                                              21

<210> SEQ ID NO 236
<211> LENGTH: 21
<212> TYPE: RNA
<213> ORGANISM: Artificial Sequence
<220> FEATURE:
<223> OTHER INFORMATION: Bgal478 sense
<220> FEATURE:
<221> NAME/KEY: modified_base
<222> LOCATION: (1)...(14)
<223> OTHER INFORMATION: n = gm
<220> FEATURE:
<221> NAME/KEY: modified_base
<222> LOCATION: (20)...(21)
<223> OTHER INFORMATION: n = deoxythymidine

<400> SEQUENCE: 236
naagnccaga cncnaauuan n                                              21

<210> SEQ ID NO 237
<211> LENGTH: 21
<212> TYPE: RNA
<213> ORGANISM: Artificial Sequence
<220> FEATURE:
<223> OTHER INFORMATION: Bgal478 antisense
<220> FEATURE:
<221> NAME/KEY: modified_base
<222> LOCATION: (5)...(17)
<223> OTHER INFORMATION: n = um
<220> FEATURE:
<221> NAME/KEY: modified_base
<222> LOCATION: (20)...(21)
<223> OTHER INFORMATION: n = deoxythymidine

<400> SEQUENCE: 237
uaauncgcgn cuggccnucn n                                              21

<210> SEQ ID NO 238
<211> LENGTH: 21
<212> TYPE: RNA
<213> ORGANISM: Artificial Sequence
<220> FEATURE:
<223> OTHER INFORMATION: COP1-2 sense with overhang
<220> FEATURE:
<221> NAME/KEY: modified_base
<222> LOCATION: (20)...(21)
<223> OTHER INFORMATION: n = deoxythymidine
```

-continued

```
<400> SEQUENCE: 238
ggaaugcuug uccaaguuun n                                              21

<210> SEQ ID NO 239
<211> LENGTH: 21
<212> TYPE: RNA
<213> ORGANISM: Artificial Sequence
<220> FEATURE:
<223> OTHER INFORMATION: COP1-2 antisense with overhang
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxyguanosine

<400> SEQUENCE: 239
aaacuuggac aagcauuccn n                                              21

<210> SEQ ID NO 240
<211> LENGTH: 21
<212> TYPE: RNA
<213> ORGANISM: Artificial Sequence
<220> FEATURE:
<223> OTHER INFORMATION: COP1-3 sense with overhang
<220> FEATURE:
<221> NAME/KEY: modified_base
<222> LOCATION: (20)...(21)
<223> OTHER INFORMATION: n = deoxythymidine

<400> SEQUENCE: 240
gcaacgacuu cguaugcccn n                                              21

<210> SEQ ID NO 241
<211> LENGTH: 21
<212> TYPE: RNA
<213> ORGANISM: Artificial Sequence
<220> FEATURE:
<223> OTHER INFORMATION: COP1-3 antisense with overhang
<220> FEATURE:
<221> NAME/KEY: modified_base
<222> LOCATION: (20)...(21)
<223> OTHER INFORMATION: n = deoxythymidine

<400> SEQUENCE: 241
gggcauacga agucguugcn n                                              21

<210> SEQ ID NO 242
<211> LENGTH: 21
<212> TYPE: RNA
<213> ORGANISM: Artificial Sequence
<220> FEATURE:
<223> OTHER INFORMATION: WEE1-1 sense with overhang
<220> FEATURE:
<221> NAME/KEY: modified_base
<222> LOCATION: (20)...(21)
<223> OTHER INFORMATION: n = deoxythymidine

<400> SEQUENCE: 242
gguauauuca uucaaugucn n                                              21

<210> SEQ ID NO 243
<211> LENGTH: 21
<212> TYPE: RNA
<213> ORGANISM: Artificial Sequence
<220> FEATURE:
```

-continued

```
<223> OTHER INFORMATION: WEE1-1 antisense with overhang
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxycytosine

<400> SEQUENCE: 243
gacauugaau gaauauaccn n                                              21

<210> SEQ ID NO 244
<211> LENGTH: 21
<212> TYPE: RNA
<213> ORGANISM: Artificial Sequence
<220> FEATURE:
<223> OTHER INFORMATION: WEE1-3 sense with overhang
<220> FEATURE:
<221> NAME/KEY: modified_base
<222> LOCATION: (20)...(21)
<223> OTHER INFORMATION: n = deoxythymidine

<400> SEQUENCE: 244
ggacaguguc gucguagaan n                                              21

<210> SEQ ID NO 245
<211> LENGTH: 21
<212> TYPE: RNA
<213> ORGANISM: Artificial Sequence
<220> FEATURE:
<223> OTHER INFORMATION: WEE1-3 antisense with overhang
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxyguanosine

<400> SEQUENCE: 245
uucuacgacg acacuguccn n                                              21

<210> SEQ ID NO 246
<211> LENGTH: 21
<212> TYPE: RNA
<213> ORGANISM: Artificial Sequence
<220> FEATURE:
<223> OTHER INFORMATION: COP1 antisense
<220> FEATURE:
<221> NAME/KEY: modified_base
<222> LOCATION: (9)...(15)
<223> OTHER INFORMATION: n = um
<220> FEATURE:
<221> NAME/KEY: modified_base
<222> LOCATION: (20)...(21)
<223> OTHER INFORMATION: n = deoxythymidine

<400> SEQUENCE: 246
agacugcunu acggnguccn n                                              21

<210> SEQ ID NO 247
<211> LENGTH: 21
<212> TYPE: RNA
<213> ORGANISM: Artificial Sequence
<220> FEATURE:
<223> OTHER INFORMATION: COP1 antisense
<220> FEATURE:
<221> NAME/KEY: modified_base
```

```
<222> LOCATION: (6)...(6)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (14)...(14)
<223> OTHER INFORMATION: n = gm
<220> FEATURE:
<221> NAME/KEY: modified_base
<222> LOCATION: (17)...(17)
<223> OTHER INFORMATION: n = um
<220> FEATURE:
<221> NAME/KEY: modified_base
<222> LOCATION: (20)...(21)
<223> OTHER INFORMATION: n = deoxythymidine

<400> SEQUENCE: 247
agacuncuun acgnugnccn n                                              21

<210> SEQ ID NO 248
<211> LENGTH: 21
<212> TYPE: RNA
<213> ORGANISM: Artificial Sequence
<220> FEATURE:
<223> OTHER INFORMATION: COP1 sense
<220> FEATURE:
<221> NAME/KEY: modified_base
<222> LOCATION: (2)...(2)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (20)...(21)
<223> OTHER INFORMATION: n = deoxythymidine

<400> SEQUENCE: 248
gnacaccgna aancagucun n                                              21

<210> SEQ ID NO 249
<211> LENGTH: 21
<212> TYPE: RNA
<213> ORGANISM: Artificial Sequence
<220> FEATURE:
<223> OTHER INFORMATION: WEE1-1 sense

<400> SEQUENCE: 249
ggcuggaugg augcauuuau u                                              21

<210> SEQ ID NO 250
<211> LENGTH: 21
<212> TYPE: RNA
<213> ORGANISM: Artificial Sequence
<220> FEATURE:
<223> OTHER INFORMATION: WEE1-3 sense
<220> FEATURE:
<221> NAME/KEY: modified_base
<222> LOCATION: (4)...(16)
<223> OTHER INFORMATION: n = um

<400> SEQUENCE: 250
ggcnggangg angcanuuau u                                              21
```

```
<210> SEQ ID NO 251
<211> LENGTH: 21
<212> TYPE: RNA
<213> ORGANISM: Artificial Sequence
<220> FEATURE:
<223> OTHER INFORMATION: WEE1-4 sense
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (4)...(17)
<223> OTHER INFORMATION: n = um

<400> SEQUENCE: 251
ngcnggaugg augcaunuau u                                              21

<210> SEQ ID NO 252
<211> LENGTH: 21
<212> TYPE: RNA
<213> ORGANISM: Artificial Sequence
<220> FEATURE:
<223> OTHER INFORMATION: WEE1 antisense
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (17)...(17)
<223> OTHER INFORMATION: n = gm

<400> SEQUENCE: 252
uaaangcauc cauccanccu c                                              21

<210> SEQ ID NO 253
<211> LENGTH: 21
<212> TYPE: RNA
<213> ORGANISM: Artificial Sequence
<220> FEATURE:
<223> OTHER INFORMATION: WEE1 antisense
<220> FEATURE:
<221> NAME/KEY: modified_base
<222> LOCATION: (9)...(13)
<223> OTHER INFORMATION: n = um
<220> FEATURE:
<221> NAME/KEY: modified_base
<222> LOCATION: (17)...(17)
<223> OTHER INFORMATION: n = gm

<400> SEQUENCE: 253
uaaaugcanc canccanccu c                                              21

<210> SEQ ID NO 254
<211> LENGTH: 21
<212> TYPE: RNA
<213> ORGANISM: Artificial Sequence
<220> FEATURE:
<223> OTHER INFORMATION: WEE1 antisense
<220> FEATURE:
<221> NAME/KEY: modified_base
<222> LOCATION: (6)...(17)
<223> OTHER INFORMATION: n = gm

<400> SEQUENCE: 254
uaaauncauc cauccanccu c                                              21

<210> SEQ ID NO 255
<211> LENGTH: 21
```

```
<212> TYPE: RNA
<213> ORGANISM: Artificial Sequence
<220> FEATURE:
<223> OTHER INFORMATION: WEE1 antisense

<400> SEQUENCE: 255
uaaaugcauc cauccagccu c                                         21

<210> SEQ ID NO 256
<211> LENGTH: 21
<212> TYPE: RNA
<213> ORGANISM: Artificial Sequence
<220> FEATURE:
<223> OTHER INFORMATION: WEE1-60 sense

<400> SEQUENCE: 256
gcuggcgaac aaauguaaac a                                         21

<210> SEQ ID NO 257
<211> LENGTH: 21
<212> TYPE: RNA
<213> ORGANISM: Artificial Sequence
<220> FEATURE:
<223> OTHER INFORMATION: WEE1-60 antisense

<400> SEQUENCE: 257
uuuacauuug uucgccagca c                                         21

<210> SEQ ID NO 258
<211> LENGTH: 21
<212> TYPE: RNA
<213> ORGANISM: Artificial Sequence
<220> FEATURE:
<223> OTHER INFORMATION: WEE1-1828 sense

<400> SEQUENCE: 258
cuccucaagu gaauauuaau c                                         21

<210> SEQ ID NO 259
<211> LENGTH: 21
<212> TYPE: RNA
<213> ORGANISM: Artificial Sequence
<220> FEATURE:
<223> OTHER INFORMATION: WEE1-1828 antisense

<400> SEQUENCE: 259
uuaauauuca cuugaggagu c                                         21

<210> SEQ ID NO 260
<211> LENGTH: 21
<212> TYPE: RNA
<213> ORGANISM: Artificial Sequence
<220> FEATURE:
<223> OTHER INFORMATION: WEE1-1937 sense

<400> SEQUENCE: 260
cauggaagcc agugauuaug a                                         21

<210> SEQ ID NO 261
<211> LENGTH: 21
<212> TYPE: RNA
<213> ORGANISM: Artificial Sequence
<220> FEATURE:
<223> OTHER INFORMATION: WEE1-1937 antisense

<400> SEQUENCE: 261
```
auaaucacug gcuuccaugu c                                            21

<210> SEQ ID NO 262
<211> LENGTH: 21
<212> TYPE: RNA
<213> ORGANISM: Artificial Sequence
<220> FEATURE:
<223> OTHER INFORMATION: WEE1-2017 sense

<400> SEQUENCE: 262
cccgguauac aacagaauuu c                                            21

<210> SEQ ID NO 263
<211> LENGTH: 21
<212> TYPE: RNA
<213> ORGANISM: Artificial Sequence
<220> FEATURE:
<223> OTHER INFORMATION: WEE1-2017 antisense

<400> SEQUENCE: 263
aauucuguug uauaccggga c                                            21

<210> SEQ ID NO 264
<211> LENGTH: 21
<212> TYPE: RNA
<213> ORGANISM: Artificial Sequence
<220> FEATURE:
<223> OTHER INFORMATION: WEE1-2018 sense

<400> SEQUENCE: 264
ccgguauaca acagaauuuc a                                            21

<210> SEQ ID NO 265
<211> LENGTH: 21
<212> TYPE: RNA
<213> ORGANISM: Artificial Sequence
<220> FEATURE:
<223> OTHER INFORMATION: WEE1-2018 antisense

<400> SEQUENCE: 265
aaauucuguu guauaccggg a                                            21

<210> SEQ ID NO 266
<211> LENGTH: 21
<212> TYPE: RNA
<213> ORGANISM: Artificial Sequence
<220> FEATURE:
<223> OTHER INFORMATION: WEE1-2094

<400> SEQUENCE: 266
aggcuggaug gaugcauuua u                                            21

<210> SEQ ID NO 267
<211> LENGTH: 21
<212> TYPE: RNA
<213> ORGANISM: Artificial Sequence
<220> FEATURE:
<223> OTHER INFORMATION: WEE1-2094 antisense

<400> SEQUENCE: 267
aaaugcaucc auccagccuc u                                            21

<210> SEQ ID NO 268
<211> LENGTH: 21
<212> TYPE: RNA
<213> ORGANISM: Artificial Sequence

```
<220> FEATURE:
<223> OTHER INFORMATION: WEE1-2104 sense

<400> SEQUENCE: 268
gaugcauuua ugccauuaag c                                              21

<210> SEQ ID NO 269
<211> LENGTH: 21
<212> TYPE: RNA
<213> ORGANISM: Artificial Sequence
<220> FEATURE:
<223> OTHER INFORMATION: WEE1-2104 antisense

<400> SEQUENCE: 269
uuaauggcau aaaugcaucc a                                              21

<210> SEQ ID NO 270
<211> LENGTH: 21
<212> TYPE: RNA
<213> ORGANISM: Artificial Sequence
<220> FEATURE:
<223> OTHER INFORMATION: WEE1-2105 sense

<400> SEQUENCE: 270
augcauuuau gccauuaagc g                                              21

<210> SEQ ID NO 271
<211> LENGTH: 21
<212> TYPE: RNA
<213> ORGANISM: Artificial Sequence
<220> FEATURE:
<223> OTHER INFORMATION: WEE1-2105 antisense

<400> SEQUENCE: 271
cuuaauggca uaaaugcauc c                                              21

<210> SEQ ID NO 272
<211> LENGTH: 21
<212> TYPE: RNA
<213> ORGANISM: Artificial Sequence
<220> FEATURE:
<223> OTHER INFORMATION: WEE1-2208 sense

<400> SEQUENCE: 272
ucucauguag uucgauauuu c                                              21

<210> SEQ ID NO 273
<211> LENGTH: 21
<212> TYPE: RNA
<213> ORGANISM: Artificial Sequence
<220> FEATURE:
<223> OTHER INFORMATION: WEE1-2208 antisense

<400> SEQUENCE: 273
aauaucgaac uacaugagaa u                                              21

<210> SEQ ID NO 274
<211> LENGTH: 21
<212> TYPE: RNA
<213> ORGANISM: Artificial Sequence
<220> FEATURE:
<223> OTHER INFORMATION: WEE1-2372 sense

<400> SEQUENCE: 274
ccgaggcuug agguauauuc a                                              21
```

```
<210> SEQ ID NO 275
<211> LENGTH: 21
<212> TYPE: RNA
<213> ORGANISM: Artificial Sequence
<220> FEATURE:
<223> OTHER INFORMATION: WEE1-2372 antisense

<400> SEQUENCE: 275
aauauaccuc aagccucggc c                                              21

<210> SEQ ID NO 276
<211> LENGTH: 21
<212> TYPE: RNA
<213> ORGANISM: Artificial Sequence
<220> FEATURE:
<223> OTHER INFORMATION: WEE1-2402 sense

<400> SEQUENCE: 276
uuugguucac auggauauaa a                                              21

<210> SEQ ID NO 277
<211> LENGTH: 21
<212> TYPE: RNA
<213> ORGANISM: Artificial Sequence
<220> FEATURE:
<223> OTHER INFORMATION: WEE1-2402 antisense

<400> SEQUENCE: 277
uauauccaug ugaaccaaag a                                              21

<210> SEQ ID NO 278
<211> LENGTH: 21
<212> TYPE: RNA
<213> ORGANISM: Artificial Sequence
<220> FEATURE:
<223> OTHER INFORMATION: WEE1-2748 sense

<400> SEQUENCE: 278
gugcuuuccc aagaauuuac a                                              21

<210> SEQ ID NO 279
<211> LENGTH: 21
<212> TYPE: RNA
<213> ORGANISM: Artificial Sequence
<220> FEATURE:
<223> OTHER INFORMATION: WEE1-3003 antisense

<400> SEQUENCE: 279
uaaauucuug ggaaagcacu u                                              21

<210> SEQ ID NO 280
<211> LENGTH: 21
<212> TYPE: RNA
<213> ORGANISM: Artificial Sequence
<220> FEATURE:
<223> OTHER INFORMATION: WEE1-3003 sense

<400> SEQUENCE: 280
uccaccaccc agaguaauag a                                              21

<210> SEQ ID NO 281
<211> LENGTH: 21
<212> TYPE: RNA
<213> ORGANISM: Artificial Sequence
<220> FEATURE:
<223> OTHER INFORMATION: WEE1-3003 antisense
```

```
<400> SEQUENCE: 281
uauuacucug gguggugggac c                                              21

<210> SEQ ID NO 282
<211> LENGTH: 21
<212> TYPE: RNA
<213> ORGANISM: Artificial Sequence
<220> FEATURE:
<223> OTHER INFORMATION: WEE1-3057 sense

<400> SEQUENCE: 282
ucugucagcc uuacuauaua c                                               21

<210> SEQ ID NO 283
<211> LENGTH: 21
<212> TYPE: RNA
<213> ORGANISM: Artificial Sequence
<220> FEATURE:
<223> OTHER INFORMATION: WEE1-3057 antisense

<400> SEQUENCE: 283
auauaguaag gcugacagag c                                               21

<210> SEQ ID NO 284
<211> LENGTH: 21
<212> TYPE: RNA
<213> ORGANISM: Artificial Sequence
<220> FEATURE:
<223> OTHER INFORMATION: WEE1-3119 sense

<400> SEQUENCE: 284
gaggaagcua gguugaaauc a                                               21

<210> SEQ ID NO 285
<211> LENGTH: 21
<212> TYPE: RNA
<213> ORGANISM: Artificial Sequence
<220> FEATURE:
<223> OTHER INFORMATION: WEE1-3119 antisense

<400> SEQUENCE: 285
auuucaaccu agcuuccucu u                                               21

<210> SEQ ID NO 286
<211> LENGTH: 21
<212> TYPE: RNA
<213> ORGANISM: Artificial Sequence
<220> FEATURE:
<223> OTHER INFORMATION: WEE1-3337

<400> SEQUENCE: 286
ugguggugug cugcuuauag u                                               21

<210> SEQ ID NO 287
<211> LENGTH: 21
<212> TYPE: RNA
<213> ORGANISM: Artificial Sequence
<220> FEATURE:
<223> OTHER INFORMATION: WEE1-3337 antisense

<400> SEQUENCE: 287
uauaagcagc acaccaccac a                                               21

<210> SEQ ID NO 288
```

```
<211> LENGTH: 21
<212> TYPE: RNA
<213> ORGANISM: Artificial Sequence
<220> FEATURE:
<223> OTHER INFORMATION: WEE1-3497 sense

<400> SEQUENCE: 288
guguguccau cuuauauuuc u                                              21

<210> SEQ ID NO 289
<211> LENGTH: 21
<212> TYPE: RNA
<213> ORGANISM: Artificial Sequence
<220> FEATURE:
<223> OTHER INFORMATION: WEE1-3497 antisense

<400> SEQUENCE: 289
aaauauaaga uggacacaca g                                              21

<210> SEQ ID NO 290
<211> LENGTH: 21
<212> TYPE: RNA
<213> ORGANISM: Artificial Sequence
<220> FEATURE:
<223> OTHER INFORMATION: WEE1-3607 sense

<400> SEQUENCE: 290
agguauugcc uugugaauuu g                                              21

<210> SEQ ID NO 291
<211> LENGTH: 21
<212> TYPE: RNA
<213> ORGANISM: Artificial Sequence
<220> FEATURE:
<223> OTHER INFORMATION: WEE1-3607 antisense

<400> SEQUENCE: 291
agguauugcc uugugaauuu g                                              21

<210> SEQ ID NO 292
<211> LENGTH: 21
<212> TYPE: RNA
<213> ORGANISM: Artificial Sequence
<220> FEATURE:
<223> OTHER INFORMATION: WEE1-3608 sense

<400> SEQUENCE: 292
gguauugccu ugugaauuug c                                              21

<210> SEQ ID NO 293
<211> LENGTH: 21
<212> TYPE: RNA
<213> ORGANISM: Artificial Sequence
<220> FEATURE:
<223> OTHER INFORMATION: WEE1-3608 antisense

<400> SEQUENCE: 293
aaauucacaa ggcaauaccu c                                              21

<210> SEQ ID NO 294
<211> LENGTH: 21
<212> TYPE: RNA
<213> ORGANISM: Artificial Sequence
<220> FEATURE:
<223> OTHER INFORMATION: WEE1-3058 sense
<220> FEATURE:
<221> NAME/KEY: modified_base
```

```
<222> LOCATION: (2)...(2)
<223> OTHER INFORMATION: n = um
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (11)...(16)
<223> OTHER INFORMATION: n = um

<400> SEQUENCE: 294
cnnucagccu nacuanauac u                                              21

<210> SEQ ID NO 295
<211> LENGTH: 21
<212> TYPE: RNA
<213> ORGANISM: Artificial Sequence
<220> FEATURE:
<223> OTHER INFORMATION: WEE1-3058 sense
<220> FEATURE:
<221> NAME/KEY: modified_base
<222> LOCATION: (4)...(4)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (14)...(14)
<223> OTHER INFORMATION: n = um

<400> SEQUENCE: 295
cugncanccu uacnauauac u                                              21

<210> SEQ ID NO 296
<211> LENGTH: 21
<212> TYPE: RNA
<213> ORGANISM: Artificial Sequence
<220> FEATURE:
<223> OTHER INFORMATION: WEE1-3058 antisense
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (14)...(14)
<223> OTHER INFORMATION: n = um

<400> SEQUENCE: 296
uauauagnaa gncngacaga g                                              21

<210> SEQ ID NO 297
<211> LENGTH: 21
<212> TYPE: RNA
<213> ORGANISM: Artificial Sequence
<220> FEATURE:
<223> OTHER INFORMATION: WEE1-3058 antisense
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
```

```
<221> NAME/KEY: modified_base
<222> LOCATION: (14)...(14)
<223> OTHER INFORMATION: n = um
<220> FEATURE:
<221> NAME/KEY: modified_base
<222> LOCATION: (15)...(15)
<223> OTHER INFORMATION: n = gm

<400> SEQUENCE: 297
uauananuaa ggcnnacaga g                                              21

<210> SEQ ID NO 298
<211> LENGTH: 21
<212> TYPE: RNA
<213> ORGANISM: Artificial Sequence
<220> FEATURE:
<223> OTHER INFORMATION: WEE1-3058 antisense
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (14)...(14)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 298
uauananuaa ggcngacana g                                              21

<210> SEQ ID NO 299
<211> LENGTH: 21
<212> TYPE: RNA
<213> ORGANISM: Artificial Sequence
<220> FEATURE:
<223> OTHER INFORMATION: COP1-739 sense

<400> SEQUENCE: 299
agaguuugga ggacaauaau a                                              21

<210> SEQ ID NO 300
<211> LENGTH: 21
<212> TYPE: RNA
<213> ORGANISM: Artificial Sequence
<220> FEATURE:
<223> OTHER INFORMATION: COP1-739 antisense

<400> SEQUENCE: 300
uuauuguccu ccaaacucug a                                              21

<210> SEQ ID NO 301
<211> LENGTH: 21
<212> TYPE: RNA
<213> ORGANISM: Artificial Sequence
<220> FEATURE:
<223> OTHER INFORMATION: COP1-740 sense

<400> SEQUENCE: 301
gaguuuggag gacaauaaua g                                              21

<210> SEQ ID NO 302
<211> LENGTH: 21
```

```
<212> TYPE: RNA
<213> ORGANISM: Artificial Sequence
<220> FEATURE:
<223> OTHER INFORMATION: COP1-740 antisense

<400> SEQUENCE: 302
auuauugucc uccaaacucu g                                              21

<210> SEQ ID NO 303
<211> LENGTH: 21
<212> TYPE: RNA
<213> ORGANISM: Artificial Sequence
<220> FEATURE:
<223> OTHER INFORMATION: COP1-795

<400> SEQUENCE: 303
gaccaucugu auccuaauuu c                                              21

<210> SEQ ID NO 304
<211> LENGTH: 21
<212> TYPE: RNA
<213> ORGANISM: Artificial Sequence
<220> FEATURE:
<223> OTHER INFORMATION: COP1-795 antisense

<400> SEQUENCE: 304
aauuaggaua cagaugguca a                                              21

<210> SEQ ID NO 305
<211> LENGTH: 21
<212> TYPE: RNA
<213> ORGANISM: Artificial Sequence
<220> FEATURE:
<223> OTHER INFORMATION: COP1-1060 sense

<400> SEQUENCE: 305
agguugcaag aagaaauaag a                                              21

<210> SEQ ID NO 306
<211> LENGTH: 21
<212> TYPE: RNA
<213> ORGANISM: Artificial Sequence
<220> FEATURE:
<223> OTHER INFORMATION: COP1-1060 antisense

<400> SEQUENCE: 306
uuauuucuuc uugcaaccuu g                                              21

<210> SEQ ID NO 307
<211> LENGTH: 21
<212> TYPE: RNA
<213> ORGANISM: Artificial Sequence
<220> FEATURE:
<223> OTHER INFORMATION: COP1-1213 sense

<400> SEQUENCE: 307
caucacacag uaguauuauu g                                              21

<210> SEQ ID NO 308
<211> LENGTH: 21
<212> TYPE: RNA
<213> ORGANISM: Artificial Sequence
<220> FEATURE:
<223> OTHER INFORMATION: COP1-1213 antisense

<400> SEQUENCE: 308
```
auaauacuac ugugugaugg a                                21

<210> SEQ ID NO 309
<211> LENGTH: 21
<212> TYPE: RNA
<213> ORGANISM: Artificial Sequence
<220> FEATURE:
<223> OTHER INFORMATION: COP1-1286 sense

<400> SEQUENCE: 309
gaaacagccu ugguauaaua g                                21

<210> SEQ ID NO 310
<211> LENGTH: 21
<212> TYPE: RNA
<213> ORGANISM: Artificial Sequence
<220> FEATURE:
<223> OTHER INFORMATION: COP1-1286 antisense

<400> SEQUENCE: 310
auuauaccaa ggcuguuucu u                                21

<210> SEQ ID NO 311
<211> LENGTH: 21
<212> TYPE: RNA
<213> ORGANISM: Artificial Sequence
<220> FEATURE:
<223> OTHER INFORMATION: COP1-1412 sense

<400> SEQUENCE: 311
aagccaguug gaugaauuuc a                                21

<210> SEQ ID NO 312
<211> LENGTH: 21
<212> TYPE: RNA
<213> ORGANISM: Artificial Sequence
<220> FEATURE:
<223> OTHER INFORMATION: COP1-1412 antisense

<400> SEQUENCE: 312
aaauucaucc aacuggcuug c                                21

<210> SEQ ID NO 313
<211> LENGTH: 21
<212> TYPE: RNA
<213> ORGANISM: Artificial Sequence
<220> FEATURE:
<223> OTHER INFORMATION: COP1-1801 sense

<400> SEQUENCE: 313
guuggagugu ugacuuuaau u                                21

<210> SEQ ID NO 314
<211> LENGTH: 21
<212> TYPE: RNA
<213> ORGANISM: Artificial Sequence
<220> FEATURE:
<223> OTHER INFORMATION: COP1-1801 antisense

<400> SEQUENCE: 314
uuaaagucaa cacuccaaca c                                21

<210> SEQ ID NO 315
<211> LENGTH: 21
<212> TYPE: RNA
<213> ORGANISM: Artificial Sequence

```
<220> FEATURE:
<223> OTHER INFORMATION: COP1-1802 sense

<400> SEQUENCE: 315
uuggaguguu gacuuuaauu u                                              21

<210> SEQ ID NO 316
<211> LENGTH: 21
<212> TYPE: RNA
<213> ORGANISM: Artificial Sequence
<220> FEATURE:
<223> OTHER INFORMATION: COP1-1802 antisense

<400> SEQUENCE: 316
auuaaaguca acacuccaac a                                              21

<210> SEQ ID NO 317
<211> LENGTH: 21
<212> TYPE: RNA
<213> ORGANISM: Artificial Sequence
<220> FEATURE:
<223> OTHER INFORMATION: COP1-1803 sense

<400> SEQUENCE: 317
uggaguguug acuuuaauuu g                                              21

<210> SEQ ID NO 318
<211> LENGTH: 21
<212> TYPE: RNA
<213> ORGANISM: Artificial Sequence
<220> FEATURE:
<223> OTHER INFORMATION: COP1-1803 antisense

<400> SEQUENCE: 318
aauuaaaguc aacacuccaa c                                              21

<210> SEQ ID NO 319
<211> LENGTH: 21
<212> TYPE: RNA
<213> ORGANISM: Artificial Sequence
<220> FEATURE:
<223> OTHER INFORMATION: COP1-1804 sense

<400> SEQUENCE: 319
ggaguguuga cuuuaauuug a                                              21

<210> SEQ ID NO 320
<211> LENGTH: 21
<212> TYPE: RNA
<213> ORGANISM: Artificial Sequence
<220> FEATURE:
<223> OTHER INFORMATION: COP1-1804 antisense

<400> SEQUENCE: 320
aaauuaaagu caacacucca a                                              21

<210> SEQ ID NO 321
<211> LENGTH: 21
<212> TYPE: RNA
<213> ORGANISM: Artificial Sequence
<220> FEATURE:
<223> OTHER INFORMATION: COP1-1923 sense

<400> SEQUENCE: 321
aaugugugcu guguuaaauu c                                              21
```

```
<210> SEQ ID NO 322
<211> LENGTH: 21
<212> TYPE: RNA
<213> ORGANISM: Artificial Sequence
<220> FEATURE:
<223> OTHER INFORMATION: COP1-1923 antisense

<400> SEQUENCE: 322
auuuaacaca gcacacauua g                                                    21

<210> SEQ ID NO 323
<211> LENGTH: 21
<212> TYPE: RNA
<213> ORGANISM: Artificial Sequence
<220> FEATURE:
<223> OTHER INFORMATION: COP1-1924 sense

<400> SEQUENCE: 323
augugugcug uguuaaauuc a                                                    21

<210> SEQ ID NO 324
<211> LENGTH: 21
<212> TYPE: RNA
<213> ORGANISM: Artificial Sequence
<220> FEATURE:
<223> OTHER INFORMATION: COP1-1924 antisense

<400> SEQUENCE: 324
aauuuaacac agcacacauu a                                                    21

<210> SEQ ID NO 325
<211> LENGTH: 21
<212> TYPE: RNA
<213> ORGANISM: Artificial Sequence
<220> FEATURE:
<223> OTHER INFORMATION: COP1-2075 sense

<400> SEQUENCE: 325
ugugaguggu gaggaaauug u                                                    21

<210> SEQ ID NO 326
<211> LENGTH: 21
<212> TYPE: RNA
<213> ORGANISM: Artificial Sequence
<220> FEATURE:
<223> OTHER INFORMATION: COP1-2075 antisense

<400> SEQUENCE: 326
aauuuccuca ccacucacaa a                                                    21

<210> SEQ ID NO 327
<211> LENGTH: 21
<212> TYPE: RNA
<213> ORGANISM: Artificial Sequence
<220> FEATURE:
<223> OTHER INFORMATION: COP1-2198 sense

<400> SEQUENCE: 327
ggcuuccaau ggagauuaua u                                                    21

<210> SEQ ID NO 328
<211> LENGTH: 21
<212> TYPE: RNA
<213> ORGANISM: Artificial Sequence
<220> FEATURE:
<223> OTHER INFORMATION: COP1-2198 antisense
```

```
<400> SEQUENCE: 328
auaaucucca uuggaagcca g                                              21

<210> SEQ ID NO 329
<211> LENGTH: 21
<212> TYPE: RNA
<213> ORGANISM: Artificial Sequence
<220> FEATURE:
<223> OTHER INFORMATION: COP1-2412 sense

<400> SEQUENCE: 329
aacagucagg guacaauuaa g                                              21

<210> SEQ ID NO 330
<211> LENGTH: 21
<212> TYPE: RNA
<213> ORGANISM: Artificial Sequence
<220> FEATURE:
<223> OTHER INFORMATION: COP1-2412 antisense

<400> SEQUENCE: 330
uaauuguacc cugacuguua g                                              21

<210> SEQ ID NO 331
<211> LENGTH: 21
<212> TYPE: RNA
<213> ORGANISM: Artificial Sequence
<220> FEATURE:
<223> OTHER INFORMATION: COP1-2413 sense

<400> SEQUENCE: 331
acagucaggg uacaauuaag g                                              21

<210> SEQ ID NO 332
<211> LENGTH: 21
<212> TYPE: RNA
<213> ORGANISM: Artificial Sequence
<220> FEATURE:
<223> OTHER INFORMATION: COP1-2413 antisense

<400> SEQUENCE: 332
uuaauuguac ccugacuguu a                                              21

<210> SEQ ID NO 333
<211> LENGTH: 21
<212> TYPE: RNA
<213> ORGANISM: Artificial Sequence
<220> FEATURE:
<223> OTHER INFORMATION: COP1-2452 sense

<400> SEQUENCE: 333
ggguuaacuc aagucaaauu g                                              21

<210> SEQ ID NO 334
<211> LENGTH: 21
<212> TYPE: RNA
<213> ORGANISM: Artificial Sequence
<220> FEATURE:
<223> OTHER INFORMATION: COP1-2452 antisense

<400> SEQUENCE: 334
auuugacuug aguuaacccu u                                              21

<210> SEQ ID NO 335
```

```
<211> LENGTH: 21
<212> TYPE: RNA
<213> ORGANISM: Artificial Sequence
<220> FEATURE:
<223> OTHER INFORMATION: COP1-2453

<400> SEQUENCE: 335
gguuaacuca agucaaauug u                                              21

<210> SEQ ID NO 336
<211> LENGTH: 21
<212> TYPE: RNA
<213> ORGANISM: Artificial Sequence
<220> FEATURE:
<223> OTHER INFORMATION: COP1-2453 antisense

<400> SEQUENCE: 336
aauuugacuu gaguuaaccc u                                              21

<210> SEQ ID NO 337
<211> LENGTH: 21
<212> TYPE: RNA
<213> ORGANISM: Artificial Sequence
<220> FEATURE:
<223> OTHER INFORMATION: COP1-2474 sense

<400> SEQUENCE: 337
acuugauccu gcugaaauac a                                              21

<210> SEQ ID NO 338
<211> LENGTH: 21
<212> TYPE: RNA
<213> ORGANISM: Artificial Sequence
<220> FEATURE:
<223> OTHER INFORMATION: COP1-2474 antisense

<400> SEQUENCE: 338
uauuucagca ggaucaagua c                                              21

<210> SEQ ID NO 339
<211> LENGTH: 21
<212> TYPE: RNA
<213> ORGANISM: Artificial Sequence
<220> FEATURE:
<223> OTHER INFORMATION: COP1-2705 sense

<400> SEQUENCE: 339
ugugauaggg aaacaaauuc u                                              21

<210> SEQ ID NO 340
<211> LENGTH: 21
<212> TYPE: RNA
<213> ORGANISM: Artificial Sequence
<220> FEATURE:
<223> OTHER INFORMATION: COP1-2705 antisense

<400> SEQUENCE: 340
aauuuguuuc ccuaucacaa a                                              21

<210> SEQ ID NO 341
<211> LENGTH: 21
<212> TYPE: RNA
<213> ORGANISM: Artificial Sequence
<220> FEATURE:
<223> OTHER INFORMATION: COP1-1181 sense
<220> FEATURE:
<221> NAME/KEY: modified_base
```

```
<222> LOCATION: (3)...(8)
<223> OTHER INFORMATION: n = gm
<220> FEATURE:
<221> NAME/KEY: modified_base
<222> LOCATION: (13)...(13)
<223> OTHER INFORMATION: n = um
<220> FEATURE:
<221> NAME/KEY: modified_base
<222> LOCATION: (20)...(20)
<223> OTHER INFORMATION: n = gm

<400> SEQUENCE: 341
uancacanug ccncaauuun a                                              21

<210> SEQ ID NO 342
<211> LENGTH: 21
<212> TYPE: RNA
<213> ORGANISM: Artificial Sequence
<220> FEATURE:
<223> OTHER INFORMATION: COP1-1181 sense
<220> FEATURE:
<221> NAME/KEY: modified_base
<222> LOCATION: (1)...(19)
<223> OTHER INFORMATION: n = um

<400> SEQUENCE: 342
nagcacagug ccncaannng a                                              21

<210> SEQ ID NO 343
<211> LENGTH: 21
<212> TYPE: RNA
<213> ORGANISM: Artificial Sequence
<220> FEATURE:
<223> OTHER INFORMATION: COP1-1181 sense
<220> FEATURE:
<221> NAME/KEY: modified_base
<222> LOCATION: (1)...(1)
<223> OTHER INFORMATION: n = um
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (17)...(17)
<223> OTHER INFORMATION: n = um
<220> FEATURE:
<221> NAME/KEY: modified_base
<222> LOCATION: (20)...(20)
<223> OTHER INFORMATION: n = gm

<400> SEQUENCE: 343
nancacagug ccucaanuun a                                              21

<210> SEQ ID NO 344
<211> LENGTH: 21
<212> TYPE: RNA
<213> ORGANISM: Artificial Sequence
<220> FEATURE:
<223> OTHER INFORMATION: COP1-1181 antisense
<220> FEATURE:
<221> NAME/KEY: modified_base
<222> LOCATION: (5)...(13)
<223> OTHER INFORMATION: n = um
<220> FEATURE:
<221> NAME/KEY: modified_base
<222> LOCATION: (14)...(14)
<223> OTHER INFORMATION: n = gm
<220> FEATURE:
<221> NAME/KEY: modified_base
<222> LOCATION: (20)...(20)
<223> OTHER INFORMATION: n = um
```

```
<400> SEQUENCE: 344
aaaungaggc acnnugcuan c                                             21

<210> SEQ ID NO 345
<211> LENGTH: 21
<212> TYPE: RNA
<213> ORGANISM: Artificial Sequence
<220> FEATURE:
<223> OTHER INFORMATION: COP1-1181 antisense
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 345
aaauugagnc acugngcnau c                                             21

<210> SEQ ID NO 346
<211> LENGTH: 21
<212> TYPE: RNA
<213> ORGANISM: Artificial Sequence
<220> FEATURE:
<223> OTHER INFORMATION: COP1-1181 antisense
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (13)...(20)
<223> OTHER INFORMATION: n = um

<400> SEQUENCE: 346
aaauugagnc acngugcuan c                                             21

<210> SEQ ID NO 347
<211> LENGTH: 21
<212> TYPE: RNA
<213> ORGANISM: Artificial Sequence
<220> FEATURE:
<223> OTHER INFORMATION: COP1-1181 antisense
<220> FEATURE:
<221> NAME/KEY: modified_base
<222> LOCATION: (4)...(5)
<223> OTHER INFORMATION: n = um
<220> FEATURE:
<221> NAME/KEY: modified_base
<222> LOCATION: (6)...(16)
<223> OTHER INFORMATION: n = gm
<220> FEATURE:
<221> NAME/KEY: modified_base
<222> LOCATION: (18)...(20)
<223> OTHER INFORMATION: n = um

<400> SEQUENCE: 347
aaannnaggc acuguncnan c                                             21

<210> SEQ ID NO 348
<211> LENGTH: 20
<212> TYPE: DNA
<213> ORGANISM: Artificial Sequence
<220> FEATURE:
<223> OTHER INFORMATION: COP1 forward primer

<400> SEQUENCE: 348
gcacgttagc atcaagacga                                               20
```

```
<210> SEQ ID NO 349
<211> LENGTH: 20
<212> TYPE: DNA
<213> ORGANISM: Artificial Sequence
<220> FEATURE:
<223> OTHER INFORMATION: COP1 reverse primer

<400> SEQUENCE: 349
acaatcccgg tcaaattcaa                                                 20

<210> SEQ ID NO 350
<211> LENGTH: 20
<212> TYPE: DNA
<213> ORGANISM: Artificial Sequence
<220> FEATURE:
<223> OTHER INFORMATION: CSN5 forward primer

<400> SEQUENCE: 350
tctgctgaag atggtgatgc                                                 20

<210> SEQ ID NO 351
<211> LENGTH: 20
<212> TYPE: DNA
<213> ORGANISM: Artificial Sequence
<220> FEATURE:
<223> OTHER INFORMATION: CSN5 reverse primer

<400> SEQUENCE: 351
gccaacctgt tttgcatttt                                                 20

<210> SEQ ID NO 352
<211> LENGTH: 21
<212> TYPE: RNA
<213> ORGANISM: Artificial Sequence
<220> FEATURE:
<223> OTHER INFORMATION: CSN5-1 sense
<220> FEATURE:
<221> NAME/KEY: modified_base
<222> LOCATION: (20)...(21)
<223> OTHER INFORMATION: n = deoxythymidine

<400> SEQUENCE: 352
ccauuacuuu aaguacugcn n                                               21

<210> SEQ ID NO 353
<211> LENGTH: 21
<212> TYPE: RNA
<213> ORGANISM: Artificial Sequence
<220> FEATURE:
<223> OTHER INFORMATION: CSN5-1 antisense
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxyguanosine

<400> SEQUENCE: 353
gcaguacuua aaguaauggn n                                               21

<210> SEQ ID NO 354
<211> LENGTH: 21
<212> TYPE: RNA
<213> ORGANISM: Artificial Sequence
<220> FEATURE:
```

```
<223> OTHER INFORMATION: CSN5-3 sense
<220> FEATURE:
<221> NAME/KEY: modified_base
<222> LOCATION: (20)...(21)
<223> OTHER INFORMATION: n = deoxythymidine

<400> SEQUENCE: 354
ccgaaaauca gaagacaaan n                                              21

<210> SEQ ID NO 355
<211> LENGTH: 21
<212> TYPE: RNA
<213> ORGANISM: Artificial Sequence
<220> FEATURE:
<223> OTHER INFORMATION: CSN5-3 antisense
<220> FEATURE:
<221> NAME/KEY: modified_base
<222> LOCATION: (20)...(20)
<223> OTHER INFORMATION: n = deoxythymidine
<220> FEATURE:
<221> NAME/KEY: modified_base
<222> LOCATION: (21)...(21)
<223> OTHER INFORMATION: n = deoxycytidine

<400> SEQUENCE: 355
uuugucuucu gauuuucggn n                                              21
```